United States Patent
Kardorff et al.

(10) Patent No.: US 6,310,245 B1
(45) Date of Patent: Oct. 30, 2001

(54) 3-AMINOCARBONYL/3-AMINOTHIOCARBONYL-SUBSTITUTED 2-BENZOYL-CYCLOHEXAN-1,3-DIONES WITH HERBICIDAL EFFECT

(75) Inventors: Uwe Kardorff, Mannheim; Regina Luise Hill, Speyer; Michael Rack, Heidelberg; Wolfgang von Deyn, Neustadt; Stefan Engel, Idstein; Martina Otten; Matthias Witschel, both of Ludwigshafen; Ernst Baumann, Dudenhofen; Joachim Rheinheimer, Ludwigshafen; Guido Mayer; Ulf Misslitz, both of Neustadt; Karl-Otto Westphalen, Speyer; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,637
(22) PCT Filed: Dec. 19, 1997
(86) PCT No.: PCT/EP97/07211
§ 371 Date: Jun. 23, 1999
§ 102(e) Date: Jun. 23, 1999
(87) PCT Pub. No.: WO98/29383
PCT Pub. Date: Jul. 9, 1998

(30) Foreign Application Priority Data

Jan. 3, 1997 (DE) .............................................. 197 00 097

(51) Int. Cl.[7] .......................... C07C 233/65; A01N 37/18
(52) U.S. Cl. .......................... 564/169; 504/289; 504/292; 504/293; 504/294; 504/337; 549/28; 549/62; 549/65; 549/378; 549/424; 560/9; 560/20; 560/23; 560/36; 560/37; 562/455
(58) Field of Search ............................ 564/169; 504/337, 504/289, 292, 293, 294; 549/28, 62, 65, 378, 424; 574/621, 432, 445, 451, 452; 560/9, 20, 23, 36, 37; 562/455

(56) References Cited

U.S. PATENT DOCUMENTS 4,943,310   7/1990   Angermann et al. .

FOREIGN PATENT DOCUMENTS

| | | |
|---|---|---|
| 2204667 | 3/1996 | (CA) . |
| 137 963 | 4/1985 | (EP) . |
| 278 742 | 8/1988 | (EP) . |
| 298 680 | 1/1989 | (EP) . |
| 97/46530 | 12/1997 | (WO) . |

OTHER PUBLICATIONS

Crossfire, Beilstein, XP002063835, 1970.

Primary Examiner—Shailendra Kumar
(74) Attorney, Agent, or Firm—Keil & Weinkauf

(57) ABSTRACT

The invention relates to 2-benzoylcyclohexane-1,3-diones of the formula I

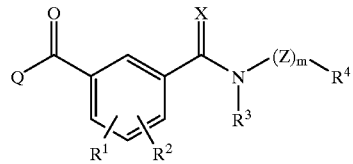

where $R_1$, $R^2$ are hydrogen, nitro, halogen, cyano, thiocyanato, alkyl, haloalkyl, alkoxyalkyl, alkenyl, alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, alkyl, haloalkyl, alkenyl or alkynyl;

$R^4$ is hydrogen, unsubstituted or substituted alkyl, cycloalkyl, alkenyl, cycloalkenyl, alkynyl, —$COR^9$, —$CO_2R^9$, —$COSR^9$ or —$CONR^8R^9$;

X is oxygen or sulfur;

Z is oxygen or $NR^8$;

m is 0 or 1;

n is 0, 1 or 2;

$R^5$ is hydrogen, alkyl, haloalkyl, alkoxyalkyl, alkenyl or alkynyl;

$R^6$ is alkyl or haloalkyl;

$R^7$ is alkyl, haloalkyl, alkoxyalkyl, alkenyl or alkynyl;

$R^8$ is hydrogen or alkyl;

$R^9$ is alkyl, alkenyl, alkynyl, phenyl or benzyl;

$R^{10}$ is alkyl, haloalkyl, alkenyl or alkynyl;

Q is an unsubstituted or substituted cyclohexane-1,3-dione ring which is linked in the 2-position;

where m is 1 if $R^3$ is hydrogen;

and the agriculturally useful salts thereof;

processes and intermediates for the preparation of the compounds of the formula I; compositions comprising them; and the use of these derivatives or compositions comprising them for controlling undesired plants.

19 Claims, No Drawings

3-AMINOCARBONYL/3-AMINOTHIOCARBONYL-SUBSTITUTED 2-BENZOYL-CYCLOHEXAN-1,3-DIONES WITH HERBICIDAL EFFECT

This application is a 371 of PCT/EP97/07211, filed Dec. 19, 1997.

The present invention relates to 2-benzoylcyclohexane-1,3-diones of the formula I

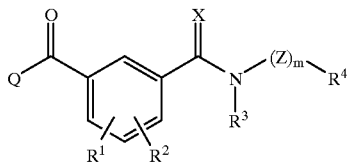

where the variables have the following meanings:

$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —S(O)$_n R^7$, —$SO_2 OR^5$, —$SO_2 NR^5 R^8$, —$NR^8 SO_2 R^6$ or —$NR^8 COR^6$;

$R^3$ is hydrogen, $C_1$–$C_6$-alkyl, $C_1$–$C_6$-haloalkyl, $C_3$–$C_6$-alkenyl or $C_3$–$C_6$-alkynyl;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8 R^9$, it being possible for the abovementioned alkyl, cycloalkyl, alkenyl, cycloalkenyl and alkynyl radicals and for $R^9$ of the radicals —$COR^9$, —$CO_2R^9$, —$COSR^9$ and —$CONR^8 R^9$ to be partially or fully halogenated and/or to have attached to them one to three of the following groups:
hydroxyl, mercapto, amino, cyano, $R^{10}$, —$OR^{10}$, —$SR^{10}$, —$NR^8 R^{10}$, =$NOR^{10}$, —$OCOR^{10}$, —$SCOR^{10}$, —$NR^8 COR^{10}$, —$CO_2 R^{10}$, —$COSR^{10}$, —$CONR^8 R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, phenyl-$C_1$–$C_4$-alkyl, hetaryl, phenoxy, phenyl-$C_1$–$C_4$-alkoxy and hetaryloxy, it being possible for the eight last-mentioned radicals, in turn, to be substituted;

X is oxygen or sulfur;
Z is oxygen or $NR^8$;
m is 0 or 1;
n is 0, 1 or 2;
$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
$R^6$ is $C_1$–$C_6$-alkyl or $C_1$–$C_6$-haloalkyl;
$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
$R^8$ is hydrogen or $C_1$–$C_6$-alkyl;
$R^9$ is $C_1$–$C_6$-alkyl, $C_3$–$C_6$-alkenyl, $C_3$–$C_6$-alkynyl, phenyl or benzyl;
$R^{10}$ is $C_1$–$C_6$-alkyl, $C_1$–$C_6$-haloalkyl, $C_3$–$C_6$-alkenyl or $C_3$–$C_6$-alkynyl;
Q is an unsubstituted or substituted cyclohexane-1,3-dione ring which is linked in the 2-position;
where m is 1 if $R^3$ is hydrogen;
and to the agriculturally useful salts thereof.

Moreover, the invention relates to processes and to intermediates for the preparation of compounds of the formula I, to compositions comprising them, and to the use of the compounds of the formula I and of compositions comprising them for controlling harmful plants.

2-Benzoylcyclohexane-1,3-diones have been disclosed in the literature, for example in EP-A 278 742, EP-A 298 680, EP-A 320 864 and WO 96/14285.

However, the herbicidal properties of the prior-art compounds and their tolerance by crop plants are only moderately satisfactory.

It is an object of the present invention to provide novel, in particular herbicidally active, compounds which have improved properties.

We have found that this object is achieved by the 2-benzoylcyclohexane-1,3-diones of the formula I and their herbicidal activity.

Furthermore, there have been found herbicidal compositions which comprise the compounds I and which have a very good herbicidal activity. Moreover, there have been found processes for the preparation of these compositions and methods of controlling undesired vegetation using the compounds I.

Depending on the substitution pattern, the compounds of the formula I can also contain one or more chiral centers, in which case they are present as enantiomer or diastereomer mixtures. The invention relates to the pure enantiomers or diastereomers and also to mixtures of these.

The compounds of the formula I can also exist in the form of their agriculturally useful salts, the type of salt generally being unimportant. In general, suitable salts are salts of those cations or the acid addition salts of those acids whose cations, or anions, respectively, do not adversely affect the herbicidal activity of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$–$C_4$-alkyl or hydroxy-$C_1$–$C_4$-alkyl and/or a phenyl or benzyl, preferably diisopropylammonium, tetramethylammonium, tetrabutylammonium, trimethylbenzylammonium, in addition phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of useful acid addition salts are mainly chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate, and the anions of $C_1$–$C_4$-alkanoic acids, preferably formate, acetate, propionate and butyrate.

Compounds of the formula I according to the invention to be emphasised are those where the variable Q is a cyclohexane-1,3-dione ring of the formula II

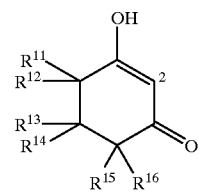

where II also represents the tautomeric formulae II', and II'',

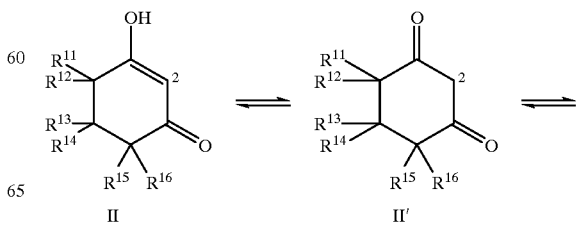

-continued

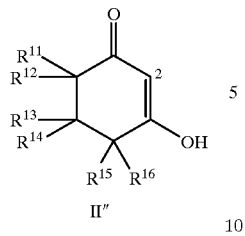

II″ which is linked in the 2-position and where
$R^{11}$, $R^{12}$, $R^{14}$ and $R^{16}$ are hydrogen or $C_1$–$C_4$-alkyl;
$R^{13}$ is hydrogen, $C_1$–$C_4$-alkyl or $C_3$–$C_4$-cycloalkyl, it being possible for the two last-mentioned groups to have attached to them one to three of the following substituents:
halogen, $C_1$–$C_4$-alkylthio or $C_1$–$C_4$-alkoxy;
or
is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,4-dioxan-2-yl, 1,3-oxathiolan-2-yl, 1,3-oxathian-2-yl, 1,3-dithiolan-2-yl or 1,3-dithian-2-yl, it being possible for the 6 last-mentioned radicals to be substituted by one to three $C_1$–$C_4$-alkyl radicals;
$R^{15}$ is hydrogen, $C_1$–$C_4$-alkyl or $C_1$–$C_6$-alkoxycarbonyl;
or
$R^{13}$ and $R^{16}$ together form a π bond or a three to six-membered carbocyclic ring;
or
the $CR^{13}R^{14}$ unit can be replaced by C=O.

Compounds of the formula I according to the invention equally to be emphasized are those where
$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and for $R^9$ of the radicals —$COR^9$, —$CO_2R^9$, —$COSR^9$ and —$CONR^8R^9$ to be partially or fully halogenated and/or to have attached to them one to three of the following groups:
hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, phenyl-$C_1$–$C_4$-alkyl, hetaryl, phenoxy, phenyl-$C_1$–$C_4$-alkoxy and hetaryloxy, it being possible for the eight last-mentioned radicals, in turn, to be partially or fully halogenated and/or to have attached to them one to three radicals selected from the group which follows:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

The organic moieties mentioned for the substituents $R^1$–$R^{16}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylthio, alkylsulfonyl, alkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably have attached to them one to five identical or different halogen atoms. Halogen is in each case fluorine, chlorine, bromine or iodine.

Other examples of meanings are:
$C_2$–$C_4$-alkyl: ethyl, propyl, 1-methylethyl, butyl, 1-methylpropyl, 2-methylpropyl and 1,1-dimethylethyl;
$C_1$–$C_4$-alkyl, and the alkyl moieties of $C_1$–$C_4$-alkylcarbonyl: $C_2$–$C_4$-alkyl as mentioned above, and also methyl;
$C_2$–$C_6$-alkyl, and the alkyl moieties of $C_1$–$C_6$-alkoxy-$C_2$–$C_6$-alkyl: $C_2$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;
$C_1$–$C_6$-alkyl, and the alkyl moieties of $C_1$–$C_6$-alkoxy-$C_1$–$C_6$-alkyl: $C_2$–$C_6$-alkyl as mentioned above, and also methyl;
$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;
$C_1$–$C_6$-haloalkyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;
$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;
$C_1$–$C_6$-alkoxy, and the alkoxy moieties of $C_1$–$C_6$-alkoxy-$C_1$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methoxybutoxy [sic], 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;
$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylthio: methylthio, ethylthio, propylthio, 1-methylethylthio, butylthio, 1-methylpropylthio, 2-methylpropylthio and 1,1-dimethylethylthio;

$C_1$–$C_4$-alkylsulfonyl ($C_1$–$C_4$-alkyl-S(=O)$_2$-): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl;

$C_3$–$C_4$-cycloalkyl: cyclopropyl and cyclobutyl;

$C_3$–$C_6$-cycloalkyl: $C_3$–$C_4$-cycloalkyl as mentioned above, and also cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and the heterocyclyl radicals in heterocyclyloxy: three to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5- dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and the hetaryl radicals in hetaryloxy: aromatic mono- or polycyclic radicals which, besides carbon ring members, additionally can contain one to four nitrogen atoms or one to three nitrogen atoms and an oxygen or a sulfur atom or an oxygen or a sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and the corresponding benzo-fused derivatives.

All phenyl and hetaryl rings are preferably unsubstituted or have attached to them one to three halogen atoms and/or one or two radicals selected from the group which follows: nitro, cyano, methyl, trifluoromethyl, methoxy, trifluoromethoxy and methoxycarbonyl.

With a view to the use of the compounds of the formula I according to the invention as herbicides, the variables preferably have the following meanings, in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
especially preferably nitro, halogen, eg. fluorine, chlorine or bromine, $C_1$–$C_6$-haloalkyl, eg. trifluoromethyl, —$OR^5$ or —$SO_2R^7$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
especially preferably hydrogen, nitro, halogen, eg. fluorine, chlorine or bromine, $C_1$–$C_6$-alkyl, eg. methyl or ethyl, $C_1$–$C_6$-haloalkyl, eg. trifluoromethyl, —$OR^5$ or —$SO_2R^7$;

$R^3$ is hydrogen, $C_1$–$C_6$-alkyl, eg. methyl, ethyl, propyl or butyl, or $C_1$–$C_6$-haloalkyl, eg. difluoromethyl or trifluoromethyl;

$R^4$ is hydrogen, $C_1$–$C_6$-alkyl, $C_3$–$C_6$-cycloalkyl, $C_3$–$C_6$-alkenyl or $C_3$–$C_6$-alkynyl, it being possible for the 4 last-mentioned substituents to be partially or fully halogenated and/or to have attached to them one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, phenyl-$C_1$–$C_4$-alkyl, hetaryl, phenoxy, phenyl-$C_1$–$C_4$-alkoxy or hetaryloxy, it being possible for the eight last-mentioned radicals, in turn, to be partially or fully halogenated and/or to have attached to them one to three radicals selected from the group which follows:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

X is oxygen or sulfur;
especially preferably oxygen;
Z is oxygen, NH or $NCH_3$;
m is 0 or 1
n is 0 or 2
$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
especially preferably methyl, ethyl, trifluoromethyl, difluoromethyl, methoxyethyl, allyl or propargyl;
$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
especially preferably methyl, ethyl, trifluoromethyl, difluoromethyl, methoxyethyl, allyl or propargyl;
$R^8$ is hydrogen or $C_1$–$C_6$-alkyl;
$R^{10}$ is $C_1$–$C_6$-alkyl, $C_1$–$C_6$-haloalkyl, $C_3$–$C_6$-alkenyl or $C_3$–$C_6$-alkynyl;
$R^{11}$, $R^{12}$, $R^{14}$, $R^{16}$ are hydrogen or $C_1$–$C_4$-alkyl;
especially preferably hydrogen, methyl or ethyl;
$R^{13}$ is hydrogen, $C_1$–$C_4$-alkyl, $C_3$–$C_4$-cycloalkyl, it being possible for the two last-mentioned groups to be unsubstituted or to have attached to them one to three of the following substituents: halogen, $C_1$–$C_4$-alkoxy or $C_1$–$C_4$-alkylthio;
tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,4-dioxan-2-yl, 1,3-oxathiolan-2-yl, 1,3-oxathian-2-yl, 1,3-dithian-2-yl or 1,3-dithiolan-2-yl, it being possible for the six last-mentioned groups to have attached to them in each case one to three $C_1$–$C_4$-alkyl radicals;
especially preferably hydrogen, methyl, ethyl, cyclopropyl, di(methoxy)methyl, di(ethoxy)methyl, 2-ethylthiopropyl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,4-dioxan-2-yl, 5,5-dimethyl-1-3-dioxan-2-yl, 1,3-oxathiolan-2-yl, 1,3-oxathian-2-yl, 1,3-dithiolan-2-yl, 5,5-dimethyl-1,3-dithian-2-yl or 1-methylthiocyclopropyl;
$R^{15}$ is hydrogen, $C_1$–$C_4$-alkyl or $C_1$–$C_4$-alkoxycarbonyl;
especially preferably hydrogen, methyl or methoxycarbonyl.

Equally, it may be advantageous for $R^{13}$ and $R^{16}$ to form a π bond so that a double bond system results.

Also, the $CR^{13}R^{14}$ unit can be replaced advantageously by C=O.

Especially preferred compounds of the formula I are where m=1. Also especially preferred are compounds where m=0 and $R^3$, $R^4$ ≠ hydrogen.

Particularly preferred compounds of the formula I are those where m=1.

Extraordinarily preferred are compounds of the formula Ia (= I where $R^1$ is bonded in the 4-position of the phenyl ring and $R^2$ in the 2-position of the phenyl ring).

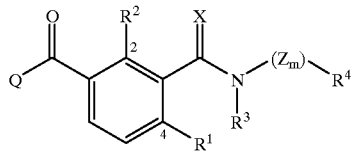

Particularly extraordinarily preferred are the compounds of the formula Ia where the variables $R^1$ to $R^3$, Q, X, Z and m have the meanings mentioned above and
$R^4$ is hydrogen, $C_1$–$C_6$-alkyl, $C_3$–$C_6$-cycloalkyl, $C_3$–$C_6$-alkenyl or $C_3$–$C_6$-alkynyl, it being possible for the 4 last-mentioned substituents to be partially or fully halogenated and/or to have attached to them one to three of the following groups: hydroxyl, mercapto, amino, cyano, —$OR^{10}$, =$NOR^{10}$, —$OCOR^{10}$, —$CO_2R^{10}$, —$COSR^{10}$, —$CONR^8R^{10}$, $C_1$–$C_4$-alkyliminooxy, $C_1$–$C_4$-alkylcarbonyl, $C_1$–$C_4$-alkoxy-$C_2$–$C_6$-alkoxycarbonyl, heterocyclyl, heterocyclyloxy, phenyl, phenyl-$C_1$–$C_4$-alkyl, hetaryl, phenoxy, phenyl-$C_1$–$C_4$-alkoxy or hetaryloxy, it being possible for the eight last-mentioned radicals, in turn, to be partially or fully halogenated and/or to have attached to them one to three radicals selected from the group which follows:
nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl.

Most particularly most extraordinarily preferred are the compounds Ia1 (≙ I where $R^1$=Cl, $R^{11}$, $R^{12}$, $R^{13}$, $R^{14}$, $R^{15}$, $R^{16}$=H, X=oxygen and m=1, where $R^1$ is bonded in the 4-position of the phenyl ring and $R^2$ in the 2-position of the phenyl ring), in particular the compounds of Table 1.

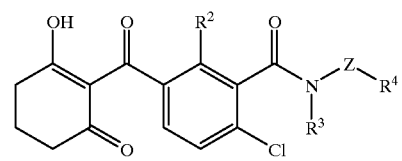

TABLE 1

| No. | $R^2$ | $R^3$ | $R^4$ | Z |
|---|---|---|---|---|
| Ia1.1 | Cl | H | $CH_3$ | O |
| Ia1.2 | Cl | $CH_3$ | $CH_3$ | O |
| Ia1.3 | Cl | $CH_2CH_3$ | $CH_3$ | O |
| Ia1.4 | Cl | $(CH_2)_2CH_3$ | $CH_3$ | O |
| Ia1.5 | Cl | $(CH_2)_3CH_3$ | $CH_3$ | O |
| Ia1.6 | Cl | H | $C_2H_5$ | O |
| Ia1.7 | Cl | $CH_3$ | $C_2H_5$ | O |
| Ia1.8 | Cl | $CH_2CH_3$ | $C_2H_5$ | O |
| Ia1.9 | Cl | $(CH_2)_2CH_3$ | $C_2H_5$ | O |
| Ia1.10 | Cl | $(CH_2)_3CH_3$ | $C_2H_5$ | O |
| Ia1.11 | Cl | H | $(CH_2)_2CH_3$ | O |
| Ia1.12 | Cl | $CH_3$ | $(CH_2)_2CH_3$ | O |
| Ia1.13 | Cl | $CH_2CH_3$ | $(CH_2)_2CH_3$ | O |
| Ia1.14 | Cl | $(CH_2)_2CH_3$ | $(CH_2)_2CH_3$ | O |
| Ia1.15 | Cl | $(CH_2)_3CH_3$ | $(CH_2)_2CH_3$ | O |
| Ia1.16 | Cl | H | $CH(CH_3)_2$ | O |
| Ia1.17 | Cl | $CH_3$ | $CH(CH_3)_2$ | O |
| Ia1.18 | Cl | $CH_2CH_3$ | $CH(CH_3)_2$ | O |
| Ia1.19 | Cl | $(CH_2)_2CH_3$ | $CH(CH_3)_2$ | O |
| Ia1.20 | Cl | $(CH_2)_3CH_3$ | $CH(CH_3)_2$ | O |
| Ia1.21 | Cl | H | $(CH_2)_3CH_3$ | O |
| Ia1.22 | Cl | $CH_3$ | $(CH_2)_3CH_3$ | O |
| Ia1.23 | Cl | $CH_2CH_3$ | $(CH_2)_3CH_3$ | O |
| Ia1.24 | Cl | $(CH_2)_2CH_3$ | $(CH_2)_3CH_3$ | O |
| Ia1.25 | Cl | $(CH_2)_3CH_3$ | $(CH_2)_3CH_3$ | O |
| Ia1.26 | Cl | H | $CH_2CH(CH_3)_2$ | O |
| Ia1.27 | Cl | $CH_3$ | $CH_2CH(CH_3)_2$ | O |
| Ia1.28 | Cl | $CH_2CH_3$ | $CH_2CH(CH_3)_2$ | O |
| Ia1.29 | Cl | $(CH_2)_2CH_3$ | $CH_2CH(CH_3)_2$ | O |
| Ia1.30 | Cl | $(CH_2)_3CH_3$ | $CH_2CH(CH_3)_2$ | O |
| Ia1.31 | Cl | H | $CH(CH_3)CH_2CH_3$ | O |
| Ia1.32 | Cl | $CH_3$ | $CH(CH_3)CH_2CH_3$ | O |
| Ia1.33 | Cl | $CH_2CH_3$ | $CH(CH_3)CH_2CH_3$ | O |
| Ia1.34 | Cl | $(CH_2)_2CH_3$ | $CH(CH_3)CH_2CH_3$ | O |
| Ia1.35 | Cl | $(CH_2)_3CH_3$ | $CH(CH_3)CH_2CH_3$ | O |
| Ia1.36 | Cl | H | $(CH_2)_2$—$C_6H_5$ | O |
| Ia1.37 | Cl | $CH_3$ | $(CH_2)_2$—$C_6H_5$ | O |
| Ia1.38 | Cl | $CH_2CH_3$ | $(CH_2)_2$—$C_6H_5$ | O |
| Ia1.39 | Cl | $(CH_2)_2CH_3$ | $(CH_2)_2$—$C_6H_5$ | O |
| Ia1.40 | Cl | $(CH_2)_3CH_3$ | $(CH_2)_2$—$C_6H_5$ | O |
| Ia1.41 | Cl | H | $CH_2CH(CH_3)$—$C_6H_5$ | O |
| Ia1.42 | Cl | $CH_3$ | $CH_2CH(CH_3)$—$C_6H_5$ | O |
| Ia1.43 | Cl | $CH_2CH_3$ | $CH_2CH(CH_3)$—$C_6H_5$ | O |
| Ia1.44 | Cl | $(CH_2)_2CH_3$ | $CH_2CH(CH_3)$—$C_6H_5$ | O |
| Ia1.45 | Cl | $(CH_2)_3CH_3$ | $CH_2CH(CH_3)$—$C_6H_5$ | O |
| Ia1.46 | Cl | H | $CH(CH_3)CH_2$—$C_6H_5$ | O |
| Ia1.47 | Cl | $CH_3$ | $CH(CH_3)CH_2$—$C_6H_5$ | O |
| Ia1.48 | Cl | $CH_2CH_3$ | $CH(CH_3)CH_2$—$C_6H_5$ | O |

TABLE 1-continued

| No. | $R^2$ | $R^3$ | $R^4$ | Z |
|---|---|---|---|---|
| Ia1.49 | Cl | $(CH_2)_2CH_3$ | $CH(CH_3)CH_2$—$C_6H_5$ | O |
| Ia1.50 | Cl | $(CH_2)_3CH_3$ | $CH(CH_3)CH_2$—$C_6H_5$ | O |
| Ia1.51 | Cl | H | $CH(CH_3)CH(CH_3)$—$C_6H_5$ | O |
| Ia1.52 | Cl | $CH_3$ | $CH(CH_3)CH(CH_3)$—$C_6H_5$ | O |
| Ia1.53 | Cl | $CH_2CH_3$ | $CH(CH_3)CH(CH_3)$—$C_6H_5$ | O |
| Ia1.54 | Cl | $(CH_2)_2CH_3$ | $CH(CH_3)CH(CH_3)$—$C_6H_5$ | O |
| Ia1.55 | Cl | $(CH_2)_3CH_3$ | $CH(CH_3)CH(CH_3)$—$C_6H_5$ | O |
| Ia1.56 | Cl | H | $(CH_2)_2$-(4-Cl—$C_6H_4$) | O |
| Ia1.57 | Cl | $CH_3$ | $(CH_2)_2$-(4-Cl—$C_6H_4$) | O |
| Ia1.58 | Cl | $CH_2CH_3$ | $(CH_2)_2$-(4-Cl—$C_6H_4$) | O |
| Ia1.59 | Cl | $(CH_2)_2CH_3$ | $(CH_2)_2$-(4-Cl—$C_6H_4$) | O |
| Ia1.60 | Cl | $(CH_2)_3CH_3$ | $(CH_2)_2$-(4-Cl—$C_6H_4$) | O |
| Ia1.61 | Cl | H | $CH_2CH(CH_3)$-(4-Cl—$C_6H_4$) | O |
| Ia1.62 | Cl | $CH_3$ | $CH_2CH(CH_3)$-(4-Cl—$C_6H_4$) | O |
| Ia1.63 | Cl | $CH_2CH_3$ | $CH_2CH(CH_3)$-(4-Cl—$C_6H_4$) | O |
| Ia1.64 | Cl | $(CH_2)_2CH_3$ | $CH_2CH(CH_3)$-(4-Cl—$C_6H_4$) | O |
| Ia1.65 | Cl | $(CH_2)_3CH_3$ | $CH_2CH(CH_3)$-(4-Cl—$C_6H_4$) | O |
| Ia1.66 | Cl | H | $CH(CH_3)CH_2$-(4-Cl—$C_6H_4$) | O |
| Ia1.67 | Cl | $CH_3$ | $CH(CH_3)CH_2$-(4-Cl—$C_6H_4$) | O |
| Ia1.68 | Cl | $CH_2CH_3$ | $CH(CH_3)CH_2$-(4-Cl—$C_6H_4$) | O |
| Ia1.69 | Cl | $(CH_2)_2CH_3$ | $CH(CH_3)CH_2$-(4-Cl—$C_6H_4$) | O |
| Ia1.70 | Cl | $(CH_2)_3CH_3$ | $CH(CH_3)CH_2$-(4-Cl—$C_6H_4$) | O |
| Ia1.71 | Cl | H | $CH(CH_3)CH(CH_3)$-(4-Cl—$C_6H_4$) | O |
| Ia1.72 | Cl | $CH_3$ | $CH(CH_3)CH(CH_3)$-(4-Cl—$C_6H_4$) | O |
| Ia1.73 | Cl | $CH_2CH_3$ | $CH(CH_3)CH(CH_3)$-(4-Cl—$C_6H_4$) | O |
| Ia1.74 | Cl | $(CH_2)_2CH_3$ | $CH(CH_3)CH(CH_3)$-(4-Cl—$C_6H_4$) | O |
| Ia1.75 | Cl | $(CH_2)_3CH_3$ | $CH(CH_3)CH(CH_3)$-(4-Cl—$C_6H_4$) | O |
| Ia1.76 | Cl | H | $(CH_2)_2$-(2,4-$Cl_2$—$C_6H_3$) | O |
| Ia1.77 | Cl | $CH_3$ | $(CH_2)_2$-(2,4-$Cl_2$—$C_6H_3$) | O |
| Ia1.78 | Cl | $CH_2CH_3$ | $(CH_2)_2$-(2,4-$Cl_2$—$C_6H_3$) | O |
| Ia1.79 | Cl | $(CH_2)_2CH_3$ | $(CH_2)_2$-(2,4-$Cl_2$—$C_6H_3$) | O |
| Ia1.80 | Cl | $(CH_2)_3CH_3$ | $(CH_2)_2$-(2,4-$Cl_2$—$C_6H_3$) | O |
| Ia1.81 | Cl | H | $CH_2CH(CH_3)$-(2,4-$Cl_2$—$C_6H_3$) | O |
| Ia1.82 | Cl | $CH_3$ | $CH_2CH(CH_3)$-(2,4-$Cl_2$—$C_6H_3$) | O |
| Ia1.83 | Cl | $CH_2CH_3$ | $CH_2CH(CH_3)$-(2,4-$Cl_2$—$C_6H_3$) | O |
| Ia1.84 | Cl | $(CH_2)_2CH_3$ | $CH_2CH(CH_3)$-(2,4-$Cl_2$—$C_6H_3$) | O |
| Ia1.85 | Cl | $(CH_2)_3CH_3$ | $CH_2CH(CH_3)$-(2,4-$Cl_2$—$C_6H_3$) | O |
| Ia1.86 | Cl | H | $CH(CH_3)CH_2$-(2,4-$Cl_2$—$C_6H_3$) | O |
| Ia1.87 | Cl | $CH_3$ | $CH(CH_3)CH_2$-(2,4-$Cl_2$—$C_6H_3$) | O |
| Ia1.88 | Cl | $CH_2CH_3$ | $CH(CH_3)CH_2$-(2,4-$Cl_2$—$C_6H_3$) | O |
| Ia1.89 | Cl | $(CH_2)_2CH_3$ | $CH(CH_3)CH_2$-(2,4-$Cl_2$—$C_6H_3$) | O |
| Ia1.90 | Cl | $(CH_2)_3CH_3$ | $CH(CH_3)CH_2$-(2,4-$Cl_2$—$C_6H_3$) | O |
| Ia1.91 | Cl | H | $CH(CH_3)CH(CH_3)$-(2,4-$Cl_2$—$C_6H_3$) | O |
| Ia1.92 | Cl | $CH_3$ | $CH(CH_3)CH(CH_3)$-(2,4-$Cl_2$—$C_6H_3$) | O |
| Ia1.93 | Cl | $CH_2CH_3$ | $CH(CH_3)CH(CH_3)$-(2,4-$Cl_2$—$C_6H_3$) | O |
| Ia1.94 | Cl | $(CH_2)_2CH_3$ | $CH(CH_3)CH(CH_3)$-(2,4-$Cl_2$—$C_6H_3$) | O |
| Ia1.95 | Cl | $(CH_2)_3CH_3$ | $CH(CH_3)CH(CH_3)$-(2,4-$Cl_2$—$C_6H_3$) | O |
| Ia1.96 | Cl | H | $(CH_2)_2$—O—$C_6H_5$ | O |
| Ia1.97 | Cl | $CH_3$ | $(CH_2)_2$—O—$C_6H_5$ | O |
| Ia1.98 | Cl | $CH_2CH_3$ | $(CH_2)_2$—O—$C_6H_5$ | O |
| Ia1.99 | Cl | $(CH_2)_2CH_3$ | $(CH_2)_2$—O—$C_6H_5$ | O |
| Ia1.100 | Cl | $(CH_2)_3CH_3$ | $(CH_2)_2$—O—$C_6H_5$ | O |
| Ia1.101 | Cl | H | $CH_2CH(CH_3)$—O—$C_6H_5$ | O |
| Ia1.102 | Cl | $CH_3$ | $CH_2CH(CH_3)$—O—$C_6H_5$ | O |
| Ia1.103 | Cl | $CH_2CH_3$ | $CH_2CH(CH_3)$—O—$C_6H_5$ | O |
| Ia1.104 | Cl | $(CH_2)_2CH_3$ | $CH_2CH(CH_3)$—O—$C_6H_5$ | O |
| Ia1.105 | Cl | $(CH_2)_3CH_3$ | $CH_2CH(CH_3)$—O—$C_6H_5$ | O |
| Ia1.106 | Cl | H | $CH(CH_3)CH_2$—O—$C_6H_5$ | O |
| Ia1.107 | Cl | $CH_3$ | $CH(CH_3)CH_2$—O—$C_6H_5$ | O |
| Ia1.108 | Cl | $CH_2CH_3$ | $CH(CH_3)CH_2$—O—$C_6H_5$ | O |
| Ia1.109 | Cl | $(CH_2)_2CH_3$ | $CH(CH_3)CH_2$—O—$C_6H_5$ | O |
| Ia1.110 | Cl | $(CH_2)_3CH_3$ | $CH(CH_3)CH_2$—O—$C_6H_5$ | O |
| Ia1.111 | Cl | H | $CH(CH_3)CH(CH_3)$—O—$C_6H_5$ | O |
| Ia1.112 | Cl | $CH_3$ | $CH(CH_3)CH(CH_3)$—O—$C_6H_5$ | O |
| Ia1.113 | Cl | $CH_2CH_3$ | $CH(CH_3)CH(CH_3)$—O—$C_6H_5$ | O |
| Ia1.114 | Cl | $(CH_2)_2CH_3$ | $CH(CH_3)CH(CH_3)$—O—$C_6H_5$ | O |
| Ia1.115 | Cl | $(CH_2)_3CH_3$ | $CH(CH_3)CH(CH_3)$—O—$C_6H_5$ | O |
| Ia1.116 | Cl | H | $(CH_2)_2$—O-(4-Cl—$C_6H_4$) | O |
| Ia1.117 | Cl | $CH_3$ | $(CH_2)_2$—O-(4-Cl—$C_6H_4$) | O |
| Ia1.118 | Cl | $CH_2CH_3$ | $(CH_2)_2$—O-(4-Cl—$C_6H_4$) | O |
| Ia1.119 | Cl | $(CH_2)_2CH_3$ | $(CH_2)2$—O-(4-Cl—$C_6H_4$) | O |
| Ia1.120 | Cl | $(CH_2)_3CH_3$ | $(CH_2)2$—O-(4-Cl—$C_6H_4$) | O |
| Ia1.121 | Cl | H | $CH_2CH(CH_3)$—O-(4-Cl-$C_6H_4$) | O |
| Ia1.122 | Cl | $CH_3$ | $CH_2CH(CH_3)$—O-(4-Cl—$C_6H_4$) | O |
| Ia1.123 | Cl | $CH_2CH_3$ | $CH_2CH(CH_3)$—O-(4-Cl-$C_6H_4$) | O |
| Ia1.124 | Cl | $(CH_2)_2CH_3$ | $CH_2CH(CH_3)$—O-(4-Cl-$C_6H_4$) | O |
| Ia1.125 | Cl | $(CH_2)_3CH_3$ | $CH_2CH(CH_3)$—O-( 4-Cl—$C_6H_4$) | O |

TABLE 1-continued

| No. | R² | R³ | R⁴ | Z |
|---|---|---|---|---|
| Ia1.126 | Cl | H | CH(CH₃)CH₂—O-(4-Cl-C₆H₄) | O |
| Ia1.127 | Cl | CH₃ | CH(CH₃)CH₂—O-(4-Cl-C₆H₄) | O |
| Ia1.128 | Cl | CH₂CH₃ | CH(CH₃)CH₂—O-(4-Cl—C₆H₄) | O |
| Ia1.129 | Cl | (CH₂)₂CH₃ | CH(CH₃)CH₂—O-(4-Cl—C₆H₄) | O |
| Ia1.130 | Cl | (CH₂)₃CH₃ | CH(CH₃)CH₂—O-(4-Cl—C₆H₄) | O |
| Ia1.131 | Cl | H | CH(CH₃)CH(CH₃)—O-(4-Cl—C₆H₄) | O |
| Ia1.132 | Cl | CH₃ | CH(CH₃)CH(CH₃)—O-(4-Cl—C₆H₄) | O |
| Ia1.133 | Cl | CH₂CH₃ | CH(CH₃)CH(CH₃)—O-(4-Cl—C₆H₄) | O |
| Ia1.134 | Cl | (CH₂)₂CH₃ | CH(CH₃)CH(CH₃)—O-(4-Cl—C₆H₄) | O |
| Ia1.135 | Cl | (CH₂)₃CH₃ | CH(CH₃)CH(CH₃)—O-(4-Cl—C₆H₄) | O |
| Ia1.136 | Cl | H | (CH₂)₂—O-(2,4-Cl₂—C₆H₃) | O |
| Ia1.137 | Cl | CH₃ | (CH₂)₂—O-(2,4-Cl₂—C₆H₃) | O |
| Ia1.138 | Cl | CH₂CH₃ | (CH₂)₂—O-(2,4-Cl₂—C₆H₃) | O |
| Ia1.139 | Cl | (CH₂)₂CH₃ | (CH₂)₂—O-(2,4-Cl₂—C₆H₃) | O |
| Ia1.140 | Cl | (CH₂)₃CH₃ | (CH₂)₂—O-(2,4-Cl₂—C₆H₃) | O |
| Ia1.141 | Cl | H | CH₂CH(CH₃)—O-(2,4-Cl₂—C₆H₃) | O |
| Ia1.142 | Cl | CH₃ | CH₂CH(CH₃)—O-(2,4-Cl₂—C₆H₃) | O |
| Ia1.143 | Cl | CH₂CH₃ | CH₂CH(CH₃)—O-(2,4-Cl₂—C₆H₃) | O |
| Ia1.144 | Cl | (CH₂)₂CH₃ | CH₂CH(CH₃)—O-(2,4-Cl₂—C₆H₃) | O |
| Ia1.145 | Cl | (CH₂)₃CH₃ | CH₂CH(CH₃)—O-(2,4-Cl₂—C₆H₃) | O |
| Ia1.146 | Cl | H | CH(CH₃)CH₂—O-(2,4-Cl₂—C₆H₃) | O |
| Ia1.147 | Cl | CH₃ | CH(CH₃)CH₂—O-(2,4-Cl₂—C₆H₃) | O |
| Ia1.148 | Cl | CH₂CH₃ | CH(CH₃)CH₂—O-(2,4-Cl₂—C₆H₃) | O |
| Ia1.149 | Cl | (CH₂)₂CH₃ | CH(CH₃)CH₂—O-(2,4-Cl₂—C₆H₃) | O |
| Ia1.150 | Cl | (CH₂)₃CH₃ | CH(CH₃)CH₂—O-(2,4-Cl₂—C₆H₃) | O |
| Ia1.151 | Cl | H | CH(CH₃)CH(CH₃)—O-(2,4-Cl₂—C₆H₃) | O |
| Ia1.152 | Cl | CH₃ | CH(CH₃)CH(CH₃)—O-(2,4-Cl₂—C₆H₃) | O |
| Ia1.153 | Cl | CH₂CH₃ | CH(CH₃)CH(CH₃)—O-(2,4-Cl₂—C₆H₃) | O |
| Ia1.154 | Cl | (CH₂)₂CH₃ | CH(CH₃)CH(CH₃)—O-(2,4-Cl₂—C₆H₃) | O |
| Ia1.155 | Cl | (CH₂)₃CH₃ | CH(CH₃)CH(CH₃)—O-(2,4-Cl₂—C₆H₃) | O |
| Ia1.156 | Cl | H | CH₃ | NH |
| Ia1.157 | Cl | CH₃ | CH₃ | NH |
| Ia1.158 | Cl | CH₂CH₃ | CH₃ | NH |
| Ia1.159 | Cl | (CH₂)₂CH₃ | CH₃ | NH |
| Ia1.160 | Cl | (CH₂)₃CH₃ | CH₃ | NH |
| Ia1.161 | Cl | H | C₂H₅ | NH |
| Ia1.162 | Cl | CH₃ | C₂H₅ | NH |
| Ia1.163 | Cl | CH₂CH₃ | C₂H₅ | NH |
| Ia1.164 | Cl | (CH₂)₂CH₃ | C₂H₅ | NH |
| Ia1.165 | Cl | (CH₂)₃CH₃ | C₂H₅ | NH |
| Ia1.166 | Cl | H | (CH₂)₂CH₃ | NH |
| Ia1.167 | Cl | CH₃ | (CH₂)₂CH₃ | NH |
| Ia1.168 | Cl | CH₂CH₃ | (CH₂)₂CH₃ | NH |
| Ia1.169 | Cl | (CH₂)₂CH₃ | (CH₂)₂CH₃ | NH |
| Ia1.170 | Cl | (CH₂)₃CH₃ | (CH₂)₂CH₃ | NH |
| Ia1.171 | Cl | H | CH(CH₃)₂ | NH |
| Ia1.172 | Cl | CH₃ | CH(CH₃)₂ | NH |
| Ia1.173 | Cl | CH₂CH₃ | CH(CH₃)₂ | NH |
| Ia1.174 | Cl | (CH₂)₂CH₃ | CH(CH₃)₂ | NH |
| Ia1.175 | Cl | (CH₂)₃CH₃ | CH(CH₃)₂ | NH |
| Ia1.176 | Cl | H | (CH₂)₃CH₃ | NH |
| Ia1.177 | Cl | CH₃ | (CH₂)₃CH₃ | NH |
| Ia1.178 | Cl | CH₂CH₃ | (CH₂)₃CH₃ | NH |
| Ia1.179 | Cl | (CH₂)₂CH₃ | (CH₂)₃CH₃ | NH |
| Ia1.180 | Cl | (CH₂)₃CH₃ | (CH₂)₃CH₃ | NH |
| Ia1.181 | Cl | H | CH₂CH(CH₃)₂ | NH |
| Ia1.182 | Cl | CH₃ | CH₂CH(CH₃)₂ | NH |
| Ia1.183 | Cl | CH₂CH₃ | CH₂CH(CH₃)₂ | NH |
| Ia1.184 | Cl | (CH₂)₂CH₃ | CH₂CH(CH₃)₂ | NH |
| Ia1.185 | Cl | (CH₂)₃CH₃ | CH₂CH(CH₃)₂ | NH |
| Ia1.186 | Cl | H | CH(CH₃)CH₂CH₃ | NH |
| Ia1.187 | Cl | CH₃ | CH(CH₃)CH₂CH₃ | NH |
| Ia1.188 | Cl | CH₂CH₃ | CH(CH₃)CH₂CH₃ | NH |
| Ia1.189 | Cl | (CH₂)₂CH₃ | CH(CH₃)CH₂CH₃ | NH |
| Ia1.190 | Cl | (CH₂)₃CH₃ | CH(CH₃)CH₂CH₃ | NH |
| Ia1.191 | Cl | H | (CH₂)₂—C₆H₅ | NH |
| Ia1.192 | Cl | CH₃ | (CH₂)₂—C₆H₅ | NH |
| Ia1.193 | Cl | CH₂CH₃ | (CH₂)₂—C₆H₅ | NH |
| Ia1.194 | Cl | (CH₂)₂CH₃ | (CH₂)₂—C₆H₅ | NH |
| Ia1.195 | Cl | (CH₂)₃CH₃ | (CH₂)₂—C₆H₅ | NH |
| Ia1.196 | Cl | H | CH₂CH(CH₃)—C₆H₅ | NH |
| Ia1.197 | Cl | CH₃ | CH₂CH(CH₃)—C₆H₅ | NH |
| Ia1.198 | Cl | CH₂CH₃ | CH₂CH(CH₃)—C₆H₅ | NH |
| Ia1.199 | Cl | (CH₂)₂CH₃ | CH₂CH(CH₃)—C₆H₅ | NH |
| Ia1.200 | Cl | (CH₂)₃CH₃ | CH₂CH(CH₃)—C₆H₅ | NH |
| Ia1.201 | Cl | H | CH(CH₃)CH₂—C₆H₅ | NH |
| Ia1.202 | Cl | CH₃ | CH(CH₃)CH₂—C₆H₅ | NH |

TABLE 1-continued

| No. | R² | R³ | R⁴ | Z |
|---|---|---|---|---|
| Ia1.203 | Cl | CH₂CH₃ | CH(CH₃)CH₂—C₆H₅ | NH |
| Ia1.204 | Cl | (CH₂)₂CH₃ | CH(CH₃)CH₂—C₆H₅ | NH |
| Ia1.205 | Cl | (CH₂)₃CH₃ | CH(CH₃)CH₂—C₆H₅ | NH |
| Ia1.206 | Cl | H | CH(CH₃)CH(CH₃)—C₆H₅ | NH |
| Ia1.207 | Cl | CH₃ | CH(CH₃)CH(CH₃)—C₆H₅ | NH |
| Ia1.208 | Cl | CH₂CH₃ | CH(CH₃)CH(CH₃)—C₆H₅ | NH |
| Ia1.209 | Cl | (CH₂)₂CH₃ | CH(CH₃)CH(CH₃)—C₆H₅ | NH |
| Ia1.210 | Cl | (CH₂)₃CH₃ | CH(CH₃)CH(CH₃)—C₆H₅ | NH |
| Ia1.211 | Cl | H | (CH₂)₂-(4-Cl—C₆H₄) | NH |
| Ia1.212 | Cl | CH₃ | (CH₂)₂-(4-Cl—C₆H₄) | NH |
| Ia1.213 | Cl | CH₂CH₃ | (CH₂)₂-(4-Cl—C₆H₄) | NH |
| Ia1.214 | Cl | (CH₂)₂CH₃ | (CH₂)₂-(4-Cl—C₆H₄) | NH |
| Ia1.215 | Cl | (CH₂)₃CH₃ | (CH₂)₂-(4-Cl—C₆H₄) | NH |
| Ia1.216 | Cl | H | CH₂CH(CH₃)-(4-Cl—C₆H₄) | NH |
| Ia1.217 | Cl | CH₃ | CH₂CH(CH₃)-(4-Cl—C₆H₄) | NH |
| Ia1.218 | Cl | CH₂CH₃ | CH₂CH(CH₃)-(4-Cl—C₆H₄) | |
| Ia1.219 | Cl | (CH₂)₂CH₃ | CH₂CH(CH₃)-(4-Cl—C₆H₄) | NH |
| Ia1.220 | Cl | (CH₂)₃CH₃ | CH₂CH(CH₃)-(4-Cl—C₆H₄) | NH |
| Ia1.221 | Cl | H | CH(CH₃)CH₂-(4-Cl—C₆H₄) | NH |
| Ia1.222 | Cl | CH₃ | CH(CH₃)CH₂-(4-Cl—C₆H₄) | NH |
| Ia1.223 | Cl | CH₂CH₃ | CH(CH₃)CH₂-(4-Cl—C₆H₄) | NH |
| Ia1.224 | Cl | (CH₂)₂CH₃ | CH(CH₃)CH₂-(4-Cl—C₆H₄) | NH |
| Ia1.225 | Cl | (CH₂)₃CH₃ | CH(CH₃)CH₂-(4-Cl—C₆H₄) | NH |
| Ia1.226 | Cl | H | CH(CH₃)CH(CH₃)-(4-Cl—C₆H₄) | NH |
| Ia1.227 | Cl | CH₃ | CH(CH₃)CH(CH₃)-(4-Cl—C₆H₄) | NH |
| Ia1.228 | Cl | CH₂CH₃ | CH(CH₃)CH(CH₃)-(4-Cl—C₆H₄) | NH |
| Ia1.229 | Cl | (CH₂)₂CH₃ | CH(CH₃)CH(CH₃)-(4-Cl—C₆H₄) | NH |
| Ia1.230 | Cl | (CH₂)₃CH₃ | CH(CH₃)CH(CH₃)-(4-Cl—C₆H₄) | NH |
| Ia1.231 | Cl | H | (CH₂)₂-(2,4-Cl₂—C₆H₃) | NH |
| Ia1.232 | Cl | CH₃ | (CH₂)₂-(2,4-Cl₂—C₆H₃) | NH |
| Ia1.233 | Cl | CH₂CH₃ | (CH₂)₂-(2,4-Cl₂—C₆H₃) | NH |
| Ia1.234 | Cl | (CH₂)₂CH₃ | (CH₂)₂-(2,4-Cl₂—C₆H₃) | NH |
| Ia1.235 | Cl | (CH₂)₃CH₃ | (CH₂)₂-(2,4-Cl₂—C₆H₃) | NH |
| Ia1.236 | Cl | H | CH₂CH(CH₃)-(2,4-Cl₂—C₆H₃) | NH |
| Ia1.237 | Cl | CH₃ | CH₂CH(CH₃)-(2,4-Cl₂—C₆H₃) | NH |
| Ia1.238 | Cl | CH₂CH₃ | CH₂CH(CH₃)-(2,4-Cl₂—C₆H₃) | NH |
| Ia1.239 | Cl | (CH₂)₂CH₃ | CH₂CH(CH₃)-(2,4-Cl₂—C₆H₃) | NH |
| Ia1.240 | Cl | (CH₂)₃CH₃ | CH₂CH(CH₃)-(2,4-Cl₂—C₆H₃) | NH |
| Ia1.241 | Cl | H | CH(CH₃)CH₂-(2,4-Cl₂—C₆H₃) | NH |
| Ia1.242 | Cl | CH₃ | CH(CH₃)CH₂-(2,4-Cl₂—C₆H₃) | NH |
| Ia1.243 | Cl | CH₂CH₃ | CH(CH₃)CH₂-(2,4-Cl₂—C₆H₃) | NH |
| Ia1.244 | Cl | (CH₂)₂CH₃ | CH(CH₃)CH₂-(2,4-Cl₂—C₆H₃) | NH |
| Ia1.245 | Cl | (CH₂)₃CH₃ | CH(CH₃)CH₂-(2,4-Cl₂—C₆H₃) | NH |
| Ia1.246 | Cl | H | CH(CH₃)CH(CH₃)-(2,4-Cl₂—C₆H₃) | NH |
| Ia1.247 | Cl | CH₃ | CH(CH₃)CH(CH₃)-(2,4-Cl₂—C₆H₃) | NH |
| Ia1.248 | Cl | CH₂CH₃ | CH(CH₃)CH(CH₃)-(2,4-Cl₂—C₆H₃) | NH |
| Ia1.249 | Cl | (CH₂)₂CH₃ | CH(CH₃)CH(CH₃)-(2,4-Cl₂—C₆H₃) | NH |
| Ia1.250 | Cl | (CH₂)₃CH₃ | CH(CH₃)CH(CH₃)-(2,4-Cl₂—C₆H₃) | NH |
| Ia1.251 | Cl | H | (CH₂)₂—O—C₆H₅ | NH |
| Ia1.252 | Cl | CH₃ | (CH₂)₂—O—C₆H₅ | NH |
| Ia1.253 | Cl | CH₂CH₃ | (CH₂)₂—O—C₆H₅ | NH |
| Ia1.254 | Cl | (CH₂)₂CH₃ | (CH₂)₂—O—C₆H₅ | NH |
| Ia1.255 | Cl | (CH₂)₃CH₃ | (CH₂)₂—O—C₆H₅ | NH |
| Ia1.256 | Cl | H | CH₂CH(CH₃)—O—C₆H₅ | NH |
| Ia1.257 | Cl | CH₃ | CH₂CH(CH₃)—O—C₆H₅ | NH |
| Ia1.258 | Cl | CH₂CH₃ | CH₂CH(CH₃)—O—C₆H₅ | NH |
| Ia1.259 | Cl | (CH₂)₂CH₃ | CH₂CH(CH₃)—O—C₆H₅ | NH |
| Ia1.260 | Cl | (CH₂)₃CH₃ | CH₂CH(CH₃)—O—C₆H₅ | NH |
| Ia1.261 | Cl | H | CH(CH₃)CH₂—O—C₆H₅ | NH |
| Ia1.262 | Cl | CH₃ | CH(CH₃)CH₂—O—C₆H₅ | NH |
| Ia1.263 | Cl | CH₂CH₃ | CH(CH₃)CH₂—O—C₆H₅ | NH |
| Ia1.264 | Cl | (CH₂)₂CH₃ | CH(CH₃)CH₂—O—C₆H₅ | NH |
| Ia1.265 | Cl | (CH₂)₃CH₃ | CH(CH₃)CH₂—O—C₆H₅ | NH |
| Ia1.266 | Cl | H | CH(CH₃)CH(CH₃)—O—C₆H₅ | NH |
| Ia1.267 | Cl | CH₃ | CH(CH₃)CH(CH₃)—O—C₆H₅ | NH |
| Ia1.268 | Cl | CH₂CH₃ | CH(CH₃)CH(CH₃)—O—C₆H₅ | NH |
| Ia1.269 | Cl | (CH₂)₂CH₃ | CH(CH₃)CH(CH₃)—O—C₆H₅ | NH |
| Ia1.270 | Cl | (CH₂)₃CH₃ | CH(CH₃)CH(CH₃)—O—C₆H₅ | NH |
| Ia1.271 | Cl | H | (CH₂)₂—O-(4-Cl—C₆H₄) | NH |
| Ia1.272 | Cl | CH₃ | (CH₂)₂—O-(4-Cl—C₆H₄) | NH |
| Ia1.273 | Cl | CH₂CH₃ | (CH₂)₂—O-(4-Cl—C₆H₄) | NH |
| Ia1.274 | Cl | (CH₂)₂CH₃ | (CH₂)₂—O-(4-Cl—C₆H₄) | NH |
| Ia1.275 | Cl | (CH₂)₃CH₃ | (CH₂)₂—O-(4-Cl—C₆H₄) | NH |
| Ia1.276 | Cl | H | CH₂CH(CH₃)—O-(4-Cl—C₆H₄) | NH |
| Ia1.277 | Cl | CH₃ | CH₂CH(CH₃)—O-(4-Cl—C₆H₄) | NH |
| Ia1.278 | Cl | CH₂CH₃ | CH₂CH(CH₃)—O-(4-Cl—C₆H₄) | NH |
| Ia1.279 | Cl | (CH₂)₂CH₃ | CH₂CH(CH₃)—O-(4-Cl—C₆H₄) | NH |

TABLE 1-continued

| No. | R² | R³ | R⁴ | Z |
|---|---|---|---|---|
| Ia1.280 | Cl | (CH₂)₃CH₃ | CH₂CH(CH₃)—O-(4-Cl—C₆H₄) | NH |
| Ia1.281 | Cl | H | CH(CH₃)CH₂—O-(4-Cl—C₆H₄) | NH |
| Ia1.282 | Cl | CH₃ | CH(CH₃)CH₂—O-(4-Cl—C₆H₄) | NH |
| Ia1.283 | Cl | CH₂CH₃ | CH(CH₃)CH₂—O-(4-Cl—C₆H₄) | NH |
| Ia1.284 | Cl | (CH₂)₂CH₃ | CH(CH₃)CH₂—O-(4-Cl—C₆H₄) | NH |
| Ia1.285 | Cl | (CH₂)₃CH₃ | CH(CH₃)CH₂—O-(4-Cl—C₆H₄) | NH |
| Ia1.286 | Cl | H | CH(CH₃)CH(CH₃)—O-(4-Cl—C₆H₄) | NH |
| Ia1.287 | Cl | CH₃ | CH(CH₃)CH(CH₃)—O-(4-Cl—C₆H₄) | NH |
| Ia1.288 | Cl | CH₂CH₃ | CH(CH₃)CH(CH₃)—O-(4-Cl—C₆H₄) | NH |
| Ia1.289 | Cl | (CH₂)₂CH₃ | CH(CH₃)CH(CH₃)—O-(4-Cl—C₆H₄) | NH |
| Ia1.290 | Cl | (CH₂)₃CH₃ | CH(CH₃)CH(CH₃)—O-(4-Cl—C₆H₄) | NH |
| Ia1.291 | Cl | H | (CH₂)₂—O-(2,4-Cl₂—C₆H₃) | NH |
| Ia1.292 | Cl | CH₃ | (CH₂)₂—O-(2,4-Cl₂—C₆H₃) | NH |
| Ia1.293 | Cl | CH₂CH₃ | (CH₂)₂—O-(2,4-Cl₂—C₆H₃) | NH |
| Ia1.294 | Cl | (CH₂)₂CH₃ | (CH₂)₂—O-(2,4-Cl₂—C₆H₃) | NH |
| Ia1.295 | Cl | (CH₂)₃CH₃ | (CH₂)₂—O-(2,4-Cl₂—C₆H₃) | NH |
| Ia1.296 | Cl | H | CH₂CH(CH₃)—O-(2,4-Cl₂—C₆H₃) | NH |
| Ia1.297 | Cl | CH₃ | CH₂CH(CH₃)—O-(2,4-Cl₂—C₆H₃) | NH |
| Ia1.298 | Cl | CH₂CH₃ | CH₂CH(CH₃)—O-(2,4-Cl₂—C₆H₃) | NH |
| Ia1.299 | Cl | (CH₂)₂CH₃ | CH₂CH(CH₃)—O-(2,4-Cl₂—C₆H₃) | NH |
| Ia1.300 | Cl | (CH₂)₃CH₃ | CH₂CH(CH₃)—O-(2,4-Cl₂—C₆H₃) | NH |
| Ia1.301 | Cl | H | CH(CH₃)CH₂—O-(2,4-Cl₂—C₆H₃) | NH |
| Ia1.302 | Cl | CH₃ | CH(CH₃)CH₂—O-(2,4-Cl₂—C₆H₃) | NH |
| Ia1.303 | Cl | CH₂CH₃ | CH(CH₃)CH₂—O-(2,4-Cl₂—C₆H₃) | NH |
| Ia1.304 | Cl | (CH₂)₂CH₃ | CH(CH₃)CH₂—O-(2,4-Cl₂—C₆H₃) | NH |
| Ia1.305 | Cl | (CH₂)₃CH₃ | CH(CH₃)CH₂—O-(2,4-Cl₂—C₆H₃) | NH |
| Ia1.306 | Cl | H | CH(CH₃)CH(CH₃)—O-(2,4-Cl₂—C₆H₃) | NH |
| Ia1.307 | Cl | CH₃ | CH(CH₃)CH(CH₃)—O-(2,4-Cl₂—C₆H₃) | NH |
| Ia1.308 | Cl | CH₂CH₃ | CH(CH₃)CH(CH₃)—O-(2,4-Cl₂—C₆H₃) | NH |
| Ia1.309 | Cl | (CH₂)₂CH₃ | CH(CH₃)CH(CH₃)—O-(2,4-Cl₂—C₆H₃) | NH |
| Ia1.310 | Cl | (CH₂)₃CH₃ | CH(CH₃)CH(CH₃)—O-(2,4-Cl₂—C₆H₃) | NH |
| Ia1.311 | Cl | H | CH₃ | NCH₃ |
| Ia1.312 | Cl | CH₃ | CH₃ | NCH₃ |
| Ia1.313 | Cl | CH₂CH₃ | CH₃ | NCH₃ |
| Ia1.314 | Cl | (CH₂)₂CH₃ | CH₃ | NCH₃ |
| Ia1.315 | Cl | (CH₂)₃CH₃ | CH₃ | NCH₃ |
| Ia1.316 | Cl | H | C₂H₅ | NCH₃ |
| Ia1.317 | Cl | CH₃ | C₂H₅ | NCH₃ |
| Ia1.318 | Cl | CH₂CH₃ | C₂H₅ | NCH₃ |
| Ia1.319 | Cl | (CH₂)₂CH₃ | C₂H₅ | NCH₃ |
| Ia1.320 | Cl | (CH₂)₃CH₃ | C₂H₅ | NCH₃ |
| Ia1.321 | Cl | H | (CH₂)₂CH₃ | NCH₃ |
| Ia1.322 | Cl | CH₃ | (CH₂)₂CH₃ | NCH₃ |
| Ia1.323 | Cl | CH₂CH₃ | (CH₂)₂CH₃ | NCH₃ |
| Ia1.324 | Cl | (CH₂)₂CH₃ | (CH₂)₂CH₃ | NCH₃ |
| Ia1.325 | Cl | (CH₂)₃CH₃ | (CH₂)₂CH₃ | NCH₃ |
| Ia1.326 | Cl | H | CH(CH₃)₂ | NCH₃ |
| Ia1.327 | Cl | CH₃ | CH(CH₃)₂ | NCH₃ |
| Ia1.328 | Cl | CH₂CH₃ | CH(CH₃)₂ | NCH₃ |
| Ia1.329 | Cl | (CH₂)₂CH₃ | CH(CH₃)₂ | NCH₃ |
| Ia1.330 | Cl | (CH₂)₃CH₃ | CH(CH₃)₂ | NCH₃ |
| Ia1.331 | Cl | H | (CH₂)₃CH₃ | NCH₃ |
| Ia1.332 | Cl | CH₃ | (CH₂)₃CH₃ | NCH₃ |
| Ia1.333 | Cl | CH₂CH₃ | (CH₂)₃CH₃ | NCH₃ |
| Ia1.334 | Cl | (CH₂)₂CH₃ | (CH₂)₃CH₃ | NCH₃ |
| Ia1.335 | Cl | (CH₂)₃CH₃ | (CH₂)₃CH₃ | NCH₃ |
| Ia1.336 | Cl | H | CH₂CH(CH₃)₂ | NCH₃ |
| Ia1.337 | Cl | CH₃ | CH₂CH(CH₃)₂ | NCH₃ |
| Ia1.338 | Cl | CH₂CH₃ | CH₂CH(CH₃)₂ | NCH₃ |
| Ia1.339 | Cl | (CH₂)₂CH₃ | CH₂CH(CH₃)₂ | NCH₃ |
| Ia1.340 | Cl | (CH₂)₃CH₃ | CH₂CH(CH₃)₂ | NCH₃ |
| Ia1.341 | Cl | H | CH(CH₃)CH₂CH₃ | NCH₃ |
| Ia1.342 | Cl | CH₃ | CH(CH₃)CH₂CH₃ | NCH₃ |
| Ia1.343 | Cl | CH₂CH₃ | CH(CH₃)CH₂CH₃ | NCH₃ |
| Ia1.344 | Cl | (CH₂)₂CH₃ | CH(CH₃)CH₂CH₃ | NCH₃ |
| Ia1.345 | Cl | (CH₂)₃CH₃ | CH(CH₃)CH₂CH₃ | NCH₃ |
| Ia1.346 | Cl | H | (CH₂)₂—C₆H₅ | NCH₃ |
| Ia1.347 | Cl | CH₃ | (CH₂)₂—C₆H₅ | NCH₃ |
| Ia1.348 | Cl | CH₂CH₃ | (CH₂)₂—C₆H₅ | NCH₃ |
| Ia1.349 | Cl | (CH₂)₂CH₃ | (CH₂)₂—C₆H₅ | NCH₃ |
| Ia1.350 | Cl | (CH₂)₃CH₃ | (CH₂)₂—C₆H₅ | NCH₃ |
| Ia1.351 | Cl | H | CH₂CH(CH₃)—C₆H₅ | NCH₃ |
| Ia1.352 | Cl | CH₃ | CH₂CH(CH₃)—C₆H₅ | NCH₃ |
| Ia1.353 | Cl | CH₂CH₃ | CH₂CH(CH₃)—C₆H₅ | NCH₃ |
| Ia1.354 | Cl | (CH₂)₂CH₃ | CH₂CH(CH₃)—C₆H₅ | NCH₃ |
| Ia1.355 | Cl | (CH₂)₃CH₃ | CH₂CH(CH₃)—C₆H₅ | NCH₃ |
| Ia1.356 | Cl | H | CH(CH₃)CH₂—C₆H₅ | NCH₃ |

TABLE 1-continued

| No. | R² | R³ | R⁴ | Z |
|---|---|---|---|---|
| Ia1.357 | Cl | CH₃ | CH(CH₃)CH₂—C₆H₅ | NCH₃ |
| Ia1.358 | Cl | CH₂CH₃ | CH(CH₃)CH₂—C₆H₅ | NCH₃ |
| Ia1.359 | Cl | (CH₂)₂CH₃ | CH(CH₃)CH₂—C₆H₅ | NCH₃ |
| Ia1.360 | Cl | (CH₂)₃CH₃ | CH(CH₃)CH₂—C₆H₅ | NCH₃ |
| Ia1.361 | Cl | H | CH(CH₃)CH(CH₃)—C₆H₅ | NCH₃ |
| Ia1.362 | Cl | CH₃ | CH(CH₃)CH(CH₃)—C₆H₅ | NCH₃ |
| Ia1.363 | Cl | CH₂CH₃ | CH(CH₃)CH(CH₃)—C₆H₅ | NCH₃ |
| Ia1.364 | Cl | (CH₂)₂CH₃ | CH(CH₃)CH(CH₃)—C₆H₅ | NCH₃ |
| Ia1.365 | Cl | (CH2)₃CH₃ | CH(CH₃)CH(CH₃)—C₆H₅ | NCH₃ |
| Ia1.366 | Cl | H | (CH₂)₂-(4-Cl—C₆H₄) | NCH₃ |
| Ia1.367 | Cl | CH₃ | (CH₂)₂-(4-Cl—C₆H₄) | NCH₃ |
| Ia1.368 | Cl | CH₂CH₃ | (CH₂)₂-(4-Cl—C₆H₄) | NCH₃ |
| Ia1.369 | Cl | (CH₂)₂CH₃ | (CH₂)₂-(4-Cl—C₆H₄) | NCH₃ |
| Ia1.370 | Cl | (CH₂)₃CH₃ | (CH₂)₂-(4-Cl—C₆H₄) | NCH₃ |
| Ia1.371 | Cl | H | CH₂CH(CH₃)-(4-Cl—C₆H₄) | NCH₃ |
| Ia1.372 | Cl | CH₃ | CH₂CH(CH₃)-(4-Cl—C₆H₄) | NCH₃ |
| Ia1.373 | Cl | CH₂CH₃ | CH₂CH(CH₃)-(4-Cl—C₆H₄) | NCH₃ |
| Ia1.374 | Cl | (CH₂)₂CH₃ | CH₂CH(CH₃)-(4-Cl—C₆H₄) | NCH₃ |
| Ia1.375 | Cl | (CH₂)₃CH₃ | CH₂CH(CH₃)-(4-Cl—C₆H₄) | NCH₃ |
| Ia1.376 | Cl | H | CH(CH₃)CH₂-(4-Cl—C₆H₄) | NCH₃ |
| Ia1.377 | Cl | CH₃ | CH(CH₃)CH₂-(4-Cl—C₆H₄) | NCH₃ |
| Ia1.378 | Cl | CH₂CH₃ | CH(CH₃)CH₂-(4-Cl—C₆H₄) | NCH₃ |
| Ia1.379 | Cl | (CH₂)₂CH₃ | CH(CH₃)CH₂-(4-Cl—C₆H₄) | NCH₃ |
| Ia1.380 | Cl | (CH₂)₃CH₃ | CH(CH₃)CH₂-(4-Cl—C₆H₄) | NCH₃ |
| Ia1.381 | Cl | H | CH(CH₃)CH(CH₃)-(4-Cl—C₆H₄) | NCH₃ |
| Ia1.382 | Cl | CH₃ | CH(CH₃)CH(CH₃)-(4-Cl—C₆H₄) | NCH₃ |
| Ia1.383 | Cl | CH₂CH₃ | CH(CH₃)CH(CH₃)-(4-Cl—C₆H₄) | NCH₃ |
| Ia1.384 | Cl | (CH₂)₂CH₃ | CH(CH₃)CH(CH₃)-(4-Cl—C₆H₄) | NCH₃ |
| Ia1.385 | Cl | (CH₂)₃CH₃ | CH(CH₃)CH(CH₃)-(4-Cl—C₆H₄) | NCH₃ |
| Ia1.386 | Cl | H | (CH₂)₂-(2,4-Cl₂—C₆H₃) | NCH₃ |
| Ia1.387 | Cl | CH₃ | (CH₂)₂-(2,4-Cl₂—C₆H₃) | NCH₃ |
| Ia1.388 | Cl | CH₂CH₃ | (CH₂)₂-(2,4-Cl₂—C₆H₃) | NCH₃ |
| Ia1.389 | Cl | (CH₂)₂CH₃ | (CH₂)₂-(2,4-Cl₂—C₆H₃) | NCH₃ |
| Ia1.390 | Cl | (CH₂)₃CH₃ | (CH₂)₂-(2,4-Cl₂—C₆H₃) | NCH₃ |
| Ia1.391 | Cl | H | CH₂CH(CH₃)-(2,4-Cl₂—C₆H₃) | NCH₃ |
| Ia1.392 | Cl | CH₃ | CH₂CH(CH₃)-(2,4-Cl₂—C₆H₃) | NCH₃ |
| Ia1.393 | Cl | CH₂CH₃ | CH₂CH(CH₃)-(2,4-Cl₂—C₆H₃) | NCH₃ |
| Ia1.394 | Cl | (CH₂)₂CH₃ | CH₂CH(CH₃)-(2,4-Cl₂—C₆H₃) | NCH₃ |
| Ia1.395 | Cl | (CH₂)₃CH₃ | CH₂CH(CH₃)-(2,4-Cl₂—C₆H₃) | NCH₃ |
| Ia1.396 | Cl | H | CH(CH₃)CH₂-(2,4-Cl₂—C₆H₃) | NCH₃ |
| Ia1.397 | Cl | CH₃ | CH(CH₃)CH₂-(2,4-Cl₂—C₆H₃) | NCH₃ |
| Ia1.398 | Cl | CH₂CH₃ | CH(CH₃)CH₂-(2,4-Cl₂—C₆H₃) | NCH₃ |
| Ia1.399 | Cl | (CH₂)₂CH₃ | CH(CH₃)CH₂-(2,4-Cl₂—C₆H₃) | NCH₃ |
| Ia1.400 | Cl | (CH₂)₃CH₃ | CH(CH₃)CH₂-(2,4-Cl₂—C₆H₃) | NCH₃ |
| Ia1.401 | Cl | H | CH(CH₃)CH(CH₃)-(2,4-Cl₂—C₆H₃) | NCH₃ |
| Ia1.402 | Cl | CH₃ | CH(CH₃)CH(CH₃)-(2,4-Cl₂—C₆H₃) | NCH₃ |
| Ia1.403 | Cl | CH₂CH₃ | CH(CH₃)CH(CH₃)-(2,4-Cl₂—C₆H₃) | NCH₃ |
| Ia1.404 | Cl | (CH₂)₂CH₃ | CH(CH₃)CH(CH₃)-(2,4-Cl₂—C₆H₃) | NCH₃ |
| Ia1.405 | Cl | (CH₂)₃CH₃ | CH(CH₃)CH(CH₃)-(2,4-Cl₂—C₆H₃) | NCH₃ |
| Ia1.406 | Cl | H | (CH₂)₂—O—C₆H₅ | NCH₃ |
| Ia1.407 | Cl | CH₃ | (CH₂)₂—O—C₆H₅ | NCH₃ |
| Ia1.408 | Cl | CH₂CH₃ | (CH₂)₂—O—C₆H₅ | NCH₃ |
| Ia1.409 | Cl | (CH₂)₂CH₃ | (CH₂)₂—O—C₆H₅ | NCH₃ |
| Ia1.410 | Cl | (CH₂)₃CH₃ | (CH₂)₂—O—C₆H₅ | NCH₃ |
| Ia1.411 | Cl | H | CH₂CH(CH₃)—O—C₆H₅ | NCH₃ |
| Ia1.412 | Cl | CH₃ | CH₂CH(CH₃)—O—C₆H₅ | NCH₃ |
| Ia1.413 | Cl | CH₂CH₃ | CH₂CH(CH₃)—O—C₆H₅ | NCH₃ |
| Ia1.414 | Cl | (CH₂)₂CH₃ | CH₂CH(CH₃)—O—C₆H₅ | NCH₃ |
| Ia1.415 | Cl | (CH₂)₃CH₃ | CH₂CH(CH₃)—O—C₆H₅ | NCH₃ |
| Ia1.416 | Cl | H | CH(CH₃)CH₂—O—C₆H₅ | NCH₃ |
| Ia1.417 | Cl | CH₃ | CH(CH₃)CH₂—O—C₆H₅ | NCH₃ |
| Ia1.418 | Cl | CH₂CH₃ | CH(CH₃)CH₂—O—C₆H₅ | NCH₃ |
| Ia1.419 | Cl | (CH₂)₂CH₃ | CH(CH₃)CH₂—O—C₆H₅ | NCH₃ |
| Ia1.420 | Cl | (CH₂)₃CH₃ | CH(CH₃)CH₂—O—C₆H₅ | NCH₃ |
| Ia1.421 | Cl | H | CH(CH₃)CH(CH₃)—O—C₆H₅ | NCH₃ |
| Ia1.422 | Cl | CH₃ | CH(CH₃)CH(CH₃)—O—C₆H₅ | NCH₃ |
| Ia1.423 | Cl | CH₂CH₃ | CH(CH₃)CH(CH₃)—O—C₆H₅ | NCH₃ |
| Ia1.424 | Cl | (CH₂)₂CH₃ | CH(CH₃)CH(CH₃)—O—C₆H₅ | NCH₃ |
| Ia1.425 | Cl | (CH₂)₃CH₃ | CH(CH₃)CH(CH₃)—O—C₆H₅ | NCH₃ |
| Ia1.426 | Cl | H | (CH₂)₂—O-(4-Cl—C₆H₄) | NCH₃ |
| Ia1.427 | Cl | CH₃ | (CH₂)₂—O-(4-Cl—C₆H₄) | NCH₃ |
| Ia1.428 | Cl | CH₂CH₃ | (CH₂)₂—O-(4-Cl—C₆H₄) | NCH₃ |
| Ia1.429 | Cl | (CH₂)₂CH₃ | (CH₂)₂—O-(4-Cl—C₆H₄) | NCH₃ |
| Ia1.430 | Cl | (CH₂)₃CH₃ | (CH₂)₂—O-(4-Cl—C₆H₄) | NCH₃ |
| Ia1.431 | Cl | H | CH₂CH(CH₃)—O-(4-Cl—C₆H₄) | NCH₃ |
| Ia1.432 | Cl | CH₃ | CH₂CH(CH₃)—O-(4-Cl—C₆H₄) | NCH₃ |
| Ia1.433 | Cl | CH₂CH₃ | CH₂CH(CH₃)—O-(4-Cl—C₆H₄) | NCH₃ |

TABLE 1-continued

| No. | R² | R³ | R⁴ | Z |
|---|---|---|---|---|
| Ia1.434 | Cl | (CH₂)₂CH₃ | CH₂CH(CH₃)—O-(4-Cl—C₆H₄) | NCH₃ |
| Ia1.435 | Cl | (CH₂)₃CH₃ | CH₂CH(CH₃)—O-(4-Cl—C₆H₄) | NCH₃ |
| Ia1.436 | Cl | H | CH(CH₃)CH₂—O-(4-Cl—C₆H₄) | NCH₃ |
| Ia1.437 | Cl | CH₃ | CH(CH₃)CH₂—O-(4-Cl—C₆H₄) | NCH₃ |
| Ia1.438 | Cl | CH₂CH₃ | CH(CH₃)CH₂—O-(4-Cl—C₆H₄) | NCH₃ |
| Ia1.439 | Cl | (CH₂)₂CH₃ | CH(CH₃)CH₂—O-(4-Cl—C₆H₄) | NCH₃ |
| Ia1.440 | Cl | (CH₂)₃CH₃ | CH(CH₃)CH₂—O-(4-Cl—C₆H₄) | NCH₃ |
| Ia1.441 | Cl | H | CH(CH₃)CH(CH₃)—O-(4-Cl—C₆H₄) | NCH₃ |
| Ia1.442 | Cl | CH₃ | CH(CH₃)CH(CH₃)—O-(4-Cl—C₆H₄) | NCH₃ |
| Ia1.443 | Cl | CH₂CH₃ | CH(CH₃)CH(CH₃)—O-(4-Cl—C₆H₄) | NCH₃ |
| Ia1.444 | Cl | (CH₂)₂CH₃ | CH(CH₃)CH(CH₃)—O-(4-Cl—C₆H₄) | NCH₃ |
| Ia1.445 | Cl | (CH₂)₃CH₃ | CH(CH₃)CH(CH₃)—O-(4-Cl—C₆H₄) | NCH₃ |
| Ia1.446 | Cl | H | (CH₂)₂—O-(2,4-Cl₂—C₆H₃) | NCH₃ |
| Ia1.447 | Cl | CH₃ | (CH₂)₂—O-(2,4-Cl₂—C₆H₃) | NCH₃ |
| Ia1.448 | Cl | CH₂CH₃ | (CH₂)₂—O-(2,4-Cl₂—C₆H₃) | NCH₃ |
| Ia1.449 | Cl | (CH₂)₂CH₃ | (CH₂)₂—O-(2,4-Cl₂—C₆H₃) | NCH₃ |
| Ia1.450 | Cl | (CH₂)₃CH₃ | (CH₂)₂—O-(2,4-Cl₂—C₆H₃) | NCH₃ |
| Ia1.451 | Cl | H | CH₂CH(CH₃)—O-(2,4-Cl₂—C₆H₃) | NCH₃ |
| Ia1.452 | Cl | CH₃ | CH₂CH(CH₃)—O-(2,4-Cl₂—C₆H₃) | NCH₃ |
| Ia1.453 | Cl | CH₂CH₃ | CH₂CH(CH₃)—O-(2,4-Cl₂—C₆H₃) | NCH₃ |
| Ia1.454 | Cl | (CH₂)₂CH₃ | CH₂CH(CH₃)—O-(2,4-Cl₂—C₆H₃) | NCH₃ |
| Ia1.455 | Cl | (CH₂)₃CH₃ | CH₂CH(CH₃)—O-(2,4-Cl₂—C₆H₃) | NCH₃ |
| Ia1.456 | Cl | H | CH(CH₃)CH₂—O-(2,4-Cl₂—C₆H₃) | NCH₃ |
| Ia1.457 | Cl | CH₃ | CH(CH₃)CH₂—O-(2,4-Cl₂—C₆H₃) | NCH₃ |
| Ia1.458 | Cl | CH₂CH₃ | CH(CH₃)CH₂—O-(2,4-Cl₂—C₆H₃) | NCH₃ |
| Ia1.459 | Cl | (CH₂)₂CH₃ | CH(CH₃)CH₂—O-(2,4-Cl₂—C₆H₃) | NCH₃ |
| Ia1.460 | Cl | (CH₂)₃CH₃ | CH(CH₃)CH₂—O-(2,4-Cl₂—C₆H₃) | NCH₃ |
| Ia1.461 | Cl | H | CH(CH₃)CH(CH₃)—O-(2,4-Cl₂—C₆H₃) | NCH₃ |
| Ia1.462 | Cl | CH₃ | CH(CH₃)CH(CH₃)—O-(2,4-Cl₂—C₆H₃) | NCH₃ |
| Ia1.463 | Cl | CH₂CH₃ | CH(CH₃)CH(CH₃)—O-(2,4-Cl₂—C₆H₃) | NCH₃ |
| Ia1.464 | Cl | (CH₂)₂CH₃ | CH(CH₃)CH(CH₃)—O-(2,4-Cl₂—C₆H₃) | NCH₃ |
| Ia1.465 | Cl | (CH₂)₃CH₃ | CH(CH₃)CH(CH₃)—O-(2,4-Cl₂—C₆H₃) | NCH₃ |
| Ia1.466 | CH₃ | H | CH₃ | O |
| Ia1.467 | CH₃ | CH₃ | CH₃ | O |
| Ia1.468 | CH₃ | CH₂CH₃ | CH₃ | O |
| Ia1.469 | CH₃ | (CH₂)₂CH₃ | CH₃ | O |
| Ia1.470 | CH₃ | (CH₂)₃CH₃ | CH₃ | O |
| Ia1.471 | CH₃ | H | C₂H₅ | O |
| Ia1.472 | CH₃ | CH₃ | C₂H₅ | O |
| Ia1.473 | CH₃ | CH₂CH₃ | C₂H₅ | O |
| Ia1.474 | CH₃ | (CH₂)₂CH₃ | C₂H₅ | O |
| Ia1.475 | CH₃ | (CH₂)₃CH₃ | C₂H₅ | O |
| Ia1.476 | CH₃ | H | (CH₂)₂CH₃ | O |
| Ia1.477 | CH₃ | CH₃ | (CH₂)₂CH₃ | O |
| Ia1.478 | CH₃ | CH₂CH₃ | (CH₂)₂CH₃ | O |
| Ia1.479 | CH₃ | (CH₂)₂CH₃ | (CH₂)₂CH₃ | O |
| Ia1.480 | CH₃ | (CH₂)₃CH₃ | (CH₂)₂CH₃ | O |
| Ia1.481 | CH₃ | H | CH(CH₃)₂ | O |
| Ia1.482 | CH₃ | CH₃ | CH(CH₃)₂ | O |
| Ia1.483 | CH₃ | CH₂CH₃ | CH(CH₃)₂ | O |
| Ia1.484 | CH₃ | (CH₂)₂CH₃ | CH(CH₃)₂ | O |
| Ia1.485 | CH₃ | (CH₂)₃CH₃ | CH(CH₃)₂ | O |
| Ia1.486 | CH₃ | H | (CH₂)₃CH₃ | O |
| Ia1.487 | CH₃ | CH₃ | (CH₂)₃CH₃ | O |
| Ia1.488 | CH₃ | CH₂CH₃ | (CH₂)₃CH₃ | O |
| Ia1.489 | CH₃ | (CH₂)₂CH₃ | (CH₂)₃CH₃ | O |
| Ia1.490 | CH₃ | (CH₂)₃CH₃ | (CH₂)₃CH₃ | O |
| Ia1.491 | CH₃ | H | CH₂CH(CH₃)₂ | O |
| Ia1.492 | CH₃ | CH₃ | CH₂CH(CH₃)₂ | O |
| Ia1.493 | CH₃ | CH₂CH₃ | CH₂CH(CH₃)₂ | O |
| Ia1.494 | CH₃ | (CH₂)₂CH₃ | CH₂CH(CH₃)₂ | O |
| Ia1.495 | CH₃ | (CH₂)₃CH₃ | CH₂CH(CH₃)₂ | O |
| Ia1.496 | CH₃ | H | CH(CH₃)CH₂CH₃ | O |
| Ia1.497 | CH₃ | CH₃ | CH(CH₃)CH₂CH₃ | O |
| Ia1.498 | CH₃ | CH₂CH₃ | CH(CH₃)CH₂CH₃ | O |
| Ia1.499 | CH₃ | (CH₂)₂CH₃ | CH(CH₃)CH₂CH₃ | O |
| Ia1.500 | CH₃ | (CH₂)₃CH₃ | CH(CH₃)CH₂CH₃ | O |
| Ia1.501 | CH₃ | H | (CH₂)₂—C₆H₅ | O |
| Ia1.502 | CH₃ | CH₃ | (CH₂)₂—C₆H₅ | O |
| Ia1.503 | CH₃ | CH₂CH₃ | (CH₂)₂—C₆H₅ | O |
| Ia1.504 | CH₃ | (CH₂)₂CH₃ | (CH₂)₂—C₆H₅ | O |
| Ia1.505 | CH₃ | (CH₂)₃CH₃ | (CH₂)₂—C₆H₅ | O |
| Ia1.506 | CH₃ | H | CH₂CH(CH₃)—C₆H₅ | O |
| Ia1.507 | CH₃ | CH₃ | CH₂CH(CH₃)—C₆H₅ | O |
| Ia1.508 | CH₃ | CH₂CH₃ | CH₂CH(CH₃)—C₆H₅ | O |
| Ia1.509 | CH₃ | (CH₂)₂CH₃ | CH₂CH(CH₃)—C₆H₅ | O |
| Ia1.510 | CH₃ | (CH₂)₃CH₃ | CH₂CH(CH₃)—C₆H₅ | O |

TABLE 1-continued

| No. | $R^2$ | $R^3$ | $R^4$ | Z |
|---|---|---|---|---|
| Ia1.511 | $CH_3$ | H | $CH(CH_3)CH_2—C_6H_5$ | O |
| Ia1.512 | $CH_3$ | $CH_3$ | $CH(CH_3)CH_2—C_6H_5$ | O |
| Ia1.513 | $CH_3$ | $CH_2CH_3$ | $CH(CH_3)CH_2—C_6H_5$ | O |
| Ia1.514 | $CH_3$ | $(CH_2)_2CH_3$ | $CH(CH_3)CH_2—C_6H_5$ | O |
| Ia1.515 | $CH_3$ | $(CH_2)_3CH_3$ | $CH(CH_3)CH_2—C_6H_5$ | O |
| Ia1.516 | $CH_3$ | H | $CH(CH_3)CH(CH_3)—C_6H_5$ | O |
| Ia1.517 | $CH_3$ | $CH_3$ | $CH(CH_3)CH(CH_3)—C_6H_5$ | O |
| Ia1.518 | $CH_3$ | $CH_2CH_3$ | $CH(CH_3)CH(CH_3)—C_6H_5$ | O |
| Ia1.519 | $CH_3$ | $(CH_2)_2CH_3$ | $CH(CH_3)CH(CH_3)—C_6H_5$ | O |
| Ia1.520 | $CH_3$ | $(CH_2)_3CH_3$ | $CH(CH_3)CH(CH_3)—C_6H_5$ | O |
| Ia1.521 | $CH_3$ | H | $(CH_2)_2$-(4-Cl—$C_6H_4$) | O |
| Ia1.522 | $CH_3$ | $CH_3$ | $(CH_2)_2$-(4-Cl—$C_6H_4$) | O |
| Ia1.523 | $CH_3$ | $CH_2CH_3$ | $(CH_2)_2$-(4-Cl—$C_6H_4$) | O |
| Ia1.524 | $CH_3$ | $(CH_2)_2CH_3$ | $(CH_2)_2$-(4-Cl—$C_6H_4$) | O |
| Ia1.525 | $CH_3$ | $(CH_2)_3CH_3$ | $(CH_2)_2$-(4-Cl—$C_6H_4$) | O |
| Ia1.526 | $CH_3$ | H | $CH_2CH(CH_3)$-(4-Cl—$C_6H_4$) | O |
| Ia1.527 | $CH_3$ | $CH_3$ | $CH_2CH(CH_3)$-(4-Cl—$C_6H_4$) | O |
| Ia1.528 | $CH_3$ | $CH_2CH_3$ | $CH_2CH(CH_3)$-(4-Cl—$C_6H_4$) | O |
| Ia1.529 | $CH_3$ | $(CH_2)_2CH_3$ | $CH_2CH(CH_3)$-(4-Cl—$C_6H_4$) | O |
| Ia1.530 | $CH_3$ | $(CH_2)_3CH_3$ | $CH_2CH(CH_3)$-(4-Cl—$C_6H_4$) | O |
| Ia1.531 | $CH_3$ | H | $CH(CH_3)CH_2$-(4-Cl—$C_6H_4$) | O |
| Ia1.532 | $CH_3$ | $CH_3$ | $CH(CH_3)CH_2$-(4-Cl—$C_6H_4$) | O |
| Ia1.533 | $CH_3$ | $CH_2CH_3$ | $CH(CH_3)CH_2$-(4-Cl—$C_6H_4$) | O |
| Ia1.534 | $CH_3$ | $(CH_2)_2CH_3$ | $CH(CH_3)CH_2$-(4-Cl—$C_6H_4$) | O |
| Ia1.535 | $CH_3$ | $(CH_2)_3CH_3$ | $CH(CH_3)CH_2$-(4-Cl—$C_6H_4$) | O |
| Ia1.536 | $CH_3$ | H | $CH(CH_3)CH(CH_3)$-(4-Cl—$C_6H_4$) | O |
| Ia1.537 | $CH_3$ | $CH_3$ | $CH(CH_3)CH(CH_3)$-(4-Cl—$C_6H_4$) | O |
| Ia1.538 | $CH_3$ | $CH_2CH_3$ | $CH(CH_3)CH(CH_3)$-(4-Cl—$C_6H_4$) | O |
| Ia1.539 | $CH_3$ | $(CH_2)_2CH_3$ | $CH(CH_3)CH(CH_3)$-(4-Cl—$C_6H_4$) | O |
| Ia1.540 | $CH_3$ | $(CH_2)_3CH_3$ | $CH(CH_3)CH(CH_3)$-(4-Cl—$C_6H_4$) | O |
| Ia1.541 | $CH_3$ | H | $(CH_2)_2$-(2,4-$Cl_2$—$C_6H_3$) | O |
| Ia1.542 | $CH_3$ | $CH_3$ | $(CH_2)_2$-(2,4-$Cl_2$—$C_6H_3$) | O |
| Ia1.543 | $CH_3$ | $CH_2CH_3$ | $(CH_2)_2$-(2,4-$Cl_2$—$C_6H_3$) | O |
| Ia1.544 | $CH_3$ | $(CH_2)_2CH_3$ | $(CH_2)_2$-(2,4-$Cl_2$—$C_6H_3$) | O |
| Ia1.545 | $CH_3$ | $(CH_2)_3CH_3$ | $(CH_2)_2$-(2,4-$Cl_2$—$C_6H_3$) | O |
| Ia1.546 | $CH_3$ | H | $CH_2CH(CH_3)$-(2,4-$Cl_2$—$C_6H_3$) | O |
| Ia1.547 | $CH_3$ | $CH_3$ | $CH_2CH(CH_3)$-(2,4-$Cl_2$—$C_6H_3$) | O |
| Ia1.548 | $CH_3$ | $CH_2CH_3$ | $CH_2CH(CH_3)$-(2,4-$Cl_2$—$C_6H_3$) | O |
| Ia1.549 | $CH_3$ | $(CH_2)_2CH_3$ | $CH_2CH(CH_3)$-(2,4-$Cl_2$—$C_6H_3$) | O |
| Ia1.550 | $CH_3$ | $(CH_2)_3CH_3$ | $CH_2CH(CH_3)$-(2,4-$Cl_2$—$C_6H_3$) | O |
| Ia1.551 | $CH_3$ | H | $CH(CH_3)CH_2$-(2,4-$Cl_2$—$C_6H_3$) | O |
| Ia1.552 | $CH_3$ | $CH_3$ | $CH(CH_3)CH_2$-(2,4-$Cl_2$—$C_6H_3$) | O |
| Ia1.553 | $CH_3$ | $CH_2CH_3$ | $CH(CH_3)CH_2$-(2,4-$Cl_2$—$C_6H_3$) | O |
| Ia1.554 | $CH_3$ | $(CH_2)_2CH_3$ | $CH(CH_3)CH_2$-(2,4-$Cl_2$—$C_6H_3$) | O |
| Ia1.555 | $CH_3$ | $(CH_2)_3CH_3$ | $CH(CH_3)CH_2$-(2,4-$Cl_2$—$C_6H_3$) | O |
| Ia1.556 | $CH_3$ | H | $CH(CH_3)CH(CH_3)$-(2,4-$Cl_2$—$C_6H_3$) | O |
| Ia1.557 | $CH_3$ | $CH_3$ | $CH(CH_3)CH(CH_3)$-(2,4-$Cl_2$—$C_6H_3$) | O |
| Ia1.558 | $CH_3$ | $CH_2CH_3$ | $CH(CH_3)CH(CH_3)$-(2,4-$Cl_2$—$C_6H_3$) | O |
| Ia1.559 | $CH_3$ | $(CH_2)_2CH_3$ | $CH(CH_3)CH(CH_3)$-(2,4-$Cl_2$—$C_6H_3$) | O |
| Ia1.560 | $CH_3$ | $(CH_2)_3CH_3$ | $CH(CH_3)CH(CH_3)$-(2,4-$Cl_2$—$C_6H_3$) | O |
| Ia1.561 | $CH_3$ | H | $(CH_2)_2—O—C_6H_5$ | O |
| Ia1.562 | $CH_3$ | $CH_3$ | $(CH_2)_2—O—C_6H_5$ | O |
| Ia1.563 | $CH_3$ | $CH_2CH_3$ | $(CH_2)_2—O—C_6H_5$ | O |
| Ia1.564 | $CH_3$ | $(CH_2)_2CH_3$ | $(CH_2)_2—O—C_6H_5$ | O |
| Ia1.565 | $CH_3$ | $(CH_2)_3CH_3$ | $(CH_2)_2—O—C_6H_5$ | O |
| Ia1.566 | $CH_3$ | H | $CH_2CH(CH_3)—O—C_6H_5$ | O |
| Ia1.567 | $CH_3$ | $CH_3$ | $CH_2CH(CH_3)—O—C_6H_5$ | O |
| Ia1.568 | $CH_3$ | $CH_2CH_3$ | $CH_2CH(CH_3)—O—C_6H_5$ | O |
| Ia1.569 | $CH_3$ | $(CH_2)_2CH_3$ | $CH_2CH(CH_3)—O—C_6H_5$ | O |
| Ia1.570 | $CH_3$ | $(CH_2)_3CH_3$ | $CH_2CH(CH_3)—O—C_6H_5$ | O |
| Ia1.571 | $CH_3$ | H | $CH(CH_3)CH_2—O—C_6H_5$ | O |
| Ia1.572 | $CH_3$ | $CH_3$ | $CH(CH_3)CH_2—O—C_6H_5$ | O |
| Ia1.573 | $CH_3$ | $CH_2CH_3$ | $CH(CH_3)CH_2—O—C_6H_5$ | O |
| Ia1.574 | $CH_3$ | $(CH_2)_2CH_3$ | $CH(CH_3)CH_2—O—C_6H_5$ | O |
| Ia1.575 | $CH_3$ | $(CH_2)_3CH_3$ | $CH(CH_3)CH_2—O—C_6H_5$ | O |
| Ia1.576 | $CH_3$ | H | $CH(CH_3)CH(CH_3)—O—C_6H_5$ | O |
| Ia1.577 | $CH_3$ | $CH_3$ | $CH(CH_3)CH(CH_3)—O—C_6H_5$ | O |
| Ia1.578 | $CH_3$ | $CH_2CH_3$ | $CH(CH_3)CH(CH_3)—O—C_6H_5$ | O |
| Ia1.579 | $CH_3$ | $(CH_2)_2CH_3$ | $CH(CH_3)CH(CH_3)—O—C_6H_5$ | O |
| Ia1.580 | $CH_3$ | $(CH_2)_3CH_3$ | $CH(CH_3)CH(CH_3)—O—C_6H_5$ | O |
| Ia1.581 | $CH_3$ | H | $(CH_2)_2—O$-(4-Cl—$C_6H_4$) | O |
| Ia1.582 | $CH_3$ | $CH_3$ | $(CH_2)_2—O$-(4-Cl—$C_6H_4$) | O |
| Ia1.583 | $CH_3$ | $CH_2CH_3$ | $(CH_2)_2—O$-(4-Cl—$C_6H_4$) | O |
| Ia1.584 | $CH_3$ | $(CH_2)_2CH_3$ | $(CH_2)_2—O$-(4-Cl—$C_6H_4$) | O |
| Ia1.585 | $CH_3$ | $(CH_2)_3CH_3$ | $(CH_2)_2—O$-(4-Cl—$C_6H_4$) | O |
| Ia1.586 | $CH_3$ | H | $CH_2CH(CH_3)—O$-(4-Cl—$C_6H_4$) | O |
| Ia1.587 | $CH_3$ | $CH_3$ | $CH_2CH(CH_3)—O$-(4-Cl—$C_6H_4$) | O |

TABLE 1-continued

| No. | $R^2$ | $R^3$ | $R^4$ | Z |
|---|---|---|---|---|
| Ia1.588 | $CH_3$ | $CH_2CH_3$ | $CH_2CH(CH_3)$—O-(4-Cl—$C_6H_4$) | O |
| Ia1.589 | $CH_3$ | $(CH_2)_2CH_3$ | $CH_2CH(CH_3)$—O-(4-Cl—$C_6H_4$) | O |
| Ia1.590 | $CH_3$ | $(CH_2)_3CH_3$ | $CH_2CH(CH_3)$—O-(4-Cl—$C_6H_4$) | O |
| Ia1.591 | $CH_3$ | H | $CH(CH_3)CH_2$—O-(4-Cl—$C_6H_4$) | O |
| Ia1.592 | $CH_3$ | $CH_3$ | $CH(CH_3)CH_2$—O-(4-Cl—$C_6H_4$) | O |
| Ia1.593 | $CH_3$ | $CH_2CH_3$ | $CH(CH_3)CH_2$—O-(4-Cl—$C_6H_4$) | O |
| Ia1.594 | $CH_3$ | $(CH_2)_2CH_3$ | $CH(CH_3)CH_2$—O-(4-Cl—$C_6H_4$) | O |
| Ia1.595 | $CH_3$ | $(CH_2)_3CH_3$ | $CH(CH_3)CH_2$—O-(4-Cl—$C_6H_4$) | O |
| Ia1.596 | $CH_3$ | H | $CH(CH_3)CH(CH_3)$—O-(4-Cl—$C_6H_4$) | O |
| Ia1.597 | $CH_3$ | $CH_3$ | $CH(CH_3)CH(CH_3)$—O-(4-Cl—$C_6H_4$) | O |
| Ia1.598 | $CH_3$ | $CH_2CH_3$ | $CH(CH_3)CH(CH_3)$—O-(4-Cl—$C_6H_4$) | O |
| Ia1.599 | $CH_3$ | $(CH_2)_2CH_3$ | $CH(CH_3)CH(CH_3)$—O-(4-Cl—$C_6H_4$) | O |
| Ia1.600 | $CH_3$ | $(CH_2)_3CH_3$ | $CH(CH_3)CH(CH_3)$—O-(4-Cl—$C_6H_4$) | O |
| Ia1.601 | $CH_3$ | H | $(CH_2)_2$—O-(2,4-$Cl_2$—$C_6H_3$) | O |
| Ia1.602 | $CH_3$ | $CH_3$ | $(CH_2)_2$—O-(2,4-$Cl_2$—$C_6H_3$) | O |
| Ia1.603 | $CH_3$ | $CH_2CH_3$ | $(CH_2)_2$—O-(2,4-$Cl_2$—$C_6H_3$) | O |
| Ia1.604 | $CH_3$ | $(CH_2)_2CH_3$ | $(CH_2)_2$—O-(2,4-$Cl_2$—$C_6H_3$) | O |
| Ia1.605 | $CH_3$ | $(CH_2)_3CH_3$ | $(CH_2)_2$—O-(2,4-$Cl_2$—$C_6H_3$) | O |
| Ia1.606 | $CH_3$ | H | $CH_2CH(CH_3)$—O-(2,4-$Cl_2$—$C_6H_3$) | O |
| Ia1.607 | $CH_3$ | $CH_3$ | $CH_2CH(CH_3)$—O-(2,4-$Cl_2$—$C_6H_3$) | O |
| Ia1.608 | $CH_3$ | $CH_2CH_3$ | $CH_2CH(CH_3)$—O-(2,4-$Cl_2$—$C_6H_3$) | O |
| Ia1.609 | $CH_3$ | $(CH_2)_2CH_3$ | $CH_2CH(CH_3)$—O-(2,4-$Cl_2$—$C_6H_3$) | O |
| Ia1.610 | $CH_3$ | $(CH_2)_3CH_3$ | $CH_2CH(CH_3)$—O-(2,4-$Cl_2$—$C_6H_3$) | O |
| Ia1.611 | $CH_3$ | H | $CH(CH_3)CH_2$—O-(2,4-$Cl_2$—$C_6H_3$) | O |
| Ia1.612 | $CH_3$ | $CH_3$ | $CH(CH_3)CH_2$—O-(2,4-$Cl_2$—$C_6H_3$) | O |
| Ia1.613 | $CH_3$ | $CH_2CH_3$ | $CH(CH_3)CH_2$—O-(2,4-$Cl_2$—$C_6H_3$) | O |
| Ia1.614 | $CH_3$ | $(CH_2)_2CH_3$ | $CH(CH_3)CH_2$—O-(2,4-$Cl_2$—$C_6H_3$) | O |
| Ia1.615 | $CH_3$ | $(CH_2)_3CH_3$ | $CH(CH_3)CH_2$—O-(2,4-$Cl_2$—$C_6H_3$) | O |
| Ia1.616 | $CH_3$ | H | $CH(CH_3)CH(CH_3)$—O-(2,4-$Cl_2$—$C_6H_3$) | O |
| Ia1.617 | $CH_3$ | $CH_3$ | $CH(CH_3)CH(CH_3)$—O-(2,4-$Cl_2$—$C_6H_3$) | O |
| Ia1.618 | $CH_3$ | $CH_2CH_3$ | $CH(CH_3)CH(CH_3)$—O-(2,4-$Cl_2$—$C_6H_3$) | O |
| Ia1.619 | $CH_3$ | $(CH_2)_2CH_3$ | $CH(CH_3)CH(CH_3)$—O-(2,4-$Cl_2$—$C_6H_3$) | O |
| Ia1.620 | $CH_3$ | $(CH_2)_3CH_3$ | $CH(CH_3)CH(CH_3)$—O-(2,4-$Cl_2$—$C_6H_3$) | O |
| Ia1.621 | $CH_3$ | H | $CH_3$ | NH |
| Ia1.622 | $CH_3$ | $CH_3$ | $CH_3$ | NH |
| Ia1.623 | $CH_3$ | $CH_2CH_3$ | $CH_3$ | NH |
| Ia1.624 | $CH_3$ | $(CH_2)_2CH_3$ | $CH_3$ | NH |
| Ia1.625 | $CH_3$ | $(CH_2)_3CH_3$ | $CH_3$ | NH |
| Ia1.626 | $CH_3$ | H | $C_2H_5$ | NH |
| Ia1.627 | $CH_3$ | $CH_3$ | $C_2H_5$ | NH |
| Ia1.628 | $CH_3$ | $CH_2CH_3$ | $C_2H_5$ | NH |
| Ia1.629 | $CH_3$ | $(CH_2)_2CH_3$ | $C_2H_5$ | NH |
| Ia1.630 | $CH_3$ | $(CH_2)_3CH_3$ | $C_2H_5$ | NH |
| Ia1.631 | $CH_3$ | H | $(CH_2)_2CH_3$ | NH |
| Ia1.632 | $CH_3$ | $CH_3$ | $(CH_2)_2CH_3$ | NH |
| Ia1.633 | $CH_3$ | $CH_2CH_3$ | $(CH_2)_2CH_3$ | NH |
| Ia1.634 | $CH_3$ | $(CH_2)_2CH_3$ | $(CH_2)_2CH_3$ | NH |
| Ia1.635 | $CH_3$ | $(CH_2)_3CH_3$ | $(CH_2)_2CH_3$ | NH |
| Ia1.636 | $CH_3$ | H | $CH(CH_3)_2$ | NH |
| Ia1.637 | $CH_3$ | $CH_3$ | $CH(CH_3)_2$ | NH |
| Ia1.638 | $CH_3$ | $CH_2CH_3$ | $CH(CH_3)_2$ | NH |
| Ia1.639 | $CH_3$ | $(CH_2)_2CH_3$ | $CH(CH_3)_2$ | NH |
| Ia1.640 | $CH_3$ | $(CH_2)_3CH_3$ | $CH(CH_3)_2$ | NH |
| Ia1.641 | $CH_3$ | H | $(CH_2)_3CH_3$ | NH |
| Ia1.642 | $CH_3$ | $CH_3$ | $(CH_2)_3CH_3$ | NH |
| Ia1.643 | $CH_3$ | $CH_2CH_3$ | $(CH_2)_3CH_3$ | NH |
| Ia1.644 | $CH_3$ | $(CH_2)_2CH_3$ | $(CH_2)_3CH_3$ | NH |
| Ia1.645 | $CH_3$ | $(CH_2)_3CH_3$ | $(CH_2)_3CH_3$ | NH |
| Ia1.646 | $CH_3$ | H | $CH_2CH(CH_3)_2$ | NH |
| Ia1.647 | $CH_3$ | $CH_3$ | $CH_2CH(CH_3)_2$ | NH |
| Ia1.648 | $CH_3$ | $CH_2CH_3$ | $CH_2CH(CH_3)_2$ | NH |
| Ia1.649 | $CH_3$ | $(CH_2)_2CH_3$ | $CH_2CH(CH_3)_2$ | NH |
| Ia1.650 | $CH_3$ | $(CH_2)_3CH_3$ | $CH_2CH(CH_3)_2$ | NH |
| Ia1.651 | $CH_3$ | H | $CH(CH_3)CH_2CH_3$ | NH |
| Ia1.652 | $CH_3$ | $CH_3$ | $CH(CH_3)CH_2CH_3$ | NH |
| Ia1.653 | $CH_3$ | $CH_2CH_3$ | $CH(CH_3)CH_2CH_3$ | NH |
| Ia1.654 | $CH_3$ | $(CH_2)_2CH_3$ | $CH(CH_3)CH_2CH_3$ | NH |
| Ia1.655 | $CH_3$ | $(CH_2)_3CH_3$ | $CH(CH_3)CH_2CH_3$ | NH |
| Ia1.656 | $CH_3$ | H | $(CH_2)_2$—$C_6H_5$ | NH |
| Ia1.657 | $CH_3$ | $CH_3$ | $(CH_2)_2$—$C_6H_5$ | NH |
| Ia1.658 | $CH_3$ | $CH_2CH_3$ | $(CH_2)_2$—$C_6H_5$ | NH |
| Ia1.659 | $CH_3$ | $(CH_2)_2CH_3$ | $(CH_2)_2$—$C_6H_5$ | NH |
| Ia1.660 | $CH_3$ | $(CH_2)_3CH_3$ | $(CH_2)_2$—$C_6H_5$ | NH |
| Ia1.661 | $CH_3$ | H | $CH_2CH(CH_3)$—$C_6H_5$ | NH |
| Ia1.662 | $CH_3$ | $CH_3$ | $CH_2CH(CH_3)$—$C_6H_5$ | NH |
| Ia1.663 | $CH_3$ | $CH_2CH_3$ | $CH_2CH(CH_3)$—$C_6H_5$ | NH |
| Ia1.664 | $CH_3$ | $(CH_2)_2CH_3$ | $CH_2CH(CH_3)$—$C_6H_5$ | NH |

TABLE 1-continued

| No. | R² | R³ | R⁴ | Z |
|---|---|---|---|---|
| Ia1.665 | CH₃ | (CH₂)₃CH₃ | CH₂CH(CH₃)—C₆H₅ | NH |
| Ia1.666 | CH₃ | H | CH(CH₃)CH₂—C₆H₅ | NH |
| Ia1.667 | CH₃ | CH₃ | CH(CH₃)CH₂—C₆H₅ | NH |
| Ia1.668 | CH₃ | CH₂CH₃ | CH(CH₃)CH₂—C₆H₅ | NH |
| Ia1.669 | CH₃ | (CH₂)₂CH₃ | CH(CH₃)CH₂—C₆H₅ | NH |
| Ia1.670 | CH₃ | (CH₂)₃CH₃ | CH(CH₃)CH₂—C₆H₅ | NH |
| Ia1.671 | CH₃ | H | CH(CH₃)CH(CH₃)—C₆H₅ | NH |
| Ia1.672 | CH₃ | CH₃ | CH(CH₃)CH(CH₃)—C₆H₅ | NH |
| Ia1.673 | CH₃ | CH₂CH₃ | CH(CH₃)CH(CH₃)—C₆H₅ | NH |
| Ia1.674 | CH₃ | (CH₂)₂CH₃ | CH(CH₃)CH(CH₃)—C₆H₅ | NH |
| Ia1.675 | CH₃ | (CH₂)₃CH₃ | CH(CH₃)CH(CH₃)—C₆H₅ | NH |
| Ia1.676 | CH₃ | H | (CH₂)₂-(4-Cl—C₆H₄) | NH |
| Ia1.677 | CH₃ | CH₃ | (CH₂)₂-(4-Cl—C₆H₄) | NH |
| Ia1.678 | CH₃ | CH₂CH₃ | (CH₂)₂-(4-Cl—C₆H₄) | NH |
| Ia1.679 | CH₃ | (CH₂)₂CH₃ | (CH₂)₂-(4-Cl—C₆H₄) | NH |
| Ia1.680 | CH₃ | (CH₂)₃CH₃ | (CH₂)₂-(4-Cl—C₆H₄) | NH |
| Ia1.681 | CH₃ | H | CH₂CH(CH₃)-(4-Cl—C₆H₄) | NH |
| Ia1.682 | CH₃ | CH₃ | CH₂CH(CH₃)-(4-Cl—C₆H₄) | NH |
| Ia1.683 | CH₃ | CH₂CH₃ | CH₂CH(CH₃)-(4-Cl—C₆H₄) | NH |
| Ia1.684 | CH₃ | (CH₂)₂CH₃ | CH₂CH(CH₃)-(4-Cl—C₆H₄) | NH |
| Ia1.685 | CH₃ | (CH₂)₃CH₃ | CH₂CH(CH₃)-(4-Cl—C₆H₄) | NH |
| Ia1.686 | CH₃ | H | CH(CH₃)CH₂-(4-Cl—C₆H₄) | NH |
| Ia1.687 | CH₃ | CH₃ | CH(CH₃)CH₂-(4-Cl—C₆H₄) | NH |
| Ia1.688 | CH₃ | CH₂CH₃ | CH(CH₃)CH₂-(4-Cl—C₆H₄) | NH |
| Ia1.689 | CH₃ | (CH₂)₂CH₃ | CH(CH₃)CH₂-(4-Cl—C₆H₄) | NH |
| Ia1.690 | CH₃ | (CH₂)₃CH₃ | CH(CH₃)CH₂-(4-Cl—C₆H₄) | NH |
| Ia1.691 | CH₃ | H | CH(CH₃)CH(CH₃)-(4-Cl—C₆H₄) | NH |
| Ia1.692 | CH₃ | CH₃ | CH(CH₃)CH(CH₃)-(4-Cl—C₆H₄) | NH |
| Ia1.693 | CH₃ | CH₂CH₃ | CH(CH₃)CH(CH₃)-(4-Cl—C₆H₄) | NH |
| Ia1.694 | CH₃ | (CH₂)₂CH₃ | CH(CH₃)CH(CH₃)-(4-Cl—C₆H₄) | NH |
| Ia1.695 | CH₃ | (CH₂)₃CH₃ | CH(CH₃)CH(CH₃)-(4-Cl—C₆H₄) | NH |
| Ia1.696 | CH₃ | H | (CH₂)₂-(2,4-Cl₂—C₆H₃) | NH |
| Ia1.697 | CH₃ | CH₃ | (CH₂)₂-(2,4-Cl₂—C₆H₃) | NH |
| Ia1.698 | CH₃ | CH₂CH₃ | (CH₂)₂-(2,4-Cl₂—C₆H₃) | NH |
| Ia1.699 | CH₃ | (CH₂)₂CH₃ | (CH₂)₂-(2,4-Cl₂—C₆H₃) | NH |
| Ia1.700 | CH₃ | (CH₂)₃CH₃ | (CH₂)₂-(2,4-Cl₂—C₆H₃) | NH |
| Ia1.701 | CH₃ | H | CH₂CH(CH₃)-(2,4-Cl₂—C₆H₃) | NH |
| Ia1.702 | CH₃ | CH₃ | CH₂CH(CH₃)-(2,4-Cl₂—C₆H₃) | NH |
| Ia1.703 | CH₃ | CH₂CH₃ | CH₂CH(CH₃)-(2,4-Cl₂—C₆H₃) | NH |
| Ia1.704 | CH₃ | (CH₂)₂CH₃ | CH₂CH(CH₃)-(2,4-Cl₂—C₆H₃) | NH |
| Ia1.705 | CH₃ | (CH₂)₃CH₃ | CH₂CH(CH₃)-(2,4-Cl₂—C₆H₃) | NH |
| Ia1.706 | CH₃ | H | CH(CH₃)CH₂-(2,4-Cl₂—C₆H₃) | NH |
| Ia1.707 | CH₃ | CH₃ | CH(CH₃)CH₂-(2,4-Cl₂—C₆H₃) | NH |
| Ia1.708 | CH₃ | CH₂CH₃ | CH(CH₃)CH₂-(2,4-Cl₂—C₆H₃) | NH |
| Ia1.709 | CH₃ | (CH₂)₂CH₃ | CH(CH₃)CH₂-(2,4-Cl₂—C₆H₃) | NH |
| Ia1.710 | CH₃ | (CH₂)₃CH₃ | CH(CH₃)CH₂-(2,4-Cl₂—C₆H₃) | NH |
| Ia1.711 | CH₃ | H | CH(CH₃)CH(CH₃)-(2,4-Cl₂—C₆H₃) | NH |
| Ia1.712 | CH₃ | CH₃ | CH(CH₃)CH(CH₃)-(2,4-Cl₂—C₆H₃) | NH |
| Ia1.713 | CH₃ | CH₂CH₃ | CH(CH₃)CH(CH₃)-(2,4-Cl₂—C₆H₃) | NH |
| Ia1.714 | CH₃ | (CH₂)₂CH₃ | CH(CH₃)CH(CH₃)-(2,4-Cl₂—C₆H₃) | NH |
| Ia1.715 | CH₃ | (CH₂)₃CH₃ | CH(CH₃)CH(CH₃)-(2,4-Cl₂—C₆H₃) | NH |
| Ia1.716 | CH₃ | H | (CH₂)₂—O—C₆H₅ | NH |
| Ia1.717 | CH₃ | CH₃ | (CH₂)₂—O—C₆H₅ | NH |
| Ia1.718 | CH₃ | CH₂CH₃ | (CH₂)₂—O—C₆H₅ | NH |
| Ia1.719 | CH₃ | (CH₂)₂CH₃ | (CH₂)₂—O—C₆H₅ | NH |
| Ia1.720 | CH₃ | (CH₂)₃CH₃ | (CH₂)₂—O—C₆H₅ | NH |
| Ia1.721 | CH₃ | H | CH₂CH(CH₃)—O—C₆H₅ | NH |
| Ia1.722 | CH₃ | CH₃ | CH₂CH(CH₃)—O—C₆H₅ | NH |
| Ia1.723 | CH₃ | CH₂CH₃ | CH₂CH(CH₃)—O—C₆H₅ | NH |
| Ia1.724 | CH₃ | (CH₂)₂CH₃ | CH₂CH(CH₃)—O—C₆H₅ | NH |
| Ia1.725 | CH₃ | (CH₂)₃CH₃ | CH₂CH(CH₃)—O—C₆H₅ | NH |
| Ia1.726 | CH₃ | H | CH(CH₃)CH₂—O—C₆H₅ | NH |
| Ia1.727 | CH₃ | CH₃ | CH(CH₃)CH₂—O—C₆H₅ | NH |
| Ia1.728 | CH₃ | CH₂CH₃ | CH(CH₃)CH₂—O—C₆H₅ | NH |
| Ia1.729 | CH₃ | (CH₂)₂CH₃ | CH(CH₃)CH₂—O—C₆H₅ | NH |
| Ia1.730 | CH₃ | (CH₂)₃CH₃ | CH(CH₃)CH₂—O—C₆H₅ | NH |
| Ia1.731 | CH₃ | H | CH(CH₃)CH(CH₃)—O—C₆H₅ | NH |
| Ia1.732 | CH₃ | CH₃ | CH(CH₃)CH(CH₃)—O—C₆H₅ | NH |
| Ia1.733 | CH₃ | CH₂CH₃ | CH(CH₃)CH(CH₃)—O—C₆H₅ | NH |
| Ia1.734 | CH₃ | (CH₂)₂CH₃ | CH(CH₃)CH(CH₃)—O—C₆H₅ | NH |
| Ia1.735 | CH₃ | (CH₂)₃CH₃ | CH(CH₃)CH(CH₃)—O—C₆H₅ | NH |
| Ia1.736 | CH₃ | H | (CH₂)₂—O-(4-Cl—C₆H₄) | NH |
| Ia1.737 | CH₃ | CH₃ | (CH₂)₂—O-(4-Cl—C₆H₄) | NH |
| Ia1.738 | CH₃ | CH₂CH₃ | (CH₂)₂—O-(4-Cl—C₆H₄) | NH |
| Ia1.739 | CH₃ | (CH₂)₂CH₃ | (CH₂)₂—O-(4-Cl—C₆H₄) | NH |
| Ia1.740 | CH₃ | (CH₂)₃CH₃ | (CH₂)₂—O-(4-Cl—C₆H₄) | NH |
| Ia1.741 | CH₃ | H | CH₂CH(CH₃)—O-(4-Cl—C₆H₄) | NH |

TABLE 1-continued

| No. | R² | R³ | R⁴ | Z |
|---|---|---|---|---|
| Ia1.742 | CH₃ | CH₃ | CH₂CH(CH₃)—O-(4-Cl—C₆H₄) | NH |
| Ia1.743 | CH₃ | CH₂CH₃ | CH₂CH(CH₃)—O-(4-Cl—C₆H₄) | NH |
| Ia1.744 | CH₃ | (CH₂)₂CH₃ | CH₂CH(CH₃)—O-(4-Cl—C₆H₄) | NH |
| Ia1.745 | CH₃ | (CH₂)₃CH₃ | CH₂CH(CH₃)—O-(4-Cl—C₆H₄) | NH |
| Ia1.746 | CH₃ | H | CH(CH₃)CH₂—O-(4-Cl—C₆H₄) | NH |
| Ia1.747 | CH₃ | CH₃ | CH(CH₃)CH₂—O-(4-Cl—C₆H₄) | NH |
| Ia1.748 | CH₃ | CH₂CH₃ | CH(CH₃)CH₂—O-(4-Cl—C₆H₄) | NH |
| Ia1.749 | CH₃ | (CH₂)₂CH₃ | CH(CH₃)CH₂—O-(4-Cl—C₆H₄) | NH |
| Ia1.750 | CH₃ | (CH₂)₃CH₃ | CH(CH₃)CH₂—O-(4-Cl—C₆H₄) | NH |
| Ia1.751 | CH₃ | H | CH(CH₃)CH(CH₃)—O-(4-Cl—C₆H₄) | NH |
| Ia1.752 | CH₃ | CH₃ | CH(CH₃)CH(CH₃)—O-(4-Cl—C₆H₄) | NH |
| Ia1.753 | CH₃ | CH₂CH₃ | CH(CH₃)CH(CH₃)—O-(4-Cl—C₆H₄) | NH |
| Ia1.754 | CH₃ | (CH₂)₂CH₃ | CH(CH₃)CH(CH₃)—O-(4-Cl—C₆H₄) | NH |
| Ia1.755 | CH₃ | (CH₂)₃CH₃ | CH(CH₃)CH(CH₃)—O-(4-Cl—C₆H₄) | NH |
| Ia1.756 | CH₃ | H | (CH₂)₂—O-(2,4-Cl₂—C₆H₃) | NH |
| Ia1.757 | CH₃ | CH₃ | (CH₂)₂—O-(2,4-Cl₂—C₆H₃) | NH |
| Ia1.758 | CH₃ | CH₂CH₃ | (CH₂)₂—O-(2,4-Cl₂—C₆H₃) | NH |
| Ia1.759 | CH₃ | (CH₂)₂CH₃ | (CH₂)₂—O-(2,4-Cl₂—C₆H₃) | NH |
| Ia1.760 | CH₃ | (CH₂)₃CH₃ | (CH₂)₂—O-(2,4-Cl₂—C₆H₃) | NH |
| Ia1.761 | CH₃ | H | CH₂CH(CH₃)—O-(2,4-Cl₂—C₆H₃) | NH |
| Ia1.762 | CH₃ | CH₃ | CH₂CH(CH₃)—O-(2,4-Cl₂—C₆H₃) | NH |
| Ia1.763 | CH₃ | CH₂CH₃ | CH₂CH(CH₃)—O-(2,4-Cl₂—C₆H₃) | NH |
| Ia1.764 | CH₃ | (CH₂)₂CH₃ | CH₂CH(CH₃)—O-(2,4-Cl₂—C₆H₃) | NH |
| Ia1.765 | CH₃ | (CH₂)₃CH₃ | CH₂CH(CH₃)—O-(2,4-Cl₂—C₆H₃) | NH |
| Ia1.766 | CH₃ | H | CH(CH₃)CH₂—O-(2,4-Cl₂—C₆H₃) | NH |
| Ia1.767 | CH₃ | CH₃ | CH(CH₃)CH₂—O-(2,4-Cl₂—C₆H₃) | NH |
| Ia1.768 | CH₃ | CH₂CH₃ | CH(CH₃)CH₂—O-(2,4-Cl₂—C₆H₃) | NH |
| Ia1.769 | CH₃ | (CH₂)₂CH₃ | CH(CH₃)CH₂—O-(2,4-Cl₂—C₆H₃) | NH |
| Ia1.770 | CH₃ | (CH₂)₃CH₃ | CH(CH₃)CH₂—O-(2,4-Cl₂—C₆H₃) | NH |
| Ia1.771 | CH₃ | H | CH(CH₃)CH(CH₃)—O-(2,4-Cl₂—C₆H₃) | NH |
| Ia1.772 | CH₃ | CH₃ | CH(CH₃)CH(CH₃)—O-(2,4-Cl₂—C₆H₃) | NH |
| Ia1.773 | CH₃ | CH₂CH₃ | CH(CH₃)CH(CH₃)—O-(2,4-Cl₂—C₆H₃) | NH |
| Ia1.774 | CH₃ | (CH₂)₂CH₃ | CH(CH₃)CH(CH₃)—O-(2,4-Cl₂—C₆H₃) | NH |
| Ia1.775 | CH₃ | (CH₂)₃CH₃ | CH(CH₃)CH(CH₃)—O-(2,4-Cl₂—C₆H₃) | NH |
| Ia1.776 | CH₃ | H | CH₃ | NCH₃ |
| Ia1.777 | CH₃ | CH₃ | CH₃ | NCH₃ |
| Ia1.778 | CH₃ | CH₂CH₃ | CH₃ | NCH₃ |
| Ia1.779 | CH₃ | (CH₂)₂CH₃ | CH₃ | NCH₃ |
| Ia1.780 | CH₃ | (CH₂)₃CH₃ | CH₃ | NCH₃ |
| Ia1.781 | CH₃ | H | C₂H₅ | NCH₃ |
| Ia1.782 | CH₃ | CH₃ | C₂H₅ | NCH₃ |
| Ia1.783 | CH₃ | CH₂CH₃ | C₂H₅ | NCH₃ |
| Ia1.784 | CH₃ | (CH₂)₂CH₃ | C₂H₅ | NCH₃ |
| Ia1.785 | CH₃ | (CH₂)₃CH₃ | C₂H₅ | NCH₃ |
| Ia1.786 | CH₃ | H | (CH₂)₂CH₃ | NCH₃ |
| Ia1.787 | CH₃ | CH₃ | (CH₂)₂CH₃ | NCH₃ |
| Ia1.788 | CH₃ | CH₂CH₃ | (CH₂)₂CH₃ | NCH₃ |
| Ia1.789 | CH₃ | (CH₂)₂CH₃ | (CH₂)₂CH₃ | NCH₃ |
| Ia1.790 | CH₃ | (CH₂)₃CH₃ | (CH₂)₂CH₃ | NCH₃ |
| Ia1.791 | CH₃ | H | CH(CH₃)₂ | NCH₃ |
| Ia1.792 | CH₃ | CH₃ | CH(CH₃)₂ | NCH₃ |
| Ia1.793 | CH₃ | CH₂CH₃ | CH(CH₃)₂ | NCH₃ |
| Ia1.794 | CH₃ | (CH₂)₂CH₃ | CH(CH₃)₂ | NCH₃ |
| Ia1.795 | CH₃ | (CH₂)₃CH₃ | CH(CH₃)₂ | NCH₃ |
| Ia1.796 | CH₃ | H | (CH₂)₃CH₃ | NCH₃ |
| Ia1.797 | CH₃ | CH₃ | (CH₂)₃CH₃ | NCH₃ |
| Ia1.798 | CH₃ | CH₂CH₃ | (CH₂)₃CH₃ | NCH₃ |
| Ia1.799 | CH₃ | (CH₂)₂CH₃ | (CH₂)₃CH₃ | NCH₃ |
| Ia1.800 | CH₃ | (CH₂)₃CH₃ | (CH₂)₃CH₃ | NCH₃ |
| Ia1.801 | CH₃ | H | CH₂CH(CH₃)₂ | NCH₃ |
| Ia1.802 | CH₃ | CH₃ | CH₂CH(CH₃)₂ | NCH₃ |
| Ia1.803 | CH₃ | CH₂CH₃ | CH₂CH(CH₃)₂ | NCH₃ |
| Ia1.804 | CH₃ | (CH₂)₂CH₃ | CH₂CH(CH₃)₂ | NCH₃ |
| Ia1.805 | CH₃ | (CH₂)₃CH₃ | CH₂CH(CH₃)₂ | NCH₃ |
| Ia1.806 | CH₃ | H | CH(CH₃)CH₂CH₃ | NCH₃ |
| Ia1.807 | CH₃ | CH₃ | CH(CH₃)CH₂CH₃ | NCH₃ |
| Ia1.808 | CH₃ | CH₂CH₃ | CH(CH₃)CH₂CH₃ | NCH₃ |
| Ia1.809 | CH₃ | (CH₂)₂CH₃ | CH(CH₃)CH₂CH₃ | NCH₃ |
| Ia1.810 | CH₃ | (CH₂)₃CH₃ | CH(CH₃)CH₂CH₃ | NCH₃ |
| Ia1.811 | CH₃ | H | (CH₂)₂—C₆H₅ | NCH₃ |
| Ia1.812 | CH₃ | CH₃ | (CH₂)₂—C₆H₅ | NCH₃ |
| Ia1.813 | CH₃ | CH₂CH₃ | (CH₂)₂—C₆H₅ | NCH₃ |
| Ia1.814 | CH₃ | (CH₂)₂CH₃ | (CH₂)₂—C₆H₅ | NCH₃ |
| Ia1.815 | CH₃ | (CH₂)₃CH₃ | (CH₂)₂—C₆H₅ | NCH₃ |
| Ia1.816 | CH₃ | H | CH₂CH(CH₃)—C₆H₅ | NCH₃ |
| Ia1.817 | CH₃ | CH₃ | CH₂CH(CH₃)—C₆H₅ | NCH₃ |
| Ia1.818 | CH₃ | CH₂CH₃ | CH₂CH(CH₃)—C₆H₅ | NCH₃ |

TABLE 1-continued

| No. | R² | R³ | R⁴ | Z |
|---|---|---|---|---|
| Ia1.819 | CH₃ | (CH₂)₂CH₃ | CH₂CH(CH₃)—C₆H₅ | NCH₃ |
| Ia1.820 | CH₃ | (CH₂)₃CH₃ | CH₂CH(CH₃)—C₆H₅ | NCH₃ |
| Ia1.821 | CH₃ | H | CH(CH₃)CH₂—C₆H₅ | NCH₃ |
| Ia1.822 | CH₃ | CH₃ | CH(CH₃)CH₂—C₆H₅ | NCH₃ |
| Ia1.823 | CH₃ | CH₂CH₃ | CH(CH₃)CH₂—C₆H₅ | NCH₃ |
| Ia1.824 | CH₃ | (CH₂)₂CH₃ | CH(CH₃)CH₂—C₆H₅ | NCH₃ |
| Ia1.825 | CH₃ | (CH₂)₃CH₃ | CH(CH₃)CH₂—C₆H₅ | NCH₃ |
| Ia1.826 | CH₃ | H | CH(CH₃)CH(CH₃)—C₆H₅ | NCH₃ |
| Ia1.827 | CH₃ | CH₃ | CH(CH₃)CH(CH₃)—C₆H₅ | NCH₃ |
| Ia1.828 | CH₃ | CH₂CH₃ | CH(CH₃)CH(CH₃)—C₆H₅ | NCH₃ |
| Ia1.829 | CH₃ | (CH₂)₂CH₃ | CH(CH₃)CH(CH₃)—C₆H₅ | NCH₃ |
| Ia1.830 | CH₃ | (CH₂)₃CH₃ | CH(CH₃)CH(CH₃)—C₆H₅ | NCH₃ |
| Ia1.831 | CH₃ | H | (CH₂)₂-(4-Cl—C₆H₄) | NCH₃ |
| Ia1.832 | CH₃ | CH₃ | (CH₂)₂-(4-Cl—C₆H₄) | NCH₃ |
| Ia1.833 | CH₃ | CH₂CH₃ | (CH₂)₂-(4-Cl—C₆H₄) | NCH₃ |
| Ia1.834 | CH₃ | (CH₂)₂CH₃ | (CH₂)₂-(4-Cl—C₆H₄) | NCH₃ |
| Ia1.835 | CH₃ | (CH₂)₃CH₃ | (CH₂)₂-(4-Cl—C₆H₄) | NCH₃ |
| Ia1.836 | CH₃ | H | CH₂CH(CH₃)-(4-Cl—C₆H₄) | NCH₃ |
| Ia1.837 | CH₃ | CH₃ | CH₂CH(CH₃)-(4-Cl—C₆H₄) | NCH₃ |
| Ia1.838 | CH₃ | CH₂CH₃ | CH₂CH(CH₃)-(4-Cl—C₆H₄) | NCH₃ |
| Ia1.839 | CH₃ | (CH₂)₂CH₃ | CH₂CH(CH₃)-(4-Cl—C₆H₄) | NCH₃ |
| Ia1.840 | CH₃ | (CH₂)₃CH₃ | CH₂CH(CH₃)-(4-Cl—C₆H₄) | NCH₃ |
| Ia1.841 | CH₃ | H | CH(CH₃)CH₂-(4-Cl—C₆H₄) | NCH₃ |
| Ia1.842 | CH₃ | CH₃ | CH(CH₃)CH₂-(4-Cl—C₆H₄) | NCH₃ |
| Ia1.843 | CH₃ | CH₂CH₃ | CH(CH₃)CH₂-(4-Cl—C₆H₄) | NCH₃ |
| Ia1.844 | CH₃ | (CH₂)₂CH₃ | CH(CH₃)CH₂-(4-Cl—C₆H₄) | NCH₃ |
| Ia1.845 | CH₃ | (CH₂)₃CH₃ | CH(CH₃)CH₂-(4-Cl—C₆H₄) | NCH₃ |
| Ia1.846 | CH₃ | H | CH(CH₃)CH(CH₃)-(4-Cl—C₆H₄) | NCH₃ |
| Ia1.847 | CH₃ | CH₃ | CH(CH₃)CH(CH₃)-(4-Cl—C₆H₄) | NCH₃ |
| Ia1.848 | CH₃ | CH₂CH₃ | CH(CH₃)CH(CH₃)-(4-Cl—C₆H₄) | NCH₃ |
| Ia1.849 | CH₃ | (CH₂)₂CH₃ | CH(CH₃)CH(CH₃)-(4-Cl—C₆H₄) | NCH₃ |
| Ia1.850 | CH₃ | (CH₂)₃CH₃ | CH(CH₃)CH(CH₃)-(4-Cl—C₆H₄) | NCH₃ |
| Ia1.851 | CH₃ | H | (CH₂)₂-(2,4-Cl₂—C₆H₃) | NCH₃ |
| Ia1.852 | CH₃ | CH₃ | (CH₂)₂-(2,4-Cl₂—C₆H₃) | NCH₃ |
| Ia1.853 | CH₃ | CH₂CH₃ | (CH₂)₂-(2,4-Cl₂—C₆H₃) | NCH₃ |
| Ia1.854 | CH₃ | (CH₂)₂CH₃ | (CH₂)₂-(2,4-Cl₂—C₆H₃) | NCH₃ |
| Ia1.855 | CH₃ | (CH₂)₃CH₃ | (CH₂)₂-(2,4-Cl₂—C₆H₃) | NCH₃ |
| Ia1.856 | CH₃ | H | CH₂CH(CH₃)-(2,4-Cl₂—C₆H₃) | NCH₃ |
| Ia1.857 | CH₃ | CH₃ | CH₂CH(CH₃)-(2,4-Cl₂—C₆H₃) | NCH₃ |
| Ia1.858 | CH₃ | CH₂CH₃ | CH₂CH(CH₃)-(2,4-Cl₂—C₆H₃) | NCH₃ |
| Ia1.859 | CH₃ | (CH₂)₂CH₃ | CH₂CH(CH₃)-(2,4-Cl₂—C₆H₃) | NCH₃ |
| Ia1.860 | CH₃ | (CH₂)₃CH₃ | CH₂CH(CH₃)-(2,4-Cl₂—C₆H₃) | NCH₃ |
| Ia1.861 | CH₃ | H | CH(CH₃)CH₂-(2,4-Cl₂—C₆H₃) | NCH₃ |
| Ia1.862 | CH₃ | CH₃ | CH(CH₃)CH₂-(2,4-Cl₂—C₆H₃) | NCH₃ |
| Ia1.863 | CH₃ | CH₂CH₃ | CH(CH₃)CH₂-(2,4-Cl₂—C₆H₃) | NCH₃ |
| Ia1.864 | CH₃ | (CH₂)₂CH₃ | CH(CH₃)CH₂-(2,4-Cl₂—C₆H₃) | NCH₃ |
| Ia1.865 | CH₃ | (CH₂)₃CH₃ | CH(CH₃)CH₂-(2,4-Cl₂—C₆H₃) | NCH₃ |
| Ia1.866 | CH₃ | H | CH(CH₃)CH(CH₃)-(2,4-Cl₂—C₆H₃) | NCH₃ |
| Ia1.867 | CH₃ | CH₃ | CH(CH₃)CH(CH₃)-(2,4-Cl₂—C₆H₃) | NCH₃ |
| Ia1.868 | CH₃ | CH₂CH₃ | CH(CH₃)CH(CH₃)-(2,4-Cl₂—C₆H₃) | NCH₃ |
| Ia1.869 | CH₃ | (CH₂)₂CH₃ | CH(CH₃)CH(CH₃)-(2,4-Cl₂—C₆H₃) | NCH₃ |
| Ia1.870 | CH₃ | (CH₂)₃CH₃ | CH(CH₃)CH(CH₃)-(2,4-Cl₂—C₆H₃) | NCH₃ |
| Ia1.871 | CH₃ | H | (CH₂)₂—O—C₆H₅ | NCH₃ |
| Ia1.872 | CH₃ | CH₃ | (CH₂)₂—O—C₆H₅ | NCH₃ |
| Ia1.873 | CH₃ | CH₂CH₃ | (CH₂)₂—O—C₆H₅ | NCH₃ |
| Ia1.874 | CH₃ | (CH₂)₂CH₃ | (CH₂)₂—O—C₆H₅ | NCH₃ |
| Ia1.875 | CH₃ | (CH₂)₃CH₃ | (CH₂)₂—O—C₆H₅ | NCH₃ |
| Ia1.876 | CH₃ | H | CH₂CH(CH₃)—O—C₆H₅ | NCH₃ |
| Ia1.877 | CH₃ | CH₃ | CH₂CH(CH₃)—O—C₆H₅ | NCH₃ |
| Ia1.878 | CH₃ | CH₂CH₃ | CH₂CH(CH₃)—O—C₆H₅ | NCH₃ |
| Ia1.879 | CH₃ | (CH₂)₂CH₃ | CH₂CH(CH₃)—O—C₆H₅ | NCH₃ |
| Ia1.880 | CH₃ | (CH₂)₃CH₃ | CH₂CH(CH₃)—O—C₆H₅ | NCH₃ |
| Ia1.881 | CH₃ | H | CH(CH₃)CH₂—O—C₆H₅ | NCH₃ |
| Ia1.882 | CH₃ | CH₃ | CH(CH₃)CH₂—O—C₆H₅ | NCH₃ |
| Ia1.883 | CH₃ | CH₂CH₃ | CH(CH₃)CH₂—O—C₆H₅ | NCH₃ |
| Ia1.884 | CH₃ | (CH₂)₂CH₃ | CH(CH₃)CH₂—O—C₆H₅ | NCH₃ |
| Ia1.885 | CH₃ | (CH₂)₃CH₃ | CH(CH₃)CH₂—O—C₆H₅ | NCH₃ |
| Ia1.886 | CH₃ | H | CH(CH₃)CH(CH₃)—O—C₆H₅ | NCH₃ |
| Ia1.887 | CH₃ | CH₃ | CH(CH₃)CH(CH₃)—O—C₆H₅ | NCH₃ |
| Ia1.888 | CH₃ | CH₂CH₃ | CH(CH₃)CH(CH₃)—O—C₆H₅ | NCH₃ |
| Ia1.889 | CH₃ | (CH₂)₂CH₃ | CH(CH₃)CH(CH₃)—O—C₆H₅ | NCH₃ |
| Ia1.890 | CH₃ | (CH₂)₃CH₃ | CH(CH₃)CH(CH₃)—O—C₆H₅ | NCH₃ |
| Ia1.891 | CH₃ | H | (CH₂)₂—O-(4-Cl—C₆H₄) | NCH₃ |
| Ia1.892 | CH₃ | CH₃ | (CH₂)₂—O-(4-Cl—C₆H₄) | NCH₃ |
| Ia1.893 | CH₃ | CH₂CH₃ | (CH₂)₂—O-(4-Cl—C₆H₄) | NCH₃ |
| Ia1.894 | CH₃ | (CH₂)₂CH₃ | (CH₂)₂—O-(4-Cl—C₆H₄) | NCH₃ |
| Ia1.895 | CH₃ | (CH₂)₃CH₃ | (CH₂)₂—O-(4-Cl—C₆H₄) | NCH₃ |

TABLE 1-continued

| No. | R² | R³ | R⁴ | Z |
|---|---|---|---|---|
| Ia1.896 | CH₃ | H | CH₂CH(CH₃)—O-(4-Cl—C₆H₄) | NCH₃ |
| Ia1.897 | CH₃ | CH₃ | CH₂CH(CH₃)—O-(4-Cl—C₆H₄) | NCH₃ |
| Ia1.898 | CH₃ | CH₂CH₃ | CH₂CH(CH₃)—O-(4-Cl—C₆H₄) | NCH₃ |
| Ia1.899 | CH₃ | (CH₂)₂CH₃ | CH₂CH(CH₃)—O-(4-Cl—C₆H₄) | NCH₃ |
| Ia1.900 | CH₃ | (CH₂)₃CH₃ | CH₂CH(CH₃)—O-(4-Cl—C₆H₄) | NCH₃ |
| Ia1.901 | CH₃ | H | CH(CH₃)CH₂—O-(4-Cl—C₆H₄) | NCH₃ |
| Ia1.902 | CH₃ | CH₃ | CH(CH₃)CH₂—O-(4-Cl—C₆H₄) | NCH₃ |
| Ia1.903 | CH₃ | CH₂CH₃ | CH(CH₃)CH₂—O-(4-Cl—C₆H₄) | NCH₃ |
| Ia1.904 | CH₃ | (CH₂)₂CH₃ | CH(CH₃)CH₂—O-(4-Cl—C₆H₄) | NCH₃ |
| Ia1.905 | CH₃ | (CH₂)₃CH₃ | CH(CH₃)CH₂—O-(4-Cl—C₆H₄) | NCH₃ |
| Ia1.906 | CH₃ | H | CH(CH₃)CH(CH₃)—O-(4-Cl—C₆H₄) | NCH₃ |
| Ia1.907 | CH₃ | CH₃ | CH(CH₃)CH(CH₃)—O-(4-Cl—C₆H₄) | NCH₃ |
| Ia1.908 | CH₃ | CH₂CH₃ | CH(CH₃)CH(CH₃)—O-(4-Cl—C₆H₄) | NCH₃ |
| Ia1.909 | CH₃ | (CH₂)₂CH₃ | CH(CH₃)CH(CH₃)—O-(4-Cl—C₆H₄) | NCH₃ |
| Ia1.910 | CH₃ | (CH₂)₃CH₃ | CH(CH₃)CH(CH₃)—O-(4-Cl—C₆H₄) | NCH₃ |
| Ia1.911 | CH₃ | H | (CH₂)₂—O-(2,4-Cl₂—C₆H₃) | NCH₃ |
| Ia1.912 | CH₃ | CH₃ | (CH₂)₂—O-(2,4-Cl₂—C₆H₃) | NCH₃ |
| Ia1.913 | CH₃ | CH₂CH₃ | (CH₂)₂—O-(2,4-Cl₂—C₆H₃) | NCH₃ |
| Ia1.914 | CH₃ | (CH₂)₂CH₃ | (CH₂)₂—O-(2,4-Cl₂—C₆H₃) | NCH₃ |
| Ia1.915 | CH₃ | (CH₂)₃CH₃ | (CH₂)₂—O-(2,4-Cl₂—C₆H₃) | NCH₃ |
| Ia1.916 | CH₃ | H | CH₂CH(CH₃)—O-(2,4-Cl₂—C₆H₃) | NCH₃ |
| Ia1.917 | CH₃ | CH₃ | CH₂CH(CH₃)—O-(2,4-Cl₂—C₆H₃) | NCH₃ |
| Ia1.918 | CH₃ | CH₂CH₃ | CH₂CH(CH₃)—O-(2,4-Cl₂—C₆H₃) | NCH₃ |
| Ia1.919 | CH₃ | (CH₂)₂CH₃ | CH₂CH(CH₃)—O-(2,4-Cl₂—C₆H₃) | NCH₃ |
| Ia1.920 | CH₃ | (CH₂)₃CH₃ | CH₂CH(CH₃)—O-(2,4-Cl₂—C₆H₃) | NCH₃ |
| Ia1.921 | CH₃ | H | CH(CH₃)CH₂—O-(2,4-Cl₂—C₆H₃) | NCH₃ |
| Ia1.922 | CH₃ | CH₃ | CH(CH₃)CH₂—O-(2,4-Cl₂—C₆H₃) | NCH₃ |
| Ia1.923 | CH₃ | CH₂CH₃ | CH(CH₃)CH₂—O-(2,4-Cl₂—C₆H₃) | NCH₃ |
| Ia1.924 | CH₃ | (CH₂)₂CH₃ | CH(CH₃)CH₂—O-(2,4-Cl₂—C₆H₃) | NCH₃ |
| Ia1.925 | CH₃ | (CH₂)₃CH₃ | CH(CH₃)CH₂—O-(2,4-Cl₂—C₆H₃) | NCH₃ |
| Ia1.926 | CH₃ | H | CH(CH₃)CH(CH₃)—O-(2,4-Cl₂—C₆H₃) | NCH₃ |
| Ia1.927 | CH₃ | CH₃ | CH(CH₃)CH(CH₃)—O-(2,4-Cl₂—C₆H₃) | NCH₃ |
| Ia1.928 | CH₃ | CH₂CH₃ | CH(CH₃)CH(CH₃)—O-(2,4-Cl₂—C₆H₃) | NCH₃ |
| Ia1.929 | CH₃ | (CH₂)₂CH₃ | CH(CH₃)CH(CH₃)—O-(2,4-Cl₂—C₆H₃) | NCH₃ |
| Ia1.930 | CH₃ | (CH₂)₃CH₃ | CH(CH₃)CH(CH₃)—O-(2,4-Cl₂—C₆H₃) | NCH₃ |
| Ia1.931 | OCH₃ | H | CH₃ | O |
| Ia1.932 | OCH₃ | CH₃ | CH₃ | O |
| Ia1.933 | OCH₃ | CH₂CH₃ | CH₃ | O |
| Ia1.934 | OCH₃ | (CH₂)₂CH₃ | CH₃ | O |
| Ia1.935 | OCH₃ | (CH₂)₃CH₃ | CH₃ | O |
| Ia1.936 | OCH₃ | H | C₂H₅ | O |
| Ia1.937 | OCH₃ | CH₃ | C₂H₅ | O |
| Ia1.938 | OCH₃ | CH₂CH₃ | C₂H₅ | O |
| Ia1.939 | OCH₃ | (CH₂)₂CH₃ | C₂H₅ | O |
| Ia1.940 | OCH₃ | (CH₂)₃CH₃ | C₂H₅ | O |
| Ia1.941 | OCH₃ | H | (CH₂)₂CH₃ | O |
| Ia1.942 | OCH₃ | CH₃ | (CH₂)₂CH₃ | O |
| Ia1.943 | OCH₃ | CH₂CH₃ | (CH₂)₂CH₃ | O |
| Ia1.944 | OCH₃ | (CH₂)₂CH₃ | (CH₂)₂CH₃ | O |
| Ia1.945 | OCH₃ | (CH₂)₃CH₃ | (CH₂)₂CH₃ | O |
| Ia1.946 | OCH₃ | H | CH(CH₃)₂ | O |
| Ia1.947 | OCH₃ | CH₃ | CH(CH₃)₂ | O |
| Ia1.948 | OCH₃ | CH₂CH₃ | CH(CH₃)₂ | O |
| Ia1.949 | OCH₃ | (CH₂)₂CH₃ | CH(CH₃)₂ | O |
| Ia1.950 | OCH₃ | (CH₂)₃CH₃ | CH(CH₃)₂ | O |
| Ia1.951 | OCH₃ | H | (CH₂)₃CH₃ | O |
| Ia1.952 | OCH₃ | CH₃ | (CH₂)₃CH₃ | O |
| Ia1.953 | OCH₃ | CH₂CH₃ | (CH₂)₃CH₃ | O |
| Ia1.954 | OCH₃ | (CH₂)₂CH₃ | (CH₂)₃CH₃ | O |
| Ia1.955 | OCH₃ | (CH₂)₃CH₃ | (CH₂)₃CH₃ | O |
| Ia1.956 | OCH₃ | H | CH₂CH(CH₃)₂ | O |
| Ia1.957 | OCH₃ | CH₃ | CH₂CH(CH₃)₂ | O |
| Ia1.958 | OCH₃ | CH₂CH₃ | CH₂CH(CH₃)₂ | O |
| Ia1.959 | OCH₃ | (CH₂)₂CH₃ | CH₂CH(CH₃)₂ | O |
| Ia1.960 | OCH₃ | (CH₂)₃CH₃ | CH₂CH(CH₃)₂ | O |
| Ia1.961 | OCH₃ | H | CH(CH₃)CH₂CH₃ | O |
| Ia1.962 | OCH₃ | CH₃ | CH(CH₃)CH₂CH₃ | O |
| Ia1.963 | OCH₃ | CH₂CH₃ | CH(CH₃)CH₂CH₃ | O |
| Ia1.964 | OCH₃ | (CH₂)₂CH₃ | CH(CH₃)CH₂CH₃ | O |
| Ia1.965 | OCH₃ | (CH₂)₃CH₃ | CH(CH₃)CH₂CH₃ | O |
| Ia1.966 | OCH₃ | H | (CH₂)₂—C₆H₅ | O |
| Ia1.967 | OCH₃ | CH₃ | (CH₂)₂—C₆H₅ | O |
| Ia1.968 | OCH₃ | CH₂CH₃ | (CH₂)₂—C₆H₅ | O |
| Ia1.969 | OCH₃ | (CH₂)₂CH₃ | (CH₂)₂—C₆H₅ | O |
| Ia1.970 | OCH₃ | (CH₂)₃CH₃ | (CH₂)₂—C₆H₅ | O |
| Ia1.971 | OCH₃ | H | CH₂CH(CH₃)—C₆H₅ | O |
| Ia1.972 | OCH₃ | CH₃ | CH₂CH(CH₃)—C₆H₅ | O |

TABLE 1-continued

| No. | R² | R³ | R⁴ | Z |
|---|---|---|---|---|
| Ia1.973 | OCH₃ | CH₂CH₃ | CH₂CH(CH₃)—C₆H₅ | O |
| Ia1.974 | OCH₃ | (CH₂)₂CH₃ | CH₂CH(CH₃)—C₆H₅ | O |
| Ia1.975 | OCH₃ | (CH₂)₃CH₃ | CH₂CH(CH₃)—C₆H₅ | O |
| Ia1.976 | OCH₃ | H | CH(CH₃)CH₂—C₆H₅ | O |
| Ia1.977 | OCH₃ | CH₃ | CH(CH₃)CH₂—C₆H₅ | O |
| Ia1.978 | OCH₃ | CH₂CH₃ | CH(CH₃)CH₂—C₆H₅ | O |
| Ia1.979 | OCH₃ | (CH₂)₂CH₃ | CH(CH₃)CH₂—C₆H₅ | O |
| Ia1.980 | OCH₃ | (CH₂)₃CH₃ | CH(CH₃)CH₂—C₆H₅ | O |
| Ia1.981 | OCH₃ | H | CH(CH₃)CH(CH₃)—C₆H₅ | O |
| Ia1.982 | OCH₃ | CH₃ | CH(CH₃)CH(CH₃)—C₆H₅ | O |
| Ia1.983 | OCH₃ | CH₂CH₃ | CH(CH₃)CH(CH₃)—C₆H₅ | O |
| Ia1.984 | OCH₃ | (CH₂)₂CH₃ | CH(CH₃)CH(CH₃)—C₆H₅ | O |
| Ia1.985 | OCH₃ | (CH₂)₃CH₃ | CH(CH₃)CH(CH₃)—C₆H₅ | O |
| Ia1.986 | OCH₃ | H | (CH₂)₂-(4-Cl—C₆H₄) | O |
| Ia1.987 | OCH₃ | CH₃ | (CH₂)₂-(4-Cl—C₆H₄) | O |
| Ia1.988 | OCH₃ | CH₂CH₃ | (CH₂)₂-(4-Cl—C₆H₄) | O |
| Ia1.989 | OCH₃ | (CH₂)₂CH₃ | (CH₂)₂-(4-Cl—C₆H₄) | O |
| Ia1.990 | OCH₃ | (CH₂)₃CH₃ | (CH₂)₂-(4-Cl—C₆H₄) | O |
| Ia1.991 | OCH₃ | H | CH₂CH(CH₃)-(4-Cl—C₆H₄) | O |
| Ia1.992 | OCH₃ | CH₃ | CH₂CH(CH₃)-(4-Cl—C₆H₄) | O |
| Ia1.993 | OCH₃ | CH₂CH₃ | CH₂CH(CH₃)-(4-Cl—C₆H₄) | O |
| Ia1.994 | OCH₃ | (CH₂)₂CH₃ | CH₂CH(CH₃)-(4-Cl—C₆H₄) | O |
| Ia1.995 | OCH₃ | (CH₂)₃CH₃ | CH₂CH(CH₃)-(4-Cl—C₆H₄) | O |
| Ia1.996 | OCH₃ | H | CH(CH₃)CH₂-(4-Cl—C₆H₄) | O |
| Ia1.997 | OCH₃ | CH₃ | CH(CH₃)CH₂-(4-Cl—C₆H₄) | O |
| Ia1.998 | OCH₃ | CH₂CH₃ | CH(CH₃)CH₂-(4-Cl—C₆H₄) | O |
| Ia1.999 | OCH₃ | (CH₂)₂CH₃ | CH(CH₃)CH₂-(4-Cl—C₆H₄) | O |
| Ia1.1000 | OCH₃ | (CH₂)₃CH₃ | CH(CH₃)CH₂-(4-Cl—C₆H₄) | O |
| Ia1.1001 | OCH₃ | H | CH(CH₃)CH(CH₃)-(4-Cl—C₆H₄) | O |
| Ia1.1002 | OCH₃ | CH₃ | CH(CH₃)CH(CH₃)-(4-Cl—C₆H₄) | O |
| Ia1.1003 | OCH₃ | CH₂CH₃ | CH(CH₃)CH(CH₃)-(4-Cl—C₆H₄) | O |
| Ia1.1004 | OCH₃ | (CH₂)₂CH₃ | CH(CH₃)CH(CH₃)-(4-Cl—C₆H₄) | O |
| Ia1.1005 | OCH₃ | (CH₂)₃CH₃ | CH(CH₃)CH(CH₃)-(4-Cl—C₆H₄) | O |
| Ia1.1006 | OCH₃ | H | (CH₂)₂-(2,4-Cl₂—C₆H₃) | O |
| Ia1.1007 | OCH₃ | CH₃ | (CH₂)₂-(2,4-Cl₂—C₆H₃) | O |
| Ia1.1008 | OCH₃ | CH₂CH₃ | (CH₂)₂-(2,4-Cl₂—C₆H₃) | O |
| Ia1.1009 | OCH₃ | (CH₂)₂CH₃ | (CH₂)₂-(2,4-Cl₂—C₆H₃) | O |
| Ia1.1010 | OCH₃ | (CH₂)₃CH₃ | (CH₂)₂-(2,4-Cl₂—C₆H₃) | O |
| Ia1.1011 | OCH₃ | H | CH₂CH(CH₃)-(2,4-Cl₂—C₆H₃) | O |
| Ia1.1012 | OCH₃ | CH₃ | CH₂CH(CH₃)-(2,4-Cl₂—C₆H₃) | O |
| Ia1.1013 | OCH₃ | CH₂CH₃ | CH₂CH(CH₃)-(2,4-Cl₂—C₆H₃) | O |
| Ia1.1014 | OCH₃ | (CH₂)₂CH₃ | CH₂CH(CH₃)-(2,4-Cl₂—C₆H₃) | O |
| Ia1.1015 | OCH₃ | (CH₂)₃CH₃ | CH₂CH(CH₃)-(2,4-Cl₂—C₆H₃) | O |
| Ia1.1016 | OCH₃ | H | CH(CH₃)CH₂-(2,4-Cl₂—C₆H₃) | O |
| Ia1.1017 | OCH₃ | CH₃ | CH(CH₃)CH₂-(2,4-Cl₂—C₆H₃) | O |
| Ia1.1018 | OCH₃ | CH₂CH₃ | CH(CH₃)CH₂-(2,4-Cl₂—C₆H₃) | O |
| Ia1.1019 | OCH₃ | (CH₂)₂CH₃ | CH(CH₃)CH₂-(2,4-Cl₂—C₆H₃) | O |
| Ia1.1020 | OCH₃ | (CH₂)₃CH₃ | CH(CH₃)CH₂-(2,4-Cl₂—C₆H₃) | O |
| Ia1.1021 | OCH₃ | H | CH(CH₃)CH(CH₃)-(2,4-Cl₂—C₆H₃) | O |
| Ia1.1022 | OCH₃ | CH₃ | CH(CH₃)CH(CH₃)-(2,4-Cl₂—C₆H₃) | O |
| Ia1.1023 | OCH₃ | CH₂CH₃ | CH(CH₃)CH(CH₃)-(2,4-Cl₂—C₆H₃) | O |
| Ia1.1024 | OCH₃ | (CH₂)₂CH₃ | CH(CH₃)CH(CH₃)-(2,4-Cl₂—C₆H₃) | O |
| Ia1.1025 | OCH₃ | (CH₂)₃CH₃ | CH(CH₃)CH(CH₃)-(2,4-Cl₂—C₆H₃) | O |
| Ia1.1026 | OCH₃ | H | (CH₂)₂—O—C₆H₅ | O |
| Ia1.1027 | OCH₃ | CH₃ | (CH₂)₂—O—C₆H₅ | O |
| Ia1.1028 | OCH₃ | CH₂CH₃ | (CH₂)₂—O—C₆H₅ | O |
| Ia1.1029 | OCH₃ | (CH₂)₂CH₃ | (CH₂)₂—O—C₆H₅ | O |
| Ia1.1030 | OCH₃ | (CH₂)₃CH₃ | (CH₂)₂—O—C₆H₅ | O |
| Ia1.1031 | OCH₃ | H | CH₂CH(CH₃)—O—C₆H₅ | O |
| Ia1.1032 | OCH₃ | CH₃ | CH₂CH(CH₃)—O—C₆H₅ | O |
| Ia1.1033 | OCH₃ | CH₂CH₃ | CH₂CH(CH₃)—O—C₆H₅ | O |
| Ia1.1034 | OCH₃ | (CH₂)₂CH₃ | CH₂CH(CH₃)—O—C₆H₅ | O |
| Ia1.1035 | OCH₃ | (CH₂)₃CH₃ | CH₂CH(CH₃)—O—C₆H₅ | O |
| Ia1.1036 | OCH₃ | H | CH(CH₃)CH₂—O—C₆H₅ | O |
| Ia1.1037 | OCH₃ | CH₃ | CH(CH₃)CH₂—O—C₆H₅ | O |
| Ia1.1038 | OCH₃ | CH₂CH₃ | CH(CH₃)CH₂—O—C₆H₅ | O |
| Ia1.1039 | OCH₃ | (CH₂)₂CH₃ | CH(CH₃)CH₂—O—C₆H₅ | O |
| Ia1.1040 | OCH₃ | (CH₂)₃CH₃ | CH(CH₃)CH₂—O—C₆H₅ | O |
| Ia1.1041 | OCH₃ | H | CH(CH₃)CH(CH₃)—O—C₆H₅ | O |
| Ia1.1042 | OCH₃ | CH₃ | CH(CH₃)CH(CH₃)—O—C₆H₅ | O |
| Ia1.1043 | OCH₃ | CH₂CH₃ | CH(CH₃)CH(CH₃)—O—C₆H₅ | O |
| Ia1.1044 | OCH₃ | (CH₂)₂CH₃ | CH(CH₃)CH(CH₃)—O—C₆H₅ | O |
| Ia1.1045 | OCH₃ | (CH₂)₃CH₃ | CH(CH₃)CH(CH₃)—O—C₆H₅ | O |
| Ia1.1046 | OCH₃ | H | (CH₂)₂—O-(4-Cl—C₆H₄) | O |
| Ia1.1047 | OCH₃ | CH₃ | (CH₂)₂—O-(4-Cl—C₆H₄) | O |
| Ia1.1048 | OCH₃ | CH₂CH₃ | (CH₂)₂—O-(4-Cl—C₆H₄) | O |
| Ia1.1049 | OCH₃ | (CH₂)₂CH₃ | (CH₂)₂—O-(4-Cl—C₆H₄) | O |

TABLE 1-continued

| No. | $R^2$ | $R^3$ | $R^4$ | Z |
|---|---|---|---|---|
| Ia1.1050 | OCH$_3$ | (CH$_2$)$_3$CH$_3$ | (CH$_2$)$_2$—O-(4-Cl—C$_6$H$_4$) | O |
| Ia1.1051 | OCH$_3$ | H | CH$_2$CH(CH$_3$)—O-(4-Cl—C$_6$H$_4$) | O |
| Ia1.1052 | OCH$_3$ | CH$_3$ | CH$_2$CH(CH$_3$)—O-(4-Cl—C$_6$H$_4$) | O |
| Ia1.1053 | OCH$_3$ | CH$_2$CH$_3$ | CH$_2$CH(CH$_3$)—O-(4-Cl—C$_6$H$_4$) | O |
| Ia1.1054 | OCH$_3$ | (CH$_2$)$_2$CH$_3$ | CH$_2$CH(CH$_3$)—O-(4-Cl—C$_6$H$_4$) | O |
| Ia1.1055 | OCH$_3$ | (CH$_2$)$_3$CH$_3$ | CH$_2$CH(CH$_3$)—O-(4-Cl—C$_6$H$_4$) | O |
| Ia1.1056 | OCH$_3$ | H | CH(CH$_3$)CH$_2$—O-(4-Cl—C$_6$H$_4$) | O |
| Ia1.1057 | OCH$_3$ | CH$_3$ | CH(CH$_3$)CH$_2$—O-(4-Cl—C$_6$H$_4$) | O |
| Ia1.1058 | OCH$_3$ | CH$_2$CH$_3$ | CH(CH$_3$)CH$_2$—O-(4-Cl—C$_6$H$_4$) | O |
| Ia1.1059 | OCH$_3$ | (CH$_2$)$_2$CH$_3$ | CH(CH$_3$)CH$_2$—O-(4-Cl—C$_6$H$_4$) | O |
| Ia1.1060 | OCH$_3$ | (CH$_2$)$_3$CH$_3$ | CH(CH$_3$)CH$_2$—O-(4-Cl—C$_6$H$_4$) | O |
| Ia1.1061 | OCH$_3$ | H | CH(CH$_3$)CH(CH$_3$)-O-(4-Cl—C$_6$H$_4$) | O |
| Ia1.1062 | OCH$_3$ | CH$_3$ | CH(CH$_3$)CH(CH$_3$)—O-(4-Cl—C$_6$H$_4$) | O |
| Ia1.1063 | OCH$_3$ | CH$_2$CH$_3$ | CH(CH$_3$)CH(CH$_3$)—O-(4-Cl—C$_6$H$_4$) | O |
| Ia1.1064 | OCH$_3$ | (CH$_2$)$_2$CH$_3$ | CH(CH$_3$)CH(CH$_3$)—O-(4-Cl—C$_6$H$_4$) | O |
| Ia1.1065 | OCH$_3$ | (CH$_2$)$_3$CH$_3$ | CH(CH$_3$)CH(CH$_3$)—O-(4-Cl—C$_6$H$_4$) | O |
| Ia1.1066 | OCH$_3$ | H | (CH$_2$)$_2$—O-(2,4-Cl$_2$—C$_6$H$_3$) | O |
| Ia1.1067 | OCH$_3$ | CH$_3$ | (CH$_2$)$_2$—O-(2,4-Cl$_2$—C$_6$H$_3$) | O |
| Ia1.1068 | OCH$_3$ | CH$_2$CH$_3$ | (CH$_2$)$_2$—O-(2,4-Cl$_2$—C$_6$H$_3$) | O |
| Ia1.1069 | OCH$_3$ | (CH$_2$)$_2$CH$_3$ | (CH$_2$)$_2$—O-(2,4-Cl$_2$—C$_6$H$_3$) | O |
| Ia1.1070 | OCH$_3$ | (CH$_2$)$_3$CH$_3$ | (CH$_2$)$_2$—O-(2,4-Cl$_2$—C$_6$H$_3$) | O |
| Ia1.1071 | OCH$_3$ | H | CH$_2$CH(CH$_3$)—O-(2,4-Cl$_2$—C$_6$H$_3$) | O |
| Ia1.1072 | OCH$_3$ | CH$_3$ | CH$_2$CH(CH$_3$)—O-(2,4-Cl$_2$—C$_6$H$_3$) | O |
| Ia1.1073 | OCH$_3$ | CH$_2$CH$_3$ | CH$_2$CH(CH$_3$)—O-(2,4-Cl$_2$—C$_6$H$_3$) | O |
| Ia1.1074 | OCH$_3$ | (CH$_2$)$_2$CH$_3$ | CH$_2$CH(CH$_3$)—O-(2,4-Cl$_2$—C$_6$H$_3$) | O |
| Ia1.1075 | OCH$_3$ | (CH$_2$)$_3$CH$_3$ | CH$_2$CH(CH$_3$)—O-(2,4-Cl$_2$—C$_6$H$_3$) | O |
| Ia1.1076 | OCH$_3$ | H | CH(CH$_3$)CH$_2$—O-(2,4-Cl$_2$—C$_6$H$_3$) | O |
| Ia1.1077 | OCH$_3$ | CH$_3$ | CH(CH$_3$)CH$_2$—O-(2,4-Cl$_2$—C$_6$H$_3$) | O |
| Ia1.1078 | OCH$_3$ | CH$_2$CH$_3$ | CH(CH$_3$)CH$_2$—O-(2,4-Cl$_2$—C$_6$H$_3$) | O |
| Ia1.1079 | OCH$_3$ | (CH$_2$)$_2$CH$_3$ | CH(CH$_3$)CH$_2$—O-(2,4-Cl$_2$—C$_6$H$_3$) | O |
| Ia1.1080 | OCH$_3$ | (CH$_2$)$_3$CH$_3$ | CH(CH$_3$)CH$_2$—O-(2,4-Cl$_2$—C$_6$H$_3$) | O |
| Ia1.1081 | OCH$_3$ | H | CH(CH$_3$)CH(CH$_3$)—O-(2,4-Cl$_2$—C$_6$H$_3$) | O |
| Ia1.1082 | OCH$_3$ | CH$_3$ | CH(CH$_3$)CH(CH$_3$)—O-(2,4-Cl$_2$—C$_6$H$_3$) | O |
| Ia1.1083 | OCH$_3$ | CH$_2$CH$_3$ | CH(CH$_3$)CH(CH$_3$)—O-(2,4-Cl$_2$—C$_6$H$_3$) | O |
| Ia1.1084 | OCH$_3$ | (CH$_2$)$_2$CH$_3$ | CH(CH$_3$)CH(CH$_3$)—O-(2,4-Cl$_2$—C$_6$H$_3$) | O |
| Ia1.1085 | OCH$_3$ | (CH$_2$)$_3$CH$_3$ | CH(CH$_3$)CH(CH$_3$)—O-(2,4-Cl$_2$—C$_6$H$_3$) | O |
| Ia1.1086 | OCH$_3$ | H | CH$_3$ | NH |
| Ia1.1087 | OCH$_3$ | CH$_3$ | CH$_3$ | NH |
| Ia1.1088 | OCH$_3$ | CH$_2$CH$_3$ | CH$_3$ | NH |
| Ia1.1089 | OCH$_3$ | (CH$_2$)$_2$CH$_3$ | CH$_3$ | NH |
| Ia1.1090 | OCH$_3$ | (CH$_2$)$_3$CH$_3$ | CH$_3$ | NH |
| Ia1.1091 | OCH$_3$ | H | C$_2$H$_5$ | NH |
| Ia1.1092 | OCH$_3$ | CH$_3$ | C$_2$H$_5$ | NH |
| Ia1.1093 | OCH$_3$ | CH$_2$CH$_3$ | C$_2$H$_5$ | NH |
| Ia1.1094 | OCH$_3$ | (CH$_2$)$_2$CH$_3$ | C$_2$H$_5$ | NH |
| Ia1.1095 | OCH$_3$ | (CH$_2$)$_3$CH$_3$ | C$_2$H$_5$ | NH |
| Ia1.1096 | OCH$_3$ | H | (CH$_2$)$_2$CH$_3$ | NH |
| Ia1.1097 | OCH$_3$ | CH$_3$ | (CH$_2$)$_2$CH$_3$ | NH |
| Ia1.1098 | OCH$_3$ | CH$_2$CH$_3$ | (CH$_2$)$_2$CH$_3$ | NH |
| Ia1.1099 | OCH$_3$ | (CH$_2$)$_2$CH$_3$ | (CH$_2$)$_2$CH$_3$ | NH |
| Ia1.1100 | OCH$_3$ | (CH$_2$)$_3$CH$_3$ | (CH$_2$)$_2$CH$_3$ | NH |
| Ia1.1101 | OCH$_3$ | H | CH(CH$_3$)$_2$ | NH |
| Ia1.1102 | OCH$_3$ | CH$_3$ | CH(CH$_3$)$_2$ | NH |
| Ia1.1103 | OCH$_3$ | CH$_2$CH$_3$ | CH(CH$_3$)$_2$ | NH |
| Ia1.1104 | OCH$_3$ | (CH$_2$)$_2$CH$_3$ | CH(CH$_3$)$_2$ | NH |
| Ia1.1105 | OCH$_3$ | (CH$_2$)$_3$CH$_3$ | CH(CH$_3$)$_2$ | NH |
| Ia1.1106 | OCH$_3$ | H | (CH$_2$)$_3$CH$_3$ | NH |
| Ia1.1107 | OCH$_3$ | CH$_3$ | (CH$_2$)$_3$CH$_3$ | NH |
| Ia1.1108 | OCH$_3$ | CH$_2$CH$_3$ | (CH$_2$)$_3$CH$_3$ | NH |
| Ia1.1109 | OCH$_3$ | (CH$_2$)$_2$CH$_3$ | (CH$_2$)$_3$CH$_3$ | NH |
| Ia1.1110 | OCH$_3$ | (CH$_2$)$_3$CH$_3$ | (CH$_2$)$_3$CH$_3$ | NH |
| Ia1.1111 | OCH$_3$ | H | CH$_2$CH(CH$_3$)$_2$ | NH |
| Ia1.1112 | OCH$_3$ | CH$_3$ | CH$_2$CH(CH$_3$)$_2$ | NH |
| Ia1.1113 | OCH$_3$ | CH$_2$CH$_3$ | CH$_2$CH(CH$_3$)$_2$ | NH |
| Ia1.1114 | OCH$_3$ | (CH$_2$)$_2$CH$_3$ | CH$_2$CH(CH$_3$)$_2$ | NH |
| Ia1.1115 | OCH$_3$ | (CH$_2$)$_3$CH$_3$ | CH$_2$CH(CH$_3$)$_2$ | NH |
| Ia1.1116 | OCH$_3$ | H | CH(CH$_3$)CH$_2$CH$_3$ | NH |
| Ia1.1117 | OCH$_3$ | CH$_3$ | CH(CH$_3$)CH$_2$CH$_3$ | NH |
| Ia1.1118 | OCH$_3$ | CH$_2$CH$_3$ | CH(CH$_3$)CH$_2$CH$_3$ | NH |
| Ia1.1119 | OCH$_3$ | (CH$_2$)$_2$CH$_3$ | CH(CH$_3$)CH$_2$CH$_3$ | NH |
| Ia1.1120 | OCH$_3$ | (CH$_2$)$_3$CH$_3$ | CH(CH$_3$)CH$_2$CH$_3$ | NH |
| Ia1.1121 | OCH$_3$ | H | (CH$_2$)$_2$—C$_6$H$_5$ | NH |
| Ia1.1122 | OCH$_3$ | CH$_3$ | (CH$_2$)$_2$—C$_6$H$_5$ | NH |
| Ia1.1123 | OCH$_3$ | CH$_2$CH$_3$ | (CH$_2$)$_2$—C$_6$H$_5$ | NH |
| Ia1.1124 | OCH$_3$ | (CH$_2$)$_2$CH$_3$ | (CH$_2$)$_2$—C$_6$H$_5$ | NH |
| Ia1.1125 | OCH$_3$ | (CH$_2$)$_3$CH$_3$ | (CH$_2$)$_2$—C$_6$H$_5$ | NH |
| Ia1.1126 | OCH$_3$ | H | CH$_2$CH(CH$_3$)—C$_6$H$_5$ | NH |

TABLE 1-continued

| No. | $R^2$ | $R^3$ | $R^4$ | Z |
|---|---|---|---|---|
| Ia1.1127 | OCH$_3$ | CH$_3$ | CH$_2$CH(CH$_3$)—C$_6$H$_5$ | NH |
| Ia1.1128 | OCH$_3$ | CH$_2$CH$_3$ | CH$_2$CH(CH$_3$)—C$_6$H$_5$ | NH |
| Ia1.1129 | OCH$_3$ | (CH$_2$)$_2$CH$_3$ | CH$_2$CH(CH$_3$)—C$_6$H$_5$ | NH |
| Ia1.1130 | OCH$_3$ | (CH$_2$)$_3$CH$_3$ | CH$_2$CH(CH$_3$)—C$_6$H$_5$ | NH |
| Ia1.1131 | OCH$_3$ | H | CH(CH$_3$)CH$_2$—C$_6$H$_5$ | NH |
| Ia1.1132 | OCH$_3$ | CH$_3$ | CH(CH$_3$)CH$_2$—C$_6$H$_5$ | NH |
| Ia1.1133 | OCH$_3$ | CH$_2$CH$_3$ | CH(CH$_3$)CH$_2$—C$_6$H$_5$ | NH |
| Ia1.1134 | OCH$_3$ | (CH$_2$)$_2$CH$_3$ | CH(CH$_3$)CH$_2$—C$_6$H$_5$ | NH |
| Ia1.1135 | OCH$_3$ | (CH$_2$)$_3$CH$_3$ | CH(CH$_3$)CH$_2$—C$_6$H$_5$ | NH |
| Ia1.1136 | OCH$_3$ | H | CH(CH$_3$)CH(CH$_3$)—C$_6$H$_5$ | NH |
| Ia1.1137 | OCH$_3$ | CH$_3$ | CH(CH$_3$)CH(CH$_3$)—C$_6$H$_5$ | NH |
| Ia1.1138 | OCH$_3$ | CH$_2$CH$_3$ | CH(CH$_3$)CH(CH$_3$)—C$_6$H$_5$ | NH |
| Ia1.1139 | OCH$_3$ | (CH$_2$)$_2$CH$_3$ | CH(CH$_3$)CH(CH$_3$)—C$_6$H$_5$ | NH |
| Ia1.1140 | OCH$_3$ | (CH$_2$)$_3$CH$_3$ | CH(CH$_3$)CH(CH$_3$)—C$_6$H$_5$ | NH |
| Ia1.1141 | OCH$_3$ | H | (CH$_2$)$_2$-(4-Cl—C$_6$H$_4$) | NH |
| Ia1.1142 | OCH$_3$ | CH$_3$ | (CH$_2$)$_2$-(4-Cl—C$_6$H$_4$) | NH |
| Ia1.1143 | OCH$_3$ | CH$_2$CH$_3$ | (CH$_2$)$_2$-(4-Cl—C$_6$H$_4$) | NH |
| Ia1.1144 | OCH$_3$ | (CH$_2$)$_2$CH$_3$ | (CH$_2$)$_2$-(4-Cl—C$_6$H$_4$) | NH |
| Ia1.1145 | OCH$_3$ | (CH$_2$)$_3$CH$_3$ | (CH$_2$)$_2$-(4-Cl—C$_6$H$_4$) | NH |
| Ia1.1146 | OCH$_3$ | H | CH$_2$CH(CH$_3$)-(4-Cl—C$_6$H$_4$) | NH |
| Ia1.1147 | OCH$_3$ | CH$_3$ | CH$_2$CH(CH$_3$)-(4-Cl—C$_6$H$_4$) | NH |
| Ia1.1148 | OCH$_3$ | CH$_2$CH$_3$ | CH$_2$CH(CH$_3$)-(4-Cl—C$_6$H$_4$) | NH |
| Ia1.1149 | OCH$_3$ | (CH$_2$)$_2$CH$_3$ | CH$_2$CH(CH$_3$)-(4-Cl—C$_6$H$_4$) | NH |
| Ia1.1150 | OCH$_3$ | (CH$_2$)$_3$CH$_3$ | CH$_2$CH(CH$_3$)-(4-Cl—C$_6$H$_4$) | NH |
| Ia1.1151 | OCH$_3$ | H | CH(CH$_3$)CH$_2$-(4-Cl—C$_6$H$_4$) | NH |
| Ia1.1152 | OCH$_3$ | CH$_3$ | CH(CH$_3$)CH$_2$-(4-Cl—C$_6$H$_4$) | NH |
| Ia1.1153 | OCH$_3$ | CH$_2$CH$_3$ | CH(CH$_3$)CH$_2$-(4-Cl—C$_6$H$_4$) | NH |
| Ia1.1154 | OCH$_3$ | (CH$_2$)$_2$CH$_3$ | CH(CH$_3$)CH$_2$-(4-Cl—C$_6$H$_4$) | NH |
| Ia1.1155 | OCH$_3$ | (CH$_2$)$_3$CH$_3$ | CH(CH$_3$)CH$_2$-(4-Cl—C$_6$H$_4$) | NH |
| Ia1.1156 | OCH$_3$ | H | CH(CH$_3$)CH(CH$_3$)-(4-Cl—C$_6$H$_4$) | NH |
| Ia1.1157 | OCH$_3$ | CH$_3$ | CH(CH$_3$)CH(CH$_3$)-(4-Cl—C$_6$H$_4$) | NH |
| Ia1.1158 | OCH$_3$ | CH$_2$CH$_3$ | CH(CH$_3$)CH(CH$_3$)-(4-Cl—C$_6$H$_4$) | NH |
| Ia1.1159 | OCH$_3$ | (CH$_2$)$_2$CH$_3$ | CH(CH$_3$)CH(CH$_3$)-(4-Cl—C$_6$H$_4$) | NH |
| Ia1.1160 | OCH$_3$ | (CH$_2$)$_3$CH$_3$ | CH(CH$_3$)CH(CH$_3$)-(4-Cl—C$_6$H$_4$) | NH |
| Ia1.1161 | OCH$_3$ | H | (CH$_2$)$_2$-(2,4-Cl$_2$—C$_6$H$_3$) | NH |
| Ia1.1162 | OCH$_3$ | CH$_3$ | (CH$_2$)$_2$-(2,4-Cl$_2$—C$_6$H$_3$) | NH |
| Ia1.1163 | OCH$_3$ | CH$_2$CH$_3$ | (CH$_2$)$_2$-(2,4-Cl$_2$—C$_6$H$_3$) | NH |
| Ia1.1164 | OCH$_3$ | (CH$_2$)$_2$CH$_3$ | (CH$_2$)$_2$-(2,4-Cl$_2$—C$_6$H$_3$) | NH |
| Ia1.1165 | OCH$_3$ | (CH$_2$)$_3$CH$_3$ | (CH$_2$)$_2$-(2,4-Cl$_2$—C$_6$H$_3$) | NH |
| Ia1.1166 | OCH$_3$ | H | CH$_2$CH(CH$_3$)-(2,4-Cl$_2$—C$_6$H$_3$) | NH |
| Ia1.1167 | OCH$_3$ | CH$_3$ | CH$_2$CH(CH$_3$)-(2,4-Cl$_2$—C$_6$H$_3$) | NH |
| Ia1.1168 | OCH$_3$ | CH$_2$CH$_3$ | CH$_2$CH(CH$_3$)-(2,4-Cl$_2$—C$_6$H$_3$) | NH |
| Ia1.1169 | OCH$_3$ | (CH$_2$)$_2$CH$_3$ | CH$_2$CH(CH$_3$)-(2,4-Cl$_2$—C$_6$H$_3$) | NH |
| Ia1.1170 | OCH$_3$ | (CH$_2$)$_3$CH$_3$ | CH$_2$CH(CH$_3$)-(2,4-Cl$_2$—C$_6$H$_3$) | NH |
| Ia1.1171 | OCH$_3$ | H | CH(CH$_3$)CH$_2$-(2,4-Cl$_2$—C$_6$H$_3$) | NH |
| Ia1.1172 | OCH$_3$ | CH$_3$ | CH(CH$_3$)CH$_2$-(2,4-Cl$_2$—C$_6$H$_3$) | NH |
| Ia1.1173 | OCH$_3$ | CH$_2$CH$_3$ | CH(CH$_3$)CH$_2$-(2,4-Cl$_2$—C$_6$H$_3$) | NH |
| Ia1.1174 | OCH$_3$ | (CH$_2$)$_2$CH$_3$ | CH(CH$_3$)CH$_2$-(2,4-Cl$_2$—C$_6$H$_3$) | NH |
| Ia1.1175 | OCH$_3$ | (CH$_2$)$_3$CH$_3$ | CH(CH$_3$)CH$_2$-(2,4-Cl$_2$—C$_6$H$_3$) | NH |
| Ia1.1176 | OCH$_3$ | H | CH(CH$_3$)CH(CH$_3$)-(2,4-Cl$_2$—C$_6$H$_3$) | NH |
| Ia1.1177 | OCH$_3$ | CH$_3$ | CH(CH$_3$)CH(CH$_3$)-(2,4-Cl$_2$—C$_6$H$_3$) | NH |
| Ia1.1178 | OCH$_3$ | CH$_2$CH$_3$ | CH(CH$_3$)CH(CH$_3$)-(2,4-Cl$_2$—C$_6$H$_3$) | NH |
| Ia1.1179 | OCH$_3$ | (CH$_2$)$_2$CH$_3$ | CH(CH$_3$)CH(CH$_3$)-(2,4-Cl$_2$—C$_6$H$_3$) | NH |
| Ia1.1180 | OCH$_3$ | (CH$_2$)$_3$CH$_3$ | CH(CH$_3$)CH(CH$_3$)-(2,4-Cl$_2$—C$_6$H$_3$) | NH |
| Ia1.1181 | OCH$_3$ | H | (CH$_2$)$_2$—O—C$_6$H$_5$ | NH |
| Ia1.1182 | OCH$_3$ | CH$_3$ | (CH$_2$)$_2$—O—C$_6$H$_5$ | NH |
| Ia1.1183 | OCH$_3$ | CH$_2$CH$_3$ | (CH$_2$)$_2$—O—C$_6$H$_5$ | NH |
| Ia1.1184 | OCH$_3$ | (CH$_2$)$_2$CH$_3$ | (CH$_2$)$_2$—O—C$_6$H$_5$ | NH |
| Ia1.1185 | OCH$_3$ | (CH$_2$)$_3$CH$_3$ | (CH$_2$)$_2$—O—C$_6$H$_5$ | NH |
| Ia1.1186 | OCH$_3$ | H | CH$_2$CH(CH$_3$)—O—C$_6$H$_5$ | NH |
| Ia1.1187 | OCH$_3$ | CH$_3$ | CH$_2$CH(CH$_3$)—O—C$_6$H$_5$ | NH |
| Ia1.1188 | OCH$_3$ | CH$_2$CH$_3$ | CH$_2$CH(CH$_3$)—O—C$_6$H$_5$ | NH |
| Ia1.1189 | OCH$_3$ | (CH$_2$)$_2$CH$_3$ | CH$_2$CH(CH$_3$)—O—C$_6$H$_5$ | NH |
| Ia1.1190 | OCH$_3$ | (CH$_2$)$_3$CH$_3$ | CH$_2$CH(CH$_3$)—O—C$_6$H$_5$ | NH |
| Ia1.1191 | OCH$_3$ | H | CH(CH$_3$)CH$_2$—O—C$_6$H$_5$ | NH |
| Ia1.1192 | OCH$_3$ | CH$_3$ | CH(CH$_3$)CH$_2$—O—C$_6$H$_5$ | NH |
| Ia1.1193 | OCH$_3$ | CH$_2$CH$_3$ | CH(CH$_3$)CH$_2$—O—C$_6$H$_5$ | NH |
| Ia1.1194 | OCH$_3$ | (CH$_2$)$_2$CH$_3$ | CH(CH$_3$)CH$_2$—O—C$_6$H$_5$ | NH |
| Ia1.1195 | OCH$_3$ | (CH$_2$)$_3$CH$_3$ | CH(CH$_3$)CH$_2$—O—C$_6$H$_5$ | NH |
| Ia1.1196 | OCH$_3$ | H | CH(CH$_3$)CH(CH$_3$)—O—C$_6$H$_5$ | NH |
| Ia1.1197 | OCH$_3$ | CH$_3$ | CH(CH$_3$)CH(CH$_3$)—O—C$_6$H$_5$ | NH |
| Ia1.1198 | OCH$_3$ | CH$_2$CH$_3$ | CH(CH$_3$)CH(CH$_3$)—O—C$_6$H$_5$ | NH |
| Ia1.1199 | OCH$_3$ | (CH$_2$)$_2$CH$_3$ | CH(CH$_3$)CH(CH$_3$)—O—C$_6$H$_5$ | NH |
| Ia1.1200 | OCH$_3$ | (CH$_2$)$_3$CH$_3$ | CH(CH$_3$)CH(CH$_3$)—O—C$_6$H$_5$ | NH |
| Ia1.1201 | OCH$_3$ | H | (CH$_2$)$_2$—O-(4-Cl—C$_6$H$_4$) | NH |
| Ia1.1202 | OCH$_3$ | CH$_3$ | (CH$_2$)$_2$—O-(4-Cl—C$_6$H$_4$) | NH |
| Ia1.1203 | OCH$_3$ | CH$_2$CH$_3$ | (CH$_2$)$_2$—O-(4-Cl—C$_6$H$_4$) | NH |

TABLE 1-continued

| No. | R² | R³ | R⁴ | Z |
|---|---|---|---|---|
| Ia1.1204 | OCH₃ | (CH₂)₂CH₃ | (CH₂)₂—O-(4-Cl—C₆H₄) | NH |
| Ia1.1205 | OCH₃ | (CH₂)₃CH₃ | (CH₂)₂—O-(4-Cl—C₆H₄) | NH |
| Ia1.1206 | OCH₃ | H | CH₂CH(CH₃)—O-(4-Cl—C₆H₄) | NH |
| Ia1.1207 | OCH₃ | CH₃ | CH₂CH(CH₃)—O-(4-Cl—C₆H₄) | NH |
| Ia1.1208 | OCH₃ | CH₂CH₃ | CH₂CH(CH₃)—O-(4-Cl—C₆H₄) | NH |
| Ia1.1209 | OCH₃ | (CH₂)₂CH₃ | CH₂CH(CH₃)—O-(4-Cl—C₆H₄) | NH |
| Ia1.1210 | OCH₃ | (CH₂)₃CH₃ | CH₂CH(CH₃)—O-(4-Cl—C₆H₄) | NH |
| Ia1.1211 | OCH₃ | H | CH(CH₃)CH₂—O-(4-Cl—C₆H₄) | NH |
| Ia1.1212 | OCH₃ | CH₃ | CH(CH₃)CH₂—O-(4-Cl—C₆H₄) | NH |
| Ia1.1213 | OCH₃ | CH₂CH₃ | CH(CH₃)CH₂—O-(4-Cl—C₆H₄) | NH |
| Ia1.1214 | OCH₃ | (CH₂)₂CH₃ | CH(CH₃)CH₂—O-(4-Cl—C₆H₄) | NH |
| Ia1.1215 | OCH₃ | (CH₂)₃CH₃ | CH(CH₃)CH₂—O-(4-Cl—C₆H₄) | NH |
| Ia1.1216 | OCH₃ | H | CH(CH₃)CH(CH₃)—O-(4-Cl—C₆H₄) | NH |
| Ia1.1217 | OCH₃ | CH₃ | CH(CH₃)CH(CH₃)—O-(4-Cl—C₆H₄) | NH |
| Ia1.1218 | OCH₃ | CH₂CH₃ | CH(CH₃)CH(CH₃)—O-(4-Cl—C₆H₄) | NH |
| Ia1.1219 | OCH₃ | (CH₂)₂CH₃ | CH(CH₃)CH(CH₃)—O-(4-Cl—C₆H₄) | NH |
| Ia1.1220 | OCH₃ | (CH₂)₃CH₃ | CH(CH₃)CH(CH₃)—O-(4-Cl—C₆H₄) | NH |
| Ia1.1221 | OCH₃ | H | (CH₂)₂—O-(2,4-Cl₂—C₆H₃) | NH |
| Ia1.1222 | OCH₃ | CH₃ | (CH₂)₂—O-(2,4-Cl₂—C₆H₃) | NH |
| Ia1.1223 | OCH₃ | CH₂CH₃ | (CH₂)₂—O-(2,4-Cl₂—C₆H₃) | NH |
| Ia1.1224 | OCH₃ | (CH₂)₂CH₃ | (CH₂)₂—O-(2,4-Cl₂—C₆H₃) | NH |
| Ia1.1225 | OCH₃ | (CH₂)₃CH₃ | (CH₂)₂—O-(2,4-Cl₂—C₆H₃) | NH |
| Ia1.1226 | OCH₃ | H | CH₂CH(CH₃)—O-(2,4-Cl₂—C₆H₃) | NH |
| Ia1.1227 | OCH₃ | CH₃ | CH₂CH(CH₃)—O-(2,4-Cl₂—C₆H₃) | NH |
| Ia1.1228 | OCH₃ | CH₂CH₃ | CH₂CH(CH₃)—O-(2,4-Cl₂—C₆H₃) | NH |
| Ia1.1229 | OCH₃ | (CH₂)₂CH₃ | CH₂CH(CH₃)—O-(2,4-Cl₂—C₆H₃) | NH |
| Ia1.1230 | OCH₃ | (CH₂)₃CH₃ | CH₂CH(CH₃)—O-(2,4-Cl₂—C₆H₃) | NH |
| Ia1.1231 | OCH₃ | H | CH(CH₃)CH₂—O-(2,4-Cl₂—C₆H₃) | NH |
| Ia1.1232 | OCH₃ | CH₃ | CH(CH₃)CH₂—O-(2,4-Cl₂—C₆H₃) | NH |
| Ia1.1233 | OCH₃ | CH₂CH₃ | CH(CH₃)CH₂—O-(2,4-Cl₂—C₆H₃) | NH |
| Ia1.1234 | OCH₃ | (CH₂)₂CH₃ | CH(CH₃)CH₂—O-(2,4-Cl₂—C₆H₃) | NH |
| Ia1.1235 | CCH₃ | (CH₂)₃CH₃ | CH(CH₃)CH₂—O-(2,4-Cl₂—C₆H₃) | NH |
| Ia1.1236 | OCH₃ | H | CH(CH₃)CH(CH₃)—O-(2,4-Cl₂—C₆H₃) | NH |
| Ia1.1237 | OCH₃ | CH₃ | CH(CH₃)CH(CH₃)—O-(2,4-Cl₂—C₆H₃) | NH |
| Ia1.1238 | OCH₃ | CH₂CH₃ | CH(CH₃)CH(CH₃)—O-(2,4-Cl₂—C₆H₃) | NH |
| Ia1.1239 | OCH₃ | (CH₂)₂CH₃ | CH(CH₃)CH(CH₃)—O-(2,4-Cl₂—C₆H₃) | NH |
| Ia1.1240 | OCH₃ | (CH₂)₃CH₃ | CH(CH₃)CH(CH₃)—O-(2,4-Cl₂—C₆H₃) | NH |
| Ia1.1241 | OCH₃ | H | CH₃ | NCH₃ |
| Ia1.1242 | OCH₃ | CH₃ | CH₃ | NCH₃ |
| Ia1.1243 | OCH₃ | CH₂CH₃ | CH₃ | NCH₃ |
| Ia1.1244 | OCH₃ | (CH₂)₂CH₃ | CH₃ | NCH₃ |
| Ia1.1245 | OCH₃ | (CH₂)₃CH₃ | CH₃ | NCH₃ |
| Ia1.1246 | OCH₃ | H | C₂H₅ | NCH₃ |
| Ia1.1247 | OCH₃ | CH₃ | C₂H₅ | NCH₃ |
| Ia1.1248 | OCH₃ | CH₂CH₃ | C₂H₅ | NCH₃ |
| Ia1.1249 | OCH₃ | (CH₂)₂CH₃ | C₂H₅ | NCH₃ |
| Ia1.1250 | OCH₃ | (CH₂)₃CH₃ | C₂H₅ | NCH₃ |
| Ia1.1251 | OCH₃ | H | (CH₂)₂CH₃ | NCH₃ |
| Ia1.1252 | OCH₃ | CH₃ | (CH₂)₂CH₃ | NCH₃ |
| Ia1.1253 | OCH₃ | CH₂CH₃ | (CH₂)₂CH₃ | NCH₃ |
| Ia1.1254 | OCH₃ | (CH₂)₂CH₃ | (CH₂)₂CH₃ | NCH₃ |
| Ia1.1255 | OCH₃ | (CH₂)₃CH₃ | (CH₂)₂CH₃ | NCH₃ |
| Ia1.1256 | OCH₃ | H | CH(CH₃)₂ | NCH₃ |
| Ia1.1257 | OCH₃ | CH₃ | CH(CH₃)₂ | NCH₃ |
| Ia1.1258 | OCH₃ | CH₂CH₃ | CH(CH₃)₂ | NCH₃ |
| Ia1.1259 | OCH₃ | (CH₂)₂CH₃ | CH(CH₃)₂ | NCH₃ |
| Ia1.1260 | OCH₃ | (CH₂)₃CH₃ | CH(CH₃)₂ | NCH₃ |
| Ia1.1261 | OCH₃ | H | (CH₂)₃CH₃ | NCH₃ |
| Ia1.1262 | OCH₃ | CH₃ | (CH₂)₃CH₃ | NCH₃ |
| Ia1.1263 | OCH₃ | CH₂CH₃ | (CH₂)₃CH₃ | NCH₃ |
| Ia1.1264 | OCH₃ | (CH₂)₂CH₃ | (CH₂)₃CH₃ | NCH₃ |
| Ia1.1265 | OCH₃ | (CH₂)₃CH₃ | (CH₂)₃CH₃ | NCH₃ |
| Ia1.1266 | OCH₃ | H | CH₂CH(CH₃)₂ | NCH₃ |
| Ia1.1267 | OCH₃ | CH₃ | CH₂CH(CH₃)₂ | NCH₃ |
| Ia1.1268 | OCH₃ | CH₂CH₃ | CH₂CH(CH₃)₂ | NCH₃ |
| Ia1.1269 | OCH₃ | (CH₂)₂CH₃ | CH₂CH(CH₃)₂ | NCH₃ |
| Ia1.1270 | OCH₃ | (CH₂)₃CH₃ | CH₂CH(CH₃)₂ | NCH₃ |
| Ia1.1271 | OCH₃ | H | CH(CH₃)CH₂CH₃ | NCH₃ |
| Ia1.1272 | OCH₃ | CH₃ | CH(CH₃)CH₂CH₃ | NCH₃ |
| Ia1.1273 | OCH₃ | CH₂CH₃ | CH(CH₃)CH₂CH₃ | NCH₃ |
| Ia1.1274 | OCH₃ | (CH₂)₂CH₃ | CH(CH₃)CH₂CH₃ | NCH₃ |
| Ia1.1275 | OCH₃ | (CH₂)₃CH₃ | CH(CH₃)CH₂CH₃ | NCH₃ |
| Ia1.1276 | OCH₃ | H | (CH₂)₂—C₆H₅ | NCH₃ |
| Ia1.1277 | OCH₃ | CH₃ | (CH₂)₂—C₆H₅ | NCH₃ |
| Ia1.1278 | OCH₃ | CH₂CH₃ | (CH₂)₂—C₆H₅ | NCH₃ |
| Ia1.1279 | OCH₃ | (CH₂)₂CH₃ | (CH₂)₂—C₆H₅ | NCH₃ |
| Ia1.1280 | OCH₃ | (CH₂)₃CH₃ | (CH₂)₂—C₆H₅ | NCH₃ |

TABLE 1-continued

| No. | R² | R³ | R⁴ | Z |
|---|---|---|---|---|
| Ia1.1281 | OCH₃ | H | CH₂CH(CH₃)—C₆H₅ | NCH₃ |
| Ia1.1282 | OCH₃ | CH₃ | CH₂CH(CH₃)—C₆H₅ | NCH₃ |
| Ia1.1283 | OCH₃ | CH₂CH₃ | CH₂CH(CH₃)—C₆H₅ | NCH₃ |
| Ia1.1284 | OCH₃ | (CH₂)₂CH₃ | CH₂CH(CH₃)—C₆H₅ | NCH₃ |
| Ia1.1285 | OCH₃ | (CH₂)₃CH₃ | CH₂CH(CH₃)—C₆H₅ | NCH₃ |
| Ia1.1286 | OCH₃ | H | CH(CH₃)CH₂—C₆H₅ | NCH₃ |
| Ia1.1287 | OCH₃ | CH₃ | CH(CH₃)CH₂—C₆H₅ | NCH₃ |
| Ia1.1288 | OCH₃ | CH₂CH₃ | CH(CH₃)CH₂—C₆H₅ | NCH₃ |
| Ia1.1289 | OCH₃ | (CH₂)₂CH₃ | CH(CH₃)CH₂—C₆H₅ | NCH₃ |
| Ia1.1290 | OCH₃ | (CH₂)₃CH₃ | CH(CH₃)CH₂—C₆H₅ | NCH₃ |
| Ia1.1291 | OCH₃ | H | CH(CH₃)CH(CH₃)—C₆H₅ | NCH₃ |
| Ia1.1292 | OCH₃ | CH₃ | CH(CH₃)CH(CH₃)—C₆H₅ | NCH₃ |
| Ia1.1293 | OCH₃ | CH₂CH₃ | CH(CH₃)CH(CH₃)—C₆H₅ | NCH₃ |
| Ia1.1294 | OCH₃ | (CH₂)₂CH₃ | CH(CH₃)CH(CH₃)—C₆H₅ | NCH₃ |
| Ia1.1295 | OCH₃ | (CH₂)₃CH₃ | CH(CH₃)CH(CH₃)—C₆H₅ | NCH₃ |
| Ia1.1296 | OCH₃ | H | (CH₂)₂-(4-Cl—C₆H₄) | NCH₃ |
| Ia1.1297 | OCH₃ | CH₃ | (CH₂)₂-(4-Cl—C₆H₄) | NCH₃ |
| Ia1.1298 | OCH₃ | CH₂CH₃ | (CH₂)₂-(4-Cl—C₆H₄) | NCH₃ |
| Ia1.1299 | OCH₃ | (CH₂)₂CH₃ | (CH₂)₂-(4-Cl—C₆H₄) | NCH₃ |
| Ia1.1300 | OCH₃ | (CH₂)₃CH₃ | (CH₂)₂-(4-Cl—C₆H₄) | NCH₃ |
| Ia1.1301 | OCH₃ | H | CH₂CH(CH₃)-(4-Cl—C₆H₄) | NCH₃ |
| Ia1.1302 | OCH₃ | CH₃ | CH₂CH(CH₃)-(4-Cl—C₆H₄) | NCH₃ |
| Ia1.1303 | OCH₃ | CH₂CH₃ | CH₂CH(CH₃)-(4-Cl—C₆H₄) | NCH₃ |
| Ia1.1304 | OCH₃ | (CH₂)₂CH₃ | CH₂CH(CH₃)-(4-Cl—C₆H₄) | NCH₃ |
| Ia1.1305 | OCH₃ | (CH₂)₃CH₃ | CH₂CH(CH₃)-(4-Cl—C₆H₄) | NCH₃ |
| Ia1.1306 | OCH₃ | H | CH(CH₃)CH₂-(4-Cl—C₆H₄) | NCH₃ |
| Ia1.1307 | OCH₃ | CH₃ | CH(CH₃)CH₂-(4-Cl—C₆H₄) | NCH₃ |
| Ia1.1308 | OCH₃ | CH₂CH₃ | CH(CH₃)—CH₂-(4-Cl—C₆H₄) | NCH₃ |
| Ia1.1309 | OCH₃ | (CH₂)₂CH₃ | CH(CH₃)CH₂-(4-Cl—C₆H₄) | NCH₃ |
| Ia1.1310 | OCH₃ | (CH₂)₃CH₃ | CH(CH₃)CH₂-(4-Cl—C₆H₄) | NCH₃ |
| Ia1.1311 | OCH₃ | H | CH(CH₃)CH(CH₃)-(4-Cl—C₆H₄) | NCH₃ |
| Ia1.1312 | OCH₃ | CH₃ | CH(CH₃)CH(CH₃)-(4-Cl—C₆H₄) | NCH₃ |
| Ia1.1313 | OCH₃ | CH₂CH₃ | CH(CH₃)CH(CH₃)-(4-Cl—C₆H₄) | NCH₃ |
| Ia1.1314 | OCH₃ | (CH₂)₂CH₃ | CH(CH₃)CH(CH₃)-(4-Cl—C₆H₄) | NCH₃ |
| Ia1.1315 | OCH₃ | (CH₂)₃CH₃ | CH(CH₃)CH(CH₃)-(4-Cl—C₆H₄) | NCH₃ |
| Ia1.1316 | OCH₃ | H | (CH₂)₂-(2,4-Cl₂—C₆H₃) | NCH₃ |
| Ia1.1317 | OCH₃ | CH₃ | (CH₂)₂-(2,4-Cl₂—C₆H₃) | NCH₃ |
| Ia1.1318 | OCH₃ | CH₂CH₃ | (CH₂)₂-(2,4-Cl₂—C₆H₃) | NCH₃ |
| Ia1.1319 | OCH₃ | (CH₂)₂CH₃ | (CH₂)₂-(2,4-Cl₂—C₆H₃) | NCH₃ |
| Ia1.1320 | OCH₃ | (CH₂)₃CH₃ | (CH₂)₂-(2,4-Cl₂—C₆H₃) | NCH₃ |
| Ia1.1321 | OCH₃ | H | CH₂CH(CH₃)-(2,4-Cl₂—C₆H₃) | NCH₃ |
| Ia1.1322 | OCH₃ | CH₃ | CH₂CH(CH₃)-(2,4-Cl₂—C₆H₃) | NCH₃ |
| Ia1.1323 | OCH₃ | CH₂CH₃ | CH₂CH(CH₃)-(2,4-Cl₂—C₆H₃) | NCH₃ |
| Ia1.1324 | OCH₃ | (CH₂)₂CH₃ | CH₂CH(CH₃)-(2,4-Cl₂—C₆H₃) | NCH₃ |
| Ia1.1325 | OCH₃ | (CH₂)₃CH₃ | CH₂CH(CH₃)-(2,4-Cl₂—C₆H₃) | NCH₃ |
| Ia1.1326 | OCH₃ | H | CH(CH₃)CH₂-(2,4-Cl₂—C₆H₃) | NCH₃ |
| Ia1.1327 | OCH₃ | CH₃ | CH(CH₃)CH₂-(2,4-Cl₂—C₆H₃) | NCH₃ |
| Ia1.1328 | OCH₃ | CH₂CH₃ | CH(CH₃)CH₂-(2,4-Cl₂—C₆H₃) | NCH₃ |
| Ia1.1329 | OCH₃ | (CH₂)₂CH₃ | CH(CH₃)CH₂-(2,4-Cl₂—C₆H₃) | NCH₃ |
| Ia1.1330 | OCH₃ | (CH₂)₃CH₃ | CH(CH₃)CH₂-(2,4-Cl₂—C₆H₃) | NCH₃ |
| Ia1.1331 | OCH₃ | H | CH(CH₃)CH(CH₃)-(2,4-Cl₂—C₆H₃) | NCH₃ |
| Ia1.1332 | OCH₃ | CH₃ | CH(CH₃)CH(CH₃)-(2,4-Cl₂—C₆H₃) | NCH₃ |
| Ia1.1333 | OCH₃ | CH₂CH₃ | CH(CH₃)CH(CH₃)-(2,4-Cl₂—C₆H₃) | NCH₃ |
| Ia1.1334 | OCH₃ | (CH₂)₂CH₃ | CH(CH₃)CH(CH₃)-(2,4-Cl₂—C₆H₃) | NCH₃ |
| Ia1.1335 | OCH₃ | (CH₂)₃CH₃ | CH(CH₃)CH(CH₃)-(2,4-Cl₂—C₆H₃) | NCH₃ |
| Ia1.1336 | OCH₃ | H | (CH₂)₂—O—C₆H₅ | NCH₃ |
| Ia1.1337 | OCH₃ | CH₃ | (CH₂)₂—O—C₆H₅ | NCH₃ |
| Ia1.1338 | OCH₃ | CH₂CH₃ | (CH₂)₂—O—C₆H₅ | NCH₃ |
| Ia1.1339 | OCH₃ | (CH₂)₂CH₃ | (CH₂)₂—O—C₆H₅ | NCH₃ |
| Ia1.1340 | OCH₃ | (CH₂)₃CH₃ | (CH₂)₂—O—C₆H₅ | NCH₃ |
| Ia1.1341 | OCH₃ | H | CH₂CH(CH₃)—O—C₆H₅ | NCH₃ |
| Ia1.1342 | OCH₃ | CH₃ | CH₂CH(CH₃)—O—C₆H₅ | NCH₃ |
| Ia1.1343 | OCH₃ | CH₂CH₃ | CH₂CH(CH₃)—O—C₆H₅ | NCH₃ |
| Ia1.1344 | OCH₃ | (CH₂)₂CH₃ | CH₂CH(CH₃)—O—C₆H₅ | NCH₃ |
| Ia1.1345 | OCH₃ | (CH₂)₃CH₃ | CH₂CH(CH₃)—O—C₆H₅ | NCH₃ |
| Ia1.1346 | OCH₃ | H | CH(CH₃)CH₂—O—C₆H₅ | NCH₃ |
| Ia1.1347 | OCH₃ | CH₃ | CH(CH₃)CH₂—O—C₆H₅ | NCH₃ |
| Ia1.1348 | OCH₃ | CH₂CH₃ | CH(CH₃)CH₂—O—C₆H₅ | NCH₃ |
| Ia1.1349 | OCH₃ | (CH₂)₂CH₃ | CH(CH₃)CH₂—O—C₆H₅ | NCH₃ |
| Ia1.1350 | OCH₃ | (CH₂)₃CH₃ | CH(CH₃)CH₂—O—C₆H₅ | NCH₃ |
| Ia1.1351 | OCH₃ | H | CH(CH₃)CH(CH₃)—O—C₆H₅ | NCH₃ |
| Ia1.1352 | OCH₃ | CH₃ | CH(CH₃)CH(CH₃)—O—C₆H₅ | NCH₃ |
| Ia1.1353 | OCH₃ | CH₂CH₃ | CH(CH₃)CH(CH₃)—O—C₆H₅ | NCH₃ |
| Ia1.1354 | OCH₃ | (CH₂)₂CH₃ | CH(CH₃)CH(CH₃)—O—C₆H₅ | NCH₃ |
| Ia1.1355 | OCH₃ | (CH₂)₃CH₃ | CH(CH₃)CH(CH₃)—O—C₆H₅ | NCH₃ |
| Ia1.1356 | OCH₃ | H | (CH₂)₂—O-(4-Cl—C₆H₄) | NCH₃ |
| Ia1.1357 | OCH₃ | CH₃ | (CH₂)₂—O-(4-Cl—C₆H₄) | NCH₃ |

TABLE 1-continued

| No. | R² | R³ | R⁴ | Z |
|---|---|---|---|---|
| Ia1.1358 | OCH₃ | CH₂CH₃ | (CH₂)₂—O-(4-Cl—C₆H₄) | NCH₃ |
| Ia1.1359 | OCH₃ | (CH₂)₂CH₃ | (CH₂)₂—O-(4-Cl—C₆H₄) | NCH₃ |
| Ia1.1360 | OCH₃ | (CH₂)₃CH₃ | (CH₂)₂—O-(4-Cl—C₆H₄) | NCH₃ |
| Ia1.1361 | OCH₃ | H | CH₂CH(CH₃)—O-(4-Cl—C₆H₄) | NCH₃ |
| Ia1.1362 | OCH₃ | CH₃ | CH₂CH(CH₃)—O-(4-Cl—C₆H₄) | NCH₃ |
| Ia1.1363 | OCH₃ | CH₂CH₃ | CH₂CH(CH₃)—O-(4-Cl—C₆H₄) | NCH₃ |
| Ia1.1364 | OCH₃ | (CH₂)₂CH₃ | CH₂CH(CH₃)—O-( 4-Cl—C₆H₄) | NCH₃ |
| Ia1.1365 | OCH₃ | (CH₂)₃CH₃ | CH₂CH(CH₃)—O-(4-Cl—C₆H₄) | NCH₃ |
| Ia1.1366 | OCH₃ | H | CH(CH₃)CH₂—O-(4-Cl—C₆H₄) | NCH₃ |
| Ia1.1367 | OCH₃ | CH₃ | CH(CH₃)CH₂—O-(4-Cl—C₆H₄) | NCH₃ |
| Ia1.1368 | OCH₃ | CH₂CH₃ | CH(CH₃)CH₂—O-(4-Cl—C₆H₄) | NCH₃ |
| Ia1.1369 | OCH₃ | (CH₂)₂CH₃ | CH(CH₃)CH₂—O-(4-Cl—C₆H₄) | NCH₃ |
| Ia1.1370 | OCH₃ | (CH₂)₃CH₃ | CH(CH₃)CH₂—O-(4-Cl—C₆H₄) | NCH₃ |
| Ia1.1371 | OCH₃ | H | CH(CH₃)CH(CH₃)—O-(4-Cl—C₆H₄) | NCH₃ |
| Ia1.1372 | OCH₃ | CH₃ | CH(CH₃)CH(CH₃)—O-(4-Cl—C₆H₄) | NCH₃ |
| Ia1.1373 | OCH₃ | CH₂CH₃ | CH(CH₃)CH(CH₃)—O-(4-Cl—C₆H₄) | NCH₃ |
| Ia1.1374 | OCH₃ | (CH₂)₂CH₃ | CH(CH₃)CH(CH₃)—O-(4-Cl—C₆H₄) | NCH₃ |
| Ia1.1375 | OCH₃ | (CH₂)₃CH₃ | CH(CH₃)CH(CH₃)—O-(4-Cl—C₆H₄) | NCH₃ |
| Ia1.1376 | OCH₃ | H | (CH₂)₂—O-(2,4-Cl₂—C₆H₃) | NCH₃ |
| Ia1.1377 | OCH₃ | CH₃ | (CH₂)₂—O-(2,4-Cl₂—C₆H₃) | NCH₃ |
| Ia1.1378 | OCH₃ | CH₂CH₃ | (CH₂)₂—O-(2,4-Cl₂—C₆H₃) | NCH₃ |
| Ia1.1379 | OCH₃ | (CH₂)₂CH₃ | (CH₂)₂—O-(2,4-Cl₂—C₆H₃) | NCH₃ |
| Ia1.1380 | OCH₃ | (CH₂)₃CH₃ | (CH₂)₂—O-(2,4-Cl₂—C₆H₃) | NCH₃ |
| Ia1.1381 | OCH₃ | H | CH₂CH(CH₃)—O-(2,4-Cl₂—C₆H₃) | NCH₃ |
| Ia1.1382 | OCH₃ | CH₃ | CH₂CH(CH₃)—O-(2,4-Cl₂—C₆H₃) | NCH₃ |
| Ia1.1383 | OCH₃ | CH₂CH₃ | CH₂CH(CH₃)—O-(2,4-Cl₂—C₆H₃) | NCH₃ |
| Ia1.1384 | OCH₃ | (CH₂)₂CH₃ | CH₂CH(CH₃)—O-(2,4-Cl₂—C₆H₃) | NCH₃ |
| Ia1.1385 | OCH₃ | (CH₂)₃CH₃ | CH₂CH(CH₃)—O-(2,4-Cl₂—C₆H₃) | NCH₃ |
| Ia1.1386 | OCH₃ | H | CH(CH₃)CH₂—O-(2,4-Cl₂—C₆H₃) | NCH₃ |
| Ia1.1387 | OCH₃ | CH₃ | CH(CH₃)CH₂—O-(2,4-Cl₂—C₆H₃) | NCH₃ |
| Ia1.1388 | OCH₃ | CH₂CH₃ | CH(CH₃)CH₂—O-(2,4-Cl₂—C₆H₃) | NCH₃ |
| Ia1.1389 | OCH₃ | (CH₂)₂CH₃ | CH(CH₃)CH₂—O-(2,4-Cl₂—C₆H₃) | NCH₃ |
| Ia1.1390 | OCH₃ | (CH₂)₃CH₃ | CH(CH₃)CH₂—O-(2,4-Cl₂—C₆H₃) | NCH₃ |
| Ia1.1391 | OCH₃ | H | CH(CH₃)CH(CH₃)—O-(2,4-Cl₂—C₆H₃) | NCH₃ |
| Ia1.1392 | OCH₃ | CH₃ | CH(CH₃)CH(CH₃)—O-(2,4-Cl₂—C₆H₃) | NCH₃ |
| Ia1.1393 | OCH₃ | CH₂CH₃ | CH(CH₃)CH(CH₃)—O-(2,4-Cl₂—C₆H₃) | NCH₃ |
| Ia1.1394 | OCH₃ | (CH₂)₂CH₃ | CH(CH₃)CH(CH₃)—O-(2,4-Cl₂—C₆H₃) | NCH₃ |
| Ia1.1395 | OCH₃ | (CH₂)₃CH₃ | CH(CH₃)CH(CH₃)—O-(2,4-Cl₂—C₆H₃) | NCH₃ |
| Ia1.1396 | CF₃ | H | CH₃ | O |
| Ia1.1397 | CF₃ | CH₃ | CH₃ | O |
| Ia1.1398 | CF₃ | CH₂CH₃ | CH₃ | O |
| Ia1.1399 | CF₃ | (CH₂)₂CH₃ | CH₃ | O |
| Ia1.1400 | CF₃ | (CH₂)₃CH₃ | CH₃ | O |
| Ia1.1401 | CF₃ | H | C₂H₅ | O |
| Ia1.1402 | CF₃ | CH₃ | C₂H₅ | O |
| Ia1.1403 | CF₃ | CH₂CH₃ | C₂H₅ | O |
| Ia1.1404 | CF₃ | (CH₂)₂CH₃ | C₂H₅ | O |
| Ia1.1405 | CF₃ | (CH₂)₃CH₃ | C₂H₅ | O |
| Ia1.1406 | CF₃ | H | (CH₂)₂CH₃ | O |
| Ia1.1407 | CF₃ | CH₃ | (CH₂)₂CH₃ | O |
| Ia1.1408 | CF₃ | CH₂CH₃ | (CH₂)₂CH₃ | O |
| Ia1.1409 | CF₃ | (CH₂)₂CH₃ | (CH₂)₂CH₃ | O |
| Ia1.1410 | CF₃ | (CH₂)₃CH₃ | (CH₂)₂CH₃ | O |
| Ia1.1411 | CF₃ | H | CH(CH₃)₂ | O |
| Ia1.1412 | CF₃ | CH₃ | CH(CH₃)₂ | O |
| Ia1.1413 | CF₃ | CH₂CH₃ | CH(CH₃)₂ | O |
| Ia1.1414 | CF₃ | (CH₂)₂CH₃ | CH(CH₃)₂ | O |
| Ia1.1415 | CF₃ | (CH₂)₃CH₃ | CH(CH₃)₂ | O |
| Ia1.1416 | CF₃ | H | (CH₂)₃CH₃ | O |
| Ia1.1417 | CF₃ | CH₃ | (CH₂)₃CH₃ | O |
| Ia1.1418 | CF₃ | CH₂CH₃ | (CH₂)₃CH₃ | O |
| Ia1.1419 | CF₃ | (CH₂)₂CH₃ | (CH₂)₃CH₃ | O |
| Ia1.1420 | CF₃ | (CH₂)₃CH₃ | (CH₂)₃CH₃ | O |
| Ia1.1421 | CF₃ | H | CH₂CH(CH₃)₂ | O |
| Ia1.1422 | CF₃ | CH₃ | CH₂CH(CH₃)₂ | O |
| Ia1.1423 | CF₃ | CH₂CH₃ | CH₂CH(CH₃)₂ | O |
| Ia1.1424 | CF₃ | (CH₂)₂CH₃ | CH₂CH(CH₃)₂ | O |
| Ia1.1425 | CF₃ | (CH₂)₃CH₃ | CH₂CH(CH₃)₂ | O |
| Ia1.1426 | CF₃ | H | CH(CH₃)CH₂CH₃ | O |
| Ia1.1427 | CF₃ | CH₃ | CH(CH₃)CH₂CH₃ | O |
| Ia1.1428 | CF₃ | CH₂CH₃ | CH(CH₃)CH₂CH₃ | O |
| Ia1.1429 | CF₃ | (CH₂)₂CH₃ | CH(CH₃)CH₂CH₃ | O |
| Ia1.1430 | CF₃ | (CH₂)₃CH₃ | CH(CH₃)CH₂CH₃ | O |
| Ia1.1431 | CF₃ | H | (CH₂)₂—C₆H₅ | O |
| Ia1.1432 | CF₃ | CH₃ | (CH₂)₂—C₆H₅ | O |
| Ia1.1433 | CF₃ | CH₂CH₃ | (CH₂)₂—C₆H₅ | O |
| Ia1.1434 | CF₃ | (CH₂)₂CH₃ | (CH₂)₂—C₆H₅ | O |

TABLE 1-continued

| No. | $R^2$ | $R^3$ | $R^4$ | Z |
|---|---|---|---|---|
| Ia1.1435 | $CF_3$ | $(CH_2)_3CH_3$ | $(CH_2)_2-C_6H_5$ | O |
| Ia1.1436 | $CF_3$ | H | $CH_2CH(CH_3)-C_6H_5$ | O |
| Ia1.1437 | $CF_3$ | $CH_3$ | $CH_2CH(CH_3)-C_6H_5$ | O |
| Ia1.1438 | $CF_3$ | $CH_2CH_3$ | $CH_2CH(CH_3)-C_6H_5$ | O |
| Ia1.1439 | $CF_3$ | $(CH_2)_2CH_3$ | $CH_2CH(CH_3)-C_6H_5$ | O |
| Ia1.1440 | $CF_3$ | $(CH_2)_3CH_3$ | $CH_2CH(CH_3)-C_6H_5$ | O |
| Ia1.1441 | $CF_3$ | H | $CH(CH_3)CH_2-C_6H_5$ | O |
| Ia1.1442 | $CF_3$ | $CH_3$ | $CH(CH_3)CH_2-C_6H_5$ | O |
| Ia1.1443 | $CF_3$ | $CH_2CH_3$ | $CH(CH_3)CH_2-C_6H_5$ | O |
| Ia1.1444 | $CF_3$ | $(CH_2)_2CH_3$ | $CH(CH_3)CH_2-C_6H_5$ | O |
| Ia1.1445 | $CF_3$ | $(CH_2)_3CH_3$ | $CH(CH_3)CH_2-C_6H_5$ | O |
| Ia1.1446 | $CF_3$ | H | $CH(CH_3)CH(CH_3)-C_6H_5$ | O |
| Ia1.1447 | $CF_3$ | $CH_3$ | $CH(CH_3)CH(CH_3)-C_6H_5$ | O |
| Ia1.1448 | $CF_3$ | $CH_2CH_3$ | $CH(CH_3)CH(CH_3)-C_6H_5$ | O |
| Ia1.1449 | $CF_3$ | $(CH_2)_2CH_3$ | $CH(CH_3)CH(CH_3)-C_6H_5$ | O |
| Ia1.1450 | $CF_3$ | $(CH_2)_3CH_3$ | $CH(CH_3)CH(CH_3)-C_6H_5$ | O |
| Ia1.1451 | $CF_3$ | H | $(CH_2)_2-(4-Cl-C_6H_4)$ | O |
| Ia1.1452 | $CF_3$ | $CH_3$ | $(CH_2)_2-(4-Cl-C_6H_4)$ | O |
| Ia1.1453 | $CF_3$ | $CH_2CH_3$ | $(CH_2)_2-(4-Cl-C_6H_4)$ | O |
| Ia1.1454 | $CF_3$ | $(CH_2)_2CH_3$ | $(CH_2)_2-(4-Cl-C_6H_4)$ | O |
| Ia1.1455 | $CF_3$ | $(CH_2)_3CH_3$ | $(CH_2)_2-(4-Cl-C_6H_4)$ | O |
| Ia1.1456 | $CF_3$ | H | $CH_2CH(CH_3)-(4-Cl-C_6H_4)$ | O |
| Ia1.1457 | $CF_3$ | $CH_3$ | $CH_2CH(CH_3)-(4-Cl-C_6H_4)$ | O |
| Ia1.1458 | $CF_3$ | $CH_2CH_3$ | $CH_2CH(CH_3)-(4-Cl-C_6H_4)$ | O |
| Ia1.1459 | $CF_3$ | $(CH_2)_2CH_3$ | $CH_2CH(CH_3)-(4-Cl-C_6H_4)$ | O |
| Ia1.1460 | $CF_3$ | $(CH_2)_3CH_3$ | $CH_2CH(CH_3)-(4-Cl-C_6H_4)$ | O |
| Ia1.1461 | $CF_3$ | H | $CH(CH_3)CH_2-(4-Cl-C_6H_4)$ | O |
| Ia1.1462 | $CF_3$ | $CH_3$ | $CH(CH_3)CH_2-(4-Cl-C_6H_4)$ | O |
| Ia1.1463 | $CF_3$ | $CH_2CH_3$ | $CH(CH_3)CH_2-(4-Cl-C_6H_4)$ | O |
| Ia1.1464 | $CF_3$ | $(CH_2)_2CH_3$ | $CH(CH_3)CH_2-(4-Cl-C_6H_4)$ | O |
| Ia1.1465 | $CF_3$ | $(CH_2)_3CH_3$ | $CH(CH_3)CH_2-(4-Cl-C_6H_4)$ | O |
| Ia1.1466 | $CF_3$ | H | $CH(CH_3)CH(CH_3)-(4-Cl-C_6H_4)$ | O |
| Ia1.1467 | $CF_3$ | $CH_3$ | $CH(CH_3)CH(CH_3)-(4-Cl-C_6H_4)$ | O |
| Ia1.1468 | $CF_3$ | $CH_2CH_3$ | $CH(CH_3)CH(CH_3)-(4-Cl-C_6H_4)$ | O |
| Ia1.1469 | $CF_3$ | $(CH_2)_2CH_3$ | $CH(CH_3)CH(CH_3)-(4-Cl-C_6H_4)$ | O |
| Ia1.1470 | $CF_3$ | $(CH_2)_3CH_3$ | $CH(CH_3)CH(CH_3)-(4-Cl-C_6H_4)$ | O |
| Ia1.1471 | $CF_3$ | H | $(CH_2)_2-(2,4-Cl_2-C_6H_3)$ | O |
| Ia1.1472 | $CF_3$ | $CH_3$ | $(CH_2)_2-(2,4-Cl_2-C_6H_3)$ | O |
| Ia1.1473 | $CF_3$ | $CH_2CH_3$ | $(CH_2)_2-(2,4-Cl_2-C_6H_3)$ | O |
| Ia1.1474 | $CF_3$ | $(CH_2)_2CH_3$ | $(CH_2)_2-(2,4-Cl_2-C_6H_3)$ | O |
| Ia1.1475 | $CF_3$ | $(CH_2)_3CH_3$ | $(CH_2)_2-(2,4-Cl_2-C_6H_3)$ | O |
| Ia1.1476 | $CF_3$ | H | $CH_2CH(CH_3)-(2,4-Cl_2-C_6H_3)$ | O |
| Ia1.1477 | $CF_3$ | $CH_3$ | $CH_2CH(CH_3)-(2,4-Cl_2-C_6H_3)$ | O |
| Ia1.1478 | $CF_3$ | $CH_2CH_3$ | $CH_2CH(CH_3)-(2,4-Cl_2-C_6H_3)$ | O |
| Ia1.1479 | $CF_3$ | $(CH_2)_2CH_3$ | $CH_2CH(CH_3)-(2,4-Cl_2-C_6H_3)$ | O |
| Ia1.1480 | $CF_3$ | $(CH_2)_3CH_3$ | $CH_2CH(CH_3)-(2,4-Cl_2-C_6H_3)$ | O |
| Ia1.1481 | $CF_3$ | H | $CH(CH_3)CH_2-(2,4-Cl_2-C_6H_3)$ | O |
| Ia1.1482 | $CF_3$ | $CH_3$ | $CH(CH_3)CH_2-(2,4-Cl_2-C_6H_3)$ | O |
| Ia1.1483 | $CF_3$ | $CH_2CH_3$ | $CH(CH_3)CH_2-(2,4-Cl_2-C_6H_3)$ | O |
| Ia1.1484 | $CF_3$ | $(CH_2)_2CH_3$ | $CH(CH_3)CH_2-(2,4-Cl_2-C_6H_3)$ | O |
| Ia1.1485 | $CF_3$ | $(CH_2)_3CH_3$ | $CH(CH_3)CH_2-(2,4-Cl_2-C_6H_3)$ | O |
| Ia1.1486 | $CF_3$ | H | $CH(CH_3)CH(CH_3)-(2,4-Cl_2-C_6H_3)$ | O |
| Ia1.1487 | $CF_3$ | $CH_3$ | $CH(CH_3)CH(CH_3)-(2,4-Cl_2-C_6H_3)$ | O |
| Ia1.1488 | $CF_3$ | $CH_2CH_3$ | $CH(CH_3)CH(CH_3)-(2,4-Cl_2-C_6H_3)$ | O |
| Ia1.1489 | $CF_3$ | $(CH_2)_2CH_3$ | $CH(CH_3)CH(CH_3)-(2,4-Cl_2-C_6H_3)$ | O |
| Ia1.1490 | $CF_3$ | $(CH_2)_3CH_3$ | $CH(CH_3)CH(CH_3)-(2,4-Cl_2-C_6H_3)$ | O |
| Ia1.1491 | $CF_3$ | H | $(CH_2)_2-O-C_6H_5$ | O |
| Ia1.1492 | $CF_3$ | $CH_3$ | $(CH_2)_2-O-C_6H_5$ | O |
| Ia1.1493 | $CF_3$ | $CH_2CH_3$ | $(CH_2)_2-O-C_6H_5$ | O |
| Ia1.1494 | $CF_3$ | $(CH_2)_2CH_3$ | $(CH_2)_2-O-C_6H_5$ | O |
| Ia1.1495 | $CF_3$ | $(CH_2)_3CH_3$ | $(CH_2)_2-O-C_6H_5$ | O |
| Ia1.1496 | $CF_3$ | H | $CH_2CH(CH_3)-O-C_6H_5$ | O |
| Ia1.1497 | $CF_3$ | $CH_3$ | $CH_2CH(CH_3)-O-C_6H_5$ | O |
| Ia1.1498 | $CF_3$ | $CH_2CH_3$ | $CH_2CH(CH_3)-O-C_6H_5$ | O |
| Ia1.1499 | $CF_3$ | $(CH_2)_2CH_3$ | $CH_2CH(CH_3)-O-C_6H_5$ | O |
| Ia1.1500 | $CF_3$ | $(CH_2)_3CH_3$ | $CH_2CH(CH_3)-O-C_6H_5$ | O |
| Ia1.1501 | $CF_3$ | H | $CH(CH_3)CH_2-O-C_6H_5$ | O |
| Ia1.1502 | $CF_3$ | $CH_3$ | $CH(CH_3)CH_2-O-C_6H_5$ | O |
| Ia1.1503 | $CF_3$ | $CH_2CH_3$ | $CH(CH_3)CH_2-O-C_6H_5$ | O |
| Ia1.1504 | $CF_3$ | $(CH_2)_2CH_3$ | $CH(CH_3)CH_2-O-C_6H_5$ | O |
| Ia1.1505 | $CF_3$ | $(CH_2)_3CH_3$ | $CH(CH_3)CH_2-O-C_6H_5$ | O |
| Ia1.1506 | $CF_3$ | H | $CH(CH_3)CH(CH_3)-O-C_6H_5$ | O |
| Ia1.1507 | $CF_3$ | $CH_3$ | $CH(CH_3)CH(CH_3)-O-C_6H_5$ | O |
| Ia1.1508 | $CF_3$ | $CH_2CH_3$ | $CH(CH_3)CH(CH_3)-O-C_6H_5$ | O |
| Ia1.1509 | $CF_3$ | $(CH_2)_2CH_3$ | $CH(CH_3)CH(CH_3)-O-C_6H_5$ | O |
| Ia1.1510 | $CF_3$ | $(CH_2)_3CH_3$ | $CH(CH_3)CH(CH_3)-O-C_6H_5$ | O |
| Ia1.1511 | $CF_3$ | H | $(CH_2)_2-O-(4-Cl-C_6H_4)$ | O |

TABLE 1-continued

| No. | R² | R³ | R⁴ | Z |
|---|---|---|---|---|
| Ia1.1512 | CF₃ | CH₃ | (CH₂)₂—O-(4-Cl—C₆H₄) | O |
| Ia1.1513 | CF₃ | CH₂CH₃ | (CH₂)₂—O-(4-Cl—C₆H₄) | O |
| Ia1.1514 | CF₃ | (CH₂)₂CH₃ | (CH₂)₂—O-(4-Cl—C₆H₄) | O |
| Ia1.1515 | CF₃ | (CH₂)₃CH₃ | (CH₂)₂—O-(4-Cl—C₆H₄) | O |
| Ia1.1516 | CF₃ | H | CH₂CH(CH₃)—O-(4-Cl—C₆H₄) | O |
| Ia1.1517 | CF₃ | CH₃ | CH₂CH(CH₃)—O-(4-Cl—C₆H₄) | O |
| Ia1.1518 | CF₃ | CH₂CH₃ | CH₂CH(CH₃)—O-(4-Cl—C₆H₄) | O |
| Ia1.1519 | CF₃ | (CH₂)₂CH₃ | CH₂CH(CH₃)—O-(4-Cl—C₆H₄) | O |
| Ia1.1520 | CF₃ | (CH₂)₃CH₃ | CH₂CH(CH₃)—O-(4-Cl—C₆H₄) | O |
| Ia1.1521 | CF₃ | H | CH(CH₃)CH₂—O-(4-Cl—C₆H₄) | O |
| Ia1.1522 | CF₃ | CH₃ | CH(CH₃)CH₂—O-(4-Cl—C₆H₄) | O |
| Ia1.1523 | CF₃ | CH₂CH₃ | CH(CH₃)CH₂—O-(4-Cl—C₆H₄) | O |
| Ia1.1524 | CF₃ | (CH₂)₂CH₃ | CH(CH₃)CH₂—O-(4-Cl—C₆H₄) | O |
| Ia1.1525 | CF₃ | (CH₂)₃CH₃ | CH(CH₃)CH₂—O-(4-Cl—C₆H₄) | O |
| Ia1.1526 | CF₃ | H | CH(CH₃)CH(CH₃)—O-(4-Cl—C₆H₄) | O |
| Ia1.1527 | CF₃ | CH₃ | CH(CH₃)CH(CH₃)—O-(4-Cl—C₆H₄) | O |
| Ia1.1528 | CF₃ | CH₂CH₃ | CH(CH₃)CH(CH₃)—O-(4-Cl—C₆H₄) | O |
| Ia1.1529 | CF₃ | (CH₂)₂CH₃ | CH(CH₃)CH(CH₃)—O-(4-Cl—C₆H₄) | O |
| Ia1.1530 | CF₃ | (CH₂)₃CH₃ | CH(CH₃)CH(CH₃)—O-(4-Cl—C₆H₄) | O |
| Ia1.1531 | CF₃ | H | (CH₂)₂—O-(2,4-Cl₂—C₆H₃) | O |
| Ia1.1532 | CF₃ | CH₃ | (CH₂)₂—O-(2,4-Cl₂—C₆H₃) | O |
| Ia1.1533 | CF₃ | CH₂CH₃ | (CH₂)₂—O-(2,4-Cl₂—C₆H₃) | O |
| Ia1.1534 | CF₃ | (CH₂)₂CH₃ | (CH₂)₂—O-(2,4-Cl₂—C₆H₃) | O |
| Ia1.1535 | CF₃ | (CH₂)₃CH₃ | (CH₂)₂—O-(2,4-Cl₂—C₆H₃) | O |
| Ia1.1536 | CF₃ | H | CH₂CH(CH₃)—O-(2,4-Cl₂—C₆H₃) | O |
| Ia1.1537 | CF₃ | CH₃ | CH₂CH(CH₃)—O-(2,4-Cl₂—C₆H₃) | O |
| Ia1.1538 | CF₃ | CH₂CH₃ | CH₂CH(CH₃)—O-(2,4-Cl₂—C₆H₃) | O |
| Ia1.1539 | CF₃ | (CH₂)₂CH₃ | CH₂CH(CH₃)—O-(2,4-Cl₂—C₆H₃) | O |
| Ia1.1540 | CF₃ | (CH₂)₃CH₃ | CH₂CH(CH₃)—O-(2,4-Cl₂—C₆H₃) | O |
| Ia1.1541 | CF₃ | H | CH(CH₃)CH₂—O-(2,4-Cl₂—C₆H₃) | O |
| Ia1.1542 | CF₃ | CH₃ | CH(CH₃)CH₂—O-(2,4-Cl₂—C₆H₃) | O |
| Ia1.1543 | CF₃ | CH₂CH₃ | CH(CH₃)CH₂—O-(2,4-Cl₂—C₆H₃) | O |
| Ia1.1544 | CF₃ | (CH₂)₂CH₃ | CH(CH₃)CH₂—O-(2,4-Cl₂—C₆H₃) | O |
| Ia1.1545 | CF₃ | (CH₂)₃CH₃ | CH(CH₃)CH₂—O-(2,4-Cl₂—C₆H₃) | O |
| Ia1.1546 | CF₃ | H | CH(CH₃)CH(CH₃)—O-(2,4-Cl₂—C₆H₃) | O |
| Ia1.1547 | CF₃ | CH₃ | CH(CH₃)CH(CH₃)—O-(2,4-Cl₂—C₆H₃) | O |
| Ia1.1548 | CF₃ | CH₂CH₃ | CH(CH₃)CH(CH₃)—O-(2,4-Cl₂—C₆H₃) | O |
| Ia1.1549 | CF₃ | (CH₂)₂CH₃ | CH(CH₃)CH(CH₃)—O-(2,4-Cl₂—C₆H₃) | O |
| Ia1.1550 | CF₃ | (CH₂)₃CH₃ | CH(CH₃)CH(CH₃)—O-(2,4-Cl₂—C₆H₃) | O |
| Ia1.1551 | CF₃ | H | CH₃ | NH |
| Ia1.1552 | CF₃ | CH₃ | CH₃ | NH |
| Ia1.1553 | CF₃ | CH₂CH₃ | CH₃ | NH |
| Ia1.1554 | CF₃ | (CH₂)₂CH₃ | CH₃ | NH |
| Ia1.1555 | CF₃ | (CH₂)₃CH₃ | CH₃ | NH |
| Ia1.1556 | CF₃ | H | C₂H₅ | NH |
| Ia1.1557 | CF₃ | CH₃ | C₂H₅ | NH |
| Ia1.1558 | CF₃ | CH₂CH₃ | C₂H₅ | NH |
| Ia1.1559 | CF₃ | (CH₂)₂CH₃ | C₂H₅ | NH |
| Ia1.1560 | CF₃ | (CH₂)₃CH₃ | C₂H₅ | NH |
| Ia1.1561 | CF₃ | H | (CH₂)₂CH₃ | NH |
| Ia1.1562 | CF₃ | CH₃ | (CH₂)₂CH₃ | NH |
| Ia1.1563 | CF₃ | CH₂CH₃ | (CH₂)₂CH₃ | NH |
| Ia1.1564 | CF₃ | (CH₂)₂CH₃ | (CH₂)₂CH₃ | NH |
| Ia1.1565 | CF₃ | (CH₂)₃CH₃ | (CH₂)₂CH₃ | NH |
| Ia1.1566 | CF₃ | H | CH(CH₃)₂ | NH |
| Ia1.1567 | CF₃ | CH₃ | CH(CH₃)₂ | NH |
| Ia1.1568 | CF₃ | CH₂CH₃ | CH(CH₃)₂ | NH |
| Ia1.1569 | CF₃ | (CH₂)₂CH₃ | CH(CH₃)₂ | NH |
| Ia1.1570 | CF₃ | (CH₂)₃CH₃ | CH(CH₃)₂ | NH |
| Ia1.1571 | CF₃ | H | (CH₂)₃CH₃ | NH |
| Ia1.1572 | CF₃ | CH₃ | (CH₂)₃CH₃ | NH |
| Ia1.1573 | CF₃ | CH₂CH₃ | (CH₂)₃CH₃ | NH |
| Ia1.1574 | CF₃ | (CH₂)₂CH₃ | (CH₂)₃CH₃ | NH |
| Ia1.1575 | CF₃ | (CH₂)₃CH₃ | (CH₂)₃CH₃ | NH |
| Ia1.1576 | CF₃ | H | CH₂CH(CH₃)₂ | NH |
| Ia1.1577 | CF₃ | CH₃ | CH₂CH(CH₃)₂ | NH |
| Ia1.1578 | CF₃ | CH₂CH₃ | CH₂CH(CH₃)₂ | NH |
| Ia1.1579 | CF₃ | (CH₂)₂CH₃ | CH₂CH(CH₃)₂ | NH |
| Ia1.1580 | CF₃ | (CH₂)₃CH₃ | CH₂CH(CH₃)₂ | NH |
| Ia1.1581 | CF₃ | H | CH(CH₃)CH₂CH₃ | NH |
| Ia1.1582 | CF₃ | CH₃ | CH(CH₃)CH₂CH₃ | NH |
| Ia1.1583 | CF₃ | CH₂CH₃ | CH(CH₃)CH₂CH₃ | NH |
| Ia1.1584 | CF₃ | (CH₂)₂CH₃ | CH(CH₃)CH₂CH₃ | NH |
| Ia1.1585 | CF₃ | (CH₂)₃CH₃ | CH(CH₃)CH₂CH₃ | NH |
| Ia1.1586 | CF₃ | H | (CH₂)₂—C₆H₅ | NH |
| Ia1.1587 | CF₃ | CH₃ | (CH₂)₂—C₆H₅ | NH |
| Ia1.1588 | CF₃ | CH₂CH₃ | (CH₂)₂—C₆H₅ | NH |

TABLE 1-continued

| No. | R² | R³ | R⁴ | Z |
|---|---|---|---|---|
| Ia1.1589 | CF₃ | (CH₂)₂CH₃ | (CH₂)₂—C₆H₅ | NH |
| Ia1.1590 | CF₃ | (CH₂)₃CH₃ | (CH₂)₂—C₆H₅ | NH |
| Ia1.1591 | CF₃ | H | CH₂CH(CH₃)—C₆H₅ | NH |
| Ia1.1592 | CF₃ | CH₃ | CH₂CH(CH₃)—C₆H₅ | NH |
| Ia1.1593 | CF₃ | CH₂CH₃ | CH₂CH(CH₃)—C₆H₅ | NH |
| Ia1.1594 | CF₃ | (CH₂)₂CH₃ | CH₂CH(CH₃)—C₆H₅ | NH |
| Ia1.1595 | CF₃ | (CH₂)₃CH₃ | CH₂CH(CH₃)—C₆H₅ | NH |
| Ia1.1596 | CF₃ | H | CH(CH₃)CH₂—C₆H₅ | NH |
| Ia1.1597 | CF₃ | CH₃ | CH(CH₃)CH₂—C₆H₅ | NH |
| Ia1.1598 | CF₃ | CH₂CH₃ | CH(CH₃)CH₂—C₆H₅ | NH |
| Ia1.1599 | CF₃ | (CH₂)₂CH₃ | CH(CH₃)CH₂—C₆H₅ | NH |
| Ia1.1600 | CF₃ | (CH₂)₃CH₃ | CH(CH₃)CH₂—C₆H₅ | NH |
| Ia1.1601 | CF₃ | H | CH(CH₃)CH(CH₃)—C₆H₅ | NH |
| Ia1.1602 | CF₃ | CH₃ | CH(CH₃)CH(CH₃)—C₆H₅ | NH |
| Ia1.1603 | CF₃ | CH₂CH₃ | CH(CH₃)CH(CH₃)—C₆H₅ | NH |
| Ia1.1604 | CF₃ | (CH₂)₂CH₃ | CH(CH₃)CH(CH₃)—C₆H₅ | NH |
| Ia1.1605 | CF₃ | (CH₂)₃CH₃ | CH(CH₃)CH(CH₃)—C₆H₅ | NH |
| Ia1.1606 | CF₃ | H | (CH₂)₂-(4-Cl—C₆H₄) | NH |
| Ia1.1607 | CF₃ | CH₃ | (CH₂)₂-(4-Cl—C₆H₄) | NH |
| Ia1.1608 | CF₃ | CH₂CH₃ | (CH₂)₂-(4-Cl—C₆H₄) | NH |
| Ia1.1609 | CF₃ | (CH₂)₂CH₃ | (CH₂)₂-(4-Cl—C₆H₄) | NH |
| Ia1.1610 | CF₃ | (CH₂)₃CH₃ | (CH₂)₂-(4-Cl—C₆H₄) | NH |
| Ia1.1611 | CF₃ | H | CH₂CH(CH₃)-(4-Cl—C₆H₄) | NH |
| Ia1.1612 | CF₃ | CH₃ | CH₂CH(CH₃)-(4-Cl—C₆H₄) | NH |
| Ia1.1613 | CF₃ | CH₂CH₃ | CH₂CH(CH₃)-(4-Cl—C₆H₄) | NH |
| Ia1.1614 | CF₃ | (CH₂)₂CH₃ | CH₂CH(CH₃)-(4-Cl—C₆H₄) | NH |
| Ia1.1615 | CF₃ | (CH₂)₃CH₃ | CH₂CH(CH₃)-(4-Cl—C₆H₄) | NH |
| Ia1.1616 | CF₃ | H | CH(CH₃)CH₂-(4-Cl—C₆H₄) | NH |
| Ia1.1617 | CF₃ | CH₃ | CH(CH₃)CH₂-(4-Cl—C₆H₄) | NH |
| Ia1.1618 | CF₃ | CH₂CH₃ | CH(CH₃)CH₂-(4-Cl—C₆H₄) | NH |
| Ia1.1619 | CF₃ | (CH₂)₂CH₃ | CH(CH₃)CH₂-(4-Cl—C₆H₄) | NH |
| Ia1.1620 | CF₃ | (CH₂)₃CH₃ | CH(CH₃)CH₂-(4-Cl—C₆H₄) | NH |
| Ia1.1621 | CF₃ | H | CH(CH₃)CH(CH₃)-(4-Cl—C₆H₄) | NH |
| Ia1.1622 | CF₃ | CH₃ | CH(CH₃)CH(CH₃)-(4-Cl—C₆H₄) | NH |
| Ia1.1623 | CF₃ | CH₂CH₃ | CH(CH₃)CH(CH₃)-(4-Cl—C₆H₄) | NH |
| Ia1.1624 | CF₃ | (CH₂)₂CH₃ | CH(CH₃)CH(CH₃)-(4-Cl—C₆H₄) | NH |
| Ia1.1625 | CF₃ | (CH₂)₃CH₃ | CH(CH₃)CH(CH₃)-(4-Cl—C₆H₄) | NH |
| Ia1.1626 | CF₃ | H | (CH₂)₂-(2,4-Cl₂—C₆H₃) | NH |
| Ia1.1627 | CF₃ | CH₃ | (CH₂)₂-(2,4-Cl₂—C₆H₃) | NH |
| Ia1.1628 | CF₃ | CH₂CH₃ | (CH₂)₂-(2,4-Cl₂—C₆H₃) | NH |
| Ia1.1629 | CF₃ | (CH₂)₂CH₃ | (CH₂)₂-(2,4-Cl₂—C₆H₃) | NH |
| Ia1.1630 | CF₃ | (CH₂)₃CH₃ | (CH₂)₂-(2,4-Cl₂—C₆H₃) | NH |
| Ia1.1631 | CF₃ | H | CH₂CH(CH₃)-(2,4-Cl₂—C₆H₃) | NH |
| Ia1.1632 | CF₃ | CH₃ | CH₂CH(CH₃)-(2,4-Cl₂—C₆H₃) | NH |
| Ia1.1633 | CF₃ | CH₂CH₃ | CH₂CH(CH₃)-(2,4-Cl₂—C₆H₃) | NH |
| Ia1.1634 | CF₃ | (CH₂)₂CH₃ | CH₂CH(CH₃)-(2,4-Cl₂—C₆H₃) | NH |
| Ia1.1635 | CF₃ | (CH₂)₃CH₃ | CH₂CH(CH₃)-(2,4-Cl₂—C₆H₃) | NH |
| Ia1.1636 | CF₃ | H | CH(CH₃)CH₂-(2,4-Cl₂—C₆H₃) | NH |
| Ia1.1637 | CF₃ | CH₃ | CH(CH₃)CH₂-(2,4-Cl₂—C₆H₃) | NH |
| Ia1.1638 | CF₃ | CH₂CH₃ | CH(CH₃)CH₂-(2,4-Cl₂—C₆H₃) | NH |
| Ia1.1639 | CF₃ | (CH₂)₂CH₃ | CH(CH₃)CH₂-(2,4-Cl₂—C₆H₃) | NH |
| Ia1.1640 | CF₃ | (CH₂)₃CH₃ | CH(CH₃)CH₂-(2,4-Cl₂—C₆H₃) | NH |
| Ia1.1641 | CF₃ | H | CH(CH₃)CH(CH₃)-(2,4-Cl₂—C₆H₃) | NH |
| Ia1.1642 | CF₃ | CH₃ | CH(CH₃)CH(CH₃)-(2,4-Cl₂—C₆H₃) | NH |
| Ia1.1643 | CF₃ | CH₂CH₃ | CH(CH₃)CH(CH₃)-(2,4-Cl₂—C₆H₃) | NH |
| Ia1.1644 | CF₃ | (CH₂)₂CH₃ | CH(CH₃)CH(CH₃)-(2,4-Cl₂—C₆H₃) | NH |
| Ia1.1645 | CF₃ | (CH₂)₃CH₃ | CH(CH₃)CH(CH₃)-(2,4-Cl₂—C₆H₃) | NH |
| Ia1.1646 | CF₃ | H | (CH₂)₂—O—C₆H₅ | NH |
| Ia1.1647 | CF₃ | CH₃ | (CH₂)₂—O—C₆H₅ | NH |
| Ia1.1648 | CF₃ | CH₂CH₃ | (CH₂)₂—O—C₆H₅ | NH |
| Ia1.1649 | CF₃ | (CH₂)₂CH₃ | (CH₂)₂—O—C₆H₅ | NH |
| Ia1.1650 | CF₃ | (CH₂)₃CH₃ | (CH₂)₂—O—C₆H₅ | NH |
| Ia1.1651 | CF₃ | H | CH₂CH(CH₃)—O—C₆H₅ | NH |
| Ia1.1652 | CF₃ | CH₃ | CH₂CH(CH₃)—O—C₆H₅ | NH |
| Ia1.1653 | CF₃ | CH₂CH₃ | CH₂CH(CH₃)—O—C₆H₅ | NH |
| Ia1.1654 | CF₃ | (CH₂)₂CH₃ | CH₂CH(CH₃)—O—C₆H₅ | NH |
| Ia1.1655 | CF₃ | (CH₂)₃CH₃ | CH₂CH(CH₃)—O—C₆H₅ | NH |
| Ia1.1656 | CF₃ | H | CH(CH₃)CH₂—O—C₆H₅ | NH |
| Ia1.1657 | CF₃ | CH₃ | CH(CH₃)CH₂—O—C₆H₅ | NH |
| Ia1.1658 | CF₃ | CH₂CH₃ | CH(CH₃)CH₂—O—C₆H₅ | NH |
| Ia1.1659 | CF₃ | (CH₂)₂CH₃ | CH(CH₃)CH₂—O—C₆H₅ | NH |
| Ia1.1660 | CF₃ | (CH₂)₃CH₃ | CH(CH₃)CH₂—O—C₆H₅ | NH |
| Ia1.1661 | CF₃ | H | CH(CH₃)CH(CH₃)—O—C₆H₅ | NH |
| Ia1.1662 | CF₃ | CH₃ | CH(CH₃)CH(CH₃)—O—C₆H₅ | NH |
| Ia1.1663 | CF₃ | CH₂CH₃ | CH(CH₃)CH(CH₃)—O—C₆H₅ | NH |
| Ia1.1664 | CF₃ | (CH₂)₂CH₃ | CH(CH₃)CH(CH₃)—O—C₆H₅ | NH |
| Ia1.1665 | CF₃ | (CH₂)₃CH₃ | CH(CH₃)CH(CH₃)—O—C₆H₅ | NH |

TABLE 1-continued

| No. | R² | R³ | R⁴ | Z |
|---|---|---|---|---|
| Ia1.1666 | CF₃ | H | (CH₂)₂—O-(4-Cl—C₆H₄) | NH |
| Ia1.1667 | CF₃ | CH₃ | (CH₂)₂—O-(4-Cl—C₆H₄) | NH |
| Ia1.1668 | CF₃ | CH₂CH₃ | (CH₂)₂—O-(4-Cl—C₆H₄) | NH |
| Ia1.1669 | CF₃ | (CH₂)₂CH₃ | (CH₂)₂—O-(4-Cl—C₆H₄) | NH |
| Ia1.1670 | CF₃ | (CH₂)₃CH₃ | (CH₂)₂—O-(4-Cl—C₆H₄) | NH |
| Ia1.1671 | CF₃ | H | CH₂CH(CH₃)—O-(4-Cl—C₆H₄) | NH |
| Ia1.1672 | CF₃ | CH₃ | CH₂CH(CH₃)—O-(4-Cl—C₆H₄) | NH |
| Ia1.1673 | CF₃ | CH₂CH₃ | CH₂CH(CH₃)—O-(4-Cl—C₆H₄) | NH |
| Ia1.1674 | CF₃ | (CH₂)₂CH₃ | CH₂CH(CH₃)—O-(4-Cl—C₆H₄) | NH |
| Ia1.1675 | CF₃ | (CH₂)₃CH₃ | CH₂CH(CH₃)—O-(4-Cl—C₆H₄) | NH |
| Ia1.1676 | CF₃ | H | CH(CH₃)CH₂—O-(4-Cl—C₆H₄) | NH |
| Ia1.1677 | CF₃ | CH₃ | CH(CH₃)CH₂—O-(4-Cl—C₆H₄) | NH |
| Ia1.1678 | CF₃ | CH₂CH₃ | CH(CH₃)CH₂—O-(4-Cl—C₆H₄) | NH |
| Ia1.1679 | CF₃ | (CH₂)₂CH₃ | CH(CH₃)CH₂—O-(4-Cl—C₆H₄) | NH |
| Ia1.1680 | CF₃ | (CH₂)₃CH₃ | CH(CH₃)CH₂—O-(4-Cl—C₆H₄) | NH |
| Ia1.1681 | CF₃ | H | CH(CH₃)CH(CH₃)—O-(4-Cl—C₆H₄) | NH |
| Ia1.1682 | CF₃ | CH₃ | CH(CH₃)CH(CH₃)—O-(4-Cl—C₆H₄) | NH |
| Ia1.1683 | CF₃ | CH₂CH₃ | CH(CH₃)CH(CH₃)—O-(4-Cl—C₆H₄) | NH |
| Ia1.1684 | CF₃ | (CH₂)₂CH₃ | CH(CH₃)CH(CH₃)—O-(4-Cl—C₆H₄) | NH |
| Ia1.1685 | CF₃ | (CH₂)₃CH₃ | CH(CH₃)CH(CH₃)—O-(4-Cl—C₆H₄) | NH |
| Ia1.1686 | CF₃ | H | (CH₂)₂—O-(2,4-Cl₂—C₆H₃) | NH |
| Ia1.1687 | CF₃ | CH₃ | (CH₂)₂—O-(2,4-Cl₂—C₆H₃) | NH |
| Ia1.1688 | CF₃ | CH₂CH₃ | (CH₂)₂—O-(2,4-Cl₂—C₆H₃) | NH |
| Ia1.1689 | CF₃ | (CH₂)₂CH₃ | (CH₂)₂—O-(2,4-Cl₂—C₆H₃) | NH |
| Ia1.1690 | CF₃ | (CH₂)₃CH₃ | (CH₂)₂—O-(2,4-Cl₂—C₆H₃) | NH |
| Ia1.1691 | CF₃ | H | CH₂CH(CH₃)—O-(2,4-Cl₂—C₆H₃) | NH |
| Ia1.1692 | CF₃ | CH₃ | CH₂CH(CH₃)—O-(2,4-Cl₂—C₆H₃) | NH |
| Ia1.1693 | CF₃ | CH₂CH₃ | CH₂CH(CH₃)—O-(2,4-Cl₂—C₆H₃) | NH |
| Ia1.1694 | CF₃ | (CH₂)₂CH₃ | CH₂CH(CH₃)—O-(2,4-Cl₂—C₆H₃) | NH |
| Ia1.1695 | CF₃ | (CH₂)₃CH₃ | CH₂CH(CH₃)—O-(2,4-Cl₂—C₆H₃) | NH |
| Ia1.1696 | CF₃ | H | CH(CH₃)CH₂—O-(2,4-Cl₂—C₆H₃) | NH |
| Ia1.1697 | CF₃ | CH₃ | CH(CH₃)CH₂—O-(2,4-Cl₂—C₆H₃) | NH |
| Ia1.1698 | CF₃ | CH₂CH₃ | CH(CH₃)CH₂—O-(2,4-Cl₂—C₆H₃) | NH |
| Ia1.1699 | CF₃ | (CH₂)₂CH₃ | CH(CH₃)CH₂—O-(2,4-Cl₂—C₆H₃) | NH |
| Ia1.1700 | CF₃ | (CH₂)₃CH₃ | CH(CH₃)CH₂—O-(2,4-Cl₂—C₆H₃) | NH |
| Ia1.1701 | CF₃ | H | CH(CH₃)CH(CH₃)—O-(2,4-Cl₂—C₆H₃) | NH |
| Ia1.1702 | CF₃ | CH₃ | CH(CH₃)CH(CH₃)—O-(2,4-Cl₂—C₆H₃) | NH |
| Ia1.1703 | CF₃ | CH₂CH₃ | CH(CH₃)CH(CH₃)—O-(2,4-Cl₂—C₆H₃) | NH |
| Ia1.1704 | CF₃ | (CH₂)₂CH₃ | CH(CH₃)CH(CH₃)—O-(2,4-Cl₂—C₆H₃) | NH |
| Ia1.1705 | CF₃ | (CH₂)₃CH₃ | CH(CH₃)CH(CH₃)—O-(2,4-Cl₂—C₆H₃) | NH |
| Ia1.1706 | CF₃ | H | CH₃ | NCH₃ |
| Ia1.1707 | CF₃ | CH₃ | CH₃ | NCH₃ |
| Ia1.1708 | CF₃ | CH₂CH₃ | CH₃ | NCH₃ |
| Ia1.1709 | CF₃ | (CH₂)₂CH₃ | CH₃ | NCH₃ |
| Ia1.1710 | CF₃ | (CH₂)₃CH₃ | CH₃ | NCH₃ |
| Ia1.1711 | CF₃ | H | C₂H₅ | NCH₃ |
| Ia1.1712 | CF₃ | CH₃ | C₂H₅ | NCH₃ |
| Ia1.1713 | CF₃ | CH₂CH₃ | C₂H₅ | NCH₃ |
| Ia1.1714 | CF₃ | (CH₂)₂CH₃ | C₂H₅ | NCH₃ |
| Ia1.1715 | CF₃ | (CH₂)₃CH₃ | C₂H₅ | NCH₃ |
| Ia1.1716 | CF₃ | H | (CH₂)₂CH₃ | NCH₃ |
| Ia1.1717 | CF₃ | CH₃ | (CH₂)₂CH₃ | NCH₃ |
| Ia1.1718 | CF₃ | CH₂CH₃ | (CH₂)₂CH₃ | NCH₃ |
| Ia1.1719 | CF₃ | (CH₂)₂CH₃ | (CH₂)₂CH₃ | NCH₃ |
| Ia1.1720 | CF₃ | (CH₂)₃CH₃ | (CH₂)₂CH₃ | NCH₃ |
| Ia1.1721 | CF₃ | H | CH(CH₃)₂ | NCH₃ |
| Ia1.1722 | CF₃ | CH₃ | CH(CH₃)₂ | NCH₃ |
| Ia1.1723 | CF₃ | CH₂CH₃ | CH(CH₃)₂ | NCH₃ |
| Ia1.1724 | CF₃ | (CH₂)₂CH₃ | CH(CH₃)₂ | NCH₃ |
| Ia1.1725 | CF₃ | (CH₂)₃CH₃ | CH(CH₃)₂ | NCH₃ |
| Ia1.1726 | CF₃ | H | (CH₂)₃CH₃ | NCH₃ |
| Ia1.1727 | CF₃ | CH₃ | (CH₂)₃CH₃ | NCH₃ |
| Ia1.1728 | CF₃ | CH₂CH₃ | (CH₂)₃CH₃ | NCH₃ |
| Ia1.1729 | CF₃ | (CH₂)₂CH₃ | (CH₂)₃CH₃ | NCH₃ |
| Ia1.1730 | CF₃ | (CH₂)₃CH₃ | (CH₂)₃CH₃ | NCH₃ |
| Ia1.1731 | CF₃ | H | CH₂CH(CH₃)₂ | NCH₃ |
| Ia1.1732 | CF₃ | CH₃ | CH₂CH(CH₃)₂ | NCH₃ |
| Ia1.1733 | CF₃ | CH₂CH₃ | CH₂CH(CH₃)₂ | NCH₃ |
| Ia1.1734 | CF₃ | (CH₂)₂CH₃ | CH₂CH(CH₃)₂ | NCH₃ |
| Ia1.1735 | CF₃ | (CH₂)₃CH₃ | CH₂CH(CH₃)₂ | NCH₃ |
| Ia1.1736 | CF₃ | H | CH(CH₃)CH₂CH₃ | NCH₃ |
| Ia1.1737 | CF₃ | CH₃ | CH(CH₃)CH₂CH₃ | NCH₃ |
| Ia1.1738 | CF₃ | CH₂CH₃ | CH(CH₃)CH₂CH₃ | NCH₃ |
| Ia1.1739 | CF₃ | (CH₂)₂CH₃ | CH(CH₃)CH₂CH₃ | NCH₃ |
| Ia1.1740 | CF₃ | (CH₂)₃CH₃ | CH(CH₃)CH₂CH₃ | NCH₃ |
| Ia1.1741 | CF₃ | H | (CH₂)₂—C₆H₅ | NCH₃ |
| Ia1.1742 | CF₃ | CH₃ | (CH₂)₂—C₆H₅ | NCH₃ |

TABLE 1-continued

| No. | R² | R³ | R⁴ | Z |
|---|---|---|---|---|
| Ia1.1743 | $CF_3$ | $CH_2CH_3$ | $(CH_2)_2$—$C_6H_5$ | $NCH_3$ |
| Ia1.1744 | $CF_3$ | $(CH_2)_2CH_3$ | $(CH_2)_2$—$C_6H_5$ | $NCH_3$ |
| Ia1.1745 | $CF_3$ | $(CH_2)_3CH_3$ | $(CH_2)_2$—$C_6H_5$ | $NCH_3$ |
| Ia1.1746 | $CF_3$ | H | $CH_2CH(CH_3)$—$C_6H_5$ | $NCH_3$ |
| Ia1.1747 | $CF_3$ | $CH_3$ | $CH_2CH(CH_3)$—$C_6H_5$ | $NCH_3$ |
| Ia1.1748 | $CF_3$ | $CH_2CH_3$ | $CH_2CH(CH_3)$—$C_6H_5$ | $NCH_3$ |
| Ia1.1749 | $CF_3$ | $(CH_2)_2CH_3$ | $CH_2CH(CH_3)$—$C_6H_5$ | $NCH_3$ |
| Ia1.1750 | $CF_3$ | $(CH_2)_3CH_3$ | $CH_2CH(CH_3)$—$C_6H_5$ | $NCH_3$ |
| Ia1.1751 | $CF_3$ | H | $CH(CH_3)CH_2$—$C_6H_5$ | $NCH_3$ |
| Ia1.1752 | $CF_3$ | $CH_3$ | $CH(CH_3)CH_2$—$C_6H_5$ | $NCH_3$ |
| Ia1.1753 | $CF_3$ | $CH_2CH_3$ | $CH(CH_3)CH_2$—$C_6H_5$ | $NCH_3$ |
| Ia1.1754 | $CF_3$ | $(CH_2)_2CH_3$ | $CH(CH_3)CH_2$—$C_6H_5$ | $NCH_3$ |
| Ia1.1755 | $CF_3$ | $(CH_2)_3CH_3$ | $CH(CH_3)CH_2$—$C_6H_5$ | $NCH_3$ |
| Ia1.1756 | $CF_3$ | H | $CH(CH_3)CH(CH_3)$—$C_6H_5$ | $NCH_3$ |
| Ia1.1757 | $CF_3$ | $CH_3$ | $CH(CH_3)CH(CH_3)$—$C_6H_5$ | $NCH_3$ |
| Ia1.1758 | $CF_3$ | $CH_2CH_3$ | $CH(CH_3)CH(CH_3)$—$C_6H_5$ | $NCH_3$ |
| Ia1.1759 | $CF_3$ | $(CH_2)_2CH_3$ | $CH(CH_3)CH(CH_3)$—$C_6H_5$ | $NCH_3$ |
| Ia1.1760 | $CF_3$ | $(CH_2)_3CH_3$ | $CH(CH_3)CH(CH_3)$—$C_6H_5$ | $NCH_3$ |
| Ia1.1761 | $CF_3$ | H | $(CH_2)_2$-(4-Cl—$C_6H_4$) | $NCH_3$ |
| Ia1.1762 | $CF_3$ | $CH_3$ | $(CH_2)_2$-(4-Cl—$C_6H_4$) | $NCH_3$ |
| Ia1.1763 | $CF_3$ | $CH_2CH_3$ | $(CH_2)_2$-(4-Cl—$C_6H_4$) | $NCH_3$ |
| Ia1.1764 | $CF_3$ | $(CH_2)_2CH_3$ | $(CH_2)_2$-(4-Cl—$C_6H_4$) | $NCH_3$ |
| Ia1.1765 | $CF_3$ | $(CH_2)_3CH_3$ | $(CH_2)_2$-(4-Cl—$C_6H_4$) | $NCH_3$ |
| Ia1.1766 | $CF_3$ | H | $CH_2CH(CH_3)$-(4-Cl—$C_6H_4$) | $NCH_3$ |
| Ia1.1767 | $CF_3$ | $CH_3$ | $CH_2CH(CH_3)$-(4-Cl—$C_6H_4$) | $NCH_3$ |
| Ia1.1768 | $CF_3$ | $CH_2CH_3$ | $CH_2CH(CH_3)$-(4-Cl—$C_6H_4$) | $NCH_3$ |
| Ia1.1769 | $CF_3$ | $(CH_2)_2CH_3$ | $CH_2CH(CH_3)$-(4-Cl—$C_6H_4$) | $NCH_3$ |
| Ia1.1770 | $CF_3$ | $(CH_2)_3CH_3$ | $CH_2CH(CH_3)$-(4-Cl—$C_6H_4$) | $NCH_3$ |
| Ia1.1771 | $CF_3$ | H | $CH(CH_3)CH_2$-(4-Cl—$C_6H_4$) | $NCH_3$ |
| Ia1.1772 | $CF_3$ | $CH_3$ | $CH(CH_3)CH_2$-(4-Cl—$C_6H_4$) | $NCH_3$ |
| Ia1.1773 | $CF_3$ | $CH_2CH_3$ | $CH(CH_3)CH_2$-(4-Cl—$C_6H_4$) | $NCH_3$ |
| Ia1.1774 | $CF_3$ | $(CH_2)_2CH_3$ | $CH(CH_3)CH_2$-(4-Cl—$C_6H_4$) | $NCH_3$ |
| Ia1.1775 | $CF_3$ | $(CH_2)_3CH_3$ | $CH(CH_3)CH_2$-(4-Cl—$C_6H_4$) | $NCH_3$ |
| Ia1.1776 | $CF_3$ | H | $CH(CH_3)CH(CH_3)$-(4-Cl—$C_6H_4$) | $NCH_3$ |
| Ia1.1777 | $CF_3$ | $CH_3$ | $CH(CH_3)CH(CH_3)$-(4-Cl—$C_6H_4$) | $NCH_3$ |
| Ia1.1778 | $CF_3$ | $CH_2CH_3$ | $CH(CH_3)CH(CH_3)$-(4-Cl—$C_6H_4$) | $NCH_3$ |
| Ia1.1779 | $CF_3$ | $(CH_2)_2CH_3$ | $CH(CH_3)CH(CH_3)$-(4-Cl—$C_6H_4$) | $NCH_3$ |
| Ia1.1780 | $CF_3$ | $(CH_2)_3CH_3$ | $CH(CH_3)CH(CH_3)$-(4-Cl—$C_6H_4$) | $NCH_3$ |
| Ia1.1781 | $CF_3$ | H | $(CH_2)_2$-(2,4-$Cl_2$—$C_6H_3$) | $NCH_3$ |
| Ia1.1782 | $CF_3$ | $CH_3$ | $(CH_2)_2$-(2,4-$Cl_2$—$C_6H_3$) | $NCH_3$ |
| Ia1.1783 | $CF_3$ | $CH_2CH_3$ | $(CH_2)_2$-(2,4-$Cl_2$—$C_6H_3$) | $NCH_3$ |
| Ia1.1784 | $CF_3$ | $(CH_2)_2CH_3$ | $(CH_2)_2$-(2,4-$Cl_2$—$C_6H_3$) | $NCH_3$ |
| Ia1.1785 | $CF_3$ | $(CH_2)_3CH_3$ | $(CH_2)_2$-(2,4-$Cl_2$—$C_6H_3$) | $NCH_3$ |
| Ia1.1786 | $CF_3$ | H | $CH_2CH(CH_3)$-(2,4-$Cl_2$—$C_6H_3$) | $NCH_3$ |
| Ia1.1787 | $CF_3$ | $CH_3$ | $CH_2CH(CH_3)$-(2,4-$Cl_2$—$C_6H_3$) | $NCH_3$ |
| Ia1.1788 | $CF_3$ | $CH_2CH_3$ | $CH_2CH(CH_3)$-(2,4-$Cl_2$—$C_6H_3$) | $NCH_3$ |
| Ia1.1789 | $CF_3$ | $(CH_2)_2CH_3$ | $CH_2CH(CH_3)$-(2,4-$Cl_2$—$C_6H_3$) | $NCH_3$ |
| Ia1.1790 | $CF_3$ | $(CH_2)_3CH_3$ | $CH_2CH(CH_3)$-(2,4-$Cl_2$—$C_6H_3$) | $NCH_3$ |
| Ia1.1791 | $CF_3$ | H | $CH(CH_3)CH_2$-(2,4-$Cl_2$—$C_6H_3$) | $NCH_3$ |
| Ia1.1792 | $CF_3$ | $CH_3$ | $CH(CH_3)CH_2$-(2,4-$Cl_2$—$C_6H_3$) | $NCH_3$ |
| Ia1.1793 | $CF_3$ | $CH_2CH_3$ | $CH(CH_3)CH_2$-(2,4-$Cl_2$—$C_6H_3$) | $NCH_3$ |
| Ia1.1794 | $CF_3$ | $(CH_2)_2CH_3$ | $CH(CH_3)CH_2$-(2,4-$Cl_2$—$C_6H_3$) | $NCH_3$ |
| Ia1.1795 | $CF_3$ | $(CH_2)_3CH_3$ | $CH(CH_3)CH_2$-(2,4-$Cl_2$—$C_6H_3$) | $NCH_3$ |
| Ia1.1796 | $CF_3$ | H | $CH(CH_3)CH(CH_3)$-(2,4-$Cl_2$—$C_6H_3$) | $NCH_3$ |
| Ia1.1797 | $CF_3$ | $CH_3$ | $CH(CH_3)CH(CH_3)$-(2,4-$Cl_2$—$C_6H_3$) | $NCH_3$ |
| Ia1.1798 | $CF_3$ | $CH_2CH_3$ | $CH(CH_3)CH(CH_3)$-(2,4-$Cl_2$—$C_6H_3$) | $NCH_3$ |
| Ia1.1799 | $CF_3$ | $(CH_2)_2CH_3$ | $CH(CH_3)CH(CH_3)$-(2,4-$Cl_2$—$C_6H_3$) | $NCH_3$ |
| Ia1.1800 | $CF_3$ | $(CH_2)_3CH_3$ | $CH(CH_3)CH(CH_3)$-(2,4-$Cl_2$—$C_6H_3$) | $NCH_3$ |
| Ia1.1801 | $CF_3$ | H | $(CH_2)_2$—O—$C_6H_5$ | $NCH_3$ |
| Ia1.1802 | $CF_3$ | $CH_3$ | $(CH_2)_2$—O—$C_6H_5$ | $NCH_3$ |
| Ia1.1803 | $CF_3$ | $CH_2CH_3$ | $(CH_2)_2$—O—$C_6H_5$ | $NCH_3$ |
| Ia1.1804 | $CF_3$ | $(CH_2)_2CH_3$ | $(CH_2)_2$—O—$C_6H_5$ | $NCH_3$ |
| Ia1.1805 | $CF_3$ | $(CH_2)_3CH_3$ | $(CH_2)_2$—O—$C_6H_5$ | $NCH_3$ |
| Ia1.1806 | $CF_3$ | H | $CH_2CH(CH_3)$—O—$C_6H_5$ | $NCH_3$ |
| Ia1.1807 | $CF_3$ | $CH_3$ | $CH_2CH(CH_3)$—O—$C_6H_5$ | $NCH_3$ |
| Ia1.1808 | $CF_3$ | $CH_2CH_3$ | $CH_2CH(CH_3)$—O—$C_6H_5$ | $NCH_3$ |
| Ia1.1809 | $CF_3$ | $(CH_2)_2CH_3$ | $CH_2CH(CH_3)$—O—$C_6H_5$ | $NCH_3$ |
| Ia1.1810 | $CF_3$ | $(CH_2)_3CH_3$ | $CH_2CH(CH_3)$—O—$C_6H_5$ | $NCH_3$ |
| Ia1.1811 | $CF_3$ | H | $CH(CH_3)CH_2$—O—$C_6H_5$ | $NCH_3$ |
| Ia1.1812 | $CF_3$ | $CH_3$ | $CH(CH_3)CH_2$—O—$C_6H_5$ | $NCH_3$ |
| Ia1.1813 | $CF_3$ | $CH_2CH_3$ | $CH(CH_3)CH_2$—O—$C_6H_5$ | $NCH_3$ |
| Ia1.1814 | $CF_3$ | $(CH_2)_2CH_3$ | $CH(CH_3)CH_2$—O—$C_6H_5$ | $NCH_3$ |
| Ia1.1815 | $CF_3$ | $(CH_2)_3CH_3$ | $CH(CH_3)CH_2$—O—$C_6H_5$ | $NCH_3$ |
| Ia1.1816 | $CF_3$ | H | $CH(CH_3)CH(CH_3)$—O—$C_6H_5$ | $NCH_3$ |
| Ia1.1817 | $CF_3$ | $CH_3$ | $CH(CH_3)CH(CH_3)$—O—$C_6H_5$ | $NCH_3$ |
| Ia1.1818 | $CF_3$ | $CH_2CH_3$ | $CH(CH_3)CH(CH_3)$—O—$C_6H_5$ | $NCH_3$ |
| Ia1.1819 | $CF_3$ | $(CH_2)_2CH_3$ | $CH(CH_3)CH(CH_3)$—O—$C_6H_5$ | $NCH_3$ |

TABLE 1-continued

| No. | R² | R³ | R⁴ | Z |
|---|---|---|---|---|
| Ia1.1820 | CF₃ | (CH₂)₃CH₃ | CH(CH₃)CH(CH₃)—O—C₆H₅ | NCH₃ |
| Ia1.1821 | CF₃ | H | (CH₂)₂—O-(4-Cl—C₆H₄) | NCH₃ |
| Ia1.1822 | CF₃ | CH₃ | (CH₂)₂—O-(4-Cl—C₆H₄) | NCH₃ |
| Ia1.1823 | CF₃ | CH₂CH₃ | (CH₂)₂—O-(4-Cl—C₆H₄) | NCH₃ |
| Ia1.1824 | CF₃ | (CH₂)₂CH₃ | (CH₂)₂—O-(4-Cl—C₆H₄) | NCH₃ |
| Ia1.1825 | CF₃ | (CH₂)₃CH₃ | (CH₂)₂—O-(4-Cl—C₆H₄) | NCH₃ |
| Ia1.1826 | CF₃ | H | CH₂CH(CH₃)—O-(4-Cl—C₆H₄) | NCH₃ |
| Ia1.1827 | CF₃ | CH₃ | CH₂CH(CH₃)—O-(4-Cl—C₆H₄) | NCH₃ |
| Ia1.1828 | CF₃ | CH₂CH₃ | CH₂CH (CH₃)—O-(4-Cl—C₆H₄) | NCH₃ |
| Ia1.1829 | CF₃ | (CH₂)₂CH₃ | CH₂CH(CH₃)—O-(4-Cl—C₆H₄) | NCH₃ |
| Ia1.1830 | CF₃ | (CH₂)₃CH₃ | CH₂CH(CH₃)—O-(4-Cl—C₆H₄) | NCH₃ |
| Ia1.1831 | CF₃ | H | CH(CH₃)CH₂—O-(4-Cl—C₆H₄) | NCH₃ |
| Ia1.1832 | CF₃ | CH₃ | CH(CH₃)CH₂—O-(4-Cl—C₆H₄) | NCH₃ |
| Ia1.1833 | CF₃ | CH₂CH₃ | CH (CH₃)CH₂—O-(4-Cl—C₆H₄) | NCH₃ |
| Ia1.1834 | CF₃ | (CH₂)₂CH₃ | CH(CH₃)CH₂—O-(4-Cl—C₆H₄) | NCH₃ |
| Ia1.1835 | CF₃ | (CH₂)₃CH₃ | CH(CH₃)CH₂—O-(4-Cl—C₆H₄) | NCH₃ |
| Ia1.1836 | CF₃ | H | CH(CH₃)CH(CH₃)—O-(4-Cl—C₆H₄) | NCH₃ |
| Ia1.1837 | CF₃ | CH₃ | CH(CH₃)CH(CH₃)—O-(4-Cl—C₆H₄) | NCH₃ |
| Ia1.1838 | CF₃ | CH₂CH₃ | CH(CH₃)CH(CH₃)—O-(4-Cl—C₆H₄) | NCH₃ |
| Ia1.1839 | CF₃ | (CH₂)₂CH₃ | CH(CH₃)CH(CH₃)—O-(4-Cl—C₆H₄) | NCH₃ |
| Ia1.1840 | CF₃ | (CH₂)₃CH₃ | CH(CH₃)CH(CH₃)—O-(4-Cl—C₆H₄) | NCH₃ |
| Ia1.1841 | CF₃ | H | (CH₂)₂—O-(2,4-Cl₂—C₆H₃) | NCH₃ |
| Ia1.1842 | CF₃ | CH₃ | (CH₂)₂—O-(2,4-Cl₂—C₆H₃) | NCH₃ |
| Ia1.1843 | CF₃ | CH₂CH₃ | (CH₂)₂—O-(2,4-Cl₂—C₆H₃) | NCH₃ |
| Ia1.1844 | CF₃ | (CH₂)₂CH₃ | (CH₂)₂—O-(2,4-Cl₂—C₆H₃) | NCH₃ |
| Ia1.1845 | CF₃ | (CH₂)₃CH₃ | (CH₂)₂—O-(2,4-Cl₂—C₆H₃) | NCH₃ |
| Ia1.1846 | CF₃ | H | CH₂CH(CH₃)—O-(2,4-Cl₂—C₆H₃) | NCH₃ |
| Ia1.1847 | CF₃ | CH₃ | CH₂CH(CH₃)—O-(2,4-Cl₂—C₆H₃) | NCH₃ |
| Ia1.1848 | CF₃ | CH₂CH₃ | CH₂CH(CH₃)—O-(2,4-Cl₂—C₆H₃) | NCH₃ |
| Ia1.1849 | CF₃ | (CH₂)₂CH₃ | CH₂CH(CH₃)—O-(2,4-Cl₂—C₆H₃) | NCH₃ |
| Ia1.1850 | CF₃ | (CH₂)₃CH₃ | CH₂CH(CH₃)—O-(2,4-Cl₂—C₆H₃) | NCH₃ |
| Ia1.1851 | CF₃ | H | CH(CH₃)CH₂—O-(2,4-Cl₂—C₆H₃) | NCH₃ |
| Ia1.1852 | CF₃ | CH₃ | CH(CH₃)CH₂—O-(2,4-Cl₂—C₆H₃) | NCH₃ |
| Ia1.1853 | CF₃ | CH₂CH₃ | CH(CH₃)CH₂—O-(2,4-Cl₂—C₆H₃) | NCH₃ |
| Ia1.1854 | CF₃ | (CH₂)₂CH₃ | CH(CH₃)CH₂—O-(2,4-Cl₂—C₆H₃) | NCH₃ |
| Ia1.1855 | CF₃ | (CH₂)₃CH₃ | CH(CH₃)CH₂—O-(2,4-Cl₂—C₆H₃) | NCH₃ |
| Ia1.1856 | CF₃ | H | CH(CH₃)CH(CH₃)—O-(2,4-Cl₂—C₆H₃) | NCH₃ |
| Ia1.1857 | CF₃ | CH₃ | CH(CH₃)CH(CH₃)—O-(2,4-Cl₂—C₆H₃) | NCH₃ |
| Ia1.1858 | CF₃ | CH₂CH₃ | CH(CH₃)CH(CH₃)—O-(2,4-Cl₂—C₆H₃) | NCH₃ |
| Ia1.1859 | CF₃ | (CH₂)₂CH₃ | CH(CH₃)CH(CH₃)—O-(2,4-Cl₂—C₆H₃) | NCH₃ |
| Ia1.1860 | CF₃ | (CH₂)₃CH₃ | CH(CH₃)CH(CH₃)—O-(2,4-Cl₂—C₆H₃) | NCH₃ |
| Ia1.1861 | SO₂CH₃ | H | CH₃ | O |
| Ia1.1862 | SO₂CH₃ | CH₃ | CH₃ | O |
| Ia1.1863 | SO₂CH₃ | CH₂CH₃ | CH₃ | O |
| Ia1.1864 | SO₂CH₃ | (CH₂)₂CH₃ | CH₃ | O |
| Ia1.1865 | SO₂CH₃ | (CH₂)₃CH₃ | CH₃ | O |
| Ia1.1866 | SO₂CH₃ | H | C₂H₅ | O |
| Ia1.1867 | SO₂CH₃ | CH₃ | C₂H₅ | O |
| Ia1.1868 | SO₂CH₃ | CH₂CH₃ | C₂H₅ | O |
| Ia1.1869 | SO₂CH₃ | (CH₂)₂CH₃ | C₂H₅ | O |
| Ia1.1870 | SO₂CH₃ | (CH₂)₃CH₃ | C₂H₅ | O |
| Ia1.1871 | SO₂CH₃ | H | (CH₂)₂CH₃ | O |
| Ia1.1872 | SO₂CH₃ | CH₃ | (CH₂)₂CH₃ | O |
| Ia1.1873 | SO₂CH₃ | CH₂CH₃ | (CH₂)₂CH₃ | O |
| Ia1.1874 | SO₂CH₃ | (CH₂)₂CH₃ | (CH₂)₂CH₃ | O |
| Ia1.1875 | SO₂CH₃ | (CH₂)₃CH₃ | (CH₂)₂CH₃ | O |
| Ia1.1876 | SO₂CH₃ | H | CH(CH₃)₂ | O |
| Ia1.1877 | SO₂CH₃ | CH₃ | CH(CH₃)₂ | O |
| Ia1.1878 | SO₂CH₃ | CH₂CH₃ | CH(CH₃)₂ | O |
| Ia1.1879 | SO₂CH₃ | (CH₂)₂CH₃ | CH(CH₃)₂ | O |
| Ia1.1880 | SO₂CH₃ | (CH₂)₃CH₃ | CH(CH₃)₂ | O |
| Ia1.1881 | SO₂CH₃ | H | (CH₂)₃CH₃ | O |
| Ia1.1882 | SO₂CH₃ | CH₃ | (CH₂)₃CH₃ | O |
| Ia1.1883 | SO₂CH₃ | CH₂CH₃ | (CH₂)₃CH₃ | O |
| Ia1.1884 | SO₂CH₃ | (CH₂)₂CH₃ | (CH₂)₃CH₃ | O |
| Ia1.1885 | SO₂CH₃ | (CH₂)₃CH₃ | (CH₂)₃CH₃ | O |
| Ia1.1886 | SO₂CH₃ | H | CH₂CH(CH₃)₂ | O |
| Ia1.1887 | SO₂CH₃ | CH₃ | CH₂CH(CH₃)₂ | O |
| Ia1.1888 | SO₂CH₃ | CH₂CH₃ | CH₂CH(CH₃)₂ | O |
| Ia1.1889 | SO₂CH₃ | (CH₂)₂CH₃ | CH₂CH(CH₃)₂ | O |
| Ia1.1890 | SO₂CH₃ | (CH₂)₃CH₃ | CH₂CH(CH₃)₂ | O |
| Ia1.1891 | SO₂CH₃ | H | CH(CH₃)CH₂CH₃ | O |
| Ia1.1892 | SO₂CH₃ | CH₃ | CH(CH₃)CH₂CH₃ | O |
| Ia1.1893 | SO₂CH₃ | CH₂CH₃ | CH(CH₃)CH₂CH₃ | O |
| Ia1.1894 | SO₂CH₃ | (CH₂)₂CH₃ | CH(CH₃)CH₂CH₃ | O |
| Ia1.1895 | SO₂CH₃ | (CH₂)₃CH₃ | CH(CH₃)CH₂CH₃ | O |
| Ia1.1896 | SO₂CH₃ | H | (CH₂)₂—C₆H₅ | O |

TABLE 1-continued

| No. | R² | R³ | R⁴ | Z |
|---|---|---|---|---|
| Ia1.1897 | SO₂CH₃ | CH₃ | (CH₂)₂—C₆H₅ | O |
| Ia1.1898 | SO₂CH₃ | CH₂CH₃ | (CH₂)₂—C₆H₅ | O |
| Ia1.1899 | SO₂CH₃ | (CH₂)₂CH₃ | (CH₂)₂—C₆H₅ | O |
| Ia1.1900 | SO₂CH₃ | (CH₂)₃CH₃ | (CH₂)₂—C₆H₅ | O |
| Ia1.1901 | SO₂CH₃ | H | CH₂CH(CH₃)—C₆H₅ | O |
| Ia1.1902 | SO₂CH₃ | CH₃ | CH₂CH(CH₃)—C₆H₅ | O |
| Ia1.1903 | SO₂CH₃ | CH₂CH₃ | CH₂CH(CH₃)—C₆H₅ | O |
| Ia1.1904 | SO₂CH₃ | (CH₂)₂CH₃ | CH₂CH(CH₃)—C₆H₅ | O |
| Ia1.1905 | SO₂CH₃ | (CH₂)₃CH₃ | CH₂CH(CH₃)—C₆H₅ | O |
| Ia1.1906 | SO₂CH₃ | H | CH(CH₃)CH₂—C₆H₅ | O |
| Ia1.1907 | SO₂CH₃ | CH₃ | CH(CH₃)CH₂—C₆H₅ | O |
| Ia1.1908 | SO₂CH₃ | CH₂CH₃ | CH(CH₃)CH₂—C₆H₅ | O |
| Ia1.1909 | SO₂CH₃ | (CH₂)₂CH₃ | CH(CH₃)CH₂—C₆H₅ | O |
| Ia1.1910 | SO₂CH₃ | (CH₂)₃CH₃ | CH(CH₃)CH₂—C₆H₅ | O |
| Ia1.1911 | SO₂CH₃ | H | CH(CH₃)CH(CH₃)—C₆H₅ | O |
| Ia1.1912 | SO₂CH₃ | CH₃ | CH(CH₃)CH(CH₃)—C₆H₅ | O |
| Ia1.1913 | SO₂CH₃ | CH₂CH₃ | CH(CH₃)CH(CH₃)—C₆H₅ | O |
| Ia1.1914 | SO₂CH₃ | (CH₂)₂CH₃ | CH(CH₃)CH(CH₃)—C₆H₅ | O |
| Ia1.1915 | SO₂CH₃ | (CH₂)₃CH₃ | CH(CH₃)CH(CH₃)—C₆H₅ | O |
| Ia1.1916 | SO₂CH₃ | H | (CH₂)₂-(4-Cl—C₆H₄) | O |
| Ia1.1917 | SO₂CH₃ | CH₃ | (CH₂)₂-(4-Cl—C₆H₄) | O |
| Ia1.1918 | SO₂CH₃ | CH₂CH₃ | (CH₂)₂-(4-Cl—C₆H₄) | O |
| Ia1.1919 | SO₂CH₃ | (CH₂)₂CH₃ | (CH₂)₂-(4-Cl—C₆H₄) | O |
| Ia1.1920 | SO₂CH₃ | (CH₂)₃CH₃ | (CH₂)₂-(4-Cl—C₆H₄) | O |
| Ia1.1921 | SO₂CH₃ | H | CH₂CH(CH₃)-(4-Cl—C₆H₄) | O |
| Ia1.1922 | SO₂CH₃ | CH₃ | CH₂CH(CH₃)-(4-Cl—C₆H₄) | O |
| Ia1.1923 | SO₂CH₃ | CH₂CH₃ | CH₂CH(CH₃)-(4-Cl—C₆H₄) | O |
| Ia1.1924 | SO₂CH₃ | (CH₂)₂CH₃ | CH₂CH(CH₃)-(4-Cl—C₆H₄) | O |
| Ia1.1925 | SO₂CH₃ | (CH₂)₃CH₃ | CH₂CH(CH₃)-(4-Cl—C₆H₄) | O |
| Ia1.1926 | SO₂CH₃ | H | CH(CH₃)CH₂-(4-Cl—C₆H₄) | O |
| Ia1.1927 | SO₂CH₃ | CH₃ | CH(CH₃)CH₂-(4-Cl—C₆H₄) | O |
| Ia1.1928 | SO₂CH₃ | CH₂CH₃ | CH(CH₃)CH₂-(4-Cl—C₆H₄) | O |
| Ia1.1929 | SO₂CH₃ | (CH₂)₂CH₃ | CH(CH₃)CH₂-(4-Cl—C₆H₄) | O |
| Ia1.1930 | SO₂CH₃ | (CH₂)₃CH₃ | CH(CH₃)CH₂-(4-Cl—C₆H₄) | O |
| Ia1.1931 | SO₂CH₃ | H | CH(CH₃)CH(CH₃)-(4-Cl—C₆H₄) | O |
| Ia1.1932 | SO₂CH₃ | CH₃ | CH(CH₃)CH(CH₃)-(4-Cl—C₆H₄) | O |
| Ia1.1933 | SO₂CH₃ | CH₂CH₃ | CH(CH₃)CH(CH₃)-(4-Cl—C₆H₄) | O |
| Ia1.1934 | SO₂CH₃ | (CH₂)₂CH₃ | CH(CH₃)CH(CH₃)-(4-Cl—C₆H₄) | O |
| Ia1.1935 | SO₂CH₃ | (CH₂)₃CH₃ | CH(CH₃)CH(CH₃)-(4-Cl—C₆H₄) | O |
| Ia1.1936 | SO₂CH₃ | H | (CH₂)₂-(2,4-Cl₂—C₆H₃) | O |
| Ia1.1937 | SO₂CH₃ | CH₃ | (CH₂)₂-(2,4-Cl₂—C₆H₃) | O |
| Ia1.1938 | SO₂CH₃ | CH₂CH₃ | (CH₂)₂-(2,4-Cl₂—C₆H₃) | O |
| Ia1.1939 | SO₂CH₃ | (CH₂)₂CH₃ | (CH₂)₂-(2,4-Cl₂—C₆H₃) | O |
| Ia1.1940 | SO₂CH₃ | (CH₂)₃CH₃ | (CH₂)₂-(2,4-Cl₂—C₆H₃) | O |
| Ia1.1941 | SO₂CH₃ | H | CH₂CH(CH₃)-(2,4-Cl₂—C₆H₃) | O |
| Ia1.1942 | SO₂CH₃ | CH₃ | CH₂CH(CH₃)-(2,4-Cl₂—C₆H₃) | O |
| Ia1.1943 | SO₂CH₃ | CH₂CH₃ | CH₂CH(CH₃)-(2,4-Cl₂—C₆H₃) | O |
| Ia1.1944 | SO₂CH₃ | (CH₂)₂CH₃ | CH₂CH(CH₃)-(2,4-Cl₂—C₆H₃) | |
| Ia1.1945 | SO₂CH₃ | (CH₂)₃CH₃ | CH₂CH(CH₃)-(2,4-Cl₂—C₆H₃) | O |
| Ia1.1946 | SO₂CH₃ | H | CH(CH₃)CH₂-(2,4-Cl₂—C₆H₃) | O |
| Ia1.1947 | SO₂CH₃ | CH₃ | CH(CH₃)CH₂-(2,4-Cl₂—C₆H₃) | O |
| Ia1.1948 | SO₂CH₃ | CH₂CH₃ | CH(CH₃)CH₂-(2,4-Cl₂—C₆H₃) | O |
| Ia1.1949 | SO₂CH₃ | (CH₂)₂CH₃ | CH(CH₃)CH₂-(2,4-Cl₂—C₆H₃) | O |
| Ia1.1950 | SO₂CH₃ | (CH₂)₃CH₃ | CH(CH₃)CH₂-(2,4-Cl₂—C₆H₃) | O |
| Ia1.1951 | SO₂CH₃ | H | CH(CH₃)CH(CH₃)-(2,4-Cl₂—C₆H₃) | O |
| Ia1.1952 | SO₂CH₃ | CH₃ | CH(CH₃)CH(CH₃)-(2,4-Cl₂—C₆H₃) | O |
| Ia1.1953 | SO₂CH₃ | CH₂CH₃ | CH(CH₃)CH(CH₃)-(2,4-Cl₂—C₆H₃) | O |
| Ia1.1954 | SO₂CH₃ | (CH₂)₂CH₃ | CH(CH₃)CH(CH₃)-(2,4-Cl₂—C₆H₃) | O |
| Ia1.1955 | SO₂CH₃ | (CH₂)₃CH₃ | CH(CH₃)CH(CH₃)-(2,4-Cl₂—C₆H₃) | O |
| Ia1.1956 | SO₂CH₃ | H | (CH₂)₂—O—C₆H₅ | O |
| Ia1.1957 | SO₂CH₃ | CH₃ | (CH₂)₂—O—C₆H₅ | O |
| Ia1.1958 | SO₂CH₃ | CH₂CH₃ | (CH₂)₂—O—C₆H₅ | O |
| Ia1.1959 | SO₂CH₃ | (CH₂)₂CH₃ | (CH₂)₂—O—C₆H₅ | O |
| Ia1.1960 | SO₂CH₃ | (CH₂)₃CH₃ | (CH₂)₂—O—C₆H₅ | O |
| Ia1.1961 | SO₂CH₃ | H | CH₂CH(CH₃)—O—C₆H₅ | O |
| Ia1.1962 | SO₂CH₃ | CH₃ | CH₂CH(CH₃)—O—C₆H₅ | O |
| Ia1.1963 | SO₂CH₃ | CH₂CH₃ | CH₂CH(CH₃)—O—C₆H₅ | O |
| Ia1.1964 | SO₂CH₃ | (CH₂)₂CH₃ | CH₂CH(CH₃)—O—C₆H₅ | O |
| Ia1.1965 | SO₂CH₃ | (CH₂)₃CH₃ | CH₂CH(CH₃)—O—C₆H₅ | O |
| Ia1.1966 | SO₂CH₃ | H | CH(CH₃)CH₂—O—C₆H₅ | O |
| Ia1.1967 | SO₂CH₃ | CH₃ | CH(CH₃)CH₂—O—C₆H₅ | O |
| Ia1.1968 | SO₂CH₃ | CH₂CH₃ | CH(CH₃)CH₂—O—C₆H₅ | O |
| Ia1.1969 | SO₂CH₃ | (CH₂)₂CH₃ | CH(CH₃)CH₂—O—C₆H₅ | O |
| Ia1.1970 | SO₂CH₃ | (CH₂)₃CH₃ | CH(CH₃)CH₂—O—C₆H₅ | O |
| Ia1.1971 | SO₂CH₃ | H | CH(CH₃)CH(CH₃)—O—C₆H₅ | O |
| Ia1.1972 | SO₂CH₃ | CH₃ | CH(CH₃)CH(CH₃)—O—C₆H₅ | O |
| Ia1.1973 | SO₂CH₃ | CH₂CH₃ | CH(CH₃)CH(CH₃)—O—C₆H₅ | O |

TABLE 1-continued

| No. | $R^2$ | $R^3$ | $R^4$ | Z |
|---|---|---|---|---|
| Ia1.1974 | $SO_2CH_3$ | $(CH_2)_2CH_3$ | $CH(CH_3)CH(CH_3)-O-C_6H_5$ | O |
| Ia1.1975 | $SO_2CH_3$ | $(CH_2)_3CH_3$ | $CH(CH_3)CH(CH_3)-O-C_6H_5$ | O |
| Ia1.1976 | $SO_2CH_3$ | H | $(CH_2)_2-O-(4-Cl-C_6H_4)$ | O |
| Ia1.1977 | $SO_2CH_3$ | $CH_3$ | $(CH_2)_2-O-(4-Cl-C_6H_4)$ | O |
| Ia1.1978 | $SO_2CH_3$ | $CH_2CH_3$ | $(CH_2)_2-O-(4-Cl-C_6H_4)$ | O |
| Ia1.1979 | $SO_2CH_3$ | $(CH_2)_2CH_3$ | $(CH_2)_2-O-(4-Cl-C_6H_4)$ | O |
| Ia1.1980 | $SO_2CH_3$ | $(CH_2)_3CH_3$ | $(CH_2)_2-O-(4-Cl-C_6H_4)$ | O |
| Ia1.1981 | $SO_2CH_3$ | H | $CH_2CH(CH_3)-O-(4-Cl-C_6H_4)$ | O |
| Ia1.1982 | $SO_2CH_3$ | $CH_3$ | $CH_2CH(CH_3)-O-(4-Cl-C_6H_4)$ | O |
| Ia1.1983 | $SO_2CH_3$ | $CH_2CH_3$ | $CH_2CH(CH_3)-O-(4-Cl-C_6H_4)$ | O |
| Ia1.1984 | $SO_2CH_3$ | $(CH_2)_2CH_3$ | $CH_2CH(CH_3)-O-(4-Cl-C_6H_4)$ | O |
| Ia1.1985 | $SO_2CH_3$ | $(CH_2)_3CH_3$ | $CH_2CH(CH_3)-O-(4-Cl-C_6H_4)$ | O |
| Ia1.1986 | $SO_2CH_3$ | H | $CH(CH_3)CH_2-O-(4-Cl-C_6H_4)$ | O |
| Ia1.1987 | $SO_2CH_3$ | $CH_3$ | $CH(CH_3)CH_2-O-(4-Cl-C_6H_4)$ | O |
| Ia1.1988 | $SO_2CH_3$ | $CH_2CH_3$ | $CH(CH_3)CH_2-O-(4-Cl-C_6H_4)$ | O |
| Ia1.1989 | $SO_2CH_3$ | $(CH_2)_2CH_3$ | $CH(CH_3)CH_2-O-(4-Cl-C_6H_4)$ | O |
| Ia1.1990 | $SO_2CH_3$ | $(CH_2)_3CH_3$ | $CH(CH_3)CH_2-O-(4-Cl-C_6H_4)$ | O |
| Ia1.1991 | $SO_2CH_3$ | H | $CH(CH_3)CH(CH_3)-O-(4-Cl-C_6H_4)$ | O |
| Ia1.1992 | $SO_2CH_3$ | $CH_3$ | $CH(CH_3)CH(CH_3)-O-(4-Cl-C_6H_4)$ | O |
| Ia1.1993 | $SO_2CH_3$ | $CH_2CH_3$ | $CH(CH_3)CH(CH_3)-O-(4-Cl-C_6H_4)$ | O |
| Ia1.1994 | $SO_2CH_3$ | $(CH_2)_2CH_3$ | $CH(CH_3)CH(CH_3)-O-(4-Cl-C_6H_4)$ | O |
| Ia1.1995 | $SO_2CH_3$ | $(CH_2)_3CH_3$ | $CH(CH_3)CH(CH_3)-O-(4-Cl-C_6H_4)$ | O |
| Ia1.1996 | $SO_2CH_3$ | H | $(CH_2)_2-O-(2,4-Cl_2-C_6H_3)$ | O |
| Ia1.1997 | $SO_2CH_3$ | $CH_3$ | $(CH_2)_2-O-(2,4-Cl_2-C_6H_3)$ | O |
| Ia1.1998 | $SO_2CH_3$ | $CH_2CH_3$ | $(CH_2)_2-O-(2,4-Cl_2-C_6H_3)$ | O |
| Ia1.1999 | $SO_2CH_3$ | $(CH_2)_2CH_3$ | $(CH_2)_2-O-(2,4-Cl_2-C_6H_3)$ | O |
| Ia1.2000 | $SO_2CH_3$ | $(CH_2)_3CH_3$ | $(CH_2)_2-O-(2,4-Cl_2-C_6H_3)$ | O |
| Ia1.2001 | $SO_2CH_3$ | H | $CH_2CH(CH_3)-O-(2,4-Cl_2-C_6H_3)$ | O |
| Ia1.2002 | $SO_2CH_3$ | $CH_3$ | $CH_2CH(CH_3)-O-(2,4-Cl_2-C_6H_3)$ | O |
| Ia1.2003 | $SO_2CH_3$ | $CH_2CH_3$ | $CH_2CH(CH_3)-O-(2,4-Cl_2-C_6H_3)$ | O |
| Ia1.2004 | $SO_2CH_3$ | $(CH_2)_2CH_3$ | $CH_2CH(CH_3)-O-(2,4-Cl_2-C_6H_3)$ | O |
| Ia1.2005 | $SO_2CH_3$ | $(CH_2)_3CH_3$ | $CH_2CH(CH_3)-O-(2,4-Cl_2-C_6H_3)$ | O |
| Ia1.2006 | $SO_2CH_3$ | H | $CH(CH_3)CH_2-O-(2,4-Cl_2-C_6H_3)$ | O |
| Ia1.2007 | $SO_2CH_3$ | $CH_3$ | $CH(CH_3)CH_2-O-(2,4-Cl_2-C_6H_3)$ | O |
| Ia1.2008 | $SO_2CH_3$ | $CH_2CH_3$ | $CH(CH_3)CH_2-O-(2,4-Cl_2-C_6H_3)$ | O |
| Ia1.2009 | $SO_2CH_3$ | $(CH_2)_2CH_3$ | $CH(CH_3)CH_2-O-(2,4-Cl_2-C_6H_3)$ | O |
| Ia1.2010 | $SO_2CH_3$ | $(CH_2)_3CH_3$ | $CH(CH_3)CH_2-O-(2,4-Cl_2-C_6H_3)$ | O |
| Ia1.2011 | $SO_2CH_3$ | H | $CH(CH_3)CH(CH_3)-O-(2,4-Cl_2-C_6H_3)$ | O |
| Ia1.2012 | $SO_2CH_3$ | $CH_3$ | $CH(CH_3)CH(CH_3)-O-(2,4-Cl_2-C_6H_3)$ | O |
| Ia1.2013 | $SO_2CH_3$ | $CH_2CH_3$ | $CH(CH_3)CH(CH_3)-O-(2,4-Cl_2-C_6H_3)$ | O |
| Ia1.2014 | $SO_2CH_3$ | $(CH_2)_2CH_3$ | $CH(CH_3)CH(CH_3)-O-(2,4-Cl_2-C_6H_3)$ | O |
| Ia1.2015 | $SO_2CH_3$ | $(CH_2)_3CH_3$ | $CH(CH_3)CH(CH_3)-O-(2,4-Cl_2-C_6H_3)$ | O |
| Ia1.2016 | $SO_2CH_3$ | H | $CH_3$ | NH |
| Ia1.2017 | $SO_2CH_3$ | $CH_3$ | $CH_3$ | NH |
| Ia1.2018 | $SO_2CH_3$ | $CH_2CH_3$ | $CH_3$ | NH |
| Ia1.2019 | $SO_2CH_3$ | $(CH_2)_2CH_3$ | $CH_3$ | NH |
| Ia1.2020 | $SO_2CH_3$ | $(CH_2)_3CH_3$ | $CH_3$ | NH |
| Ia1.2021 | $SO_2CH_3$ | H | $C_2H_5$ | NH |
| Ia1.2022 | $SO_2CH_3$ | $CH_3$ | $C_2H_5$ | NH |
| Ia1.2023 | $SO_2CH_3$ | $CH_2CH_3$ | $C_2H_5$ | NH |
| Ia1.2024 | $SO_2CH_3$ | $(CH_2)_2CH_3$ | $C_2H_5$ | NH |
| Ia1.2025 | $SO_2CH_3$ | $(CH_2)_3CH_3$ | $C_2H_5$ | NH |
| Ia1.2026 | $SO_2CH_3$ | H | $(CH_2)_2CH_3$ | NH |
| Ia1.2027 | $SO_2CH_3$ | $CH_3$ | $(CH_2)_2CH_3$ | NH |
| Ia1.2028 | $SO_2CH_3$ | $CH_2CH_3$ | $(CH_2)_2CH_3$ | NH |
| Ia1.2029 | $SO_2CH_3$ | $(CH_2)_2CH_3$ | $(CH_2)_2CH_3$ | NH |
| Ia1.2030 | $SO_2CH_3$ | $(CH_2)_3CH_3$ | $(CH_2)_2CH_3$ | NH |
| Ia1.2031 | $SO_2CH_3$ | H | $CH(CH_3)_2$ | NH |
| Ia1.2032 | $SO_2CH_3$ | $CH_3$ | $CH(CH_3)_2$ | NH |
| Ia1.2033 | $SO_2CH_3$ | $CH_2CH_3$ | $CH(CH_3)_2$ | NH |
| Ia1.2034 | $SO_2CH_3$ | $(CH_2)_2CH_3$ | $CH(CH_3)_2$ | NH |
| Ia1.2035 | $SO_2CH_3$ | $(CH_2)_3CH_3$ | $CH(CH_3)_2$ | NH |
| Ia1.2036 | $SO_2CH_3$ | H | $(CH_2)_3CH_3$ | NH |
| Ia1.2037 | $SO_2CH_3$ | $CH_3$ | $(CH_2)_3CH_3$ | NH |
| Ia1.2038 | $SO_2CH_3$ | $CH_2CH_3$ | $(CH_2)_3CH_3$ | NH |
| Ia1.2039 | $SO_2CH_3$ | $(CH_2)_2CH_3$ | $(CH_2)_3CH_3$ | NH |
| Ia1.2040 | $SO_2CH_3$ | $(CH_2)_3CH_3$ | $(CH_2)_3CH_3$ | NH |
| Ia1.2041 | $SO_2CH_3$ | H | $CH_2CH(CH_3)_2$ | NH |
| Ia1.2042 | $SO_2CH_3$ | $CH_3$ | $CH_2CH(CH_3)_2$ | NH |
| Ia1.2043 | $SO_2CH_3$ | $CH_2CH_3$ | $CH_2CH(CH_3)_2$ | NH |
| Ia1.2044 | $SO_2CH_3$ | $(CH_2)_2CH_3$ | $CH_2CH(CH_3)_2$ | NH |
| Ia1.2045 | $SO_2CH_3$ | $(CH_2)_3CH_3$ | $CH_2CH(CH_3)_2$ | NH |
| Ia1.2046 | $SO_2CH_3$ | H | $CH(CH_3)CH_2CH_3$ | NH |
| Ia1.2047 | $SO_2CH_3$ | $CH_3$ | $CH(CH_3)CH_2CH_3$ | NH |
| Ia1.2048 | $SO_2CH_3$ | $CH_2CH_3$ | $CH(CH_3)CH_2CH_3$ | NH |
| Ia1.2049 | $SO_2CH_3$ | $(CH_2)_2CH_3$ | $CH(CH_3)CH_2CH_3$ | NH |
| Ia1.2050 | $SO_2CH_3$ | $(CH_2)_3CH_3$ | $CH(CH_3)CH_2CH_3$ | NH |

TABLE 1-continued

| No. | R² | R³ | R⁴ | Z |
|---|---|---|---|---|
| Ia1.2051 | SO₂CH₃ | H | (CH₂)₂—C₆H₅ | NH |
| Ia1.2052 | SO₂CH₃ | CH₃ | (CH₂)₂—C₆H₅ | NH |
| Ia1.2053 | SO₂CH₃ | CH₂CH₃ | (CH₂)₂—C₆H₅ | NH |
| Ia1.2054 | SO₂CH₃ | (CH₂)₂CH₃ | (CH₂)₂—C₆H₅ | NH |
| Ia1.2055 | SO₂CH₃ | (CH₂)₃CH₃ | (CH₂)₂—C₆H₅ | NH |
| Ia1.2056 | SO₂CH₃ | H | CH₂CH(CH₃)—C₆H₅ | NH |
| Ia1.2057 | SO₂CH₃ | CH₃ | CH₂CH(CH₃)—C₆H₅ | NH |
| Ia1.2058 | SO₂CH₃ | CH₂CH₃ | CH₂CH(CH₃)—C₆H₅ | NH |
| Ia1.2059 | SO₂CH₃ | (CH₂)₂CH₃ | CH₂CH(CH₃)—C₆H₅ | NH |
| Ia1.2060 | SO₂CH₃ | (CH₂)₃CH₃ | CH₂CH(CH₃)—C₆H₅ | NH |
| Ia1.2061 | SO₂CH₃ | H | CH(CH₃)CH₂—C₆H₅ | NH |
| Ia1.2062 | SO₂CH₃ | CH₃ | CH(CH₃)CH₂—C₆H₅ | NH |
| Ia1.2063 | SO₂CH₃ | CH₂CH₃ | CH(CH₃)CH₂—C₆H₅ | NH |
| Ia1.2064 | SO₂CH₃ | (CH₂)₂CH₃ | CH(CH₃)CH₂—C₆H₅ | NH |
| Ia1.2065 | SO₂CH₃ | (CH₂)₃CH₃ | CH(CH₃)CH₂—C₆H₅ | NH |
| Ia1.2066 | SO₂CH₃ | H | CH(CH₃)CH(CH₃)—C₆H₅ | NH |
| Ia1.2067 | SO₂CH₃ | CH₃ | CH(CH₃)CH(CH₃)—C₆H₅ | NH |
| Ia1.2068 | SO₂CH₃ | CH₂CH₃ | CH(CH₃)CH(CH₃)—C₆H₅ | NH |
| Ia1.2069 | SO₂CH₃ | (CH₂)₂CH₃ | CH(CH₃)CH(CH₃)—C₆H₅ | NH |
| Ia1.2070 | SO₂CH₃ | (CH₂)₃CH₃ | CH(CH₃)CH(CH₃)—C₆H₅ | NH |
| Ia1.2071 | SO₂CH₃ | H | (CH₂)₂-(4-Cl—C₆H₄) | NH |
| Ia1.2072 | SO₂CH₃ | CH₃ | (CH₂)₂-(4-Cl—C₆H₄) | NH |
| Ia1.2073 | SO₂CH₃ | CH₂CH₃ | (CH₂)₂-(4-Cl—C₆H₄) | NH |
| Ia1.2074 | SO₂CH₃ | (CH₂)₂CH₃ | (CH₂)₂-(4-Cl—C₆H₄) | NH |
| Ia1.2075 | SO₂CH₃ | (CH₂)₃CH₃ | (CH₂)₂-(4-Cl—C₆H₄) | NH |
| Ia1.2076 | SO₂CH₃ | H | CH₂CH(CH₃)-(4-Cl—C₆H₄) | NH |
| Ia1.2077 | SO₂CH₃ | CH₃ | CH₂CH(CH₃)-(4-Cl—C₆H₄) | NH |
| Ia1.2078 | SO₂CH₃ | CH₂CH₃ | CH₂CH(CH₃)-(4-Cl—C₆H₄) | NH |
| Ia1.2079 | SO₂CH₃ | (CH₂)₂CH₃ | CH₂CH(CH₃)-(4-Cl—C₆H₄) | NH |
| Ia1.2080 | SO₂CH₃ | (CH₂)₃CH₃ | CH₂CH(CH₃)-(4-Cl—C₆H₄) | NH |
| Ia1.2081 | SO₂CH₃ | H | CH(CH₃)CH₂-(4-Cl—C₆H₄) | NH |
| Ia1.2082 | SO₂CH₃ | CH₃ | CH(CH₃)CH₂-(4-Cl—C₆H₄) | NH |
| Ia1.2083 | SO₂CH₃ | CH₂CH₃ | CH(CH₃)CH₂-(4-Cl—C₆H₄) | NH |
| Ia1.2084 | SO₂CH₃ | (CH₂)₂CH₃ | CH(CH₃)CH₂-(4-Cl—C₆H₄) | NH |
| Ia1.2085 | SO₂CH₃ | (CH₂)₃CH₃ | CH(CH₃)CH₂-(4-Cl—C₆H₄) | NH |
| Ia1.2086 | SO₂CH₃ | H | CH(CH₃)CH(CH₃)-(4-Cl—C₆H₄) | NH |
| Ia1.2087 | SO₂CH₃ | CH₃ | CH(CH₃)CH(CH₃)-(4-Cl—C₆H₄) | NH |
| Ia1.2088 | SO₂CH₃ | CH₂CH₃ | CH(CH₃)CH(CH₃)-(4-Cl—C₆H₄) | NH |
| Ia1.2089 | SO₂CH₃ | (CH₂)₂CH₃ | CH(CH₃)CH(CH₃)-(4-Cl—C₆H₄) | NH |
| Ia1.2090 | SO₂CH₃ | (CH₂)₃CH₃ | CH(CH₃)CH(CH₃)-(4-Cl—C₆H₄) | NH |
| Ia1.2091 | SO₂CH₃ | H | (CH₂)₂-(2,4-Cl₂—C₆H₃) | NH |
| Ia1.2092 | SO₂CH₃ | CH₃ | (CH₂)₂-(2,4-Cl₂—C₆H₃) | NH |
| Ia1.2093 | SO₂CH₃ | CH₂CH₃ | (CH₂)₂-(2,4-Cl₂—C₆H₃) | NH |
| Ia1.2094 | SO₂CH₃ | (CH₂)₂CH₃ | (CH₂)₂-(2,4-Cl₂—C₆H₃) | NH |
| Ia1.2095 | SO₂CH₃ | (CH₂)₃CH₃ | (CH₂)₂-(2,4-Cl₂—C₆H₃) | NH |
| Ia1.2096 | SO₂CH₃ | H | CH₂CH(CH₃)-(2,4-Cl₂—C₆H₃) | NH |
| Ia1.2097 | SO₂CH₃ | CH₃ | CH₂CH(CH₃)-(2,4-Cl₂—C₆H₃) | NH |
| Ia1.2098 | SO₂CH₃ | CH₂CH₃ | CH₂CH(CH₃)-(2,4-Cl₂—C₆H₃) | NH |
| Ia1.2099 | SO₂CH₃ | (CH₂)₂CH₃ | CH₂CH(CH₃)-(2,4-Cl₂—C₆H₃) | NH |
| Ia1.2100 | SO₂CH₃ | (CH₂)₃CH₃ | CH₂CH(CH₃)-(2,4-Cl₂—C₆H₃) | NH |
| Ia1.2101 | SO₂CH₃ | H | CH(CH₃)CH₂-(2,4-Cl₂—C₆H₃) | NH |
| Ia1.2102 | SO₂CH₃ | CH₃ | CH(CH₃)CH₂-(2,4-Cl₂—C₆H₃) | NH |
| Ia1.2103 | SO₂CH₃ | CH₂CH₃ | CH(CH₃)CH₂-(2,4-Cl₂—C₆H₃) | NH |
| Ia1.2104 | SO₂CH₃ | (CH₂)₂CH₃ | CH(CH₃)CH₂-(2,4-Cl₂—C₆H₃) | NH |
| Ia1.2105 | SO₂CH₃ | (CH₂)₃CH₃ | CH(CH₃)CH₂-(2,4-Cl₂—C₆H₃) | NH |
| Ia1.2106 | SO₂CH₃ | H | CH(CH₃)CH(CH₃)-(2,4-Cl₂—C₆H₃) | NH |
| Ia1.2107 | SO₂CH₃ | CH₃ | CH(CH₃)CH(CH₃)-(2,4-Cl₂—C₆H₃) | NH |
| Ia1.2108 | SO₂CH₃ | CH₂CH₃ | CH(CH₃)CH(CH₃)-(2,4-Cl₂—C₆H₃) | NH |
| Ia1.2109 | SO₂CH₃ | (CH₂)₂CH₃ | CH(CH₃)CH(CH₃)-(2,4-Cl₂—C₆H₃) | NH |
| Ia1.2110 | SO₂CH₃ | (CH₂)₃CH₃ | CH(CH₃)CH(CH₃)-(2,4-Cl₂—C₆H₃) | NH |
| Ia1.2111 | SO₂CH₃ | H | (CH₂)₂—O—C₆H₅ | NH |
| Ia1.2112 | SO₂CH₃ | CH₃ | (CH₂)₂—O—C₆H₅ | NH |
| Ia1.2113 | SO₂CH₃ | CH₂CH₃ | (CH₂)₂—O—C₆H₅ | NH |
| Ia1.2114 | SO₂CH₃ | (CH₂)₂CH₃ | (CH₂)₂—O—C₆H₅ | NH |
| Ia1.2115 | SO₂CH₃ | (CH₂)₃CH₃ | (CH₂)₂—O—C₆H₅ | NH |
| Ia1.2116 | SO₂CH₃ | H | CH₂CH(CH₃)—O—C₆H₅ | NH |
| Ia1.2117 | SO₂CH₃ | CH₃ | CH₂CH(CH₃)—O—C₆H₅ | NH |
| Ia1.2118 | SO₂CH₃ | CH₂CH₃ | CH₂CH(CH₃)—O—C₆H₅ | NH |
| Ia1.2119 | SO₂CH₃ | (CH₂)₂CH₃ | CH₂CH(CH₃)—O—C₆H₅ | NH |
| Ia1.2120 | SO₂CH₃ | (CH₂)₃CH₃ | CH₂CH(CH₃)—O—C₆H₅ | NH |
| Ia1.2121 | SO₂CH₃ | H | CH(CH₃)CH₂—O—C₆H₅ | NH |
| Ia1.2122 | SO₂CH₃ | CH₃ | CH(CH₃)CH₂—O—C₆H₅ | NH |
| Ia1.2123 | SO₂CH₃ | CH₂CH₃ | CH(CH₃)CH₂—O—C₆H₅ | NH |
| Ia1.2124 | SO₂CH₃ | (CH₂)₂CH₃ | CH(CH₃)CH₂—O—C₆H₅ | NH |
| Ia1.2125 | SO₂CH₃ | (CH₂)₃CH₃ | CH(CH₃) | CH₂—O—C₆H₅ NH |

TABLE 1-continued

| No. | R² | R³ | R⁴ | Z |
|---|---|---|---|---|
| Ia1.2126 | SO₂CH₃ | H | CH(CH₃)CH(CH₃)—O—C₆H₅ | NH |
| Ia1.2127 | SO₂CH₃ | CH₃ | CH(CH₃)CH(CH₃)—O—C₆H₅ | NH |
| Ia1.2128 | SO₂CH₃ | CH₂CH₃ | CH(CH₃)CH(CH₃)—O—C₆H₅ | NH |
| Ia1.2129 | SO₂CH₃ | (CH₂)₂CH₃ | CH(CH₃)CH(CH₃)—O—C₆H₅ | NH |
| Ia1.2130 | SO₂CH₃ | (CH₂)₃CH₃ | CH(CH₃)CH(CH₃)—O—C₆H₅ | NH |
| Ia1.2131 | SO₂CH₃ | H | (CH₂)₂—O-(4-Cl—C₆H₄) | NH |
| Ia1.2132 | SO₂CH₃ | CH₃ | (CH₂)₂—O-(4-Cl—C₆H₄) | NH |
| Ia1.2133 | SO₂CH₃ | CH₂CH₃ | (CH₂)₂—O-(4-Cl—C₆H₄) | NH |
| Ia1.2134 | SO₂CH₃ | (CH₂)₂CH₃ | (CH₂)₂—O-(4-Cl—C₆H₄) | NH |
| Ia1.2135 | SO₂CH₃ | (CH₂)₃CH₃ | (CH₂)₂—O-(4-Cl—C₆H₄) | NH |
| Ia1.2136 | SO₂CH₃ | H | CH₂CH(CH₃)—O-(4-Cl—C₆H₄) | NH |
| Ia1.2137 | SO₂CH₃ | CH₃ | CH₂CH(CH₃)—O-(4-Cl—C₆H₄) | NH |
| Ia1.2138 | SO₂CH₃ | CH₂CH₃ | CH₂CH(CH₃)—O-(4-Cl—C₆H₄) | NH |
| Ia1.2139 | SO₂CH₃ | (CH₂)₂CH₃ | CH₂CH(CH₃)—O-(4-Cl—C₆H₄) | NH |
| Ia1.2140 | SO₂CH₃ | (CH₂)₃CH₃ | CH₂CH(CH₃)-O-(4-Cl—C₆H₄) | NH |
| Ia1.2141 | SO₂CH₃ | H | CH(CH₃)CH₂—O-(4-Cl—C₆H₄) | NH |
| Ia1.2142 | SO₂CH₃ | CH₃ | CH(CH₃)CH₂—O-(4-Cl—C₆H₄) | NH |
| Ia1.2143 | SO₂CH₃ | CH₂CH₃ | CH(CH₃)CH₂—O-(4-Cl—C₆H₄) | NH |
| Ia1.2144 | SO₂CH₃ | (CH₂)₂CH₃ | CH(CH₃)CH₂—O-(4-Cl—C₆H₄) | NH |
| Ia1.2145 | SO₂CH₃ | (CH₂)₃CH₃ | CH(CH₃)CH₂—O-(4-Cl—C₆H₄) | NH |
| Ia1.2146 | SO₂CH₃ | H | CH(CH₃)CH(CH₃)—O-(4-Cl—C₆H₄) | NH |
| Ia1.2147 | SO₂CH₃ | CH₃ | CH(CH₃)CH(CH₃)—O-(4-Cl—C₆H₄) | NH |
| Ia1.2148 | SO₂CH₃ | CH₂CH₃ | CH(CH₃)CH(CH₃)—O-(4-Cl—C₆H₄) | NH |
| Ia1.2149 | SO₂CH₃ | (CH₂)₂CH₃ | CH(CH₃)CH(CH₃)—O-(4-Cl—C₆H₄) | NH |
| Ia1.2150 | SO₂CH₃ | (CH₂)₃CH₃ | CH(CH₃)CH(CH₃)—O-(4-Cl—C₆H₄) | NH |
| Ia1.2151 | SO₂CH₃ | H | (CH₂)₂—O-(2,4-Cl₂—C₆H₃) | NH |
| Ia1.2152 | SO₂CH₃ | CH₃ | (CH₂)₂—O-(2,4-Cl₂—C₆H₃) | NH |
| Ia1.2153 | SO₂CH₃ | CH₂CH₃ | (CH₂)₂—O-(2,4-Cl₂—C₆H₃) | NH |
| Ia1.2154 | SO₂CH₃ | (CH₂)₂CH₃ | (CH₂)₂—O-(2,4-Cl₂—C₆H₃) | NH |
| Ia1.2155 | SO₂CH₃ | (CH₂)₃CH₃ | (CH₂)₂—O-(2,4-Cl₂—C₆H₃) | NH |
| Ia1.2156 | SO₂CH₃ | H | CH₂CH(CH₃)—O-(2,4-Cl₂—C₆H₃) | NH |
| Ia1.2157 | SO₂CH₃ | CH₃ | CH₂CH(CH₃)—O-(2,4-Cl₂—C₆H₃) | NH |
| Ia1.2158 | SO₂CH₃ | CH₂CH₃ | CH₂CH(CH₃)-O-(2,4-Cl₂—C₆H₃) | NH |
| Ia1.2159 | SO₂CH₃ | (CH₂)₂CH₃ | CH₂CH(CH₃)—O-(2,4-Cl₂—C₆H₃) | NH |
| Ia1.2160 | SO₂CH₃ | (CH₂)₃CH₃ | CH₂CH(CH₃)—O-(2,4-Cl₂—C₆H₃) | NH |
| Ia1.2161 | SO₂CH₃ | H | CH(CH₃)CH₂—O-(2,4-Cl₂—C₆H₃) | NH |
| Ia1.2162 | SO₂CH₃ | CH₃ | CH(CH₃)CH₂—O-(2,4-Cl₂—C₆H₃) | NH |
| Ia1.2163 | SO₂CH₃ | CH₂CH₃ | CH(CH₃)CH₂—O-(2,4-Cl₂—C₆H₃) | NH |
| Ia1.2164 | SO₂CH₃ | (CH₂)₂CH₃ | CH(CH₃)CH₂—O-(2,4-Cl₂—C₆H₃) | NH |
| Ia1.2165 | SO₂CH₃ | (CH₂)₃CH₃ | CH(CH₃)CH₂—O-(2,4-Cl₂—C₆H₃) | NH |
| Ia1.2166 | SO₂CH₃ | H | CH(CH₃)CH(CH₃)—O-(2,4-Cl₂—C₆H₃) | NH |
| Ia1.2167 | SO₂CH₃ | CH₃ | CH(CH₃)CH(CH₃)—O-(2,4-Cl₂—C₆H₃) | NH |
| Ia1.2168 | SO₂CH₃ | CH₂CH₃ | CH(CH₃)CH(CH₃)—O-(2,4-Cl₂—C₆H₃) | NH |
| Ia1.2169 | SO₂CH₃ | (CH₂)₂CH₃ | CH(CH₃)CH(CH₃)—O-(2,4-Cl₂—C₆H₃) | NH |
| Ia1.2170 | SO₂CH₃ | (CH₂)₃CH₃ | CH(CH₃)CH(CH₃)—O-(2,4-Cl₂—C₆H₃) | NH |
| Ia1.2171 | SO₂CH₃ | H | CH₃ | NCH₃ |
| Ia1.2172 | SO₂CH₃ | CH₃ | CH₃ | NCH₃ |
| Ia1.2173 | SO₂CH₃ | CH₂CH₃ | CH₃ | NCH₃ |
| Ia1.2174 | SO₂CH₃ | (CH₂)₂CH₃ | CH₃ | NCH₃ |
| Ia1.2175 | SO₂CH₃ | (CH₂)₃CH₃ | CH₃ | NCH₃ |
| Ia1.2176 | SO₂CH₃ | H | C₂H₅ | NCH₃ |
| Ia1.2177 | SO₂CH₃ | CH₃ | C₂H₅ | NCH₃ |
| Ia1.2178 | SO₂CH₃ | CH₂CH₃ | C₂H₅ | NCH₃ |
| Ia1.2179 | SO₂CH₃ | (CH₂)₂CH₃ | C₂H₅ | NCH₃ |
| Ia1.2180 | SO₂CH₃ | (CH₂)₃CH₃ | C₂H₅ | NCH₃ |
| Ia1.2181 | SO₂CH₃ | H | (CH₂)₂CH₃ | NCH₃ |
| Ia1.2182 | SO₂CH₃ | CH₃ | (CH₂)₂CH₃ | NCH₃ |
| Ia1.2183 | SO₂CH₃ | CH₂CH₃ | (CH₂)₂CH₃ | NCH₃ |
| Ia1.2184 | SO₂CH₃ | (CH₂)₂CH₃ | (CH₂)₂CH₃ | NCH₃ |
| Ia1.2185 | SO₂CH₃ | (CH₂)₃CH₃ | (CH₂)₂CH₃ | NCH₃ |
| Ia1.2186 | SO₂CH₃ | H | CH(CH₃)₂ | NCH₃ |
| Ia1.2187 | SO₂CH₃ | CH₃ | CH(CH₃)₂ | NCH₃ |
| Ia1.2188 | SO₂CH₃ | CH₂CH₃ | CH(CH₃)₂ | NCH₃ |
| Ia1.2189 | SO₂CH₃ | (CH₂)₂CH₃ | CH(CH₃)₂ | NCH₃ |
| Ia1.2190 | SO₂CH₃ | (CH₂)₃CH₃ | CH(CH₃)₂ | NCH₃ |
| Ia1.2191 | SO₂CH₃ | H | (CH₂)₃CH₃ | NCH₃ |
| Ia1.2192 | SO₂CH₃ | CH₃ | (CH₂)₃CH₃ | NCH₃ |
| Ia1.2193 | SO₂CH₃ | CH₂CH₃ | (CH₂)₃CH₃ | NCH₃ |
| Ia1.2194 | SO₂CH₃ | (CH₂)₂CH₃ | (CH₂)₃CH₃ | NCH₃ |
| Ia1.2195 | SO₂CH₃ | (CH₂)₃CH₃ | (CH₂)₃CH₃ | NCH₃ |
| Ia1.2196 | SO₂CH₃ | H | CH₂CH(CH₃)₂ | NCH₃ |
| Ia1.2197 | SO₂CH₃ | CH₃ | CH₂CH(CH₃)₂ | NCH₃ |
| Ia1.2198 | SO₂CH₃ | CH₂CH₃ | CH₂CH(CH₃)₂ | NCH₃ |
| Ia1.2199 | SO₂CH₃ | (CH₂)₂CH₃ | CH₂CH(CH₃)₂ | NCH₃ |
| Ia1.2200 | SO₂CH₃ | (CH₂)₃CH₃ | CH₂CH(CH₃)₂ | NCH₃ |
| Ia1.2201 | SO₂CH₃ | H | CH(CH₃)CH₂CH₃ | NCH₃ |
| Ia1.2202 | SO₂CH₃ | CH₃ | CH(CH₃)CH₂CH₃ | NCH₃ |

TABLE 1-continued

| No. | R² | R³ | R⁴ | Z |
|---|---|---|---|---|
| Ia1.2203 | SO₂CH₃ | CH₂CH₃ | CH(CH₃)CH₂CH₃ | NCH₃ |
| Ia1.2204 | SO₂CH₃ | (CH₂)₂CH₃ | CH(CH₃)CH₂CH₃ | NCH₃ |
| Ia1.2205 | SO₂CH₃ | (CH₂)₃CH₃ | CH(CH₃)CH₂CH₃ | NCH₃ |
| Ia1.2206 | SO₂CH₃ | H | (CH₂)₂—C₆H₅ | NCH₃ |
| Ia1.2207 | SO₂CH₃ | CH₃ | (CH₂)₂—C₆H₅ | NCH₃ |
| Ia1.2208 | SO₂CH₃ | CH₂CH₃ | (CH₂)₂—C₆H₅ | NCH₃ |
| Ia1.2209 | SO₂CH₃ | (CH₂)₂CH₃ | (CH₂)₂—C₆H₅ | NCH₃ |
| Ia1.2210 | SO₂CH₃ | (CH₂)₃CH₃ | (CH₂)₂—C₆H₅ | NCH₃ |
| Ia1.2211 | SO₂CH₃ | H | CH₂CH(CH₃)—C₆H₅ | NCH₃ |
| Ia1.2212 | SO₂CH₃ | CH₃ | CH₂CH(CH₃)—C₆H₅ | NCH₃ |
| Ia1.2213 | SO₂CH₃ | CH₂CH₃ | CH₂CH(CH₃)—C₆H₅ | NCH₃ |
| Ia1.2214 | SO₂CH₃ | (CH₂)₂CH₃ | CH₂CH(CH₃)—C₆H₅ | NCH₃ |
| Ia1.2215 | SO₂CH₃ | (CH₂)₃CH₃ | CH₂CH(CH₃)—C₆H₅ | NCH₃ |
| Ia1.2216 | SO₂CH₃ | H | CH(CH₃)CH₂—C₆H₅ | NCH₃ |
| Ia1.2217 | SO₂CH₃ | CH₃ | CH(CH₃)CH₂—C₆H₅ | NCH₃ |
| Ia1.2218 | SO₂CH₃ | CH₂CH₃ | CH(CH₃)CH₂—C₆H₅ | NCH₃ |
| Ia1.2219 | SO₂CH₃ | (CH₂)₂CH₃ | CH(CH₃)CH₂—C₆H₅ | NCH₃ |
| Ia1.2220 | SO₂CH₃ | (CH₂)₃CH₃ | CH(CH₃)CH₂—C₆H₅ | NCH₃ |
| Ia1.2221 | SO₂CH₃ | H | CH(CH₃)CH(CH₃)—C₆H₅ | NCH₃ |
| Ia1.2222 | SO₂CH₃ | CH₃ | CH(CH₃)CH(CH₃)—C₆H₅ | NCH₃ |
| Ia1.2223 | SO₂CH₃ | CH₂CH₃ | CH(CH₃)CH(CH₃)—C₆H₅ | NCH₃ |
| Ia1.2224 | SO₂CH₃ | (CH₂)₂CH₃ | CH(CH₃)CH(CH₃)—C₆H₅ | NCH₃ |
| Ia1.2225 | SO₂CH₃ | (CH₂)₃CH₃ | CH(CH₃)CH(CH₃)—C₆H₅ | NCH₃ |
| Ia1.2226 | SO₂CH₃ | H | (CH₂)₂-(4-Cl—C₆H₄) | NCH₃ |
| Ia1.2227 | SO₂CH₃ | CH₃ | (CH₂)₂-(4-Cl—C₆H₄) | NCH₃ |
| Ia1.2228 | SO₂CH₃ | CH₂CH₃ | (CH₂)₂-(4-Cl—C₆H₄) | NCH₃ |
| Ia1.2229 | SO₂CH₃ | (CH₂)₂CH₃ | (CH₂)₂-(4-Cl—C₆H₄) | NCH₃ |
| Ia1.2230 | SO₂CH₃ | (CH₂)₃CH₃ | (CH₂)₂-(4-Cl—C₆H₄) | NCH₃ |
| Ia1.2231 | SO₂CH₃ | H | CH₂CH(CH₃)-(4-Cl—C₆H₄) | NCH₃ |
| Ia1.2232 | SO₂CH₃ | CH₃ | CH₂CH(CH₃)-(4-Cl—C₆H₄) | NCH₃ |
| Ia1.2233 | SO₂CH₃ | CH₂CH₃ | CH₂CH(CH₃)-(4-Cl—C₆H₄) | NCH₃ |
| Ia1.2234 | SO₂CH₃ | (CH₂)₂CH₃ | CH₂CH(CH₃)-(4-Cl—C₆H₄) | NCH₃ |
| Ia1.2235 | SO₂CH₃ | (CH₂)₃CH₃ | CH₂CH(CH₃)-(4-Cl—C₆H₄) | NCH₃ |
| Ia1.2236 | SO₂CH₃ | H | CH(CH₃)CH₂-(4-Cl—C₆H₄) | NCH₃ |
| Ia1.2237 | SO₂CH₃ | CH₃ | CH(CH₃)CH₂-(4-Cl—C₆H₄) | NCH₃ |
| Ia1.2238 | SO₂CH₃ | CH₂CH₃ | CH(CH₃)CH₂-(4-Cl—C₆H₄) | NCH₃ |
| Ia1.2239 | SO₂CH₃ | (CH₂)₂CH₃ | CH(CH₃)CH₂-(4-Cl—C₆H₄) | NCH₃ |
| Ia1.2240 | SO₂CH₃ | (CH₂)₃CH₃ | CH(CH₃)CH₂-(4-Cl—C₆H₄) | NCH₃ |
| Ia1.2241 | SO₂CH₃ | H | CH(CH₃)CH(CH₃)-(4-Cl—C₆H₄) | NCH₃ |
| Ia1.2242 | SO₂CH₃ | CH₃ | CH(CH₃)CH(CH₃)-(4-Cl—C₆H₄) | NCH₃ |
| Ia1.2243 | SO₂CH₃ | CH₂CH₃ | CH(CH₃)CH(CH₃)-(4-Cl—C₆H₄) | NCH₃ |
| Ia1.2244 | SO₂CH₃ | (CH₂)₂CH₃ | CH(CH₃)CH(CH₃)-(4-Cl—C₆H₄) | NCH₃ |
| Ia1.2245 | SO₂CH₃ | (CH₂)₃CH₃ | CH(CH₃)CH(CH₃)-(4-Cl—C₆H₄) | NCH₃ |
| Ia1.2246 | SO₂CH₃ | H | (CH₂)₂-(2,4-Cl₂—C₆H₃) | NCH₃ |
| Ia1.2247 | SO₂CH₃ | CH₃ | (CH₂)₂-(2,4-Cl₂—C₆H₃) | NCH₃ |
| Ia1.2248 | SO₂CH₃ | CH₂CH₃ | (CH₂)₂-(2,4-Cl₂—C₆H₃) | NCH₃ |
| Ia1.2249 | SO₂CH₃ | (CH₂)₂CH₃ | (CH₂)₂-(2,4-Cl₂—C₆H₃) | NCH₃ |
| Ia1.2250 | SO₂CH₃ | (CH₂)₃CH₃ | (CH₂)₂-(214-Cl₂—C₆H₃) | NCH₃ |
| Ia1.2251 | SO₂CH₃ | H | CH₂CH(CH₃)-(2,4-Cl₂—C₆H₃) | NCH₃ |
| Ia1.2252 | SO₂CH₃ | CH₃ | CH₂CH(CH₃)-(2,4-Cl₂—C₆H₃) | NCH₃ |
| Ia1.2253 | SO₂CH₃ | CH₂CH₃ | CH₂CH(CH₃)-(2,4-Cl₂—C₆H₃) | NCH₃ |
| Ia1.2254 | SO₂CH₃ | (CH₂)₂CH₃ | CH₂CH(CH₃)-(2,4-Cl₂—C₆H₃) | NCH₃ |
| Ia1.2255 | SO₂CH₃ | (CH₂)₃CH₃ | CH₂CH(CH₃)-( 2, 4-Cl₂—C₆H₃) | NCH₃ |
| Ia1.2256 | SO₂CH₃ | H | CH(CH₃)CH₂-(2,4-Cl₂—C₆H₃) | NCH₃ |
| Ia1.2257 | SO₂CH₃ | CH₃ | CH(CH₃)CH₂-(2,4-Cl₂—C₆H₃) | NCH₃ |
| Ia1.2258 | SO₂CH₃ | CH₂CH₃ | CH(CH₃)CH₂-(2,4-Cl₂—C₆H₃) | NCH₃ |
| Ia1.2259 | SO₂CH₃ | (CH₂)₂CH₃ | CH(CH₃)CH₂-(2,4-Cl₂—C₆H₃) | NCH₃ |
| Ia1.2260 | SO₂CH₃ | (CH₂)₃CH₃ | CH(CH₃)CH₂-(2,4-Cl₂—C₆H₃) | NCH₃ |
| Ia1.2261 | SO₂CH₃ | H | CH(CH₃)CH(CH₃)-(2,4-Cl₂—C₆H₃) | NCH₃ |
| Ia1.2262 | SO₂CH₃ | CH₃ | CH(CH₃)CH(CH₃)-(2,4-Cl₂—C₆H₃) | NCH₃ |
| Ia1.2263 | SO₂CH₃ | CH₂CH₃ | CH(CH₃)CH(CH₃)-(2,4-Cl₂—C₆H₃) | NCH₃ |
| Ia1.2264 | SO₂CH₃ | (CH₂)₂CH₃ | CH(CH₃)CH(CH₃)-(2,4-Cl₂—C₆H₃) | NCH₃ |
| Ia1.2265 | SO₂CH₃ | (CH₂)₃CH₃ | CH(CH₃)CH(CH₃)-(2,4-Cl₂—C₆H₃) | NCH₃ |
| Ia1.2266 | SO₂CH₃ | H | (CH₂)₂—O—C₆H₅ | NCH₃ |
| Ia1.2267 | SO₂CH₃ | CH₃ | (CH₂)₂—O—C₆H₅ | NCH₃ |
| Ia1.2268 | SO₂CH₃ | CH₂CH₃ | (CH₂)₂—O—C₆H₅ | NCH₃ |
| Ia1.2269 | SO₂CH₃ | (CH₂)₂CH₃ | (CH₂)₂—O—C₆H₅ | NCH₃ |
| Ia1.2270 | SO₂CH₃ | (CH₂)₃CH₃ | (CH₂) 2-O—C₆H₅ | NCH₃ |
| Ia1.2271 | SO₂CH₃ | H | CH₂CH(CH₃)—O—C₆H₅ | NCH₃ |
| Ia1.2272 | SO₂CH₃ | CH₃ | CH₂CH(CH₃)—O—C₆H₅ | NCH₃ |
| Ia1.2273 | SO₂CH₃ | CH₂CH₃ | CH₂CH (CH₃)—O—C₆H₅ | NCH₃ |
| Ia1.2274 | SO₂CH₃ | (CH₂)₂CH₃ | CH₂CH(CH₃)—O—C₆H₅ | NCH₃ |
| Ia1.2275 | SO₂CH₃ | (CH₂)₃CH₃ | CH₂CH(CH₃)—O—C₆H₅ | NCH₃ |
| Ia1.2276 | SO₂CH₃ | H | CH(CH₃)CH₂—O—C₆H₅ | NCH₃ |
| Ia1.2277 | SO₂CH₃ | CH₃ | CH(CH₃)CH₂—O—C₆H₅ | NCH₃ |
| Ia1.2278 | SO₂CH₃ | CH₂CH₃ | CH(CH₃)CH₂—O—C₆H₅ | NCH₃ |
| Ia1.2279 | SO₂CH₃ | (CH₂)₂CH₃ | CH(CH₃)CH₂—O—C₆H₅ | NCH₃ |

TABLE 1-continued

| No. | R² | R³ | R⁴ | Z |
|---|---|---|---|---|
| Ia1.2280 | SO₂CH₃ | (CH₂)₃CH₃ | CH(CH₃)CH₂—O—C₆H₅ | NCH₃ |
| Ia1.2281 | SO₂CH₃ | H | CH(CH₃)CH(CH₃)—O—C₆H₅ | NCH₃ |
| Ia1.2282 | SO₂CH₃ | CH₃ | CH(CH₃)CH(CH₃)—O—C₆H₅ | NCH₃ |
| Ia1.2283 | SO₂CH₃ | CH₂CH₃ | CH(CH₃)CH(CH₃)—O—C₆H₅ | NCH₃ |
| Ia1.2284 | SO₂CH₃ | (CH₂)₂CH₃ | CH(CH₃)CH(CH₃)—O—C₆H₅ | NCH₃ |
| Ia1.2285 | SO₂CH₃ | (CH₂)₃CH₃ | CH(CH₃)CH(CH₃)—O—C₆H₅ | NCH₃ |
| Ia1.2286 | SO₂CH₃ | H | (CH₂)₂—O-(4-Cl—C₆H₄) | NCH₃ |
| Ia1.2287 | SO₂CH₃ | CH₃ | (CH₂)₂—O-(4-Cl—C₆H₄) | NCH₃ |
| Ia1.2288 | SO₂CH₃ | CH₂CH₃ | (CH₂)₂—O-(4-Cl—C₆H₄) | NCH₃ |
| Ia1.2289 | SO₂CH₃ | (CH₂)₂CH₃ | (CH₂)₂—O-(4-Cl—C₆H₄) | NCH₃ |
| Ia1.2290 | SO₂CH₃ | (CH₂)₃CH₃ | (CH₂)₂—O-(4-Cl—C₆H₄) | NCH₃ |
| Ia1.2291 | SO₂CH₃ | H | CH₂CH(CH₃)—O-(4-Cl—C₆H₄) | NCH₃ |
| Ia1.2292 | SO₂CH₃ | CH₃ | CH₂CH(CH₃)—O-(4-Cl—C₆H₄) | NCH₃ |
| Ia1.2293 | SO₂CH₃ | CH₂CH₃ | CH₂CH(CH₃)—O-(4-Cl—C₆H₄) | NCH₃ |
| Ia1.2294 | SO₂CH₃ | (CH₂)₂CH₃ | CH₂CH(CH₃)—O-(4-Cl—C₆H₄) | NCH₃ |
| Ia1.2295 | SO₂CH₃ | (CH₂)₃CH₃ | CH₂CH(CH₃)—O-(4-Cl—C₆H₄) | NCH₃ |
| Ia1.2296 | SO₂CH₃ | H | CH(CH₃)CH₂—O-(4-Cl—C₆H₄) | NCH₃ |
| Ia1.2297 | SO₂CH₃ | CH₃ | CH(CH₃)CH₂—O-(4-Cl—C₆H₄) | NCH₃ |
| Ia1.2298 | SO₂CH₃ | CH₂CH₃ | CH(CH₃)CH₂—O-(4-Cl—C₆H₄) | NCH₃ |
| Ia1.2299 | SO₂CH₃ | (CH₂)₂CH₃ | CH(CH₃)CH₂—O-(4-Cl—C₆H₄) | NCH₃ |
| Ia1.2300 | SO₂CH₃ | (CH₂)₃CH₃ | CH(CH₃)CH₂—O-(4-Cl—C₆H₄) | NCH₃ |
| Ia1.2301 | SO₂CH₃ | H | CH(CH₃)CH(CH₃)—O-(4-Cl—C₆H₄) | NCH₃ |
| Ia1.2302 | SO₂CH₃ | CH₃ | CH(CH₃)CH(CH₃)—O-(4-Cl—C₆H₄) | NCH₃ |
| Ia1.2303 | SO₂CH₃ | CH₂CH₃ | CH(CH₃)CH(CH₃)—O-(4-Cl—C₆H₄) | NCH₃ |
| Ia1.2304 | SO₂CH₃ | (CH₂)₂CH₃ | CH(CH₃)CH(CH₃)—O-(4-Cl—C₆H₄) | NCH₃ |
| Ia1.2305 | SO₂CH₃ | (CH₂)₃CH₃ | CH(CH₃)CH(CH₃)—O-(4-Cl—C₆H₄) | NCH₃ |
| Ia1.2306 | SO₂CH₃ | H | (CH₂)₂—O-(2,4-Cl₂—C₆H₃) | NCH₃ |
| Ia1.2307 | SO₂CH₃ | CH₃ | (CH₂)₂—O-(2,4-Cl₂—C₆H₃) | NCH₃ |
| Ia1.2308 | SO₂CH₃ | CH₂CH₃ | (CH₂)₂—O-(2,4-Cl₂—C₆H₃) | NCH₃ |
| Ia1.2309 | SO₂CH₃ | (CH₂)₂CH₃ | (CH₂)₂—O-(2,4-Cl₂—C₆H₃) | NCH₃ |
| Ia1.2310 | SO₂CH₃ | (CH₂)₃CH₃ | (CH₂)₂—O-(2,4-Cl₂—C₆H₃) | NCH₃ |
| Ia1.2311 | SO₂CH₃ | H | CH₂CH(CH₃)—O-(2,4-Cl₂—C₆H₃) | NCH₃ |
| Ia1.2312 | SO₂CH₃ | CH₃ | CH₂CH(CH₃)—O-(2,4-Cl₂—C₆H₃) | NCH₃ |
| Ia1.2313 | SO₂CH₃ | CH₂CH₃ | CH₂CH(CH₃)—O-(2,4-Cl₂—C₆H₃) | NCH₃ |
| Ia1.2314 | SO₂CH₃ | (CH₂)₂CH₃ | CH₂CH(CH₃)—O-(2,4-Cl₂—C₆H₃) | NCH₃ |
| Ia1.2315 | SO₂CH₃ | (CH₂)₃CH₃ | CH₂CH(CH₃)—O-(2,4-Cl₂—C₆H₃) | NCH₃ |
| Ia1.2316 | SO₂CH₃ | H | CH(CH₃)CH₂—O-(2,4-Cl₂—C₆H₃) | NCH₃ |
| Ia1.2317 | SO₂CH₃ | CH₃ | CH(CH₃)CH₂—O-(2,4-Cl₂—C₆H₃) | NCH₃ |
| Ia1.2318 | SO₂CH₃ | CH₂CH₃ | CH(CH₃)CH₂—O-(2,4-Cl₂—C₆H₃) | NCH₃ |
| Ia1.2319 | SO₂CH₃ | (CH₂)₂CH₃ | CH(CH₃)CH₂—O-(2,4-Cl₂—C₆H₃) | NCH₃ |
| Ia1.2320 | SO₂CH₃ | (CH₂)₃CH₃ | CH(CH₃)CH₂—O-(2,4-Cl₂—C₆H₃) | NCH₃ |
| Ia1.2321 | SO₂CH₃ | H | CH(CH₃)CH(CH₃)—O-(2,4-Cl₂—C₆H₃) | NCH₃ |
| Ia1.2322 | SO₂CH₃ | CH₃ | CH(CH₃)CH(CH₃)—O-(2,4-Cl₂—C₆H₃) | NCH₃ |
| Ia1.2323 | SO₂CH₃ | CH₂CH₃ | CH(CH₃)CH(CH₃)—O-(2,4-Cl₂—C₆H₃) | NCH₃ |
| Ia1.2324 | SO₂CH₃ | (CH₂)₂CH₃ | CH(CH₃)CH(CH₃)—O-(2,4-Cl₂—C₆H₃) | NCH₃ |
| Ia1.2325 | SO₂CH₃ | (CH₂)₃CH₃ | CH(CH₃)CH(CH₃)—O-(2,4-Cl₂—C₆H₃) | NCH₃ |
| Ia1.2326 | NO₂ | H | CH₃ | O |
| Ia1.2327 | NO₂ | CH₃ | CH₃ | O |
| Ia1.2328 | NO₂ | CH₂CH₃ | CH₃ | O |
| Ia1.2329 | NO₂ | (CH₂)₂CH₃ | CH₃ | O |
| Ia1.2330 | NO₂ | (CH₂)₃CH₃ | CH₃ | O |
| Ia1.2331 | NO₂ | H | C₂H₅ | O |
| Ia1.2332 | NO₂ | CH₃ | C₂H₅ | O |
| Ia1.2333 | NO₂ | CH₂CH₃ | C₂H₅ | O |
| Ia1.2334 | NO₂ | (CH₂)₂CH₃ | C₂H₅ | O |
| Ia1.2335 | NO₂ | (CH₂)₃CH₃ | C₂H₅ | O |
| Ia1.2336 | NO₂ | H | (CH₂)₂CH₃ | O |
| Ia1.2337 | NO₂ | CH₃ | (CH₂)₂CH₃ | O |
| Ia1.2338 | NO₂ | CH₂CH₃ | (CH₂)₂CH₃ | O |
| Ia1.2339 | NO₂ | (CH₂)₂CH₃ | (CH₂)₂CH₃ | O |
| Ia1.2340 | NO₂ | (CH₂)₃CH₃ | (CH₂)₂CH₃ | O |
| Ia1.2341 | NO₂ | H | CH(CH₃)₂ | O |
| Ia1.2342 | NO₂ | CH₃ | CH(CH₃)₂ | O |
| Ia1.2343 | NO₂ | CH₂CH₃ | CH(CH₃)₂ | O |
| Ia1.2344 | NO₂ | (CH₂)₂CH₃ | CH(CH₃)₂ | O |
| Ia1.2345 | NO₂ | (CH₂)₃CH₃ | CH(CH₃)₂ | O |
| Ia1.2346 | NO₂ | H | (CH₂)₃CH₃ | O |
| Ia1.2347 | NO₂ | CH₃ | (CH₂)₃CH₃ | O |
| Ia1.2348 | NO₂ | CH₂CH₃ | (CH₂)₃CH₃ | O |
| Ia1.2349 | NO₂ | (CH₂)₂CH₃ | (CH₂)₃CH₃ | O |
| Ia1.2350 | NO₂ | (CH₂)₃CH₃ | (CH₂)₃CH₃ | O |
| Ia1.2351 | NO₂ | H | CH₂CH(CH₃)₂ | O |
| Ia1.2352 | NO₂ | CH₃ | CH₂CH(CH₃)₂ | O |
| Ia1.2353 | NO₂ | CH₂CH₃ | CH₂CH(CH₃)₂ | O |
| Ia1.2354 | NO₂ | (CH₂)₂CH₃ | CH₂CH(CH₃)₂ | O |
| Ia1.2355 | NO₂ | (CH₂)₃CH₃ | CH₂CH(CH₃)₂ | O |
| Ia1.2356 | NO₂ | H | CH(CH₃)CH₂CH₃ | O |

TABLE 1-continued

| No. | R² | R³ | R⁴ | Z |
|---|---|---|---|---|
| Ia1.2357 | NO₂ | CH₃ | CH(CH₃)CH₂CH₃ | O |
| Ia1.2358 | NO₂ | CH₂CH₃ | CH(CH₃)CH₂CH₃ | O |
| Ia1.2359 | NO₂ | (CH₂)₂CH₃ | CH(CH₃)CH₂CH₃ | O |
| Ia1.2360 | NO₂ | (CH₂)₃CH₃ | CH(CH₃)CH₂CH₃ | O |
| Ia1.2361 | NO₂ | H | (CH₂)₂—C₆H₅ | O |
| Ia1.2362 | NO₂ | CH₃ | (CH₂)₂—C₆H₅ | O |
| Ia1.2363 | NO₂ | CH₂CH₃ | (CH₂)₂—C₆H₅ | O |
| Ia1.2364 | NO₂ | (CH₂)₂CH₃ | (CH₂)₂—C₆H₅ | O |
| Ia1.2365 | NO₂ | (CH₂)₃CH₃ | (CH₂)₂—C₆H₅ | O |
| Ia1.2366 | NO₂ | H | CH₂CH(CH₃)—C₆H₅ | O |
| Ia1.2367 | NO₂ | CH₃ | CH₂CH(CH₃)—C₆H₅ | O |
| Ia1.2368 | NO₂ | CH₂CH₃ | CH₂CH(CH₃)—C₆H₅ | O |
| Ia1.2369 | NO₂ | (CH₂)₂CH₃ | CH₂CH(CH₃)—C₆H₅ | O |
| Ia1.2370 | NO₂ | (CH₂)₃CH₃ | CH₂CH(CH₃)—C₆H₅ | O |
| Ia1.2371 | NO₂ | H | CH(CH₃)CH₂—C₆H₅ | O |
| Ia1.2372 | NO₂ | CH₃ | CH(CH₃)CH₂—C₆H₅ | O |
| Ia1.2373 | NO₂ | CH₂CH₃ | CH(CH₃)CH₂—C₆H₅ | O |
| Ia1.2374 | NO₂ | (CH₂)₂CH₃ | CH(CH₃)CH₂—C₆H₅ | O |
| Ia1.2375 | NO₂ | (CH₂)₃CH₃ | CH(CH₃)CH₂—C₆H₅ | O |
| Ia1.2376 | NO₂ | H | CH(CH₃)CH(CH₃)—C₆H₅ | O |
| Ia1.2377 | NO₂ | CH₃ | CH(CH₃)CH(CH₃)—C₆H₅ | O |
| Ia1.2378 | NO₂ | CH₂CH₃ | CH(CH₃)CH(CH₃)—C₆H₅ | O |
| Ia1.2379 | NO₂ | (CH₂)₂CH₃ | CH(CH₃)CH(CH₃)—C₆H₅ | O |
| Ia1.2380 | NO₂ | (CH₂)₃CH₃ | CH(CH₃)CH(CH₃)—C₆H₅ | O |
| Ia1.2381 | NO₂ | H | (CH₂)₂-(4-Cl—C₆H₄) | O |
| Ia1.2382 | NO₂ | CH₃ | (CH₂)₂-(4-Cl—C₆H₄) | O |
| Ia1.2383 | NO₂ | CH₂CH₃ | (CH₂)₂-(4-Cl—C₆H₄) | O |
| Ia1.2384 | NO₂ | (CH₂)₂CH₃ | (CH₂)₂-(4-Cl—C₆H₄) | O |
| Ia1.2385 | NO₂ | (CH₂)₃CH₃ | (CH₂)₂-(4-Cl—C₆H₄) | O |
| Ia1.2386 | NO₂ | H | CH₂CH(CH₃)-(4-Cl—C₆H₄) | O |
| Ia1.2387 | NO₂ | CH₃ | CH₂CH(CH₃)-(4-Cl—C₆H₄) | O |
| Ia1.2388 | NO₂ | CH₂CH₃ | CH₂CH(CH₃)-(4-Cl—C₆H₄) | O |
| Ia1.2389 | NO₂ | (CH₂)₂CH₃ | CH₂CH(CH₃)-(4-Cl—C₆H₄) | O |
| Ia1.2390 | NO₂ | (CH₂)₃CH₃ | CH₂CH(CH₃)-(4-Cl—C₆H₄) | O |
| Ia1.2391 | NO₂ | H | CH(CH₃)CH₂-(4-Cl—C₆H₄) | O |
| Ia1.2392 | NO₂ | CH₃ | CH(CH₃)CH₂-(4-Cl—C₆H₄) | O |
| Ia1.2393 | NO₂ | CH₂CH₃ | CH(CH₃)CH₂-(4-Cl—C₆H₄) | O |
| Ia1.2394 | NO₂ | (CH₂)₂CH₃ | CH(CH₃)CH₂-(4-Cl—C₆H₄) | O |
| Ia1.2395 | NO₂ | (CH₂)₃CH₃ | CH(CH₃)CH₂-(4-Cl—C₆H₄) | O |
| Ia1.2396 | NO₂ | H | CH(CH₃)CH(CH₃)-(4-Cl—C₆H₄) | O |
| Ia1.2397 | NO₂ | CH₃ | CH(CH₃)CH(CH₃)-(4-Cl—C₆H₄) | O |
| Ia1.2398 | NO₂ | CH₂CH₃ | CH(CH₃)CH(CH₃)-(4-Cl—C₆H₄) | O |
| Ia1.2399 | NO₂ | (CH₂)₂CH₃ | CH(CH₃)CH(CH₃)-(4-Cl—C₆H₄) | O |
| Ia1.2400 | NO₂ | (CH₂)₃CH₃ | CH(CH₃)CH(CH₃)-(4-Cl—C₆H₄) | O |
| Ia1.2401 | NO₂ | H | (CH₂)₂-(2,4-Cl₂—C₆H₃) | O |
| Ia1.2402 | NO₂ | CH₃ | (CH₂)₂-(2,4-Cl₂—C₆H₃) | O |
| Ia1.2403 | NO₂ | CH₂CH₃ | (CH₂)₂-(2,4-Cl₂—C₆H₃) | O |
| Ia1.2404 | NO₂ | (CH₂)₂CH₃ | (CH₂)₂-(2,4-Cl₂—C₆H₃) | O |
| Ia1.2405 | NO₂ | (CH₂)₃CH₃ | (CH₂)₂-(2,4-Cl₂—C₆H₃) | O |
| Ia1.2406 | NO₂ | H | CH₂CH(CH₃)-(2,4-Cl₂—C₆H₃) | O |
| Ia1.2407 | NO₂ | CH₃ | CH₂CH(CH₃)-(2,4-Cl₂—C₆H₃) | O |
| Ia1.2408 | NO₂ | CH₂CH₃ | CH₂CH(CH₃)-(2,4-Cl₂—C₆H₃) | O |
| Ia1.2409 | NO₂ | (CH₂)₂CH₃ | CH₂CH(CH₃)-(2,4-Cl₂—C₆H₃) | O |
| Ia1.2410 | NO₂ | (CH₂)₃CH₃ | CH₂CH(CH₃)-(2,4-Cl₂—C₆H₃) | O |
| Ia1.2411 | NO₂ | H | CH(CH₃)CH₂-(2,4-Cl₂—C₆H₃) | O |
| Ia1.2412 | NO₂ | CH₃ | CH(CH₃)CH₂-(2,4-Cl₂—C₆H₃) | O |
| Ia1.2413 | NO₂ | CH₂CH₃ | CH(CH₃)CH₂-(2,4-Cl₂—C₆H₃) | O |
| Ia1.2414 | NO₂ | (CH₂)₂CH₃ | CH(CH₃)CH₂-(2,4-Cl₂—C₆H₃) | O |
| Ia1.2415 | NO₂ | (CH₂)₃CH₃ | CH(CH₃)CH₂-(2,4-Cl₂—C₆H₃) | O |
| Ia1.2416 | NO₂ | H | CH(CH₃)CH(CH₃)-(2,4-Cl₂—C₆H₃) | O |
| Ia1.2417 | NO₂ | CH₃ | CH(CH₃)CH(CH₃)-(2,4-Cl₂—C₆H₃) | O |
| Ia1.2418 | NO₂ | CH₂CH₃ | CH(CH₃)CH(CH₃)-(2,4-Cl₂—C₆H₃) | O |
| Ia1.2419 | NO₂ | (CH₂)₂CH₃ | CH(CH₃)CH(CH₃)-(2,4-Cl₂—C₆H₃) | O |
| Ia1.2420 | NO₂ | (CH₂)₃CH₃ | CH(CH₃)CH(CH₃)-(2,4-Cl₂—C₆H₃) | O |
| Ia1.2421 | NO₂ | H | (CH₂)₂—O—C₆H₅ | O |
| Ia1.2422 | NO₂ | CH₃ | (CH₂)₂—O—C₆H₅ | O |
| Ia1.2423 | NO₂ | CH₂CH₃ | (CH₂)₂—O—C₆H₅ | O |
| Ia1.2424 | NO₂ | (CH₂)₂CH₃ | (CH₂)₂—O—C₆H₅ | O |
| Ia1.2425 | NO₂ | (CH₂)₃CH₃ | (CH₂)₂—O—C₆H₅ | O |
| Ia1.2426 | NO₂ | H | CH₂CH(CH₃)—O—C₆H₅ | O |
| Ia1.2427 | NO₂ | CH₃ | CH₂CH(CH₃)—O—C₆H₅ | O |
| Ia1.2428 | NO₂ | CH₂CH₃ | CH₂CH(CH₃)—O—C₆H₅ | O |
| Ia1.2429 | NO₂ | (CH₂)₂CH₃ | CH₂CH(CH₃)—O—C₆H₅ | O |
| Ia1.2430 | NO₂ | (CH₂)₃CH₃ | CH₂CH(CH₃)—O—C₆H₅ | O |
| Ia1.2431 | NO₂ | H | CH(CH₃)CH₂—O—C₆H₅ | O |
| Ia1.2432 | NO₂ | CH₃ | CH(CH₃)CH₂—O—C₆H₅ | O |
| Ia1.2433 | NO₂ | CH₂CH₃ | CH(CH₃)CH₂—O—C₆H₅ | O |

TABLE 1-continued

| No. | R² | R³ | R⁴ | Z |
|---|---|---|---|---|
| Ia1.2434 | NO₂ | (CH₂)₂CH₃ | CH(CH₃)CH₂—O—C₆H₅ | O |
| Ia1.2435 | NO₂ | (CH₂)₃CH₃ | CH(CH₃)CH₂—O—C₆H₅ | O |
| Ia1.2436 | NO₂ | H | CH(CH₃)CH(CH₃)—O—C₆H₅ | O |
| Ia1.2437 | NO₂ | CH₃ | CH(CH₃)CH(CH₃)—O—C₆H₅ | O |
| Ia1.2438 | NO₂ | CH₂CH₃ | CH(CH₃)CH(CH₃)—O—C₆H₅ | O |
| Ia1.2439 | NO₂ | (CH₂)₂CH₃ | CH(CH₃)CH(CH₃)—O—C₆H₅ | O |
| Ia1.2440 | NO₂ | (CH₂)₃CH₃ | CH(CH₃)CH(CH₃)—O—C₆H₅ | O |
| Ia1.2441 | NO₂ | H | (CH₂)₂—O-(4-Cl—C₆H₄) | O |
| Ia1.2442 | NO₂ | CH₃ | (CH₂)₂—O-(4-Cl—C₆H₄) | O |
| Ia1.2443 | NO₂ | CH₂CH₃ | (CH₂)₂—O-(4-Cl—C₆H₄) | O |
| Ia1.2444 | NO₂ | (CH₂)₂CH₃ | (CH₂)₂—O-(4-Cl—C₆H₄) | O |
| Ia1.2445 | NO₂ | (CH₂)₃CH₃ | (CH₂)₂—O-(4-Cl—C₆H₄) | O |
| Ia1.2446 | NO₂ | H | CH₂CH(CH₃)—O-(4-Cl—C₆H₄) | O |
| Ia1.2447 | NO₂ | CH₃ | CH₂CH(CH₃)—O-(4-Cl—C₆H₄) | O |
| Ia1.2448 | NO₂ | CH₂CH₃ | CH₂CH(CH₃)—O-(4-Cl—C₆H₄) | O |
| Ia1.2449 | NO₂ | (CH₂)₂CH₃ | CH₂CH(CH₃)—O-(4-Cl—C₆H₄) | O |
| Ia1.2450 | NO₂ | (CH₂)₃CH₃ | CH₂CH(CH₃)—O-(4-Cl—C₆H₄) | O |
| Ia1.2451 | NO₂ | H | CH(CH₃)CH₂—O-(4-Cl—C₆H₄) | O |
| Ia1.2452 | NO₂ | CH₃ | CH(CH₃)CH₂—O-(4-Cl—C₆H₄) | O |
| Ia1.2453 | NO₂ | CH₂CH₃ | CH(CH₃)CH₂—O-(4-Cl—C₆H₄) | O |
| Ia1.2454 | NO₂ | (CH₂)₂CH₃ | CH(CH₃)CH₂—O-(4-Cl—C₆H₄) | O |
| Ia1.2455 | NO₂ | (CH₂)₃CH₃ | CH(CH₃)CH₂—O-(4-Cl—C₆H₄) | O |
| Ia1.2456 | NO₂ | H | CH(CH₃)CH(CH₃)—O-(4-Cl—C₆H₄) | O |
| Ia1.2457 | NO₂ | CH₃ | CH(CH₃)CH(CH₃)—O-(4-Cl—C₆H₄) | O |
| Ia1.2458 | NO₂ | CH₂CH₃ | CH(CH₃)CH(CH₃)—O-(4-Cl—C₆H₄) | O |
| Ia1.2459 | NO₂ | (CH₂)₂CH₃ | CH(CH₃)CH(CH₃)—O-(4-Cl—C₆H₄) | O |
| Ia1.2460 | NO₂ | (CH₂)₃CH₃ | CH(CH₃)CH(CH₃)—O-(4-Cl—C₆H₄) | O |
| Ia1.2461 | NO₂ | H | (CH₂)₂—O-(2,4-Cl₂—C₆H₃) | O |
| Ia1.2462 | NO₂ | CH₃ | (CH₂)₂—O-(2,4-Cl₂—C₆H₃) | O |
| Ia1.2463 | NO₂ | CH₂CH₃ | (CH₂)₂—O-(2,4-Cl₂—C₆H₃) | O |
| Ia1.2464 | NO₂ | (CH₂)₂CH₃ | (CH₂)₂—O-(2,4-Cl₂—C₆H₃) | O |
| Ia1.2465 | NO₂ | (CH₂)₃CH₃ | (CH₂)₂—O-(2,4-Cl₂—C₆H₃) | O |
| Ia1.2466 | NO₂ | H | CH₂CH(CH₃)—O-(2,4-Cl₂—C₆H₃) | O |
| Ia1.2467 | NO₂ | CH₃ | CH₂CH(CH₃)—O-(2,4-Cl₂—C₆H₃) | O |
| Ia1.2468 | NO₂ | CH₂CH₃ | CH₂CH(CH₃)—O-(2,4-Cl₂—C₆H₃) | O |
| Ia1.2469 | NO₂ | (CH₂)₂CH₃ | CH₂CH(CH₃)—O-(2,4-Cl₂—C₆H₃) | O |
| Ia1.2470 | NO₂ | (CH₂)₃CH₃ | CH₂CH(CH₃)—O-(2,4-Cl₂—C₆H₃) | O |
| Ia1.2471 | NO₂ | H | CH(CH₃)CH₂—O-(2,4-Cl₂—C₆H₃) | O |
| Ia1.2472 | NO₂ | CH₃ | CH(CH₃)CH₂—O-(2,4-Cl₂—C₆H₃) | O |
| Ia1.2473 | NO₂ | CH₂CH₃ | CH(CH₃)CH₂—O-(2,4-Cl₂—C₆H₃) | O |
| Ia1.2474 | NO₂ | (CH₂)₂CH₃ | CH(CH₃)CH₂—O-(2,4-Cl₂—C₆H₃) | O |
| Ia1.2475 | NO₂ | (CH₂)₃CH₃ | CH(CH₃)CH₂—O-(2,4-Cl₂—C₆H₃) | O |
| Ia1.2476 | NO₂ | H | CH(CH₃)CH(CH₃)—O-(2,4-Cl₂—C₆H₃) | O |
| Ia1.2477 | NO₂ | CH₃ | CH(CH₃)CH(CH₃)—O-(2,4-Cl₂—C₆H₃) | O |
| Ia1.2478 | NO₂ | CH₂CH₃ | CH(CH₃)CH(CH₃)—O-(2,4-Cl₂—C₆H₃) | O |
| Ia1.2479 | NO₂ | (CH₂)₂CH₃ | CH(CH₃)CH(CH₃)—O-(2,4-Cl₂—C₆H₃) | O |
| Ia1.2480 | NO₂ | (CH₂)₃CH₃ | CH(CH₃)CH(CH₃)—O-(2,4-Cl₂—C₆H₃) | O |
| Ia1.2481 | NO₂ | H | CH₃ | NH |
| Ia1.2482 | NO₂ | CH₃ | CH₃ | NH |
| Ia1.2483 | NO₂ | CH₂CH₃ | CH₃ | NH |
| Ia1.2484 | NO₂ | (CH₂)₂CH₃ | CH₃ | NH |
| Ia1.2485 | NO₂ | (CH₂)₃CH₃ | CH₃ | NH |
| Ia1.2486 | NO₂ | H | C₂H₅ | NH |
| Ia1.2487 | NO₂ | CH₃ | C₂H₅ | NH |
| Ia1.2488 | NO₂ | CH₂CH₃ | C₂H₅ | NH |
| Ia1.2489 | NO₂ | (CH₂)₂CH₃ | C₂H₅ | NH |
| Ia1.2490 | NO₂ | (CH₂)₃CH₃ | C₂H₅ | NH |
| Ia1.2491 | NO₂ | H | (CH₂)₂CH₃ | NH |
| Ia1.2492 | NO₂ | CH₃ | (CH₂)₂CH₃ | NH |
| Ia1.2493 | NO₂ | CH₂CH₃ | (CH₂)₂CH₃ | NH |
| Ia1.2494 | NO₂ | (CH₂)₂CH₃ | (CH₂)₂CH₃ | NH |
| Ia1.2495 | NO₂ | (CH₂)₃CH₃ | (CH₂)₂CH₃ | NH |
| Ia1.2496 | NO₂ | H | CH(CH₃)₂ | NH |
| Ia1.2497 | NO₂ | CH₃ | CH(CH₃)₂ | NH |
| Ia1.2498 | NO₂ | CH₂CH₃ | CH(CH₃)₂ | NH |
| Ia1.2499 | NO₂ | (CH₂)₂CH₃ | CH(CH₃)₂ | NH |
| Ia1.2500 | NO₂ | (CH₂)₃CH₃ | CH(CH₃)₂ | NH |
| Ia1.2501 | NO₂ | H | (CH₂)₃CH₃ | NH |
| Ia1.2502 | NO₂ | CH₃ | (CH₂)₃CH₃ | NH |
| Ia1.2503 | NO₂ | CH₂CH₃ | (CH₂)₃CH₃ | NH |
| Ia1.2504 | NO₂ | (CH₂)₂CH₃ | (CH₂)₃CH₃ | NH |
| Ia1.2505 | NO₂ | (CH₂)₃CH₃ | (CH₂)₃CH₃ | NH |
| Ia1.2506 | NO₂ | H | CH₂CH(CH₃)₂ | NH |
| Ia1.2507 | NO₂ | CH₃ | CH₂CH(CH₃)₂ | NH |
| Ia1.2508 | NO₂ | CH₂CH₃ | CH₂CH(CH₃)₂ | NH |
| Ia1.2509 | NO₂ | (CH₂)₂CH₃ | CH₂CH(CH₃)₂ | NH |
| Ia1.2510 | NO₂ | (CH₂)₃CH₃ | CH₂CH(CH₃)₂ | NH |

TABLE 1-continued

| No. | R² | R³ | R⁴ | Z |
|---|---|---|---|---|
| Ia1.2511 | NO₂ | H | CH(CH₃)CH₂CH₃ | NH |
| Ia1.2512 | NO₂ | CH₃ | CH(CH₃)CH₂CH₃ | NH |
| Ia1.2513 | NO₂ | CH₂CH₃ | CH(CH₃)CH₂CH₃ | NH |
| Ia1.2514 | NO₂ | (CH₂)₂CH₃ | CH(CH₃)CH₂CH₃ | NH |
| Ia1.2515 | NO₂ | (CH₂)₃CH₃ | CH(CH₃)CH₂CH₃ | NH |
| Ia1.2516 | NO₂ | H | (CH₂)₂—C₆H₅ | NH |
| Ia1.2517 | NO₂ | CH₃ | (CH₂)₂—C₆H₅ | NH |
| Ia1.2518 | NO₂ | CH₂CH₃ | (CH₂)₂—C₆H₅ | NH |
| Ia1.2519 | NO₂ | (CH₂)₂CH₃ | (CH₂)₂—C₆H₅ | NH |
| Ia1.2520 | NO₂ | (CH₂)₃CH₃ | (CH₂)₂—C₆H₅ | NH |
| Ia1.2521 | NO₂ | H | CH₂CH(CH₃)—C₆H₅ | NH |
| Ia1.2522 | NO₂ | CH₃ | CH₂CH(CH₃)—C₆H₅ | NH |
| Ia1.2523 | NO₂ | CH₂CH₃ | CH₂CH(CH₃)—C₆H₅ | NH |
| Ia1.2524 | NO₂ | (CH₂)₂CH₃ | CH₂CH(CH₃)—C₆H₅ | NH |
| Ia1.2525 | NO₂ | (CH₂)₃CH₃ | CH₂CH(CH₃)—C₆H₅ | NH |
| Ia1.2526 | NO₂ | H | CH(CH₃)CH₂—C₆H₅ | NH |
| Ia1.2527 | NO₂ | CH₃ | CH(CH₃)CH₂—C₆H₅ | NH |
| Ia1.2528 | NO₂ | CH₂CH₃ | CH(CH₃)CH₂—C₆H₅ | NH |
| Ia1.2529 | NO₂ | (CH₂)₂CH₃ | CH(CH₃)CH₂—C₆H₅ | NH |
| Ia1.2530 | NO₂ | (CH₂)₃CH₃ | CH(CH₃)CH₂—C₆H₅ | NH |
| Ia1.2531 | NO₂ | H | CH(CH₃)CH(CH₃)—C₆H₅ | NH |
| Ia1.2532 | NO₂ | CH₃ | CH(CH₃)CH(CH₃)—C₆H₅ | NH |
| Ia1.2533 | NO₂ | CH₂CH₃ | CH(CH₃)CH(CH₃)—C₆H₅ | NH |
| Ia1.2534 | NO₂ | (CH₂)₂CH₃ | CH(CH₃)CH(CH₃)—C₆H₅ | NH |
| Ia1.2535 | NO₂ | (CH₂)₃CH₃ | CH(CH₃)CH(CH₃)—C₆H₅ | NH |
| Ia1.2536 | NO₂ | H | (CH₂)₂-(4-Cl—C₆H₄) | NH |
| Ia1.2537 | NO₂ | CH₃ | (CH₂)₂-(4-Cl—C₆H₄) | NH |
| Ia1.2538 | NO₂ | CH₂CH₃ | (CH₂)₂-(4-Cl—C₆H₄) | NH |
| Ia1.2539 | NO₂ | (CH₂)₂CH₃ | (CH₂)₂-(4-Cl—C₆H₄) | NH |
| Ia1.2540 | NO₂ | (CH₂)₃CH₃ | (CH₂)₂-(4-Cl—C₆H₄) | NH |
| Ia1.2541 | NO₂ | H | CH₂CH(CH₃)-(4-Cl—C₆H₄) | NH |
| Ia1.2542 | NO₂ | CH₃ | CH₂CH(CH₃)-(4-Cl—C₆H₄) | NH |
| Ia1.2543 | NO₂ | CH₂CH₃ | CH₂CH(CH₃)-(4-Cl—C₆H₄) | NH |
| Ia1.2544 | NO₂ | (CH₂)₂CH₃ | CH₂CH(CH₃)-(4-Cl—C₆H₄) | NH |
| Ia1.2545 | NO₂ | (CH₂)₃CH₃ | CH₂CH(CH₃)-(4-Cl—C₆H₄) | NH |
| Ia1.2546 | NO₂ | H | CH(CH₃)CH₂-(4-Cl—C₆H₄) | NH |
| Ia1.2547 | NO₂ | CH₃ | CH(CH₃)CH₂-(4-Cl—C₆H₄) | NH |
| Ia1.2548 | NO₂ | CH₂CH₃ | CH(CH₃)CH₂-(4-Cl—C₆H₄) | NH |
| Ia1.2549 | NO₂ | (CH₂)₂CH₃ | CH(CH₃)CH₂-(4-Cl—C₆H₄) | NH |
| Ia1.2550 | NO₂ | (CH₂)₃CH₃ | CH(CH₃)CH₂-(4-Cl—C₆H₄) | NH |
| Ia1.2551 | NO₂ | H | CH(CH₃)CH(CH₃)-(4-Cl—C₆H₄) | NH |
| Ia1.2552 | NO₂ | CH₃ | CH(CH₃)CH(CH₃)-(4-Cl—C₆H₄) | NH |
| Ia1.2553 | NO₂ | CH₂CH₃ | CH(CH₃)CH(CH₃)-(4-Cl—C₆H₄) | NH |
| Ia1.2554 | NO₂ | (CH₂)₂CH₃ | CH(CH₃)CH(CH₃)-(4-Cl—C₆H₄) | NH |
| Ia1.2555 | NO₂ | (CH₂)₃CH₃ | CH(CH₃)CH(CH₃)-(4-Cl—C₆H₄) | NH |
| Ia1.2556 | NO₂ | H | (CH₂)₂-(2,4-Cl₂—C₆H₃) | NH |
| Ia1.2557 | NO₂ | CH₃ | (CH₂)₂-(2,4-Cl₂—C₆H₃) | NH |
| Ia1.2558 | NO₂ | CH₂CH₃ | (CH₂)₂-(2,4-Cl₂—C₆H₃) | NH |
| Ia1.2559 | NO₂ | (CH₂)₂CH₃ | (CH₂)₂-(2,4-Cl₂—C₆H₃) | NH |
| Ia1.2560 | NO₂ | (CH₂)₃CH₃ | (CH₂)₂-(2,4-Cl₂—C₆H₃) | NH |
| Ia1.2561 | NO₂ | H | CH₂CH(CH₃)-(2,4-Cl₂—C₆H₃) | NH |
| Ia1.2562 | NO₂ | CH₃ | CH₂CH(CH₃)-(2,4-Cl₂—C₆H₃) | NH |
| Ia1.2563 | NO₂ | CH₂CH₃ | CH₂CH(CH₃)-(2,4-Cl₂—C₆H₃) | NH |
| Ia1.2564 | NO₂ | (CH₂)₂CH₃ | CH₂CH(CH₃)-(2,4-Cl₂—C₆H₃) | NH |
| Ia1.2565 | NO₂ | (CH₂)₃CH₃ | CH₂CH(CH₃)-(2,4-Cl₂—C₆H₃) | NH |
| Ia1.2566 | NO₂ | H | CH(CH₃)CH₂-(2,4-Cl₂—C₆H₃) | NH |
| Ia1.2567 | NO₂ | CH₃ | CH(CH₃)CH₂-(2,4-Cl₂—C₆H₃) | NH |
| Ia1.2568 | NO₂ | CH₂CH₃ | CH(CH₃)CH₂-(2,4-Cl₂—C₆H₃) | NH |
| Ia1.2569 | NO₂ | (CH₂)₂CH₃ | CH(CH₃)CH₂-(2,4-Cl₂—C₆H₃) | NH |
| Ia1.2570 | NO₂ | (CH₂)₃CH₃ | CH(CH₃)CH₂-(2,4-Cl₂—C₆H₃) | NH |
| Ia1.2571 | NO₂ | H | CH(CH₃)CH(CH₃)-(2,4-Cl₂—C₆H₃) | NH |
| Ia1.2572 | NO₂ | CH₃ | CH(CH₃)CH(CH₃)-(2,4-Cl₂—C₆H₃) | NH |
| Ia1.2573 | NO₂ | CH₂CH₃ | CH(CH₃)CH(CH₃)-(2,4-Cl₂—C₆H₃) | NH |
| Ia1.2574 | NO₂ | (CH₂)₂CH₃ | CH(CH₃)CH(CH₃)-(2,4-Cl₂—C₆H₃) | NH |
| Ia1.2575 | NO₂ | (CH₂)₃CH₃ | CH(CH₃)CH(CH₃)-(2,4-Cl₂—C₆H₃) | NH |
| Ia1.2576 | NO₂ | H | (CH₂)₂—O—C₆H₅ | NH |
| Ia1.2577 | NO₂ | CH₃ | (CH₂)₂—O—C₆H₅ | NH |
| Ia1.2578 | NO₂ | CH₂CH₃ | (CH₂)₂—O—C₆H₅ | NH |
| Ia1.2579 | NO₂ | (CH₂)₂CH₃ | (CH₂)₂—O—C₆H₅ | NH |
| Ia1.2580 | NO₂ | (CH₂)₃CH₃ | (CH₂)₂—O—C₆H₅ | NH |
| Ia1.2581 | NO₂ | H | CH₂CH(CH₃)—O—C₆H₅ | NH |
| Ia1.2582 | NO₂ | CH₃ | CH₂CH(CH₃)—O—C₆H₅ | NH |
| Ia1.2583 | NO₂ | CH₂CH₃ | CH₂CH(CH₃)—O—C₆H₅ | NH |
| Ia1.2584 | NO₂ | (CH₂)₂CH₃ | CH₂CH(CH₃)—O—C₆H₅ | NH |
| Ia1.2585 | NO₂ | (CH₂)₃CH₃ | CH₂CH(CH₃)—O—C₆H₅ | NH |
| Ia1.2586 | NO₂ | H | CH(CH₃)CH₂—O—C₆H₅ | NH |
| Ia1.2587 | NO₂ | CH₃ | CH(CH₃)CH₂—O—C₆H₅ | NH |

TABLE 1-continued

| No. | $R^2$ | $R^3$ | $R^4$ | Z |
|---|---|---|---|---|
| Ia1.2588 | $NO_2$ | $CH_2CH_3$ | $CH(CH_3)CH_2$—O—$C_6H_5$ | NH |
| Ia1.2589 | $NO_2$ | $(CH_2)_2CH_3$ | $CH(CH_3)CH_2$—O—$C_6H_5$ | NH |
| Ia1.2590 | $NO_2$ | $(CH_2)_3CH_3$ | $CH(CH_3)CH_2$—O—$C_6H_5$ | NH |
| Ia1.2591 | $NO_2$ | H | $CH(CH_3)CH(CH_3)$—O—$C_6H_5$ | NH |
| Ia1.2592 | $NO_2$ | $CH_3$ | $CH(CH_3)CH(CH_3)$—O—$C_6H_5$ | NH |
| Ia1.2593 | $NO_2$ | $CH_2CH_3$ | $CH(CH_3)CH(CH_3)$—O—$C_6H_5$ | NH |
| Ia1.2594 | $NO_2$ | $(CH_2)_2CH_3$ | $CH(CH_3)CH(CH_3)$—O—$C_6H_5$ | NH |
| Ia1.2595 | $NO_2$ | $(CH_2)_3CH_3$ | $CH(CH_3)CH(CH_3)$—O—$C_6H_5$ | NH |
| Ia1.2596 | $NO_2$ | H | $(CH_2)_2$—O-(4-Cl—$C_6H_4$) | NH |
| Ia1.2597 | $NO_2$ | $CH_3$ | $(CH_2)_2$—O-(4-Cl—$C_6H_4$) | NH |
| Ia1.2598 | $NO_2$ | $CH_2CH_3$ | $(CH_2)_2$—O-(4-Cl—$C_6H_4$) | NH |
| Ia1.2599 | $NO_2$ | $(CH_2)_2CH_3$ | $(CH_2)_2$—O-(4-Cl—$C_6H_4$) | NH |
| Ia1.2600 | $NO_2$ | $(CH_2)_3CH_3$ | $(CH_2)_2$—O-(4-Cl—$C_6H_4$) | NH |
| Ia1.2601 | $NO_2$ | H | $CH_2CH(CH_3)$—O-(4-Cl—$C_6H_4$) | NH |
| Ia1.2602 | $NO_2$ | $CH_3$ | $CH_2CH(CH_3)$—O-(4-Cl—$C_6H_4$) | NH |
| Ia1.2603 | $NO_2$ | $CH_2CH_3$ | $CH_2CH(CH_3)$—O-(4-Cl—$C_6H_4$) | NH |
| Ia1.2604 | $NO_2$ | $(CH_2)_2CH_3$ | $CH_2CH(CH_3)$—O-(4-Cl—$C_6H_4$) | NH |
| Ia1.2605 | $NO_2$ | $(CH_2)_3CH_3$ | $CH_2CH(CH_3)$—O-(4-Cl—$C_6H_4$) | NH |
| Ia1.2606 | $NO_2$ | H | $CH(CH_3)CH_2$—O-(4-Cl—$C_6H_4$) | NH |
| Ia1.2607 | $NO_2$ | $CH_3$ | $CH(CH_3)CH_2$—O-(4-Cl—$C_6H_4$) | NH |
| Ia1.2608 | $NO_2$ | $CH_2CH_3$ | $CH(CH_3)CH_2$—O-(4-Cl—$C_6H_4$) | NH |
| Ia1.2609 | $NO_2$ | $(CH_2)_2CH_3$ | $CH(CH_3)CH_2$—O-(4-Cl—$C_6H_4$) | NH |
| Ia1.2610 | $NO_2$ | $(CH_2)_3CH_3$ | $CH(CH_3)CH_2$—O-(4-Cl—$C_6H_4$) | NH |
| Ia1.2611 | $NO_2$ | H | $CH(CH_3)CH(CH_3)$—O-(4-Cl—$C_6H_4$) | NH |
| Ia1.2612 | $NO_2$ | $CH_3$ | $CH(CH_3)CH(CH_3)$—O-(4-Cl—$C_6H_4$) | NH |
| Ia1.2613 | $NO_2$ | $CH_2CH_3$ | $CH(CH_3)CH(CH_3)$—O-(4-Cl—$C_6H_4$) | NH |
| Ia1.2614 | $NO_2$ | $(CH_2)_2CH_3$ | $CH(CH_3)CH(CH_3)$—O-(4-Cl—$C_6H_4$) | NH |
| Ia1.2615 | $NO_2$ | $(CH_2)_3CH_3$ | $CH(CH_3)CH(CH_3)$—O-(4-Cl—$C_6H_4$) | NH |
| Ia1.2616 | $NO_2$ | H | $(CH_2)_2$—O-(2,4-$Cl_2$—$C_6H_3$) | NH |
| Ia1.2617 | $NO_2$ | $CH_3$ | $(CH_2)_2$—O-(2,4-$Cl_2$—$C_6H_3$) | NH |
| Ia1.2618 | $NO_2$ | $CH_2CH_3$ | $(CH_2)_2$—O-(2,4-$Cl_2$—$C_6H_3$) | NH |
| Ia1.2619 | $NO_2$ | $(CH_2)_2CH_3$ | $(CH_2)_2$—O-(2,4-$Cl_2$—$C_6H_3$) | NH |
| Ia1.2620 | $NO_2$ | $(CH_2)_3CH_3$ | $(CH_2)_2$—O-(2,4-$Cl_2$—$C_6H_3$) | NH |
| Ia1.2621 | $NO_2$ | H | $CH_2CH(CH_3)$—O-(2,4-$Cl_2$—$C_6H_3$) | NH |
| Ia1.2622 | $NO_2$ | $CH_3$ | $CH_2CH(CH_3)$—O-(2,4-$Cl_2$—$C_6H_3$) | NH |
| Ia1.2623 | $NO_2$ | $CH_2CH_3$ | $CH_2CH(CH_3)$—O-(2,4-$Cl_2$—$C_6H_3$) | NH |
| Ia1.2624 | $NO_2$ | $(CH_2)_2CH_3$ | $CH_2CH(CH_3)$—O-(2,4-$Cl_2$—$C_6H_3$) | NH |
| Ia1.2625 | $NO_2$ | $(CH_2)_3CH_3$ | $CH_2CH(CH_3)$—O-(2,4-$Cl_2$—$C_6H_3$) | NH |
| Ia1.2626 | $NO_2$ | H | $CH(CH_3)CH_2$—O-(2,4-$Cl_2$—$C_6H_3$) | NH |
| Ia1.2627 | $NO_2$ | $CH_3$ | $CH(CH_3)CH_2$—O-(2,4-$Cl_2$—$C_6H_3$) | NH |
| Ia1.2628 | $NO_2$ | $CH_2CH_3$ | $CH(CH_3)CH_2$—O-(2,4-$Cl_2$—$C_6H_3$) | NH |
| Ia1.2629 | $NO_2$ | $(CH_2)_2CH_3$ | $CH(CH_3)CH_2$—O-(2,4-$Cl_2$—$C_6H_3$) | NH |
| Ia1.2630 | $NO_2$ | $(CH_2)_3CH_3$ | $CH(CH_3)CH_2$—O-(2,4-$Cl_2$—$C_6H_3$) | NH |
| Ia1.2631 | $NO_2$ | H | $CH(CH_3)CH(CH_3)$—O-(2,4-$Cl_2$—$C_6H_3$) | NH |
| Ia1.2632 | $NO_2$ | $CH_3$ | $CH(CH_3)CH(CH_3)$—O-(2,4-$Cl_2$—$C_6H_3$) | NH |
| Ia1.2633 | $NO_2$ | $CH_2CH_3$ | $CH(CH_3)CH(CH_3)$—O-(2,4-$Cl_2$—$C_6H_3$) | NH |
| Ia1.2634 | $NO_2$ | $(CH_2)_2CH_3$ | $CH(CH_3)CH(CH_3)$—O-(2,4-$Cl_2$—$C_6H_3$) | NH |
| Ia1.2635 | $NO_2$ | $(CH_2)_3CH_3$ | $CH(CH_3)CH(CH_3)$—O-(2,4-$Cl_2$—$C_6H_3$) | NH |
| Ia1.2636 | $NO_2$ | H | $CH_3$ | $NCH_3$ |
| Ia1.2637 | $NO_2$ | $CH_3$ | $CH_3$ | $NCH_3$ |
| Ia1.2638 | $NO_2$ | $CH_2CH_3$ | $CH_3$ | $NCH_3$ |
| Ia1.2639 | $NO_2$ | $(CH_2)_2CH_3$ | $CH_3$ | $NCH_3$ |
| Ia1.2640 | $NO_2$ | $(CH_2)_3CH_3$ | $CH_3$ | $NCH_3$ |
| Ia1.2641 | $NO_2$ | H | $C_2H_5$ | $NCH_3$ |
| Ia1.2642 | $NO_2$ | $CH_3$ | $C_2H_5$ | $NCH_3$ |
| Ia1.2643 | $NO_2$ | $CH_2CH_3$ | $C_2H_5$ | $NCH_3$ |
| Ia1.2644 | $NO_2$ | $(CH_2)_2CH_3$ | $C_2H_5$ | $NCH_3$ |
| Ia1.2645 | $NO_2$ | $(CH_2)_3CH_3$ | $C_2H_5$ | $NCH_3$ |
| Ia1.2646 | $NO_2$ | H | $(CH_2)_2CH_3$ | $NCH_3$ |
| Ia1.2647 | $NO_2$ | $CH_3$ | $(CH_2)_2CH_3$ | $NCH_3$ |
| Ia1.2648 | $NO_2$ | $CH_2CH_3$ | $(CH_2)_2CH_3$ | $NCH_3$ |
| Ia1.2649 | $NO_2$ | $(CH_2)_2CH_3$ | $(CH_2)_2CH_3$ | $NCH_3$ |
| Ia1.2650 | $NO_2$ | $(CH_2)_3CH_3$ | $(CH_2)_2CH_3$ | $NCH_3$ |
| Ia1.2651 | $NO_2$ | H | $CH(CH_3)_2$ | $NCH_3$ |
| Ia1.2652 | $NO_2$ | $CH_3$ | $CH(CH_3)_2$ | $NCH_3$ |
| Ia1.2653 | $NO_2$ | $CH_2CH_3$ | $CH(CH_3)_2$ | $NCH_3$ |
| Ia1.2654 | $NO_2$ | $(CH_2)_2CH_3$ | $CH(CH_3)_2$ | $NCH_3$ |
| Ia1.2655 | $NO_2$ | $(CH_2)_3CH_3$ | $CH(CH_3)_2$ | $NCH_3$ |
| Ia1.2656 | $NO_2$ | H | $(CH_2)_3CH_3$ | $NCH_3$ |
| Ia1.2657 | $NO_2$ | $CH_3$ | $(CH_2)_3CH_3$ | $NCH_3$ |
| Ia1.2658 | $NO_2$ | $CH_2CH_3$ | $(CH_2)_3CH_3$ | $NCH_3$ |
| Ia1.2659 | $NO_2$ | $(CH_2)_2CH_3$ | $(CH_2)_3CH_3$ | $NCH_3$ |
| Ia1.2660 | $NO_2$ | $(CH_2)_3CH_3$ | $(CH_2)_3CH_3$ | $NCH_3$ |
| Ia1.2661 | $NO_2$ | H | $CH_2CH(CH_3)_2$ | $NCH_3$ |
| Ia1.2662 | $NO_2$ | $CH_3$ | $CH_2CH(CH_3)_2$ | $NCH_3$ |
| Ia1.2663 | $NO_2$ | $CH_2CH_3$ | $CH_2CH(CH_3)_2$ | $NCH_3$ |
| Ia1.2664 | $NO_2$ | $(CH_2)_2CH_3$ | $CH_2CH(CH_3)_2$ | $NCH_3$ |

TABLE 1-continued

| No. | $R^2$ | $R^3$ | $R^4$ | Z |
|---|---|---|---|---|
| Ia1.2665 | $NO_2$ | $(CH_2)_3CH_3$ | $CH_2CH(CH_3)_2$ | $NCH_3$ |
| Ia1.2666 | $NO_2$ | H | $CH(CH_3)CH_2CH_3$ | $NCH_3$ |
| Ia1.2667 | $NO_2$ | $CH_3$ | $CH(CH_3)CH_2CH_3$ | $NCH_3$ |
| Ia1.2668 | $NO_2$ | $CH_2CH_3$ | $CH(CH_3)CH_2CH_3$ | $NCH_3$ |
| Ia1.2669 | $NO_2$ | $(CH_2)_2CH_3$ | $CH(CH_3)CH_2CH_3$ | $NCH_3$ |
| Ia1.2670 | $NO_2$ | $(CH_2)_3CH_3$ | $CH(CH_3)CH_2CH_3$ | $NCH_3$ |
| Ia1.2671 | $NO_2$ | H | $(CH_2)_2-C_6H_5$ | $NCH_3$ |
| Ia1.2672 | $NO_2$ | $CH_3$ | $(CH_2)_2-C_6H_5$ | $NCH_3$ |
| Ia1.2673 | $NO_2$ | $CH_2CH_3$ | $(CH_2)_2-C_6H_5$ | $NCH_3$ |
| Ia1.2674 | $NO_2$ | $(CH_2)_2CH_3$ | $(CH_2)_2-C_6H_5$ | $NCH_3$ |
| Ia1.2675 | $NO_2$ | $(CH_2)_3CH_3$ | $(CH_2)_2-C_6H_5$ | $NCH_3$ |
| Ia1.2676 | $NO_2$ | H | $CH_2CH(CH_3)-C_6H_5$ | $NCH_3$ |
| Ia1.2677 | $NO_2$ | $CH_3$ | $CH_2CH(CH_3)-C_6H_5$ | $NCH_3$ |
| Ia1.2678 | $NO_2$ | $CH_2CH_3$ | $CH_2CH(CH_3)-C_6H_5$ | $NCH_3$ |
| Ia1.2679 | $NO_2$ | $(CH_2)_2CH_3$ | $CH_2CH(CH_3)-C_6H_5$ | $NCH_3$ |
| Ia1.2680 | $NO_2$ | $(CH_2)_3CH_3$ | $CH_2CH(CH_3)-C_6H_5$ | $NCH_3$ |
| Ia1.2681 | $NO_2$ | H | $CH(CH_3)CH_2-C_6H_5$ | $NCH_3$ |
| Ia1.2682 | $NO_2$ | $CH_3$ | $CH(CH_3)CH_2-C_6H_5$ | $NCH_3$ |
| Ia1.2683 | $NO_2$ | $CH_2CH_3$ | $CH(CH_3)CH_2-C_6H_5$ | $NCH_3$ |
| Ia1.2684 | $NO_2$ | $(CH_2)_2CH_3$ | $CH(CH_3)CH_2-C_6H_5$ | $NCH_3$ |
| Ia1.2685 | $NO_2$ | $(CH_2)_3CH_3$ | $CH(CH_3)CH_2-C_6H_5$ | $NCH_3$ |
| Ia1.2686 | $NO_2$ | H | $CH(CH_3)CH(CH_3)-C_6H_5$ | $NCH_3$ |
| Ia1.2687 | $NO_2$ | $CH_3$ | $CH(CH_3)CH(CH_3)-C_6H_5$ | $NCH_3$ |
| Ia1.2688 | $NO_2$ | $CH_2CH_3$ | $CH(CH_3)CH(CH_3)-C_6H_5$ | $NCH_3$ |
| Ia1.2689 | $NO_2$ | $(CH_2)_2CH_3$ | $CH(CH_3)CH(CH_3)-C_6H_5$ | $NCH_3$ |
| Ia1.2690 | $NO_2$ | $(CH_2)_3CH_3$ | $CH(CH_3)CH(CH_3)-C_6H_5$ | $NCH_3$ |
| Ia1.2691 | $NO_2$ | H | $(CH_2)_2-(4-Cl-C_6H_4)$ | $NCH_3$ |
| Ia1.2692 | $NO_2$ | $CH_3$ | $(CH_2)_2-(4-Cl-C_6H_4)$ | $NCH_3$ |
| Ia1.2693 | $NO_2$ | $CH_2CH_3$ | $(CH_2)_2-(4-Cl-C_6H_4)$ | $NCH_3$ |
| Ia1.2694 | $NO_2$ | $(CH_2)_2CH_3$ | $(CH_2)_2-(4-Cl-C_6H_4)$ | $NCH_3$ |
| Ia1.2695 | $NO_2$ | $(CH_2)_3CH_3$ | $(CH_2)_2-(4-Cl-C_6H_4)$ | $NCH_3$ |
| Ia1.2696 | $NO_2$ | H | $CH_2CH(CH_3)-(4-Cl-C_6H_4)$ | $NCH_3$ |
| Ia1.2697 | $NO_2$ | $CH_3$ | $CH_2CH(CH_3)-(4-Cl-C_6H_4)$ | $NCH_3$ |
| Ia1.2698 | $NO_2$ | $CH_2CH_3$ | $CH_2CH(CH_3)-(4-Cl-C_6H_4)$ | $NCH_3$ |
| Ia1.2699 | $NO_2$ | $(CH_2)_2CH_3$ | $CH_2CH(CH_3)-(4-Cl-C_6H_4)$ | $NCH_3$ |
| Ia1.2700 | $NO_2$ | $(CH_2)_3CH_3$ | $CH_2CH(CH_3)-(4-Cl-C_6H_4)$ | $NCH_3$ |
| Ia1.2701 | $NO_2$ | H | $CH(CH_3)CH_2-(4-Cl-C_6H_4)$ | $NCH_3$ |
| Ia1.2702 | $NO_2$ | $CH_3$ | $CH(CH_3)CH_2-(4-Cl-C_6H_4)$ | $NCH_3$ |
| Ia1.2703 | $NO_2$ | $CH_2CH_3$ | $CH(CH_3)CH_2-(4-Cl-C_6H_4)$ | $NCH_3$ |
| Ia1.2704 | $NO_2$ | $(CH_2)_2CH_3$ | $CH(CH_3)CH_2-(4-Cl-C_6H_4)$ | $NCH_3$ |
| Ia1.2705 | $NO_2$ | $(CH_2)_3CH_3$ | $CH(CH_3)CH_2-(4-Cl-C_6H_4)$ | $NCH_3$ |
| Ia1.2706 | $NO_2$ | H | $CH(CH_3)CH(CH_3)-(4-Cl-C_6H_4)$ | $NCH_3$ |
| Ia1.2707 | $NO_2$ | $CH_3$ | $CH(CH_3)CH(CH_3)-(4-Cl-C_6H_4)$ | $NCH_3$ |
| Ia1.2708 | $NO_2$ | $CH_2CH_3$ | $CH(CH_3)CH(CH_3)-(4-Cl-C_6H_4)$ | $NCH_3$ |
| Ia1.2709 | $NO_2$ | $(CH_2)_2CH_3$ | $CH(CH_3)CH(CH_3)-(4-Cl-C_6H_4)$ | $NCH_3$ |
| Ia1.2710 | N62 | $(CH_2)_3CH_3$ | $CH(CH_3)CH(CH_3)-(4-Cl-C_6H_4)$ | $NCH_3$ |
| Ia1.2711 | $NO_2$ | H | $(CH_2)_2-(2,4-Cl_2-C_6H_3)$ | $NCH_3$ |
| Ia1.2712 | $NO_2$ | $CH_3$ | $(CH_2)_2-(2,4-Cl_2-C_6H_3)$ | $NCH_3$ |
| Ia1.2713 | $NO_2$ | $CH_2CH_3$ | $(CH_2)_2-(2,4-Cl_2-C_6H_3)$ | $NCH_3$ |
| Ia1.2714 | $NO_2$ | $(CH_2)_2CH_3$ | $(CH_2)_2-(2,4-Cl_2-C_6H_3)$ | $NCH_3$ |
| Ia1.2715 | $NO_2$ | $(CH_2)_3CH_3$ | $(CH_2)_2-(2,4-Cl_2-C_6H_3)$ | $NCH_3$ |
| Ia1.2716 | $NO_2$ | H | $CH_2CH(CH_3)-(2,4-Cl_2-C_6H_3)$ | $NCH_3$ |
| Ia1.2717 | $NO_2$ | $CH_3$ | $CH_2CH(CH_3)-(2,4-Cl_2-C_6H_3)$ | $NCH_3$ |
| Ia1.2718 | $NO_2$ | $CH_2CH_3$ | $CH_2CH(CH_3)-(2,4-Cl_2-C_6H_3)$ | $NCH_3$ |
| Ia1.2719 | $NO_2$ | $(CH_2)_2CH_3$ | $CH_2CH(CH_3)-(2,4-Cl_2-C_6H_3)$ | $NCH_3$ |
| Ia1.2720 | $NO_2$ | $(CH_2)_3CH_3$ | $CH_2CH(CH_3)-(2,4-Cl_2-C_6H_3)$ | $NCH_3$ |
| Ia1.2721 | $NO_2$ | H | $CH(CH_3)CH_2-(2,4-Cl_2-C_6H_3)$ | $NCH_3$ |
| Ia1.2722 | $NO_2$ | $CH_3$ | $CH(CH_3)CH_2-(2,4-Cl_2-C_6H_3)$ | $NCH_3$ |
| Ia1.2723 | $NO_2$ | $CH_2CH_3$ | $CH(CH_3)CH_2-(2,4-Cl_2-C_6H_3)$ | $NCH_3$ |
| Ia1.2724 | $NO_2$ | $(CH_2)_2CH_3$ | $CH(CH_3)CH_2-(2,4-Cl_2-C_6H_3)$ | $NCH_3$ |
| Ia1.2725 | $NO_2$ | $(CH_2)_3CH_3$ | $CH(CH_3)CH_2-(2,4-Cl_2-C_6H_3)$ | $NCH_3$ |
| Ia1.2726 | $NO_2$ | H | $CH(CH_3)CH(CH_3)-(2,4-Cl_2-C_6H_3)$ | $NCH_3$ |
| Ia1.2727 | $NO_2$ | $CH_3$ | $CH(CH_3)CH(CH_3)-(2,4-Cl_2-C_6H_3)$ | $NCH_3$ |
| Ia1.2728 | $NO_2$ | $CH_2CH_3$ | $CH(CH_3)CH(CH_3)-(2,4-Cl_2-C_6H_3)$ | $NCH_3$ |
| Ia1.2729 | $NO_2$ | $(CH_2)_2CH_3$ | $CH(CH_3)CH(CH_3)-(2,4-Cl_2-C_6H_3)$ | $NCH_3$ |
| Ia1.2730 | $NO_2$ | $(CH_2)_3CH_3$ | $CH(CH_3)CH(CH_3)-(2,4-Cl_2-C_6H_3)$ | $NCH_3$ |
| Ia1.2731 | $NO_2$ | H | $(CH_2)_2-O-C_6H_5$ | $NCH_3$ |
| Ia1.2732 | $NO_2$ | $CH_3$ | $(CH_2)_2-O-C_6H_5$ | $NCH_3$ |
| Ia1.2733 | $NO_2$ | $CH_2CH_3$ | $(CH_2)_2-O-C_6H_5$ | $NCH_3$ |
| Ia1.2734 | $NO_2$ | $(CH_2)_2CH_3$ | $(CH_2)_2-O-C_6H_5$ | $NCH_3$ |
| Ia1.2735 | $NO_2$ | $(CH_2)_3CH_3$ | $(CH_2)_2-O-C_6H_5$ | $NCH_3$ |
| Ia1.2736 | $NO_2$ | H | $CH_2CH(CH_3)-O-C_6H_5$ | $NCH_3$ |
| Ia1.2737 | $NO_2$ | $CH_3$ | $CH_2CH(CH_3)-O-C_6H_5$ | $NCH_3$ |
| Ia1.2738 | $NO_2$ | $CH_2CH_3$ | $CH_2CH(CH_3)-O-C_6H_5$ | $NCH_3$ |
| Ia1.2739 | $NO_2$ | $(CH_2)_2CH_3$ | $CH_2CH(CH_3)-O-C_6H_5$ | $NCH_3$ |
| Ia1.2740 | $NO_2$ | $(CH_2)_3CH_3$ | $CH_2CH(CH_3)-O-C_6H_5$ | $NCH_3$ |
| Ia1.2741 | $NO_2$ | H | $CH(CH_3)CH_2-O-C_6H_5$ | $NCH_3$ |

TABLE 1-continued

| No. | $R^2$ | $R^3$ | $R^4$ | Z |
|---|---|---|---|---|
| Ia1.2742 | $NO_2$ | $CH_3$ | $CH(CH_3)CH_2-O-C_6H_5$ | $NCH_3$ |
| Ia1.2743 | $NO_2$ | $CH_2CH_3$ | $CH(CH_3)CH_2-O-C_6H_5$ | $NCH_3$ |
| Ia1.2744 | $NO_2$ | $(CH_2)_2CH_3$ | $CH(CH_3)CH_2-O-C_6H_5$ | $NCH_3$ |
| Ia1.2745 | $NO_2$ | $(CH_2)_3CH_3$ | $CH(CH_3)CH_2-O-C_6H_5$ | $NCH_3$ |
| Ia1.2746 | $NO_2$ | H | $CH(CH_3)CH(CH_3)-O-C_6H_5$ | $NCH_3$ |
| Ia1.2747 | $NO_2$ | $CH_3$ | $CH(CH_3)CH(CH_3)-O-C_6H_5$ | $NCH_3$ |
| Ia1.2748 | $NO_2$ | $CH_2CH_3$ | $CH(CH_3)CH(CH_3)-O-C_6H_5$ | $NCH_3$ |
| Ia1.2749 | $NO_2$ | $(CH_2)_2CH_3$ | $CH(CH_3)CH(CH_3)-O-C_6H_5$ | $NCH_3$ |
| Ia1.2750 | $NO_2$ | $(CH_2)_3CH_3$ | $CH(CH_3)CH(CH_3)-O-C_6H_5$ | $NCH_3$ |
| Ia1.2751 | $NO_2$ | H | $(CH_2)_2-O-(4-Cl-C_6H_4)$ | $NCH_3$ |
| Ia1.2752 | $NO_2$ | $CH_3$ | $(CH_2)_2-O-(4-Cl-C_6H_4)$ | $NCH_3$ |
| Ia1.2753 | $NO_2$ | $CH_2CH_3$ | $(CH_2)_2-O-(4-Cl-C_6H_4)$ | $NCH_3$ |
| Ia1.2754 | $NO_2$ | $(CH_2)_2CH_3$ | $(CH_2)_2-O-(4-Cl-C_6H_4)$ | $NCH_3$ |
| Ia1.2755 | $NO_2$ | $(CH_2)_3CH_3$ | $(CH_2)_2-O-(4-Cl-C_6H_4)$ | $NCH_3$ |
| Ia1.2756 | $NO_2$ | H | $CH_2CH(CH_3)-O-(4-Cl-C_6H_4)$ | $NCH_3$ |
| Ia1.2757 | $NO_2$ | $CH_3$ | $CH_2CH(CH_3)-O-(4-Cl-C_6H_4)$ | $NCH_3$ |
| Ia1.2758 | $NO_2$ | $CH_2CH_3$ | $CH_2CH(CH_3)-O-(4-Cl-C_6H_4)$ | $NCH_3$ |
| Ia1.2759 | $NO_2$ | $(CH_2)_2CH_3$ | $CH_2CH(CH_3)-O-(4-Cl-C_6H_4)$ | $NCH_3$ |
| Ia1.2760 | $NO_2$ | $(CH_2)_3CH_3$ | $CH_2CH(CH_3)-O-(4-Cl-C_6H_4)$ | $NCH_3$ |
| Ia1.2761 | $NO_2$ | H | $CH(CH_3)CH_2-O-(4-Cl-C_6H_4)$ | $NCH_3$ |
| Ia1.2762 | $NO_2$ | $CH_3$ | $CH(CH_3)CH_2-O-(4-Cl-C_6H_4)$ | $NCH_3$ |
| Ia1.2763 | $NO_2$ | $CH_2CH_3$ | $CH(CH_3)CH_2-O-(4-Cl-C_6H_4)$ | $NCH_3$ |
| Ia1.2764 | $NO_2$ | $(CH_2)_2CH_3$ | $CH(CH_3)CH_2-O-(4-Cl-C_6H_4)$ | $NCH_3$ |
| Ia1.2765 | $NO_2$ | $(CH_2)_3CH_3$ | $CH(CH_3)CH_2-O-(4-Cl-C_6H_4)$ | $NCH_3$ |
| Ia1.2766 | $NO_2$ | H | $CH(CH_3)CH(CH_3)-O-(4-Cl-C_6H_4)$ | $NCH_3$ |
| Ia1.2767 | $NO_2$ | $CH_3$ | $CH(CH_3)CH(CH_3)-O-(4-Cl-C_6H_4)$ | $NCH_3$ |
| Ia1.2768 | $NO_2$ | $CH_2CH_3$ | $CH(CH_3)CH(CH_3)-O-(4-Cl-C_6H_4)$ | $NCH_3$ |
| Ia1.2769 | $NO_2$ | $(CH_2)_2CH_3$ | $CH(CH_3)CH(CH_3)-O-(4-Cl-C_6H_4)$ | $NCH_3$ |
| Ia1.2770 | $NO_2$ | $(CH_2)_3CH_3$ | $CH(CH_3)CH(CH_3)-O-(4-Cl-C_6H_4)$ | $NCH_3$ |
| Ia1.2771 | $NO_2$ | H | $(CH_2)_2-O-(2,4-Cl_2-C_6H_3)$ | $NCH_3$ |
| Ia1.2772 | $NO_2$ | $CH_3$ | $(CH_2)_2-O-(2,4-Cl_2-C_6H_3)$ | $NCH_3$ |
| Ia1.2773 | $NO_2$ | $CH_2CH_3$ | $(CH_2)_2-O-(2,4-Cl_2-C_6H_3)$ | $NCH_3$ |
| Ia1.2774 | $NO_2$ | $(CH_2)_2CH_3$ | $(CH_2)_2-O-(2,4-Cl_2-C_6H_3)$ | $NCH_3$ |
| Ia1.2775 | $NO_2$ | $(CH_2)_3CH_3$ | $(CH_2)_2-O-(2,4-Cl_2-C_6H_3)$ | $NCH_3$ |
| Ia1.2776 | $NO_2$ | H | $CH_2CH(CH_3)-O-(2,4-Cl_2-C_6H_3)$ | $NCH_3$ |
| Ia1.2777 | $NO_2$ | $CH_3$ | $CH_2CH(CH_3)-O-(2,4-Cl_2-C_6H_3)$ | $NCH_3$ |
| Ia1.2778 | $NO_2$ | $CH_2CH_3$ | $CH_2CH(CH_3)-O-(2,4-Cl_2-C_6H_3)$ | $NCH_3$ |
| Ia1.2779 | $NO_2$ | $(CH_2)_2CH_3$ | $CH_2CH(CH_3)-O-(2,4-Cl_2-C_6H_3)$ | $NCH_3$ |
| Ia1.2780 | $NO_2$ | $(CH_2)_3CH_3$ | $CH_2CH(CH_3)-O-(2,4-Cl_2-C_6H_3)$ | $NCH_3$ |
| Ia1.2781 | $NO_2$ | H | $CH(CH_3)CH_2-O-(2,4-Cl_2-C_6H_3)$ | $NCH_3$ |
| Ia1.2782 | $NO_2$ | $CH_3$ | $CH(CH_3)CH_2-O-(2,4-Cl_2-C_6H_3)$ | $NCH_3$ |
| Ia1.2783 | $NO_2$ | $CH_2CH_3$ | $CH(CH_3)CH_2-O-(2,4-Cl_2-C_6H_3)$ | $NCH_3$ |
| Ia1.2784 | $NO_2$ | $(CH_2)_2CH_3$ | $CH(CH_3)CH_2-O-(2,4-Cl_2-C_6H_3)$ | $NCH_3$ |
| Ia1.2785 | $NO_2$ | $(CH_2)_3CH_3$ | $CH(CH_3)CH_2-O-(2,4-Cl_2-C_6H_3)$ | $NCH_3$ |
| Ia1.2786 | $NO_2$ | H | $CH(CH_3)CH(CH_3)-O-(2,4-Cl_2-C_6H_3)$ | $NCH_3$ |
| Ia1.2787 | $NO_2$ | $CH_3$ | $CH(CH_3)CH(CH_3)-O-(2,4-Cl_2-C_6H_3)$ | $NCH_3$ |
| Ia1.2788 | $NO_2$ | $CH_2CH_3$ | $CH(CH_3)CH(CH_3)-O-(2,4-Cl_2-C_6H_3)$ | $NCH_3$ |
| Ia1.2789 | $NO_2$ | $(CH_2)_2CH_3$ | $CH(CH_3)CH(CH_3)-O-(2,4-Cl_2-C_6H_3)$ | $NCH_3$ |
| Ia1.2790 | $NO_2$ | $(CH_2)_3CH_3$ | $CH(CH_3)CH(CH_3)-O-(2,4-Cl_2-C_6H_3)$ | $NCH_3$ |

Also most particularly most extraordinarily preferred are the 2-benzoylcyclohexane-1,3-diones of the formula I which follow:

The compounds Ia2, especially the compounds Ia2.1–Ia2.2790, which differ from the corresponding compounds Ia1.1–Ia1.2790 by the fact that $R^{13}$ is methyl:

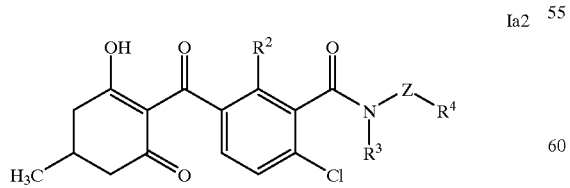

Ia2

The compounds Ia3, especially the compounds Ia3.1–Ia3.2790, which differ from the corresponding compounds Ia1.1–Ia1.2790 by the fact that $R^{13}$ and $R^{14}$ are in each case methyl:

Ia3

The compounds Ia4, especially the compounds Ia4.1–Ia4.2790, which differ from the corresponding compounds Ia1.1–Ia1.2790 by the fact that $R^{15}$ and $R^{16}$ are in each case methyl:

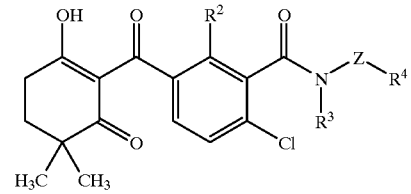

Ia4

The compounds Ia5, especially the compounds Ia5.1–Ia5.2790, which differ from the corresponding compounds Ia1.1–Ia1.2790 by the fact that the $CR^{13}R^{14}$ unit is replaced by C=O:

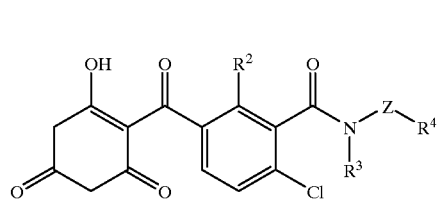

Ia5

The compounds Ia6, especially the compounds Ia6.1–Ia6.2790, which differ from the corresponding compounds Ia1.1–Ia1.2790 by the fact that $R^{11}$, $R^{15}$ and $R^{16}$ are in each case methyl and the $CR^{13}R^{14}$ unit is replaced by C=O:

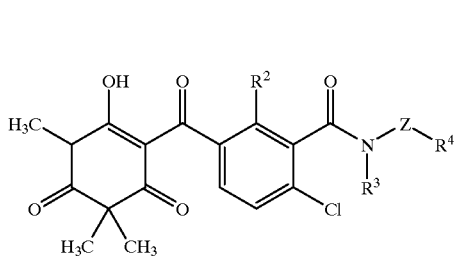

Ia6

The compounds Ia7, especially the compounds Ia7.1–Ia7.2790, which differ from the corresponding compounds Ia1.1–Ia1.2790 by the fact that $R^{11}$, $R^{12}$, $R^{15}$ and $R^{16}$ are in each case methyl and the $CR^{13}R^{14}$ unit is replaced by C=O:

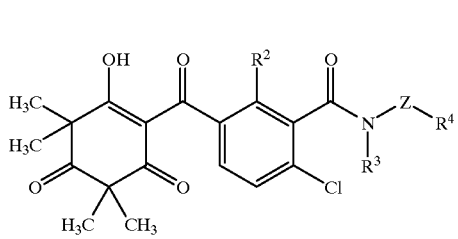

Ia7

The compounds Ia8, especially the compounds Ia8.1–Ia8.2790, which differ from the corresponding compounds Ia1.1–Ia1.2790 by the fact that $R^1$ is nitro:

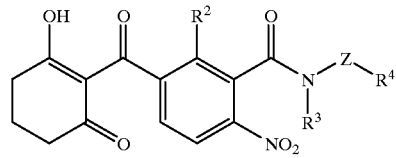

Ia8

The compounds Ia9, especially the compounds Ia9.1–Ia9.2790, which differ from the corresponding compounds Ia1.1–Ia1.2790 by the fact that $R^1$ is nitro and $R^{13}$ is methyl:

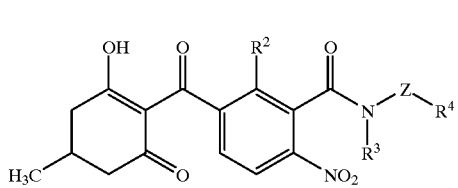

Ia9

The compounds Ia10, especially the compounds Ia10.1–Ia10.2790, which differ from the corresponding compounds Ia1.1–Ia1.2790 by the fact that $R^1$ is nitro and $R^{13}$ and $R^{14}$ are in each case methyl:

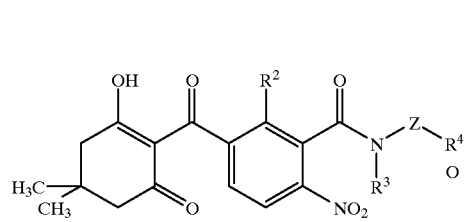

Ia10

The compounds Ia11, especially the compounds Ia11.1–Ia11.2790, which differ from the corresponding compounds Ia1.1–Ia1.2790 by the fact that $R^1$ is nitro and $R^{15}$ and $R^{16}$ are in each case methyl:

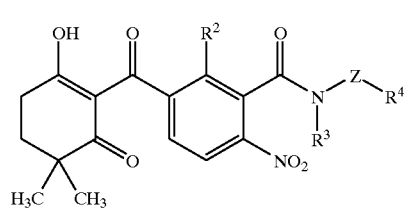

Ia11

The compounds Ia12, especially the compounds Ia12.1–Ia12.2790, which differ from the corresponding compounds Ia1.1–Ia1.2790 by the fact that $R^1$ is nitro and the $CR^{13}R^{14}$ unit is replaced by C=O:

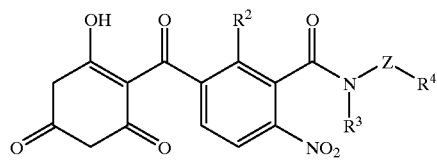

Ia12

The compounds Ia13, especially the compounds Ia13.1–Ia13.2790, which differ from the corresponding compounds Ia1.1–Ia1.2790 by the fact that $R^1$ is nitro, $R^{11}$, $R^{15}$ and $R^{16}$ are in each case methyl and the $CR^{13}R^{14}$ unit is replaced by C=O:

Ia13

The compounds Ia14, especially the compounds Ia14.1–Ia14.2790, which differ from the corresponding compounds Ia1.1–Ia1.2790 by the fact that $R^1$ is nitro, $R^{11}$, $R^{12}$, $R^{15}$ and $R^{16}$ are in each case methyl and the $CR^{13}R^{14}$ unit is replaced by C=O:

Ia14

The compounds Ia15, especially the compounds Ia15.1–Ia15.2790, which differ from the corresponding compounds Ia1.1–Ia1.2790 by the fact that $R^1$ is methylsulfonyl:

Ia15

The compounds Ia16, especially the compounds Ia16.1–Ia16.2790, which differ from the corresponding compounds Ia1.1–Ia1.2790 by the fact that $R^1$ is methylsulfonyl and $R^{13}$ is methyl:

Ia16

The compounds Ia17, especially the compounds Ia17.1–Ia17.2790, which differ from the corresponding compounds Ia1.1–Ia1.2790 by the fact that $R^1$ is methylsulfonyl and $R^{13}$ and $R^{14}$ are in each case methyl:

Ia17

The compounds Ia18, especially the compounds Ia18.1–Ia18.2790, which differ from the corresponding compounds Ia1.1–Ia1.2790 by the fact that $R^1$ is methylsulfonyl and $R^{15}$ and $R^{16}$ are in each case methyl:

Ia18

The compounds Ia19, especially the compounds Ia19.1–Ia19.2790, which differ from the corresponding compounds Ia1.1–Ia1.2790 by the fact that $R^1$ is methylsulfonyl and the $CR^{13}R^{14}$ unit is replaced by C=O:

Ia19

The compounds Ia20, especially the compounds Ia20.1–Ia20.2790, which differ from the corresponding compounds Ia1.1–Ia1.2790 by the fact that $R^1$ is methylsulfonyl, $R^{11}$, $R^{15}$ and $R^{16}$ are in each case methyl and the $CR^{13}R^{14}$ unit is replaced by C=O:

Ia20

The compounds Ia21, especially the compounds Ia21.1–Ia21.2790, which differ from the corresponding compounds Ia1.1–Ia1.2790 by the fact that $R^1$ is methylsulfonyl, $R^{11}$, $R^{12}$, $R^{15}$ and $R^{16}$ are in each case methyl and the $CR^{13}R^{14}$ unit is replaced by C=O:

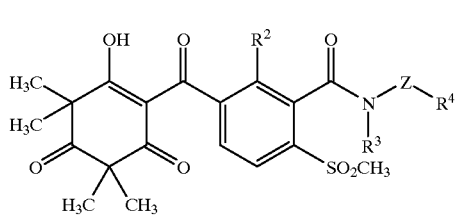
Ia21

The compounds Ia22, especially the compounds Ia22.1–Ia22.2790, which differ from the corresponding compounds Ia1.1–Ia1.2790 by the fact that $R^1$ is trifluoromethyl:

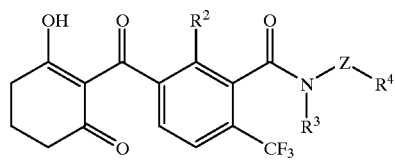
Ia22

The compounds Ia23, especially the compounds Ia23.1–Ia23.2790, which differ from the corresponding compounds Ia1.1–Ia1.2790 by the fact that $R^1$ is trifluoromethyl and $R^{13}$ is methyl:

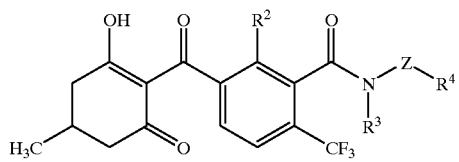
Ia23

The compounds Ia24, especially the compounds Ia24.1–Ia24.2790, which differ from the corresponding compounds Ia1.1–Ia1.2790 by the fact that $R^1$ is trifluoromethyl and $R^{13}$ and $R^{14}$ are in each case methyl:

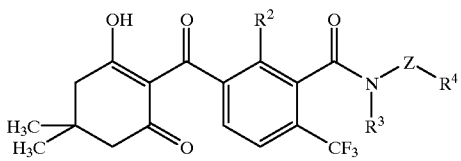
Ia24

The compounds Ia25, especially the compounds Ia25.1–Ia25.2790, which differ from the corresponding compounds Ia1.1–Ia1.2790 by the fact that $R^1$ is trifluoromethyl and $R^{15}$ and $R^{16}$ are in each case methyl:

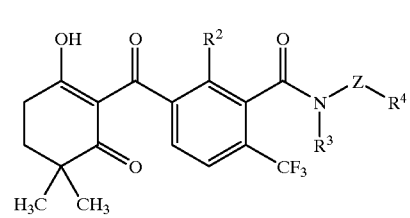
Ia25

The compounds Ia26, especially the compounds Ia26.1–Ia26.2790, which differ from the corresponding compounds Ia1.1–Ia1.2790 by the fact that $R^1$ is trifluoromethyl and the $CR^{13}R^{14}$ unit is replaced by C=O:

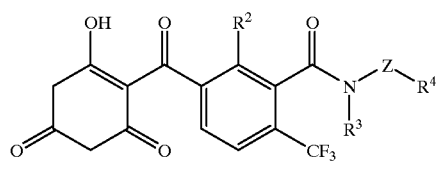
Ia26

The compounds Ia27, especially the compounds Ia27.1–Ia27.2790, which differ from the corresponding compounds Ia1.1–Ia1.2790 by the fact that $R^1$ is trifluoromethyl, $R^{11}$, $R^{15}$ and $R^{16}$ are in each case methyl and the $CR^{13}R^{14}$ unit is replaced by C=O:

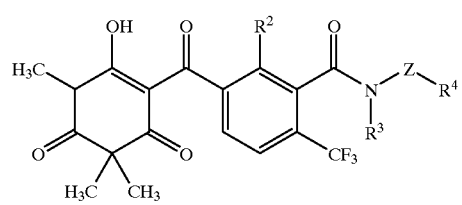
Ia27

The compounds Ia28, especially the compounds Ia28.1–Ia28.2790, which differ from the corresponding compounds Ia1.1–Ia1.2790 by the fact that $R^1$ is trifluoromethyl, $R^{11}$, $R^{12}$, $R^{15}$ and $R^{16}$ are in each case methyl and the $CR^{13}R^{14}$ unit is replaced by C=O:

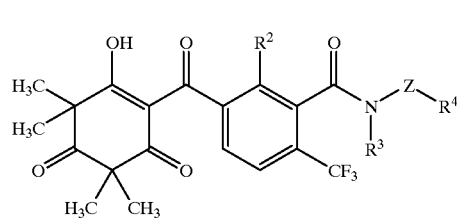
Ia28

Very most particularly extraordinarily preferred compounds are the compounds of the formula Ia' (= I, where $R^1$ is bonded in position 4 of the phenyl ring and $R^2$ is bonded in position 2 of the phenyl ring)

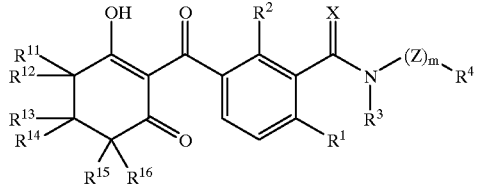

Ia' where the variables have the following meanings:

$R^1$ is halogen or $C_1$–$C_4$-alkylsulfonyl;
$R^2$ is halogen or $C_1$–$C_4$-alkyl;
$R^3$ is hydrogen or $C_1$–$C_4$-alkyl;
$R^4$ is hydrogen, $C_1$–$C_6$-alkyl, $C_3$–$C_6$-alkenyl, it being possible for the two last-mentioned substituents to be partially or fully halogenated and/or to have attached to them one to three of the following groups: phenyl, phenyl-$C_1$–$C_4$-alkyl, hetaryl or phenyloxy, it being possible for the 4 last-mentioned radicals in turn to be partially or fully halogenated;
X is oxygen;
Z is oxygen or NH;
m is 0 or 1;
$R_{12}$ $R^{12}$, $R^{14}$, $R^{15}$, $R^{16}$ are hydrogen or $C_1$–$C_4$-alkyl;
$R^{13}$ is hydrogen, $C_1$–$C_4$-alkyl, tetrahydropyran-3-yl, tetrahydrothiopyran-3-yl or 1,4-dioxan-2-yl;

If desired, the $CR^{13}R^{14}$ unit can be replaced by C=O.

The 2-benzoylcyclohexane-1,3-diones of the formula I are obtainable by various routes, for example by the following process:

Reaction of cyclohexanediones of the formula II with an activated carboxylic acid IIIα or a carboxylic acid IIIβ which is preferably activated in situ, to give the acylation product IV, followed by a rearrangement reaction.

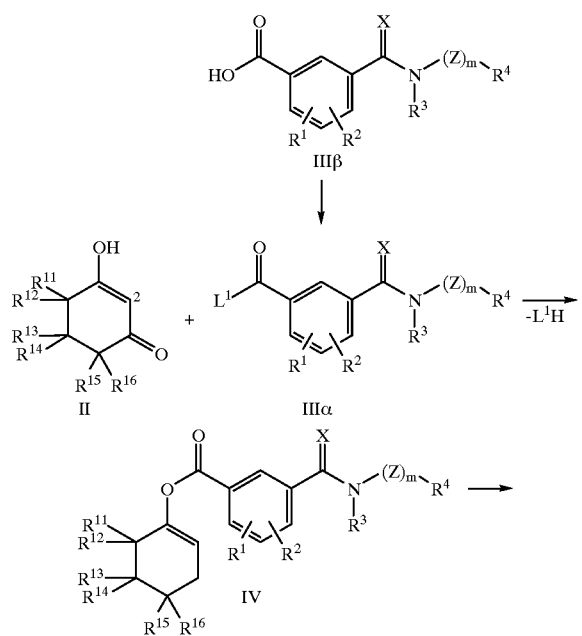

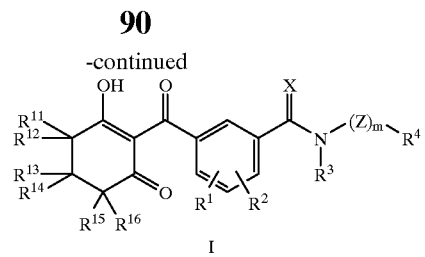

I $L^1$ is a nucleophilically displaceable leaving group such as halogen, eg. bromine, chlorine, hetaryl, eg. imidazolyl, pyridyl, carboxylate, eg. acetate, trifluoroacetate and the like.

The activated carboxylic acid can be employed directly, as in the case of the carboxylic acid halides, or generated in situ, for example with dicyclohexylcarbodiimide, triphenylphosphine/azodicarboxylic ester, 2-pyridine disulfite/triphenylphosphine, carbonyldiimidazole and the like.

It may be advantageous to carry out the acylation reaction in the presence of a base. The reactants and the auxiliary base are expediently employed in equimolar amounts for this purpose. A small excess mount of the auxiliary base, for example 1.2 to 1.5 mol equivalents based on II, may be advantageous under certain circumstances.

Suitable auxiliary bases are tertiary alkylamines, pyridine or alkali metal carbonates. Examples of solvents which can be used are chlorinated hydrocarbons such as methylene chloride, 1,2-dichloroethane, aromatic hydrocarbons such as toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide or esters such as ethyl acetate, or mixtures of these.

If carboxylic acid halides are employed as activated carboxylic acid component, it may be expedient to cool the reaction mixture to 0–10° C. when adding this reactant. The mixture is subsequently stirred at 20–100° C., preferably at 25–500° C., until the reaction is complete. Working-up is carried out in the customary manner, for example the reaction mixture is poured into water and the product of value is extracted. Solvents which are especially suitable for this purpose are methylene chloride, diethyl ether and ethyl acetate. After the organic phase has been dried and the solvent removed, the crude enol ester of the formula IV is purified, preferably by chromatography. However, it is also possible to employ the crude enol ester of the formula IV in the rearrangement reaction without further purification.

The enol esters of the formula IV are expediently subjected to a rearrangement reaction to give the compounds of the formula I at from 20 to 40° C. in a solvent and in the presence of an auxiliary base and with the aid of, or without, a cyano compound as catalyst.

Solvents which can be used are, for example, acetonitrile, ethylene chloride, 1,2-dichloroethane, ethyl acetate, toluene, or mixtures of these. The preferred solvent is acetonitrile.

Suitable auxiliary bases are tertiary amines such as triethylamine, pyridine or alkali metal carbonates such as sodium carbonate, potassium carbonate, which are preferably employed in quimolar amounts or up to a fourfold excess, based on the enol ester. By preference, triethylamine is used, preferably in twice the equimolar ratio based on the enol ester.

Suitable as "rearrangement catalysts" are inorganic cyanides such as sodium cyanide, potassium cyanide, and organic cyano compounds such as acetone cyanohydrin, trimethylsilyl cyanide. They are normally employed in an amount of from 1 to 50 mol percent, based on the enol ester. It is preferred to employ acetone cyanohydrin or trimethylsilyl cyanide, for example in an amount of from 5 to 15, preferably 10, mol percent based on the enol ester.

Work-up can be carried out in a manner known per se. For example, the reaction mixture is acidified with dilute mineral acid, eg. 5% strength hydrochloric acid or sulfuric acid, and extracted with an organic solvent, eg. methylene chloride, ethyl acetate. The organic extract can be extracted with 5–10% strength alkali metal carbonate solution, eg. sodium carbonate solution, potassium carbonate solution. The aqueous phase is acidified and the resulting precipitate filtered off with suction and/or extracted with methylene chloride or ethyl acetate, dried and concentrated. (Examples of the synthesis of enol esters of cyclohexane-1,3-diones and of the cyanide-catalyzed rearrangement reaction of the enol esters are mentioned, for example, in EP-A 186 118, U.S. Pat. No. 4 780 127).

Those cyclohexane-1,3-diones of the formula II which are used as starting materials and which are not already known can be prepared by processes known per se (for example EP-A 71 707, EP-A 142 741, EP-A 243 313, U.S. Pat. No. 4 249 937; WO 92/13821).

Novel benzoic acid derivatives of the formula III

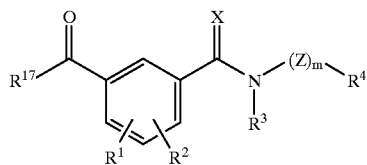

are those where the variables have the following meanings:

$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, $C_1$–$C_6$-alkyl, $C_1$–$C_6$-haloalkyl, $C_3$–$C_6$-alkenyl or $C_3$–$C_6$-alkynyl;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and for $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, phenyl-$C_1$–$C_4$-alkyl, hetaryl, phenoxy, phenyl-$C_1$–$C_4$-alkoxy and hetaryloxy, it being possible for the eight last-mentioned radicals, in turn, to be substituted;

X is oxygen or sulfur;
Z is oxygen or $NR^8$;
m is 0 or 1;
n is 0, 1 or 2;
$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;
$R^6$ is $C_1$–$C_6$-alkyl or $C_1$–$C_6$-haloalkyl;
$R^7$ is $C_1$–$C_6$-alkyl, $C_1$–$C_6$-haloalkyl, $C_4$–$C_6$-alkoxy-$C_2$–$C_6$-alkyl, $C_3$–$C_6$-alkenyl or $C_3$–$C_6$-alkynyl;

$R^8$ is hydrogen or $C_1$–$C_6$-alkyl;
$R^9$ is $C_1$–$C_6$-alkyl, $C_3$–$C_6$-alkenyl, $C_3$–$C_6$-alkynyl, phenyl or benzyl;
$R^{10}$ is $C_1$–$C_6$-alkyl, $C_1$–$C_6$-haloalkyl, $C_3$–$C_6$-alkenyl or $C_3$–$C_6$-alkynyl;
$R^{17}$ is hydroxyl or a radical which can be removed by hydrolysis,
where m is 1 if $R^3$ is hydrogen.

Examples of radicals which can be removed by hydrolysis are alkoxy, phenoxy, alkylthio and phenylthio radicals which are unsubstituted or substituted, halides, hetaryl radicals which are bonded via nitrogen, amino radicals, imino radicals which are unsubstituted or substituted.

Preferred are benzoic acid halides IIIα, where $L^1$=halogen (= III where $R^{17}$=halogen),

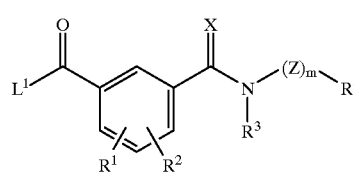

where the variables $R^1$ to $R^4$, X, Z and m have the meanings given under formula III and
$L^1$ is halogen, in particular chlorine or bromine.

Equally preferred are the benzoic acids of the formula IIIβ (= III where $R^{17}$=hydroxyl),

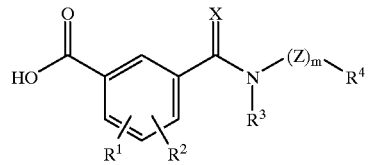

where the variables $R^1$ to $R^4$, X, Z and m have the meanings given under formula III.

Equally preferred are the benzoic esters of the formula IIIγ (= III where M=$C_1$–$C_6$-alkoxy)

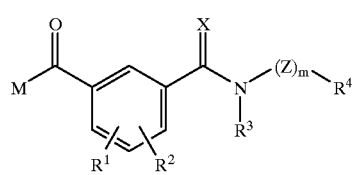

where the variables $R^1$ to $R^4$, X, Z and m have the meanings given under formula III and
M is $C_1$–$C_6$-alkoxy;

The particular embodiments of the benzoic esters of the formula III with reference to the variables $R^1$ to $R^4$, X, Z and M correspond to those of the 2-benzoylcyclohexane-1,3-diones of the formula I.

The compounds of the formula IIIα (where $L^1$ =halogen) can be synthesized by reacting benzoic acids of the formula IIIβ with halogenating reagents such as thionyl chloride, thionyl bromide, phosgene, diphosgene, triphosgene, oxalyl chloride, oxalyl bromide by methods similar to those known from the literature (cf. L. G. Fieser, M. Fieser "Reagents for Organic Synthesis", Vol. I (1967), pp. 767–769).

The benzoic acids of the formula IIIβ can be obtained, inter alia, by hydrolyzing the benzoic esters of the formula IIIγ (where M=C₁–C₆-alkoxy) by methods similar to those known from the literature.

The benzoic esters of the formula IIIγ (where X=oxygen) are obtainable by various routes, for example by the following processes:

A)

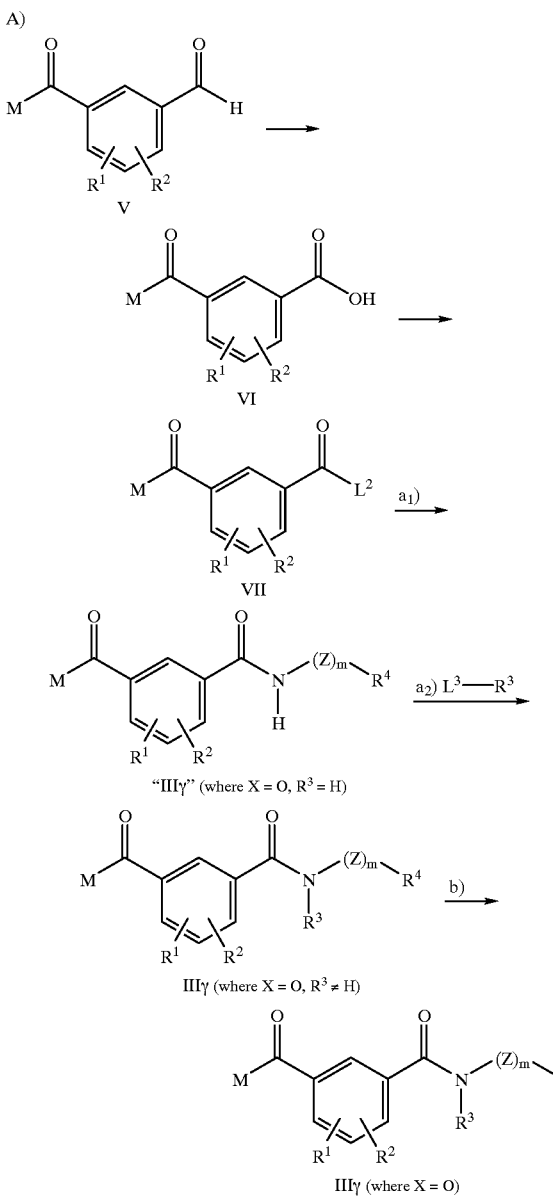

Isophthalic acid derivatives of the formula VI can be obtained in a manner known per se by oxidizing aldehydes of the formula V (J. March, "Advanced Organic Chemistry", 3rd Edition (1985), p. 629 et seq., Wiley-Interscience Publication).

Methods which are similar to those known from the literature can be used for first converting the compounds of the formula VI into the corresponding activated carboxylic acids VII where $L^2$ is a nucleophilically displaceable leaving group such as halogen, eg. bromine, chlorine, hetaryl, eg. imidazolyl, pyridyl, carboxylate, eg. acetate, trifluoroacetate and the like. Then, in case $a_1$) the product is reacted with an amino, hydroxylamine or hydrazine derivative, where $R^3$ is hydrogen. Subsequent alkylation ($a_2$) gives corresponding amide, hydroxamic acid or carbohydrazide derivatives of the formula IIIγ (where X=O and $R^3{\neq}H$) (where $L^3$ has the meaning given under $L^2$) (J. Org. Chem. (1971), 31, 284–294; J. Chem. Soc. Perk. II (1977), 1080–1084; Australian J. Chem. (1969), 22, 161–173; ibid (1974), 27, 1341–1349). In case b), the end product is obtained by direct reaction with $R^3NH$—$(Z)_m$—$R^4$ (cf. Australian J. Chem. (1974), 27, 1341–1349).

The aldehydes of the formula V can be synthesized from the corresponding toluenes of the formula VIII by processes similar to those known from the literature by converting them into the ω-halotoluene IX and subsequently oxidizing the product (cf. Synth. Commun. 22 (1992), 1967–1971).

(Hal = Cl, Br)

The carboxylic acids of the formula VI are accessible by hydrolyzing nitriles of the formula X by processes known from the literature (J. March, "Advanced Organic Chemistry", 3rd Edition (1970), p. 788, Wiley-Interscience Publication, 1985; Ann. Chem. (1970), p. 23–37).

The nitrites of the formula X can be synthesized from the corresponding aldehydes V by processes similar to those known from the literature (J. March, "Advanced Organic Chemistry", 3rd Edition (1985), pp. 806–807, Wiley-Interscience Publication). Equally, it is possible to obtain nitrites of the formula X from anilines of the formula XI by means of Sandmeyer reaction or from aryl halides of the formula XII by Rosemund/von Braun reaction with metal cyanides, in particular CUCN (J. March, "Advanced Organic Chemistry", 1985, 3rd Edition, p. 594, p. 648, Wiley-Interscience Publication).

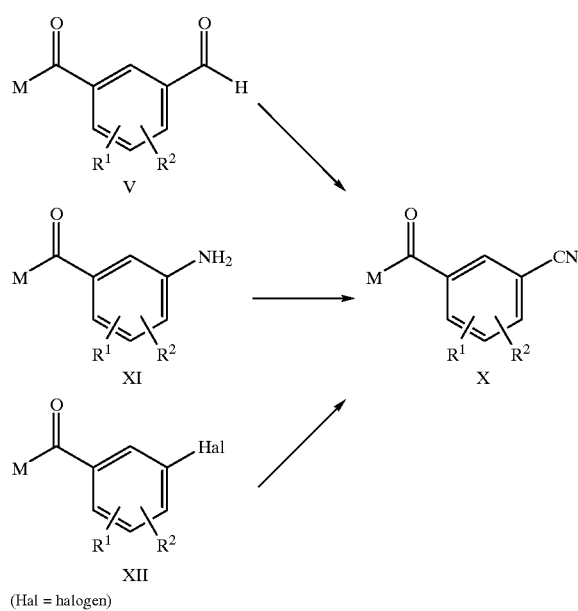

(Hal = halogen)

Preparation Examples

2-[2,4-Dichloro-3-(N-ethyl-N-propoxyaminocarbonyl)benzoyl]-1,3-cyclohexanedione (compound 2.03)

2.20 g (0.0065 mol) of 2,4-dichloro-3-(N-ethyl-N-propoxyaminocarbonyl)benzoyl chloride were added to a solution of 0.71 g (0.0070 mol) of triethylamine and 0.79 g (0.0070 mol) of 1,3-cyclohexanedione in 50 ml of methylene chloride. After the reaction solution had been stirred for 2 hours at room temperature, the solvent was removed in vacuo. The residue was purified by means of silica gel chromatography (eluent: toluene/ethyl acetate=8/2). The resulting enol ester was taken up in 50 ml of acetonitrile, and 0.50 g (0.0049 mol) of triethylamine and 0.10 g (0.0010 mol) of trimethylsilyl cyanide were added. After the mixture had been stirred for 3 hours at room temperature, the solvent was removed and the residue was taken up in methylene chloride. The organic phase was washed with dilute phosphoric acid, dried and concentrated. This gave 1.20 g of 2-[2,4-dichloro-3-(N-ethyl-N-propoxyaminocarbonyl) benzoyl]-1,3-cyclohexanedione, which was extracted by stirring with diethyl ether.

(m.p.: 180–183° C.)

Besides the 2-benzoylcyclohexane-1,3-dione of the formula I described above, other substances which were, or can be, prepared in a similar manner are listed in Table 2 which follows:

TABLE 2

Ia

| No. | Z | $R^1$ | $R^2$ | $R^3$ | $R^4$ | $R^{11}$ | $R^{12}$ | $R^{13}$ | $R^{14}$ | $R^{15}$ | $R^{16}$ | Physical data m.p. [° C.] |
|---|---|---|---|---|---|---|---|---|---|---|---|---|
| 2.01 | O | Cl | Cl | $CH_3$ | $CH_3$ | H | H | H | H | H | H | 127–128 |
| 2.02 | O | Cl | Cl | $CH_3$ | $CH_2$-(4-Cl—$C_6H_4$) | H | H | H | H | H | H | 182–183 |
| 2.03 | O | Cl | Cl | $CH_2CH_3$ | $(CH_2)_2CH_3$ | H | H | H | H | H | H | 182–183 |
| 2.04 | O | Cl | Cl | $CH_3$ | $(CH_2)_2CH_3$ | H | H | H | H | H | H | 177–178 |
| 2.05 | O | Cl | Cl | $CH_3$ | $CH_2$-(4-Cl—$C_6H_4$) | H | H | tetrahydrothiopyranyl | H | H | H | >200 |
| 2.06 | O | Cl | Cl | $CH_3$ | $CH_2$-(4-Cl—$C_6H_4$) | $CH_3$ | $CH_3$ | =O | H | $CH_3$ | $CH_3$ | 185–200 |
| 2.07 | O | Cl | Cl | $CH_3$ | $CH_2$-(4-Cl—$C_6H_4$) | H | H | 1,3-dioxanyl | H | H | H | 165–187 |
| 2.08 | O | Cl | Cl | $CH_3$ | $(CH_2)_2CH_3$ | H | H | tetrahydropyranyl | H | H | H | 50–55 |
| 2.09 | O | Cl | Cl | $CH_3$ | $CH_2$-(5-Cl-thien-2-yl) 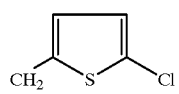 | H | H | H | H | H | H | 159–166 |

TABLE 2-continued

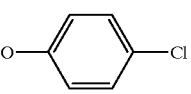

| No. | Z | R¹ | R² | R³ | R⁴ | | R¹¹ | R¹² | R¹³ | R¹⁴ | R¹⁵ | R¹⁶ | Physical data m.p. [° C.] |
|---|---|---|---|---|---|---|---|---|---|---|---|---|---|
| 2.10 | O | Cl | Cl | CH₃ | CH₂CH(CH₃)O—⟨C₆H₄⟩—Cl | | H | H | H | H | H | H | 60–67 |
| 2.11 | O | Cl | Cl | CH₃ | CH₂CH(CH₃)O—⟨C₆H₄⟩—Cl | tetrahydropyranyl-S | H | H | | H | H | H | 157–163 |
| 2.12 | O | SO₂CH₃ | Cl | CH₃ | CH₃ | | CH₃ | CH₃ | =O | | CH₃ | CH₃ | 190–210 |
| 2.13 | O | SO₂CH₃ | Cl | CH₃ | CH₃ | | H | H | H | H | H | H | >200 |
| 2.14 | O | SO₂CH₃ | Cl | CH₃ | CH₃ | | H | H | H | H | CH₃ | CH₃ | >200 |
| 2.15 | O | SO₂CH₃ | Cl | CH₃ | CH₃ | | H | H | CH₃ | CH₃ | H | H | >200 |
| 2.16 | O | SO₂CH₃ | Cl | CH₂CH₃ | CH₃ | | H | H | H | H | H | H | 160–175 |
| 2.17 | O | SO₂CH₃ | Cl | CH₂CH₃ | CH₂CH₃ | | H | H | H | H | H | H | 72–80 |
| 2.18 | O | SO₂CH₃ | Cl | CH₃ | CH₂CH₃ | | H | H | H | H | H | H | 75–113 |
| 2.19 | O | SO₂CH₃ | Cl | H | (E)-CH₂CH=CHCl | | H | H | H | H | H | H | 177–180 |
| 2.20 | O | SO₂CH₃ | Cl | CH₃ | (E)-CH₂CH=CHCl | | H | H | H | H | H | H | 195–197 |
| 2.21 | NH | SO₂CH₃ | Cl | CH₃ | H | | H | H | H | H | H | H | 168–178 |
| 2.22 | — | SO₂CH₃ | Cl | CH₃ | CH₃ | | H | H | H | H | H | H | 200–201 |
| 2.23 | — | SO₂CH₃ | Cl | CH₃ | CH₃ | | H | H | CH₃ | CH₃ | H | H | 160–162 |
| 2.24 | — | SO₂CH₃ | Cl | CH₃ | CH₃ | | H | H | H | H | CH₃ | CH₃ | 194–197 |
| 2.25 | — | SO₂CH₃ | CH₃ | CH₃ | CH₃ | | CH₃ | CH₃ | =O | | CH₃ | CH₃ | 75–130 |
| 2.26 | — | SO₂CH₃ | CH₃ | CH₃ | CH₃ | | H | H | CH₃ | CH₃ | H | H | 170–181 |
| 2.27 | — | Cl | Cl | CH₃ | CH₂CH₃ | | H | H | H | H | H | H | 193–198 |
| 2.28 | O | SO₂CH₃ | Cl | CH₂CH₃ | CH₃ | | H | H | CH₃ | CH₃ | H | H | 154–155 |
| 2.29 | O | SO₂CH₃ | Cl | H | CH₃ | | H | H | H | H | H | H | 164–168 |
| 2.30 | — | SO₂CH₃ | Cl | (CH₂)₂CH₃ | H | | H | H | H | H | H | H | 164–168 |
| 2.31 | — | SO₂CH₃ | Cl | CH₃ | H | | H | H | H | H | H | H | 180–183 |
| 2.32 | — | SO₂CH₃ | Cl | CH₃ | H | | CH₃ | CH₃ | H | H | H | H | >200 |

The syntheses of some starting materials are given below:
Methyl 2-chloro-3-(N-ethoxy-N-methylaminocarbonyl)-4-methylsulfonylbenzoate (compound 3.29)

Step a) 2-Chloro-3-methyl-4-methylthioacetophenone

A solution of 157 g (2 mol) of acetyl chloride in 420 mol of 1,2-dichloroethane was added dropwise at 15–20° C. to a suspension of 286 g (2.14 mol) of aluminum trichloride in 420 ml of 1,2-dichloroethane. A solution of 346 g (2 mol) of 2-chloro-6-methylthiotoluene in 1 l of 1,2-dichloroethane was subsequently added dropwise. After the reaction mixture had been stirred for 12 hours, it was poured into a mixture of 3 l of ice and 1 l of concentrated HCl. The mixture was extracted with methylene chloride, and the organic phase was washed with water, dried with sodium sulfate and concentrated. The residue was distilled in vacuo. This gave 256 g (60% of theory) of 2-chloro-3-methyl-4-methylthioacetophenone.

(m.p.: 460° C.)

Step b) 2-Chloro-3-methyl-4-methylsulfonylacetophenone 163.0 g (0.76 mol) of 2-chloro-3-methyl-4-methylthioacetophenone were dissolved in 1.5 l of glacial acetic acid, 18.6 g of sodium tungstate were added, and 173.3 g of 30% strength hydrogen peroxide solution were added dropwise with cooling. Stirring was continued for 2 days and the mixture was subsequently diluted with water. The solid which had precipitated was filtered off with suction, washed with water and dried. This gave 164.0 g (88% of theory) of 2-chloro-3-methyl-4-methyl-sulfonylacetophenone.

(m.p.: 110–111° C.)

Step c) 2-Chloro-3-methyl-4-methylsulfonylbenzoic acid 82 g (0.33 mol) of 2-chloro-3-methyl-4-methylsulfonyl-acetophenone were dissolved in 700 ml of dioxane, and 1 l of a 12.5% strength sodium hypochlorite solution was added at room temperature. Stirring was subsequently continued for 1 hour at 800° C. After cooling, two phases formed, of which the bottom phase was diluted with water and acidified weakly. The solid which precipitated was filtered off with suction, washed with water and dried. This gave 60 g (73% of theory) of 2-chloro-3-methyl-4-methylsulfonylbenzoic acid.

(m.p.: 230–231° C.)

Step d) Methyl 2-chloro-3-methyl-4-methylsulfonylbenzoate 100 g (0.4 mol) of 2-chloro-3-methyl-4-methyl-sulfonylbenzoic acid were dissolved in 1 l of methanol and hydrogen chloride gas was passed in for 5 hours at reflux temperature. The mixture was subsequently concentrated. This gave 88.5 g (84% of theory) of methyl 2-chloro-3-methyl-4-methylsulfonylbenzoate.

(m.p.: 107–108° C.)

Step e) Methyl 3-bromomethyl-2-chloro-4-methylsulfonylbenzoate 82 g (0.31 mol) of methyl 2-chloro-3-methyl-4-methylsulfonylbenzoate were dissolved in 2 l of tetrachloromethane, 56 g (0.31 mol) of N-bromosuccinimide were added, a little at a time, with exposure to light. The reaction mixture was filtered, the filtrate was concentrated, and the residue was taken up in 200 ml of methyl tert-butyl ether. The solution was treated with petroleum ether, and the solid which precipitated was filtered off with suction and dried. This gave 74.5 g (70% of theory) of methyl 3-bromomethyl-2-chloro-4-methylsulfonylbenzoate.

(m.p.: 74–75° C.)

Step f) Methyl 2-chloro-3-formyl-4-methylsulfonylbenzoate 42.1 g (0.36 mol) of N-methylmorpholine-N-oxide were added to a solution of 41.0 g (0.12 mol) of methyl 3-bromomethyl-2-chloro-4-methylsulfonylbenzoate in 250 ml of acetonitrile. The batch was stirred for 12 hours at room temperature and subsequently concentrated, and the residue was taken up in ethyl acetate. The solution was extracted with water, dried with sodium sulfate and concentrated. This gave 31.2 g (94% of theory) of methyl 2-chloro-3-formyl-4-methylsulfonylbenzoate (m.p.: 98–105° C.)

Step g) Methyl 2-chloro-3-hydroxycarbonyl-4-methylsulfonylbenzoate 13.8 g (0.11 mol) of sodium hydrogen phosphate monohydrate in 170 ml of water, 49.3 g (0.43 mol) of 30% strength hydrogen peroxide solution and 66.2 g (0.59 mol) of 80% strength aqueous sodium chlorite solution were added in succession at 5° C. to a solution of 115.3 g (0.42 mol) of methyl 2-chloro-3-formyl-4-methylsulfonylbenzoate and in 2000 ml of acetonitrile. The reaction solution was stirred for 1 hour at 5° C. and for 12 hours at room temperature. Then, the pH was brought to 1 with 10% strength hydrochloric acid, and 1500 ml of aqueous 40% strength sodium hydrogen sulfite solution were added. After the mixture had been stirred for 1 hour at room temperature, the aqueous phase was extracted three times with ethyl acetate. The combined organic phases were washed with sodium hydrogen sulfite solution and dried. After the solvent had been distilled off, 102.0 g of methyl 2-chloro-3-hydroxycarbonyl-4-methylsulfonylbenzoate were obtained.

($^1$H NMR (d$^6$-DMSO, δ in ppm): 3.34 (s, 3H); 3.93 (s, 3H); 8.08 (s, 2H); 14.50 (s, br., 1H))

Step h) Methyl 2-chloro-3-chlorocarbonyl-4-methylsulfonylbenzoate 2 drops of dimethylformamide and 11.9 g (0.1 mol) of thionyl chloride were added to a solution of 6.0 g (0.021 mol) of methyl 2-chloro-3-hydroxycarbonyl-4-methylsulfonylbenzoate and in 50 ml of dry toluene. The solution was refluxed for 4 hours. After the solvent had been removed in vacuo, 6.2 g of methyl 2-chloro-3-chlorocarbonyl-4-methylsulfonylbenzoate were obtained.

($^1$H NMR (CDCl$_3$; δ in ppm): 3.21 (s, 3H); 4.02 (s, 3H); 8.02 (d, 1H); 8.07 (d, 1H))

Step i) Methyl 2-chloro-3-N-ethoxyaminocarbonyl-4-methylsulfonylbenzoate (compound 3.28)

11.70 g (0.120 mol) of O-ethyl hydroxylamine hydrochloride and 12.10 g (0.120 mol) of triethylamine were added at room temperarture to a solution of 26.40 g (0.085 mol) of methyl 2-chloro-3-chlorocarbonyl-4-methylsulfonylbenzoate and in 300 ml of dichloromethane. After the reaction solution had been stirred for 4 hours at room temperature, it was washed with dilute hydrochloric acid, dried and concentrated. The resulting residue was extracted by stirring with diethyl ether. This gave 25.00 g of methyl 2-chloro-3-N-ethoxyaminocarbonyl-4-methylsulfonyl-benzoate.

(m.p.: 90–110° C.)

Step j) Methyl 2-chloro-3-(N-ethoxy-N-methylaminocarbonyl)-4-methylsulfonylbenzoate (compound 3.29)

A mixture of 20.00 g (0.060 mol) of methyl 2-chloro-3-N-ethoxyaminocarbonyl-4-methylsulfonylbenzoate and 16.60 g (0.120 mol) of potassium carbonate in 200 ml of dimethylformamide was stirred for 30 minutes at room temperature. 25.60 g (0.180 mol) of methyl iodide were subsequently added dropwise, and the mixture was stirred for 5 hours at 50° C. After the reaction mixture had cooled, it was stirred into 1 l of ice-water, the aqueous phase was extracted with ethyl acetate, and the combined organic phases were dried and concentrated. The residue was chromatographed on silica gel (eluent: toluene/ethyl acetate=8/2). This gave 3.80 g of methyl 2-chloro-3-(N-ethoxy-N-methylaminocarbonyl)-4-methyl-sulfonylbenzoate.

2,4-Dichloro-3-(N-ethyl-N-propoxy) aminocarbonylbenzoyl chloride (compound 3.21)

Step a) 2,4-Dichloro-3-methylacetophenone 235.0 g (3.0 mol) of acetyl chloride were added dropwise in the course of 2 hours to a solution of 502.0 g (3.12 mol) of 2,6-dichlorotoluene and [sic] 408.0 g (3.06 mol) of aluminum trichloride at 100° C., with stirring. After the reaction mixture had been stirred for 2 hours at 100–105° C., it was cooled and poured onto 3 l of ice and 1 l of water. The solid which precipitated in this process was filtered off with suction and washed to neutrality with 800 ml of water. After drying at 40° C., 500.0 g of 2,4-dichloro-3-methylacetophenone were obtained as crude product, which was subsequently distilled under a high vacuum.

(b.p.: 121–128° C. (4 mbar))

step b) 2,4-Dichloro-3-methylbenzoic acid

Firstly 655.2 g (4.1 mol) of bromine and subsequently 203.0 g (1.0 mol) of 2,4-dichloro-3-methylacetophenone in 1300 ml of 1,4-dioxane were added dropwise at 0–10° C. to a solution of 520.0 g (13 mol) of sodium hydroxide in 2600 ml of water. After the mixture had been stirred for 12 hours, the organic phase was separated off, the aqueous phase was treated with a 30% strength solution made with sodium pyrosulfite and water, and the pH was brought to 1 with hydrochloric acid. The precipitate which had separated out was filtered off with suction, washed with water and dried in vacuo at 60° C. This gave 197.0 g of 2,4-dichloro-3-methylbenzoic acid.

(m.p.: 173–175° C.)

Step c) Methyl 2,4-dichloro-3-methylbenzoate 60 ml of concentrated sulfuric acid were added dropwise to a solution of 424.0 g (2 mol) of 2,4-dichloro-3-methylbenzoic acid and in 1500 ml of methanol. After the reaction mixture had been refluxed for 5 hours, it was cooled and concentrated in vacuo, and the residue was subsequently taken up in 1000 ml of methylene chloride. The organic phase was washed with water, subsequently with 5% strength sodium hydrogen carbonate solution and then again with water, dried and concentrated in vacuo. This gave 401.0 g of methyl 2,4-dichloro-3-methylbenzoate.

(b.p: 103–107° C. (1–1.5 mbar))

Step d) Methyl 3-bromomethyl-2,4-dichlorobenzoate 1.0 g of azobisisobutyronitrile was added to a solution of 84.0 g (0.38 mol) of methyl 2,4-dichloro-3-methylbenzoate and 67.6 g (0.38 mol) of N-bromosuccinimide in 380 ml of carbon tetrachloride. After the reaction mixture had been refluxed for 3.5 hours, it was cooled, and the precipitate formed was filtered off with suction. The filtrate was concentrated in vacuo and the resulting residue was extracted by stirring with methyl tert-butyl ether. This gave 108.0 g of methyl 3-bromomethyl-2,4-dichlorobenzoate.

(m.p.: 51–54° C.)

Step e) Methyl 2,4-dichloro-3-formylbenzoate 696.2 g (2.97 mol) of aqueous 50% strength N-methylmorpholine N-oxide solution were added dropwise under reflux to a solution of 312.0 g (0.99 mol) of methyl 3-bromomethyl-2,4-dichlorobenzoate in 2 l of acetonitrile. After the reaction solution had been stirred for 48 hours at room temperature, it was stirred into 6 l of water. The precipitate which had separated out was filtered off with suction, washed with water and dried in vacuo. This gave 141.3 g of methyl 2,4-dichloro-3-formylbenzoate.

($^1$H NMR (CDCl$_3$, δ in ppm): 3.98 (s, 3H); 7.47 (d, 1H); 7.84 (d, 1H); 10.48 (s, 1H))

Step f) Methyl 2,4-dichloro-3-hydroxycarbonylbenzoate 5.9 g (0.043 mol) of sodium dihydrogen phosphate monohydrate in 70 ml of water, 20.5 g (0.181 mol) of 30% strength hydrogen peroxide solution and 27.3 g (0.241 mol) of 80% strength sodium chlorite solution were added in succession at 5° C. to a solution of 40.0 g (0.172 mol) of methyl 2,4-dichloro-3-formylbenzoate and in 500 ml of acetonitrile. The reaction solution was stirred for 1 hour at 5° C. and for 12 hours at room temperature. Subsequently, a pH of 1 was established with 10% strength hydrochloric acid, and 500 ml of 40% strength sodium hydrogen sulfite solution were added. After the mixture had been stirred for 1 hour at room temperature, the aqueous phase was extracted three times with ethyl acetate, the combined organic phases were washed with 1.0 l of 10% strength sodium hydrogen sulfite solution and subsequently dried. After the solvent had been distilled off, 40.0 g of methyl 2,4-dichloro-3-hydroxycarbonylbenzoate were obtained.

($^1$H NMR (d$^6$-DMSO, δ in ppm): 3.90 (s, 3H); 7.69 (d, 1H); 7.89 (d, 1H))

Step g) Methyl 3-chlorocarbonyl-2,4-dichlorobenzoate 2 drops of dimethylformamide and 11.90 g (0.1 mol) of thionyl chloride were added to a solution of 5.00 g (0.02 mol) of methyl 2,4-dichloro-3-hydroxycarbonyl-benzoate and in 50 ml of dry toluene. The solution was refluxed for 4 hours. After the solvent had been distilled off, 5.35 g of methyl 3-chlorocarbonyl-2,4-dichlorobenzoate were obtained.

Step h) Methyl 2,4-dichloro-3-(N-propoxy) aminocarbonylbenzoate (compound 3.17)

4.05 g (0.040 mol) of triethylamine and 4.50 g (0.040 mol) of propoxyamine hydrochloride were added to a solution of 10.70 g (0.040 mol) of methyl 3-chlorocarbonyl-2,4-dichlorobenzoate and [sic] 200 ml of dichloromethane. After the reaction solution had been stirred for 2 hours at room temperature, it was washed with dilute phosphoric acid, dried and concentrated. The residue obtained was chromatographed on silica gel (eluent: toluene/ethyl acetate=9/1). This gave methyl 2,4-dichloro-3-(N-propoxy) aminocarbonylbenzoate.

Step i) Methyl 2,4-dichloro-3-(N-ethyl-N-propoxy)-aminocarbonylbenzoate (compound 3.14)

A mixture of 12.50 g (0.041 mol) of methyl 2,4-dichloro-3-(N-propoxy)aminocarbonylbenzoate and 11.30 g (0.082 mol) of potassium carbonate in 100 ml of dimethylformamide was stirred for 30 minutes at room temperature. 19.20 g (0.123 mol) of ethyl iodide were subsequently added dropwise. After the reaction mixture had been heated for 5 hours at 50° C., it was cooled and stirred into 1 l of ice-water. The aqueous phase was then extracted with ethyl acetate, the combined organic phases were dried, and the solvent was distilled off in vacuo. After the residue had been chromatographed on silica gel (eluent: toluene/ethyl acetate=9/1), 7.00 g of methyl 2,4-dichloro-3-(N-ethyl-N-propoxy) aminocarbonylbenzoate were obtained.

(m.p.: 48–50° C.).

Step j) 2,4-Dichloro-3-(N-ethyl-N-propoxy) aminocarbonylbenzoic acid (compound 3.18)

A solution of 7.00 g (0.021 mol) of methyl 2,4-dichloro-3-(N-ethyl-N-propoxy)aminocarbonylbenzoate and [sic] 40 ml of 10% strength aqueous sodium hydroxide solution was stirred for 2 hours at 80° C. After the reaction mixture had cooled, it was stirred into 200 ml of ice-water, and the pH was brought to 1 with concentrated hydrochloric acid. The aqueous phase was extracted with ethyl acetate, and the combined organic phases were dried and concentrated in vacuo. This gave 5.50 g of 2,4-dichloro-3-(N-ethyl-N-propoxy)-aminocarbonylbenzoic acid.

Step k) 2,4-Dichloro-3-(N-ethyl-N-propoxy) aminocarbonylbenzoyl chloride (compound 3.21)

A solution of 4.00 g (0.0125 mol) of 2,4-dichloro-3-(N-ethyl-N-propoxy)aminocarbonylbenzoic acid and 14.90 g of thionyl chloride in 100 ml of dry toluene was stirred for 3 hours at 100° C. After the solvent had been removed in vacuo, 4.40 g of 2,4-dichloro-3-(N-ethyl-N-propoxy)-aminocarbonylbenzoyl chloride were obtained.

Methyl 2,4-dichloro-3-(N-methoxy) aminocarbonylbenzoate (compound 3.01)

20 4.60 g (0.045 mol) of triethylamine and 3.75 g (0.045 mol) of methoxyamine hydrochloride were added to a solution of 5.35 g (0.02 mol) of methyl 3-chlorocarbonyl-2,4-dichlorobenzoate and in 100 ml of dichloromethane. After the reaction solution had been stirred for 12 hours at room temperature, it was washed with dilute phosphoric acid, dried and concentrated. The resulting residue was extracted by stirring with diethyl ether. This gave 4.80 g of methyl 2,4-dichloro-3-(N-methoxy) aminocarbonylbenzoate.

(m.p.: 162–164° C.)

30 Methyl 2,4-dichloro-3-(N-propoxy) aminocarbonylbenzoate (compound 3.02)

10.7 g (0.04 mol) of methyl 3-chlorocarbonyl-2,4-dichlorobenzoate in 100 ml of methylene chloride were slowly added dropwise at 30° C. to a solution of 4.50 g (0.04 mol) of propoxyamine hydrochloride and 4.05 g (0.04 mol) of triethylamine in 200 ml of methylene chloride. After the reaction mixture had been stirred for 2 hours at room temperature, it was washed with dilute phosphoric acid, dried and concentrated. The resulting residue was chromatographed on silica gel (eluent: toluene/ethyl acetate=9/1). This gave 11.50 g of methyl 2,4-dichloro-3-(N-propoxyamino)carbonylbenzoate.

(m.p.: 80–81° C.)

Methyl 3-(N-4-chlorobenzyloxy)aminocarbonyl-2,4-dichlorobenzoate (compound 3.03)

10.70 g (0.04 mol) of methyl 3-chlorocarbonyl-2,4-dichloro-benzoate in 50 ml of methylene chloride were slowly added dropwise at approximately 30° C. to a solution of 7.76 g (0.04 mol) of 4-chlorobenzyloxyamine hydrochloride and 4.05 g (0.04 mol) of triethylamine in 200 ml of methylene chloride. After the reaction mixture had been stirred for 12 hours at room temperature, it was washed with dilute phosphoric acid, dried and concentrated. After the residue had been extracted by stirring with diethyl ether, 19.00 g of methyl 3-(4-chlorobenzyloxy)amino-carbonyl-2,4-dichlorobenzoate were obtained.
(m.p.: 120–121° C.)

Besides the compounds described above, other benzoic acid derivatives of the formula IIIa which were, or can be, prepared in a similar manner are listed in Table 3 below.

TABLE 3

IIIa (≙ III where $R^1$ is bonded in the 4-position and $R^2$ in the 2-position)

| No. | X | $R^1$ | $R^2$ | $R^3$ | $(Z)_m$—$R^4$ | $R^{17}$ | M.p. [° C.] $^1$H NMR [ppm] |
|---|---|---|---|---|---|---|---|
| 3.01 | O | Cl | Cl | H | OCH$_3$ | OCH$_3$ | 162–164 |
| 3.02 | O | Cl | Cl | H | O(CH$_2$)$_2$CH$_3$ | OCH$_3$ | 80–81 |
| 3.03 | O | Cl | Cl | H | 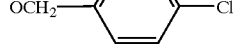 | OCH$_3$ | 120–121 |
| 3.04 | O | Cl | Cl | CH$_3$ | OCH$_3$ | OCH$_3$ | 78–80 |
| 3.05 | O | Cl | Cl | CH$_3$ | OCH$_3$ | OH | |
| 3.06 | S | Cl | Cl | CH$_3$ | OCH$_3$ | OCH$_3$ | |
| 3.07 | O | Cl | Cl | CH$_3$ | OCH$_3$ | Cl | |
| 3.08 | O | Cl | Cl | H | OCH$_3$ | OH | |
| 3.09 | O | Cl | Cl | H | OCH$_3$ | Cl | |
| 3.10 | O | Cl | Cl | CH$_3$ |  | OCH$_3$ | 121–123 |
| 3.11 | O | Cl | Cl | CH$_3$ | CH$_2$CH$_3$ | OCH$_3$ | |
| 3.12 | O | Cl | Cl | CH$_3$ | CH$_2$CH$_3$ | OH | 151–153 |
| 3.13 | O | Cl | Cl | CH$_3$ | O(CH$_2$)$_2$CH$_3$ | OCH$_3$ | 47–48 |
| 3.14 | O | Cl | Cl | C$_2$H$_5$ | O(CH$_2$)$_2$CH$_3$ | OCH$_3$ | 48–50 |
| 3.15 | O | Cl | Cl | CH$_3$ | 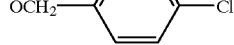 | OH | 130–131 |
| 3.16 | O | Cl | Cl | CH$_3$ | O(CH$_2$)$_2$CH$_3$ | OH | oil |
| 3.17 | O | Cl | Cl | H | O(CH$_2$)$_2$CH$_3$ | OCH$_3$ | 80–81 |
| 3.18 | O | Cl | Cl | C$_2$H$_5$ | O(CH$_2$)$_2$CH$_3$ | OH | oil |
| 3.19 | O | Cl | Cl | CH$_3$ | CH$_2$CH$_3$ | Cl | |
| 3.20 | O | Cl | Cl | CH$_3$ | 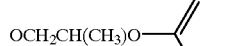 | Cl | |
| 3.21 | O | Cl | Cl | C$_2$H$_5$ | O(CH$_2$)$_2$CH$_3$ | Cl | |
| 3.22 | O | SO$_2$CH$_3$ | Cl | H | OCH$_3$ | OCH$_3$ | 160–162 |
| 3.23 | O | SO$_2$CH$_3$ | Cl | CH$_3$ | OCH$_3$ | OCH$_3$ | 102–103 |
| 3.24 | O | Cl | Cl | H | N(CH$_3$)$_2$ | OCH$_3$ | 170–176 |
| 3.25 | O | Cl | Cl | H | OCH$_2$CH(CH$_3$)O—⌬—Cl | OCH$_3$ | |
| 3.26 | O | Cl | Cl | CH$_3$ | OCH$_2$CH(CH$_3$)O—⌬—Cl | OCH$_3$ | |

TABLE 3-continued

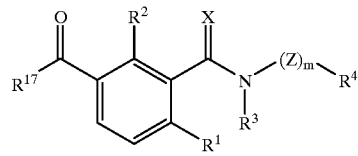

IIIa (= III where R¹ is bonded in the 4-position and R² in the 2-position)

| No. | X | R¹ | R² | R³ | $(Z)_m$—R⁴ | R¹⁷ | M.p. [° C.] ¹H NMR [ppm] |
|---|---|---|---|---|---|---|---|
| 3.27 | O | Cl | Cl | CH₃ | OCH₂CH(CH₃)O—⟨C₆H₄⟩—Cl | OH | 110–118 |
| 3.28 | O | SO₂CH₃ | Cl | H | OCH₂CH₃ | OCH₃ | 90–110 |
| 3.29 | O | SO₂CH₃ | Cl | CH₃ | OCH₂CH₃ | OCH₃ | |
| 3.30 | O | SO₂CH₃ | Cl | CH₃ | OCH₂CH₃ | OH | |
| 3.31 | O | SO₂CH₃ | Cl | CH₃ | OCH₃ | OH | |
| 3.32 | O | SO₂CH₃ | Cl | CH₃ | OCH₃ | Cl | |
| 3.33 | O | SO₂CH₃ | Cl | CH₂CH₃ | OCH₃ | OCH₃ | 140–144 |
| 3.34 | O | SO₂CH₃ | Cl | CH₂CH₃ | OCH₃ | OH | 194–197 |
| 3.35 | O | SO₂CH₃ | Cl | CH₃ | OCH₂CH₃ | OH | 98–103 |
| 3.36 | O | SO₂CH₃ | Cl | CH₂CH₃ | OCH₂CH₃ | OCH₃ | |
| 3.37 | O | SO₂CH₃ | Cl | CH₂CH₃ | OCH₂CH₃ | OH | |
| 3.38 | O | SO₂CH₃ | Cl | H | (E)-OCH₂CH=CHCl | OH | 204 |
| 3.39 | O | SO₂CH₃ | Cl | CH₃ | (E)-OCH₂CH=CHCl | OH | 57–60 |
| 3.40 | O | SO₂CH₃ | CH₃ | CH₃ | CH₃ | OH | 249–270 |
| 3.41 | O | Cl | Cl | CH₃ | N(CH₃)₂ | OCH₃ | 93 |
| 3.42 | O | SO₂CH₃ | Cl | C(CH₃)₂CH₂Cl | H | OCH₃ | 147–148 |
| 3.43 | O | SO₂CH₃ | Cl | H | OCH₃ | OH | oil |
| 3.44 | O | SO₂CH₃ | Cl | (CH₂)₂CH₃ | H | OH | 168–170 |
| 3.45 | O | SO₂CH₃ | Cl | CH₃ | NH₂ | OH | 203–205 |
| 3.46 | O | SO₂CH₃ | Cl | CH₃ | H | NHCH₃ | oil |
| 3.47 | O | SO₂CH₃ | Cl | CH₃ | H | OH | oil |

The 2-benzoylcyclohexane-1,3-diones of the formula I and their agriculturally useful salts are suitable as herbicides, both in the form of isomer mixtures and in the form of the pure isomers. The herbicidal compositions comprising compounds of the formula I effect very good control of vegetation on non-crop areas, especially at high rates of application. In crops such as wheat, rice, maize, soybeans and cotton they act against broad-leaved weeds and grass weeds without damaging the crop plants substantially. This effect is observed especially at low rates of application.

Depending on the application method in question, the compounds of the formula I, or compositions comprising them, can additionally be employed in a further number of crop plants for eliminating undesirable plants. Examples of suitable crops are the following:

Allium cepa, Ananas comosus, Arachis hypogaea, Asparagus officinalis, Beta vulgaris spec. altissima, Beta vulgaris spec. rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pisum sativum, Prunus avium, Prunus persica, Pyrus communis, Ribes syl estre [sic], Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera and Zea mays.

Moreover, the compounds of the formula I can also be used in crops which tolerate the action of herbicides due to breeding including genetic engineering methods.

The compounds of the formula I or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

The herbicidal compositions comprise a herbicidally active amount of at least one compound of the formula I or of an agriculturally useful salt of I and auxiliaries conventionally used for the formulation of crop protection products.

Suitable inert additives are essentially: mineral oil fractions of medium to high boiling point such as kerosine and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol, cyclohexanol, ketones such as cyclohexanone, and strongly polar solvents, e.g. amines such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substrates substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants (adjuvants) are the alkali metal, alkaline earth metal and ammonium salts of aromatic sulfonic acids, e.g. ligno-, phenol-, naphthalene- and dibutylnaphthalenesulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders and other solid carriers.

The concentrations of the compounds of the formula I in the ready-to-use products can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR spectrum).

The compounds I according to the invention can be formulated, for example, as follows:

I. 20 parts by weight of the compound No. 2.01 are dissolved in a mixture composed of 80 parts by weight of alkylated benzene, 10 parts by weight of the adduct of 8 to 10 mol of ethylene oxide and 1 mol of oleic acid N-monoethanolamide, parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 2.03 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 2.05 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 2.06 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

V. 3 parts by weight of the active ingredient No. 2.09 are mixed with 97 parts by weight of finely divided kaolin. This gives a dust which comprises 3% by weight of the active ingredient.

VI. 20 parts by weight of the active ingredient No. 2.11 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound 2.12 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound 2.07 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The active ingredients of the formula I, or the herbicidal compositions, can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while the active ingredients reach the leaves of undesirable plants which grow underneath, or the bare soil (post-directed, lay-by).

To widen the spectrum of action and to achieve synergistic effects, the compounds of the formula I can be mixed and applied jointly with a large number of representatives of other groups of herbicidally or growth-regulatory active ingredients. Suitable components in mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ethers, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to also apply the compounds of the formula I, alone or in combination with other herbicides, in the form of a mixture with other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The rates of application of active ingredient are from 0.001 to is 3.0, preferably 0.01 to 1.0, kg/ha active substance (a.s.), depending on the purpose of the control measures, the season, the target plants and the growth stage.

USE EXAMPLES

The herbicidal action of the 2-benzoylcyclohexane-1,3-diones of the formula I was demonstrated by the following greenhouse experiments:

The culture containers used were plastic pots containing loamy sand with approximately 3.0% of humus as substrate. The seeds of the test plants were sown separately for each species.

For the pre-emergence treatment, the active ingredients, suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were first grown to a plant height of from 3 to 15 cm, depending on the plant habit, and then treated with the active ingredients which had been suspended or emulsified in water. To this end, the test plants were either sown directly and grown in the same containers, or they were first grown separately as seedlings and transplanted into the test containers a few days prior to treatment. The rate of application for the post-emergence treatment was 0.125 or 0.0625 kg/ha a.s. Depending on the species, the plants were kept at from 10–25° C. and 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
|---|---|
| Chenopodium album | lambsquarters (goosefoot) |
| Ipomoea spp. | morning glory |
| Polygenum persicaria | ladysthumb |
| Solanum nigrum | black nightshade |
| Zea mays | Indian corn |

The compound 2.01 (Table 2), when applied post-emergence at rates of 0.125 and 0.0625 kg/ha (a.s.), had a very good effect against the abovementioned mono- and dicotyledonous harmful plants combined with good tolerance in Indian corn.

We claim:
1. A 2-benzoylcyclohexane-1,3-dione of formula I

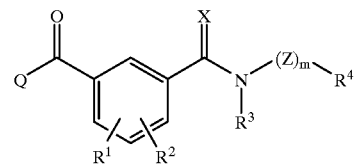

where the variables have the following meanings:
$R^1$, $R^2$ are hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$, —$OCOR^6$, —$OSO_2R^6$, —SH, —$S(O)_nR^7$, —$SO_2OR^5$, —$SO_2NR^5R^8$, —$NR^8SO_2R^6$ or —$NR^8COR^6$;

$R^3$ is hydrogen, $C_1$–$C_6$-alkyl, $C_1$–$C_6$-haloalkyl, $C_3$–$C_6$-alkenyl or $C_3$–$C_6$-alkynyl;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and for $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, phenyl-$C_1$–$C_4$-alkyl, hetaryl, phenoxy, phenyl-$C_1$–$C_4$-alkoxy and hetaryloxy, it being possible for the eight last-mentioned radicals, in turn, to be substituted;

X is oxygen or sulfur;
z is oxygen or $NR^8$;
m is 0 or 1;
n is 0, 1 or 2;
$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^6$ is $C_1$–$C_6$-alkyl or $C_1$–$C_6$-haloalkyl;

$R^7$ is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^8$ is hydrogen or $C_1$–$C_6$-alkyl;

$R^9$ is $C_1$–$C_6$-alkyl, $C_3$–$C_6$-alkenyl, $C_3$–$C_6$-alkynyl, phenyl or benzyl;

$R^{10}$ is $C_1$–$C_6$-alkyl, $C_1$–$C_6$-haloalkyl, $C_3$–$C_6$-alkenyl or $C_3$–$C_6$-alkynyl;

Q is a cyclohexane-1,3-dione ring of formula II

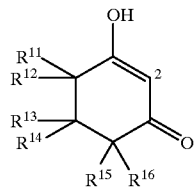

wherein $R^{11}$, $R^{12}$, $R^{14}$ and $R^{16}$ are hydrogen or $C_1$–$C_4$-alkyl;

$R^{13}$ is hydrogen, $C_1$–$C_4$-alkyl or $C_3$–$C_4$-cycloalkyl, it being possible for the two last-mentioned groups to have attached to them one to three of the following substituents: halogen, $C_1$–$C_4$-alkylthio or $C_1$–$C_4$-alkoxy; or is tetrahydropyran-2-yl, tetrahydropyran-3-yl, tetrahy-dropyran-4-yl, tetrahydrothiopyran-2-yl, tetrahydrothio-pyran-3-yl, tetrahydrothiopyran-4-yl, 1,3-dioxolan-2-yl, 1,3-dioxan-2-yl, 1,4-dioxan-2-yl, 1,3-oxathiolan-2-yl, 1,3-oxathian-2-yl, 1,3-dithiolan-2-yl or 1,3-di-thian-2-yl, it being possible for the 6 last-mentioned radicals to be substituted by one to three $C_1$–$C_4$-alkyl radicals;

$R^{15}$ is hydrogen, $C_1$–$C_4$-alkyl or $C_1$–$C_6$-alkoxycarbonyl; or $R^{13}$ and $R^{16}$ together form a π bond or a three to six-membered carbocyclic ring; or the $CR^{13}R^{14}$ unit represents a C=O group;

where m is 1 if $R^3$ is hydrogen; or an agriculturally useful salt thereof.

2. The 2-benzoylcyclohexane-1,3-dione of formula I defined in claim 1 wherein $R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^2$ is hydrogen or a radical as mentioned above for $R^1$.

3. The 2-benzoylcyclohexane-1,3-dione of formula I defined in claim 1 wherein m is 1.

4. The 2-benzoylcyclohexane-1,3-dione defined in claim 1 which is of formula Ia

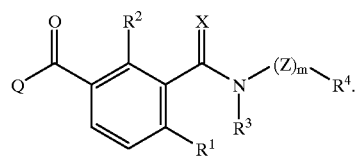

5. A process for the preparation of the 2-benzoylcyclohexane-1,3-dione of formula I defined in claim 1, which comprises acylating an unsubstituted or substituted cyclohexane-1,3-dione Q with an activated carboxylic acid IIIα or with a carboxylic acid IIIβ,

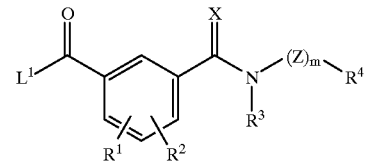

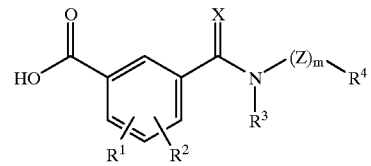

where $L^1$ is a nucleophilically displaceable leaving group, and, if appropriate, subjecting the acylation product to a rearrangement reaction in the presence of a catalyst to give the compounds I.

6. A benzoic acid derivative of formula IIIa

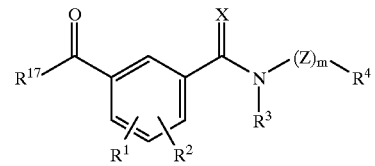

where $R^1$, $R^2$ are nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^3$ is hydrogen, $C_1$–$C_6$-alkyl, $C_1$–$C_6$-haloalkyl, $C_3$–$C_6$-alkenyl or $C_3$–$C_6$-alkynyl;

$R^4$ is hydrogen, $C_1$–$C_6$-alkyl, $C_3$–$C_6$-cycloalkyl, $C_3$–$C_6$-alkenyl, $C_4$–$C_6$-cycloalkenyl, $C_3$–$C_6$-alkynyl, —$COR^9$, —$CO_2R^9$, —$COSR^9$ or —$CONR^8R^9$, it being possible for the abovementioned alkyl, cycloalkyl, alkenyl, cycloalkenyl and alkynyl radicals and for $R^9$ of the radicals —$COR^9$, —$CO_2R^9$, —$COSR^9$ and —$CONR^8R^9$ to be partially or fully halogenated and/or to have attached to them one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, phenyl-$C_1$–$C_4$-alkyl, hetaryl, phenoxy, phenyl-$C_1$–$C_4$-alkoxy and hetaryloxy, it being possible for the eight last-mentioned radicals, in turn, to be substituted;

X is oxygen or sulfur;

Z is oxygen or $NR^8$;

m is 1;

n is 0, 1 or 2;

$R^5$ is hydrogen, $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

R 7 is $C_1$–$C_6$-alkyl, $C_1$–$C_6$-haloalkyl, $C_1$–$C_6$-alkoxy-$C_2$–$C_6$-alkyl, $C_3$–$C_6$-alkenyl or $C_3$–$C_6$-alkynyl;

$R^{17}$ is hydroxyl or a radical which can be removed by hydrolysis;

where $R^4$ is not hydrogen if Z is NH and $R^1$ and $R^2$ are chlorine.

7. The benzoic acid derivative of formula IIIa defined in claim 6, wherein $R^{17}$ is halogen, hydroxyl or $C_1$–$C_6$-alkoxy.

8. A composition comprising a herbicidally active amount of at least one 2-benzoylcyclohexane-1,3-dione of formula I or of an agriculturally useful salt of I defined in claim 1 and auxiliaries conventionally used for the formulation of crop protection products.

9. A process for the preparation of herbicidally active composition defined in claim 8, which comprises mixing a herbicidally active amount of at least one 2-benzoyl-cyclohexane-1,3-dione of formula I or of an agriculturally useful salt of I and auxiliaries conventionally used for the formulation of crop protection products.

10. A method of controlling undesirable vegetation, which comprises allowing a herbicidally active amount of at least one 2-benzoylcyclohexane-1,3-dione of formula I or of an agriculturally useful salt of I defined in claim 1 to act on plants, their environment and/or on seeds.

11. The 2-benzoylcyclohexane-1,3-dione of formula I defined in claim 1 wherein $R^3$ is hydrogen, methyl, ethyl, propyl, butyl, difluoromethyl or trifluoromethyl.

12. The 2-benzoylcyclohexane-1,3-dione of formula I defined in claim 1 wherein X is oxygen.

13. The 2-benzoylcyclohexane-1,3-dione of formula I defined in claim 1 wherein Z is oxygen, NH or N—CH$_3$.

14. The 2-benzoylcyclohexane-1,3-dione of formula I defined in claim 1 wherein $R^{11}$, $R^{12}$, $R^{14}$ and $R^{15}$ are each hydrogen, methyl or ethyl.

15. The 2-benzoylcyclohexane-1,3-dione of formula I defined in claim 1 wherein $R^{15}$ is hydrogen, methyl or ethyl.

16. The 2-benzoylcyclohexane-1,3-dione of formula I defined in claim 1 wherein $CR^{13}R^{14}$ represents a C=O group.

17. The 2-benzoylcyclohexane-1,3-dione defined in claim 1 which is of formula Ia'

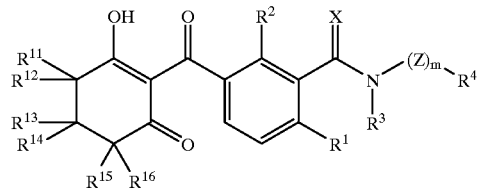

wherein $R^1$ is halogen or $C_1$–$C_4$-alkylsulfonyl;

$R^2$ is halogen or $C_1$–$C_4$-alkyl;

$R^3$ is hydrogen or $C_1$–$C_4$-alkyl;

$R^4$ is hydrogen, $C_1$–$C_6$-alkyl, $C_3$–$C_6$-alkenyl, it being possible for the two last-mentioned substituents to be partially or fully halogenated and/or to have attached to them one to three of the following froups: phenyl, phenyl-$C_1$–$C_4$-alkyl, hetaryl or phenoxy, it being possible for the 4 last-mentioned radicals to be partially or fully halogenated;

X is oxygen;

Z is oxygen or NH;

m is 0 or 1;

$R^{11}$, $R^{12}$, $R^{14}$, $R^{15}$ and $R^{16}$ are hydrogen or $C_1$–$C_4$-alkyl;

$R^{13}$ is hydrogen, $C_1$–$C_4$-alkyl, tetrahydropyran-3-yl, tetrahydro-thiopyran-3-yl or 1,4-dioxan-2-yl; or the $CR^{13}R^{14}$ unit represents a C=O group.

18. The 2-benzoylcyclohexane-1,3-dione of formula I defined in claim 1 wherein $R^{15}$ is H or $C_1$–$C_4$-alkyl.

19. The 2-benzoylcyclohexane-1,3-dione of formula I defined in claim 4 wherein $R^{15}$ is H or $C_1$–$C_4$-alkyl.

* * * * *

UNITED STATES PATENT AND TRADEMARK OFFICE
CERTIFICATE OF CORRECTION

PATENT NO. : 6,310,245 B1
DATED : Ocotober 30, 2001
INVENTOR(S) : Kardorff et al.

It is certified that error appears in the above-identified patent and that said Letters Patent is hereby corrected as shown below:

<u>Title page, Item [54] and Column 1, line 1,</u>
The title should read:
-- 3-AMINOCARBONYL/3-AMINOTHIOCARBONYL-SUBSTITUTED 2-BENZOYLCYCLOHEXANE-1,3-DIONES WITH HERBICIDAL EFFECT --

ABSTRACT,
Second line after formula I, "$R_1$" should be -- $R^1$ --.

<u>Column 111,</u>
Line 29, "tetrahy-dropyran" should be -- tetrahydropyran --.

<u>Column 114,</u>
Line 20, "froups" should be -- groups --.
Line 31, "tetrahydro-thiopyran" should be -- tetrahydrothiopyran --.

Signed and Sealed this

First Day of October, 2002

Attest:

JAMES E. ROGAN
*Attesting Officer*   *Director of the United States Patent and Trademark Office*